(12) United States Patent
Desai et al.

(10) Patent No.: US 8,367,670 B2
(45) Date of Patent: Feb. 5, 2013

(54) MODULATORS OF TOLL-LIKE RECEPTORS

(75) Inventors: Manoj C. Desai, Pleasant Hill, CA (US); Randall L. Halcomb, Foster City, CA (US); Paul Hrvatin, South San Francisco, CA (US); Hon Chung Hui, San Mateo, CA (US); Ryan McFadden, Foster City, CA (US); Paul A. Roethle, San Francisco, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 376 days.

(21) Appl. No.: 12/632,194

(22) Filed: Dec. 7, 2009

(65) Prior Publication Data

US 2010/0143301 A1   Jun. 10, 2010

Related U.S. Application Data

(60) Provisional application No. 61/121,061, filed on Dec. 9, 2008, provisional application No. 61/170,404, filed on Apr. 17, 2009, provisional application No. 61/224,386, filed on Jul. 9, 2009, provisional application No. 61/227,378, filed on Jul. 21, 2009, provisional application No. 61/242,635, filed on Sep. 15, 2009.

(51) Int. Cl.
| | |
|---|---|
| C07D 475/06 | (2006.01) |
| C07D 475/08 | (2006.01) |
| C07D 475/12 | (2006.01) |
| C07D 487/04 | (2006.01) |
| A61K 31/519 | (2006.01) |
| A61P 31/12 | (2006.01) |
| A61P 35/00 | (2006.01) |

(52) U.S. Cl. .................. 514/249; 544/258; 544/259
(58) Field of Classification Search .................. 544/258, 544/259; 514/249
See application file for complete search history.

(56) References Cited

U.S. PATENT DOCUMENTS

| | | | |
|---|---|---|---|
| 5,057,540 A | 10/1991 | Kensil et al. | |
| 5,424,311 A | 6/1995 | Billhardt-Troughton et al. | |
| 5,620,978 A | 4/1997 | Cai et al. | |
| 5,693,641 A | 12/1997 | Buckman et al. | |
| 6,299,884 B1 | 10/2001 | Van Nest et al. | |
| 6,452,325 B1 | 9/2002 | Dupont | |
| 2004/0029885 A1 | 2/2004 | Bauer et al. | |
| 2009/0263470 A1 | 10/2009 | Coller et al. | |

FOREIGN PATENT DOCUMENTS

| | | |
|---|---|---|
| EP | 1939201 A1 | 7/2008 |
| JP | 2886570 A | 5/1991 |
| WO | WO-9014837 A1 | 12/1990 |
| WO | WO-9744038 A1 | 11/1997 |
| WO | WO-9805661 A1 | 2/1998 |
| WO | WO-0000478 A1 | 1/2000 |
| WO | WO-0119825 A1 | 3/2001 |
| WO | WO-02076954 A1 | 10/2002 |
| WO | WO-03020722 A1 | 3/2003 |
| WO | WO-2004076454 A1 | 9/2004 |
| WO | WO-2005123736 A1 | 12/2005 |
| WO | WO-2006/117670 A1 | 11/2006 |
| WO | WO-2007014838 A1 | 2/2007 |
| WO | WO-2007108968 A2 | 9/2007 |
| WO | WO-2007148064 A1 | 12/2007 |
| WO | WO-2008051493 A2 | 5/2008 |
| WO | WO-2008101867 A1 | 8/2008 |
| WO | WO-2008113711 A1 | 9/2008 |
| WO | WO-2009022185 A2 | 2/2009 |
| WO | WO-2009023269 A2 | 2/2009 |
| WO | WO-2009067547 A1 | 5/2009 |

OTHER PUBLICATIONS

Barr, I.G. et al. (1998) "ISCOMs and other saponin based adjuvants," *Advanced Drug Delivery Reviews* 32:247-271.
Boyer, N. et al. (2000) "Pathogenesis, diagnosis and management of hepatitis C," *J. of Hepatology* 32(Supp. 1)98-112.
Boyle, P.H. et al. (1991) Synthesis of a 2,4-Diaminodihydrohomopteridine, 6-Acetyl-2,4-Diamino-7,8-Dihydro—9H-Pyrimido[4,5-b][1,4]Diazepine, Using a Furazano[3,4-d]Pyrimidine Precursor.
Breault, G.A. et al. (2008) "Exploring 8-benzyl pteridine-6,7-diones as inhibitors of glutamate racemase (MurI) in Gram-positive bacteria," Bioorganic & Medicinal Chemistry Letters, 18(23)6100-6103.
Calisher, C.H. et al. (1989) "Antigenic Relationships between Flaviviruses as Determined by Cross-neutralization Tests with Polyclonal Antisera," *J. gen. Virol.* 70:37-43.
Di Bisceglie, A. et al. (1999) "The Unmet Challenges of Hepatitis C," *Scientific American , Inc.* 80-85.
Dustin, L.B. "Flying Under the Radar; The Immunobiology of Hepatitis C," *Annu. Rev. Immunol.* 25:71-99, (2007).
Dymock, B. et al. (2000) "Novel approaches to the treatment of hepatitis C virus infection," *Antiviral Chemistry & Chemotherapy*, 11:79-96.
Dzierba, C. et al. (2007) Dihydropyridopyrazinones and Dihydropteridinones as Corticotropin-Releasing Factor-1 Receptor Antagonists: Structure—Activity Relationships and Computational Modeling.
Gluck, R. et al, (2002) "New technology platforms in the development of vaccines for the future," *Vaccine* 20:B10-B16.
Goodchild, A. et al. (2009) "Primary Leukocyte Screens for Innate Immune Agonists," *Journal of Biomolecular Screening* 14(6):723-730.

(Continued)

*Primary Examiner* — Bruck Kifle

(57) ABSTRACT

Provided are modulators of TLRs of Formula II:

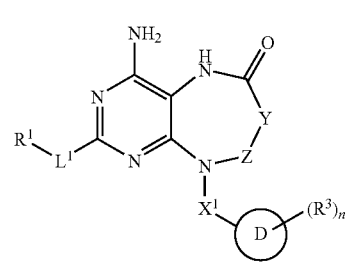

Formula II pharmaceutically acceptable salts thereof, compositions containing such compounds, and therapeutic methods that include the administration of such compounds.

19 Claims, No Drawings

OTHER PUBLICATIONS

Gordon, C.P. et al. (2005) "Control of Hepatitis C: A Medicinal Chemistry Perspective," *Journal of Medicinal Chemistry* 48(1)1-20.

Horsmans, Y. et al. (2005) "Isatoribine, an Agonist of TLR7, Reduces Plasma Virus Concentration in Chronic Hepatitis C Infection," *Hepatology* 42:724-731.

International Search Report and Written Opinion for International App. No. PCT/US20091067002, International filing date Dec. 7, 2009, mailed on Feb. 22, 2010.

Jin, G. et al. (2006) "Synthesis and immunostimulatory activity of 8-substituted amino 9-benzyladenines as potent Toll-like receptor 7 agonists," *Bioorganic & Medicinal Chemistry Letters* 16:4559-4563.

Korba, B.E. at al. (2000) "Treatment of Chronic Woodchuck Hepatitis Virus Infection in the Eastern Woodchuck (Marmota monax) With Nucleoside Analogues Is Predictive of Therapy for Chronic Hepatitis B Virus Infection in Humans," *Hepatology* 31:1165-1175.

Lee, J. et al. (2006) "Activation of anti-hepatitis C virus responses via Toll-like receptor 7," *Proc. Natl. Acad. Sci.* 103:1828-1833.

Menne, S. et al. (2007) "The woodchuck as an animal model for pathogenesis and therapy of chronic hepatitis B virus infection," *World J. Gastroenterol.* 13:104-124.

Moennig, V. et al. (1992) "The Pestiviruses," *Advances in Virus Research* 41:53-98.

Moradpour, D. et al. (2007) "Replication of hepatitis C virus," *Nature Reviews, Microbiology* 5(6) 453-463.

Nagashima, T. et al. (2004) "Solution-Phase Parallel Synthesis of an N-Alkylated Dihydropteridinone Library from Fluorous Amino Acids," *J. Comb Chem.* 6:942-949.

Scott, L.J. (2002) "Interferon-α-2b Plus Ribavirin," *Drugs* 62:507-556.

Sun, P. et al. (2009) "Functional characterization of ex vivo blood myeloid and plasmacytoid dendritic cells after infection with dengue virus," *Virology* 383:207-215.

Susvilo, I. et al. (2006) "Study on the Reaction of Methyl N-Methyl-N-(6-substituted-5-nitropyrimidin-4-yl)glycinates with Sodium Alkoxides," *J. Heterocyclic Chem.*, 43, 267-276.

Tennant, B.C. (1999) "Animal Models of Hepatitis B Virus Infection," *Clinics in Liver Disease* 3(2):241-266.

Thomas, A. et al. (2007) "Investigating Toll-Like Receptor Agonists for Potential to Treat Hepatitis C Virus Infection," *Antimicrobial Agents and Chemotherapy* 51(8) 2969-2978.

MODULATORS OF TOLL-LIKE RECEPTORS

This application is filed under 35 U.S.C. 111(a) claiming the benefit under 35 U.S.C. 119(e) of U.S. provisional applications 61/121,061 filed Dec. 9, 2008, 61/170,404 filed Apr. 17, 2009, 61/224,386 filed Jul. 9, 2009, 61/227,378 filed Jul. 21, 2009 and 61/242,635 filed Sep. 15, 2009; all of which are herein incorporated by reference in their entireties for all purposes.

FIELD OF THE INVENTION

This application relates generally to pteridinone and pyrimidinodiazepinone derivatives and pharmaceutical compositions which selectively modulate toll-like receptors (such as TLR7), and methods of making and using such compounds.

BACKGROUND OF THE INVENTION

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli*.), TLR3 is activated by double-stranded RNA, TLR4 is activated by lipopolysaccharide (i.e., LPS or endotoxin) of Gram-negative bacteria (e.g., *Salmonella* and *E. coli* 0157:H7), TLR5 is activated by flagellin of motile bacteria (e.g., *Listeria*), TLR7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-a), interleukin-1 (IL-1), and certain chemokines. Agonists of TLR-7 are immunostimulants and induce the production of endogenous interferon-a in vivo.

There are a number of diseases, disorders, and conditions linked to TLRs such that therapies using a TLR agonist are believed promising, including but not limited to melanoma, non-small cell lung carcinoma, hepatocellular carcinoma, basal cell carcinoma, renal cell carcinoma, myeloma, allergic rhinitis, asthma, COPD, ulcerative colitis, hepatic fibrosis, and viral infections such as HBV, Flaviviridae viruses, HCV, HPV, RSV, SARS, HIV, or influenza.

The treatment of Flaviviridae virus infections with TLR agonists is particularly promising. Viruses of the Flaviviridae family comprise at least three distinguishable genera including *pestiviruses, Flaviviruses*, and *hepaciviruses* (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). *Flaviviruses* are responsible for important human diseases such as dengue fever and yellow fever while *hepaciviruses* cause hepatitis C virus infections in humans. Other important viral infections caused by the Flaviviridae family include West Nile virus (WNV) Janpanese encephalitis virus (JEV), tick-borne encephalitis virus, Junjin virus, Murray Valley encephalitis, St Louis enchaplitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Bymock et al. in Antiviral Chemistry & Chemotherapy, 11:2; 79-95 (2000). Currently, there are primarily two antiviral compounds, ribavirin, a nucleoside analog, and interferon-alpha (α) (IFN), that are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., of al. *Drugs* 2002, 62, 507-556) but less than half the patients given this treatment show a persistent benefit.

HCV is recognized by innate virus-sensing mechanisms that induce a rapid IFN response (Dustin, et al., *Annu. Rev. Immunol.* 2007, 25, 71-99). It is likely that the sources of the IFN are, at least, the infected hepatocytes and particularly the plasmacytoid dendritic cells (pDC) that highly express TLR 7 receptors and secrete high amounts of IFN. Horsmans, et al. (*Hepatology*, 2005, 42, 724-731), demonstrated that a once daily 7-day treatment with the TLR 7 agonist isatoribine reduces plasma virus concentrations in HCV infected patients. Lee, et al. (*Proc. Natl. Acad. Sci. USA*, 2006, 103, 1828-1833), demonstrated that TLR 7 stimulation can induce HCV immunity by both an IFN and IFN-independent mechanisms. These workers also revealed that TLR 7 is expressed in normal as well as HCV infected hepatocytes. These combined results support the conclusion that stimulation of TLR 7 receptors, such as through the administration of a TLR 7 agonist, is a viable mechanism for effectively treating natural HCV infections. Given the need for more effective treatments for HCV infections, there is a need to develop safe and therapeutically effective TLR 7 agonists.

SUMMARY OF THE INVENTION

Provided is a compound of Formula II:

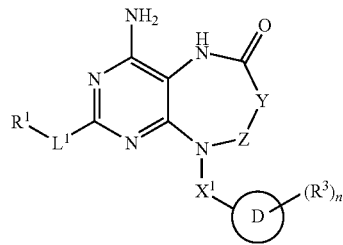

Formula II or a pharmaceutically acceptable salt or ester thereof, wherein:

Y—Z is —$CR^4R^5$—, —$CR^4R^5$—$CR^4R^5$—, —C(O)$CR^4R^5$—, —$CR^4R^5$C(O)—, —$NR^8$C(O)—, —C(O)$NR^8$—, —$CR^4R^5$S(O)$_2$—, or —$CR^5$=$CR^5$—;

$L^1$ is —$NR^8$—, —O—, —S—, —N($R^8$)C(O)—, —S(O)$_2$—, —S(O) —C(O)N($R^8$)—, —N($R^8$)S(O)$_2$—, —S(O)$_2$N($R^8$)— or a covalent bond;

$R^1$ is alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, or substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl;

$X^1$ is alkylene, substituted alkylene, heteroalkylene, substituted heteroalkylene, alkenylene, substituted alkenylene, alkynylene, substituted alkynylene, carbocyclylene, substituted carbocyclylene, heterocyclylene, substituted heterocyclylene, —$NR^8$—, —O—, —C(O)—, —S(O)—, S(O)$_2$—, or a bond;

D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$; or D is a heterocyclyl, substituted heterocyclyl, heteroaryl or substituted heteroaryl wherein said heterocyclyl, substituted heterocyclyl, heteroaryl or substituted heteroaryl comprises one to four nitrogen atoms;

each $L^2$ is independently alkylene, substituted alkylene, heteroalkylene, substituted heteroalkylene, or a covalent bond;

each $R^3$ is independently halogen, cyano, azido, nitro, alkyl, substituted alkyl, hydroxyl, amino, heteroalkyl, substituted heteroalkyl, alkoxy, haloalkyl, haloalkoxy, —CHO, —C(O)$OR^8$, —S(O)$R^8$, —S(O)$_2R^8$; —C(O)$NR^9R^{10}$, —N($R^9$)C(O)$R^8$, carbocyclyl, substituted carbocyclyl, carbocyclylalkyl, substituted carbocyclylalkyl, alkenyl, substituted alkenyl, alkynyl, substituted alkynyl, —S(O)$_2NR^9R^{10}$, —N($R^9$)S(O)$_2R^8$, —N($R^9$)S(O)$_2OR^{10}$, —OS(O)$_2NR^9R^{10}$;

n is 0, 1, 2, 3, 4 or 5;

$R^4$ and $R^5$ are each independently H, alkyl, substituted alkyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, cyano, azido, $OR^8$, —C(O)H, —C(O)$R^8$, —S(O)$R^8$, —S(O)$_2R^8$, —C(O)$OR^8$, or —C(O)$NR^9R^{10}$; or $R^4$ and $R^5$, taken together with the carbon to which they are both attached, form a carbocycle, substituted carbocycle, heterocycle or substituted heterocycle; or $R^4$ and $R^5$, when on the same carbon atom, taken together with the carbon to which they are attached are —C(O)— or —C($NR^8$)—; or two $R^4$ or two $R^5$ on adjacent carbon atoms when taken together with the carbons to which they are attached form a 3 to 6 membered carbocycle, substituted carbocycle, heterocycle or substituted heterocycle;

$R^6$ and $R^7$ are each independently H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl, —C(O)H, —C(O)$R^8$, —S(O)$R^8$, —S(O)$_2R^8$, —C(O)$OR^8$, or —C(O)$NR^9R^{10}$, S(O)$_2NR^9R^{10}$; or $R^6$ and $R^7$, taken together with the nitrogen to which they are both attached, form a substituted or unsubstituted heterocycle, which may contain one or more additional heteroatoms selected from N, O, P, or S; or $R^7$ taken together with $L^2$, and the N to which they are both attached, forms a substituted or unsubstituted 3 to 8 membered heterocycle which may contain one or more additional heteroatoms selected from N, O, S, or P;

$R^8$ is H, alkyl, substituted alkyl, haloalkyl, alkenyl, substituted alkenyl, alkynyl, substituted alkynyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; and $R^9$ and $R^{10}$ are each independently H, alkyl, substituted alkyl, alkenyl, substituted alkenyl, alkynyl, substituted alkynyl, haloalkyl, heteroalkyl, substituted heteroalkyl, carbocyclyl, substituted carbocyclyl, carbocyclylalkyl, substituted carbocyclylalkyl, heterocyclyl, substituted heterocyclyl, heterocyclylalkyl, substituted heterocyclylalkyl, arylalkyl, substituted arylalkyl, heteroarylalkyl, substituted heteroarylalkyl, carbocyclylheteroalkyl, substituted carbocyclylheteroalkyl, heterocyclylheteroalkyl, substituted heterocyclylheteroalkyl, arylheteroalkyl, substituted arylheteroalkyl, heteroarylheteroalkyl, or substituted heteroarylheteroalkyl; or $R^9$ and $R^{10}$, taken together with the nitrogen to which they are both bonded, form a substituted or unsubstituted heterocycle;

wherein each substituted alkyl, substituted alkenyl, substituted alkynyl, substituted heteroalkyl, substituted carbocyclyl, substituted carbocyclylalkyl, substituted heterocyclyl, substituted heterocyclylalkyl, substituted arylalkyl, substituted heteroarylalkyl, substituted carbocyclylheteroalkyl, substituted heterocyclylheteroalkyl, substituted arylheteroalkyl, substituted heteroarylheteroalkyl, substituted alkylene, substituted heteroalkylene, substituted alkenylene, substituted alkynylene, substituted carbocyclylene, or substituted heterocyclylene is independently substituted with one to four substituents selected from the group consisting of -halogen, —R, —O⁻, =O, —OR, —SR, —S⁻, —NR$_2$, —N(+)R$_3$, =NR, —C(halogen)$_3$, —CR(halogen)$_2$, —CR$_2$(halogen), —CN, —OCN, —SCN, —N=C=O, —NCS, —NO, —NO$_2$, =N$_2$, —N$_3$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NR, —S(=O)R, —NRS(=O)₂R, —NRS(=O)₂NRR, —NRS(=O)₂OR, —OP(=O)(OR)₂, —P(=O)(OR)₂, —P(O)(OR)(O)R, —C(=O)R, —C(=S)R, —C(=O)OR, —C(=S)OR, —C(=O)SR, —C(=S)SR, —C(=O)NRR, —C(=S)NRR, —C(=NR)NRR, and —NRC(=NR)NRR; wherein each R is independently H, alkyl, cycloalkyl, aryl, arylalkyl, or heterocyclyl.

While not wishing to be bound by theory, the inventors currently believe that the compounds of Formula II are agonists of TLR-7 and may also be agonists of other TLRs.

Another aspect of the present invention includes a method for treating a viral infection comprising administering a therapeutically effective amount of a compound of Formula II. The compound is administered to a human subject in need thereof, such as a human being who is infected with a virus of the Flaviviridae family, such as hepatitis C virus. In one embodiment, the viral infection is acute or chronic HCV infection. In one embodiment, the treatment results in one or more of a reduction in viral load or clearance of RNA.

Another aspect of the present invention includes the use of a compound of Formula II for the manufacture of a medicament for the treatment of a viral infection. Another aspect of the present invention includes a compound of Formula II for the use in treating a viral infection. In one embodiment, the viral infection is acute or chronic HCV infection. In one embodiment, the treatment results in one or more of a reduction in viral load or clearance of RNA.

In another aspect, a method for treating Flaviviridae viral infections is provided comprising administering an therapeutically effective amount of a compound of Formula II to a patient in need thereof. The compound of Formula II is administered to a human subject in need thereof, such as a human being who is infected with viruses of the Flaviviridae family. In another embodiment, the compound of Formula II is administered to a human subject in need thereof, such as a human being who is infected with a HCV virus. In one embodiment, the treatment results in the reduction of one or more of the in viral loads or clearance of RNA in the patient.

In another embodiment, provided is a method of treating and/or preventing a disease caused by a viral infection wherein the viral infection is caused by a virus selected from the group consisting of dengue virus, yellow fever virus, West Nile virus, Japanese encephalitis virus, tick-borne encephalitis virus, Junjin virus, Murray Valley encephalitis virus, St Louis encephalitis virus, Omsk hemorrhagic fever virus, bovine viral disarrhea virus, Zika virus and Hepatitis C virus; by administering to a subject in need thereof a therapeutically effective amount of a compound of Formula II, or a pharmaceutically acceptable salt thereof.

In another aspect, provided is the use of a compound of Formula II for the manufacture of a medicament for the treatment of Flaviviridae viral infections. In another aspect, provided is a compound of Formula II for use in treating a Flaviviridae viral infection. In one embodiment, the Flaviviridae viral infection is acute or chronic HCV infection. In one embodiment of each aspect of use and compound, the treatment results in the reduction of one or more of the viral loads or clearance of RNA in the patient.

In another aspect, provided is a method for treating or preventing HCV comprising administering an effective amount of a compound of Formula II to a patient in need thereof. In another aspect, provided is the use of a compound of the present invention for the manufacture of a medicament for the treatment or prevention of HCV.

In another aspect, provided is a pharmaceutical composition comprising a compound of Formula II and one or more pharmaceutically acceptable carriers or excipients. The pharmaceutical composition of Formula II may further comprise one or more additional therapeutic agents. The one or more additional therapeutic agent may be, without limitation, selected from: interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV, or mixtures thereof.

In another aspect, provided is a method for the treatment or prevention of the symptoms or effects of an HCV infection in an infected animal which comprises administering to, i.e. treating, said animal with a pharmaceutical combination composition or formulation comprising an effective amount of a Formula II compound, and a second compound having anti-HCV properties.

In another embodiment, provided are compounds of Formula II and pharmaceutically acceptable salts thereof and all racemates, enantiomers, diastereomers, tautomers, polymorphs, pseudopolymorphs and amorphous forms thereof.

In another aspect, provided are processes and novel intermediates disclosed herein which are useful for preparing Formula II compounds.

In other aspects, novel methods for synthesis, analysis, separation, isolation, purification, characterization, and testing of the compounds of Formula II are provided.

The present invention includes combinations of aspects and embodiments, as well as preferences, as herein described throughout the present specification.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

All documents referenced herein are each incorporated by reference in their entirety for all purposes.

In one embodiment of Formula II, $L^1$ is —$NR^8$—. In another embodiment of Formula II, $L^1$ is —O—. In another embodiment of Formula II, $L^1$ is —S—. In another embodiment of Formula II, $L^1$ is —$N(R^8)C(O)$—. In another embodiment of Formula II, $L^1$ is —S(O)—. In another embodiment of Formula II, $L^1$ is —$S(O)_2$—. In another embodiment of Formula II, $L^1$ is a covalent bond. In another embodiment of Formula II, $L^1$ is —$C(O)N(R^8)$—. In another embodiment of Formula II, $L^1$ is —$N(R^8)S(O)_2$—. In another embodiment of Formula II, $L^1$ is —$S(O)_2N(R^8)$—.

In one embodiment of Formula II, $R^1$ is alkyl. In another embodiment of Formula II, $R^1$ is substituted alkyl. In another embodiment of Formula II, $R^1$ is heteroalkyl. In another embodiment of Formula II, $R^1$ is substituted heteroalkyl.

In another embodiment of Formula II, $X^1$ is alkylene. In another embodiment of Formula II, $X^1$ is substituted alkylene. In another embodiment of Formula II, $X^1$ is heteroalkylene. In another embodiment of Formula II, $X^1$ is substituted heteroalkylene. In one embodiment of Formula II, $X^1$ is $C_1$-$C_6$ alkylene. In another embodiment of Formula II, $X^1$ is substituted $C_1$-$C_6$ alkylene. In another embodiment of Formula II, $X^1$ is $C_1$-$C_6$ heteroalkylene. In another embodiment of Formula II, $X^1$ is substituted $C_1$-$C_6$ heteroalkylene. In another embodiment of Formula II, $X^1$ is —$CH_2$—.

In one embodiment of Formula II, D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another embodiment of Formula II, D is a heterocyclyl or heteroaryl wherein said heterocyclyl or heteroaryl comprises one to four nitrogen atoms. In another embodiment of Formula II, D is a 3- to 12-membered carbocyclyl or 3- to 12-membered heterocyclyl wherein said carbocyclyl or heterocyclyl is substituted with -$L^2$-$NR^6R^7$. In another embodiment of Formula II, D is phenyl, biphenyl or pyridinyl wherein said phenyl, biphenyl or pyridinyl is substituted with -$L^2$-$NR^6R^7$. In another embodiment of Formula II, D is a heterocyclyl, substituted heterocyclyl, heteroaryl or substituted heteroaryl wherein said heterocyclyl, substituted heterocyclyl, heteroaryl or substituted heteroaryl comprises one to four nitrogen atoms. In another embodiment of Formula II, D is a heterocyclyl, substituted heterocyclyl, heteroaryl or substituted heteroaryl wherein said heterocyclyl, substituted heterocyclyl, heteroaryl or substituted heteroaryl is optionally substituted pyridinyl, optionally substituted piperidinyl, optionally substituted piperazinyl or optionally substituted 1,2,3,4-tetrahydroisoquinolinyl.

In one embodiment of Formula II, D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^6$ and $R^7$ independently are H, alkyl, heteroalkyl, or, together with the nitrogen atom to which they are attached, form a substituted or unsubstituted heterocyclyl. In another embodiment of Formula II, D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another embodiment of Formula II, D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$ and $R^7$ taken together with $L^2$, and the N to which they are both attached, forms a substituted or unsubstituted 3 to 8 membered heterocycle which may contain one or more additional heteroatoms selected from N, O, S, or P.

In one embodiment of Formula II, —Y—Z— is —$CR^4R^5$—. In another embodiment of Formula II, —Y—Z— is —$CR^4R^5$—$CR^4R^5$—. In another embodiment of Formula II, —Y—Z— is —$CR^4R^5$— wherein each $R^4$ or $R^5$ is independently H or $C_1$-$C_6$ alkyl. In another embodiment of Formula II, —Y—Z— is —$CH_2$—. In another embodiment of Formula II, —Y—Z— is —$(CH_2)_2$—. In another embodiment of Formula II, —Y—Z— is —C(O)—.

In one embodiment of Formula II, —Y—Z— is —$CR^4R^5$— or —$CR^4R^5$—$CR^4R^5$— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, $R^7$ taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— or —$CR^4R^5$—$CR^4R^5$— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —$CR^4R^5$— wherein each $R^4$ or $R^5$ is independently H or $CH_3$ and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -$L^2$-$NR^6R^7$. In another aspect of this embodiment, D is a 3- to 12-membered carbocyclyl or 3- to 12-membered heterocyclyl wherein said carbocyclyl or heterocyclyl is substituted with -$L^2$-$NR^6R^7$. In another aspect of this embodiment, D is phenyl, biphenyl or pyridinyl wherein said phenyl, biphenyl or pyridinyl is substituted with -$L^2$-$NR^6R^7$. In another aspect of this embodiment, $R^6$ and $R^7$ independently are H, alkyl, heteroalkyl, or, together with the nitrogen atom to which they are attached, form a substituted or unsubstituted heterocyclyl. In another aspect of this embodiment, $R^6$ and $R^7$ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, R7 taken together with $L^2$, and the N to which they are both attached, forms a substituted or unsubstituted 3 to 8 membered heterocycle which may contain one or more additional heteroatoms selected from N, O, S, or P. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^1$ is —NH— or —O—. In another aspect of this embodiment, $R^1$ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —CR⁴R⁵— wherein each R⁴ or R⁵ is independently H or CH₃ and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, L¹ is —NH— or —O—. In another aspect of this embodiment, R¹ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —CR⁴R⁵— wherein R⁴ and R⁵ taken together with the carbon to which they are attached is —C(O)— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -L²-NR⁶R⁷. In another aspect of this embodiment, D is a 3- to 12-membered carbocyclyl or 3- to 12-membered heterocyclyl wherein said carbocyclyl or heterocyclyl is substituted with -L²-NR⁶R⁷. In another aspect of this embodiment, D is phenyl, biphenyl or pyridinyl wherein said phenyl, biphenyl or pyridinyl is substituted with -L²-NR⁶R⁷. In another aspect of this embodiment, R⁶ and R⁷ independently are H, alkyl, heteroalkyl, or, together with the nitrogen atom to which they are attached, form a substituted or unsubstituted heterocyclyl. In another aspect of this embodiment, R⁶ and R⁷ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, R⁷ taken together with L², and the N to which they are both attached, forms a substituted or unsubstituted 3 to 8 membered heterocycle which may contain one or more additional heteroatoms selected from N, O, S, or P. In another aspect of this embodiment, each of R⁶ and R⁷ independently is H, alkyl, or heteroaryl. In another aspect of this embodiment, R⁶ and R⁷ taken together with the nitrogen to which they are attached form a substituted or unsubstituted 4-6 membered heterocycle comprising 0 to 2 heteroatoms selected from N, O or S. In another aspect of this embodiment, L¹ is —NH— or —O—. In another aspect of this embodiment, R¹ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —CR⁴R⁵— wherein R⁴ and R⁵ taken together with the carbon to which they are attached is —C(O)— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, is —NH— or —O—. In another aspect of this embodiment, R¹ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —CH₂CH₂— and D is carbocyclyl, substituted carbocyclyl, heterocyclyl or substituted heterocyclyl wherein said carbocyclyl, substituted carbocyclyl, heterocyclyl or substituted heterocyclyl is substituted with one or two -L²-NR⁶R⁷. In another aspect of this embodiment, D is a 3- to 12-membered carbocyclyl or 3- to 12-membered heterocyclyl wherein said carbocyclyl or heterocyclyl is substituted with -L²-NR⁶R⁷. In another aspect of this embodiment, D is phenyl, biphenyl or pyridinyl wherein said phenyl, biphenyl or pyridinyl is substituted with -L²-NR⁶R⁷. In another aspect of this embodiment, R⁶ and R⁷ independently are H, alkyl, heteroalkyl, or, together with the nitrogen atom to which they are attached, form a substituted or unsubstituted heterocyclyl. In another aspect of this embodiment, R⁶ and R⁷ taken together with the nitrogen to which they are attached form a 4- to 10-membered mono- or bicyclic, saturated, partially saturated, or unsaturated ring containing from 0 to 3 additional heteroatoms selected from N, O, or S. In another aspect of this embodiment, R⁷ taken together with L², and the N to which they are both attached, forms a substituted or unsubstituted 3 to 8 membered heterocycle which may contain one or more additional heteroatoms selected from N, O, S, or P. In another aspect of this embodiment, each of R⁶ and R⁷ independently is H, alkyl, or heteroaryl. In another aspect of this embodiment, R⁶ and R⁷ taken together with the nitrogen to which they are attached form a substituted or unsubstituted 4-6 membered heterocycle comprising 0 to 2 heteroatoms selected from N, O or S. In another aspect of this embodiment, L¹ is —NH— or —O—. In another aspect of this embodiment, R¹ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment of Formula II, —Y—Z— is —CH₂CH₂— and D is a heterocyclyl or heteroaryl wherein said heterocyclyl or heteroaryl comprises one to four nitrogen atoms. In another aspect of this embodiment, D is optionally substituted pyridinyl, optionally substituted piperidinyl, optionally substituted piperazinyl or optionally substituted 1,2,3,4-tetrahydroisoquinolinyl. In another aspect of this embodiment, L¹ is —NH— or —O—. In another aspect of this embodiment, R¹ is alkyl, substituted alkyl, heteroalkyl, substituted heteroalkyl, heterocyclylalkyl, substituted heterocyclylalkyl, carbocyclylalkyl or substituted carbocyclylalkyl.

In one embodiment, the compound of Formula II is represented by Formula Ia:

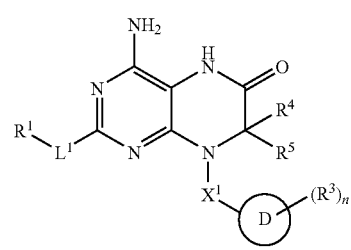

or a pharmaceutically acceptable salt thereof, wherein:
L¹ is —NH— or —O—;
R¹ is alkyl, substituted alkyl, heteroalkyl, substituted heteroalkyl, heterocyclylalkyl, substituted heterocyclylalkyl, carbocyclylalkyl or substituted carbocyclylalkyl;
each of R⁴ and R⁵ independently is H or C₁-C₆ alkyl or R⁴ and R⁵ taken together with the carbon to which they are attached is —C(O)—;
X¹ is C₁-C₆ alkylene, C₁-C₆ heteroalkylene or C₁-C₆ substituted heteroalkylene;
D is phenyl, biphenyl or pyridinyl, wherein said phenyl, biphenyl or pyridinyl is substituted with -L²-NR⁶R⁷; or
D is pyridinyl, piperidinyl, piperazinyl or 1,2,3,4-tetrahydroisoquinolinyl;

n is 0 or 1;

$R^3$ is halogen, cyano, alkyl, carbocyclyl, carbocyclylalkyl, haloalkyl, —C(O)OR$^6$, —C(O)NR$^9$R$^{10}$ or —CHO;

$L^2$ is $C_1$-$C_6$ alkylene or a covalent bond;

each of $R^6$ and $R^7$ independently is H, alkyl, or heteroaryl; or $R^6$ and $R^7$ taken together with the nitrogen to which they are attached form a substituted or unsubstituted 4-6 membered heterocycle comprising 0 to 2 heteroatoms selected from N, O or S.

In one embodiment of Formula Ia, each of $R^4$ and $R^6$ independently is H or $C_1$-$C_6$ alkyl. In another embodiment of Formula Ia, each of $R^4$ and $R^5$ is H. In another embodiment of Formula Ia, $R^4$ and $R^5$ taken together with the carbon to which they are attached is —C(O)—. In another embodiment of Formula Ia, $L^1$ is —O—. In another embodiment of Formula Ia, $L^1$ is —NH—. In another embodiment of Formula Ia, $X^1$ is $C_1$-$C_6$ alkylene. In another embodiment of Formula Ia, $X^1$ is $C_1$-$C_6$ heteroalkylene. In another embodiment of Formula Ia, $X^1$ is $C_1$-$C_6$ substituted heteroalkylene. In another embodiment of Formula Ia, $X^1$ is —CH$_2$—. In another embodiment of Formula Ia, D is phenyl, biphenyl or pyridinyl, wherein said phenyl, biphenyl or pyridinyl is substituted with -$L^2$-NR$^6$R$^7$. In another embodiment of Formula Ia, D is pyridinyl, piperidinyl, or piperazinyl. In another embodiment of Formula Ia, $L^2$ is —CH$_2$—. In another embodiment of Formula Ia, each of $R^6$ and $R^7$ independently is H, alkyl, or heteroaryl. In another embodiment of Formula Ia, $R^6$ and $R^7$ taken together with the nitrogen to which they are attached form a substituted or unsubstituted 4-6 membered heterocycle comprising 0 to 2 heteroatoms selected from N, O or S.

In one embodiment of Formula Ia, each of $R^4$ and $R^5$ independently is H or CH$_3$ and D is phenyl, biphenyl or pyridinyl, wherein said phenyl, biphenyl or pyridinyl is substituted with -$L^2$-NR$^6$R$^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is —CH$_2$—. In another aspect of this embodiment, $X^1$ is —CH$_2$—. In another aspect of this embodiment, $L^1$ is —O—. In another aspect of this embodiment, $L^1$ is —NH—.

In one embodiment of Formula Ia, each of $R^4$ and $R^5$ independently is H or CH$_3$ and D is pyridinyl, piperidinyl, or piperazinyl. In another aspect of this embodiment, $X^1$ is —CH$_2$—. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is —O—. In another aspect of this embodiment, $L^1$ is —NH—.

In one embodiment of Formula Ia, $R^4$ and $R^5$ taken together with the carbon to which they are attached is —O(O)— and D is phenyl, biphenyl or pyridinyl, wherein said phenyl, biphenyl or pyridinyl is substituted with -$L^2$-NR$^6$R$^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is —CH$_2$—. In another aspect of this embodiment, $X^1$ is —CH$_2$—. In another aspect of this embodiment, $L^1$ is —O—. In another aspect of this embodiment, $L^1$ is —NH—.

In one embodiment of Formula Ia, $R^4$ and $R^6$ taken together with the carbon to which they are attached is —C(O)— and D is pyridinyl, piperidinyl, piperazinyl or 1,2,3,4-tetrahydroisoquinolinyl. In another aspect of this embodiment, $X^1$ is —CH$_2$—. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is —O—. In another aspect of this embodiment, $L^1$ is —NH—.

In one embodiment, the compound of Formula II is represented by Formula IIa:

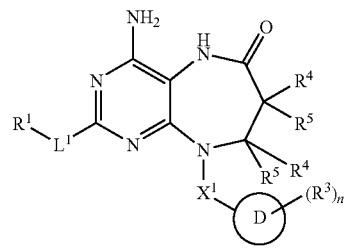

or a pharmaceutically acceptable salt thereof, wherein:

$L^1$ is —NH— or —O—;

$R^1$ is alkyl, substituted alkyl, heteroalkyl, substituted heteroalkyl, heterocyclylalkyl, substituted heterocyclylalkyl, carbocyclylalkyl or substituted carbocyclylalkyl;

each of $R^4$ and $R^5$ independently is H or $C_1$-$C_6$ alkyl or any $R^4$ and $R^5$ on the same carbon atom when taken together with the carbon to which that is —C(O)—;

$X^1$ is $C_1$-$C_6$ alkylene, $C_1$-$C_6$ heteroalkylene or $C_1$-$C_6$ substituted heteroalkylene;

D is phenyl, biphenyl or pyridinyl, wherein said phenyl, biphenyl or pyridinyl is substituted with -$L^2$-NR$^6$R$^7$; or D is pyridinyl, piperidinyl, piperazinyl or 1,2,3,4-tetrahydroisoquinolinyl;

n is 0 or 1;

$R^3$ is halogen, cyano, alkyl, carbocyclyl, carbocyclylalkyl, haloalkyl, —C(O)OR$^8$, —C(O)NR$^9$R$^{10}$ or —CHO;

$L^2$ is $C_1$-$C_6$ alkylene or a covalent bond;

each of $R^6$ and $R^7$ independently is H, alkyl, or heteroaryl; or $R^6$ and $R^7$ taken together with the nitrogen to which they are attached form a substituted or unsubstituted 4-6 membered heterocycle comprising 0 to 2 heteroatoms selected from N, O or S.

In one embodiment of Formula IIa, each of $R^4$ and $R^5$ independently is H or $C_1$-$C_5$ alkyl. In another embodiment of Formula IIa, each of $R^4$ and $R^5$ is H. In another embodiment of Formula IIa, $L^1$ is —O—. In another embodiment of Formula IIa, $L^1$ is —NH—. In another embodiment of Formula IIa, $X^1$ is $C_1$-$C_6$ alkylene. In another embodiment of Formula IIa, $X^1$ is $C_1$-$C_6$ heteroalkylene. In another embodiment of Formula IIa, $X^1$ is $C_1$-$C_6$ substituted heteroalkylene. In another embodiment of Formula IIa, $X^1$ is —CH$_2$—. In another embodiment of Formula IIa, D is phenyl, biphenyl or pyridinyl, wherein said phenyl, biphenyl or pyridinyl is substituted with -$L^2$-NR$^6$R$^7$. In another embodiment of Formula IIa, D is pyridinyl, piperidinyl, piperazinyl or 1,2,3,4-tetrahydroisoquinolinyl. In another embodiment of Formula IIa, $L^2$ is —CH$_2$—. In another embodiment of Formula IIa, each of $R^6$ and $R^7$ independently is H, alkyl, or heteroaryl. In another embodiment of Formula IIa, $R^6$ and $R^7$ taken together with the nitrogen to which they are attached form a substituted or unsubstituted 4-6 membered heterocycle comprising 0 to 2 heteroatoms selected from N, O or S.

In one embodiment of Formula IIa, each of $R^4$ and $R^5$ independently is H or $CH_3$ and D is phenyl, biphenyl or pyridinyl, wherein said phenyl, biphenyl or pyridinyl is substituted with $-L^2-NR^6R^7$. In another aspect of this embodiment, each of $R^6$ and $R^7$ independently is H, alkyl, or heteroaryl. In another aspect of this embodiment, $R^6$ and $R^7$ taken together with the nitrogen to which they are attached form a substituted or unsubstituted 4-6 membered heterocycle comprising 0 to 2 heteroatoms selected from N, O or S. In another aspect of this embodiment, $L^2$ is $-CH_2-$. In another aspect of this embodiment, $X^1$ is $-CH_2-$. In another aspect of this embodiment, $L^1$ is $-O-$. In another aspect of this embodiment, $L^1$ is $-NH-$.

In one embodiment of Formula IIa, each of $R^4$ and $R^5$ independently is H or $CH_3$ and D is pyridinyl, piperidinyl, or piperazinyl. In another aspect of this embodiment, $X^1$ is $-CH_2-$. In another aspect of this embodiment, $X^1$ is $C_1$-$C_6$ alkylene. In another aspect of this embodiment, $X^1$ is $C_1$-$C_6$ heteroalkylene. In another aspect of this embodiment, $X^1$ is $C_1$-$C_6$ substituted heteroalkylene. In another aspect of this embodiment, $L^1$ is $-O-$. In another aspect of this embodiment, $L^1$ is $-NH-$.

In another embodiment, provided are compounds of Formula II selected from the group consisting of

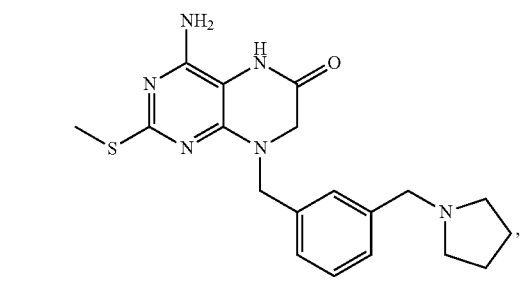

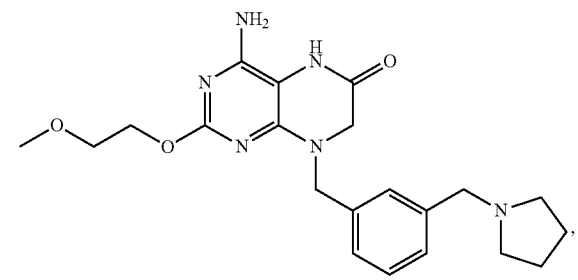

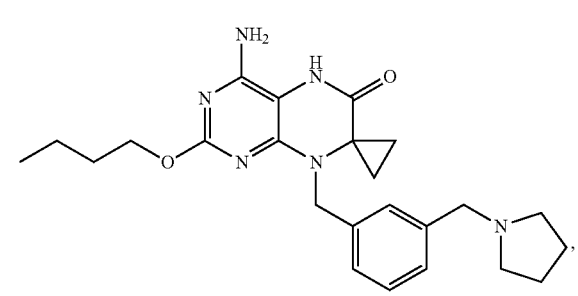

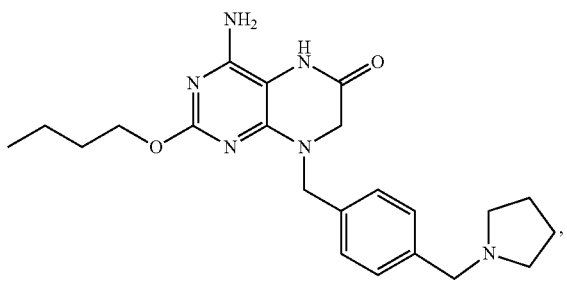

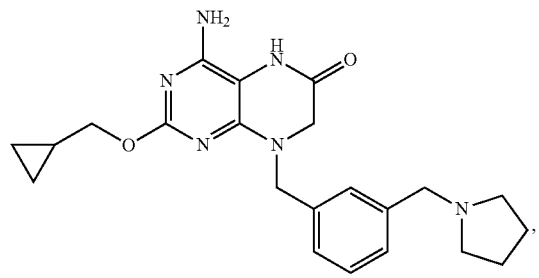

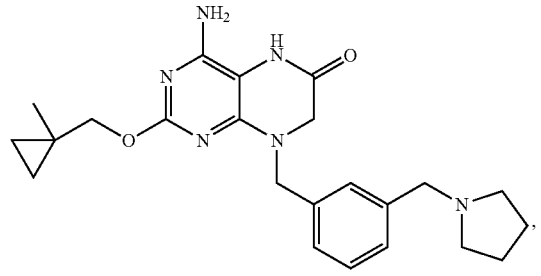

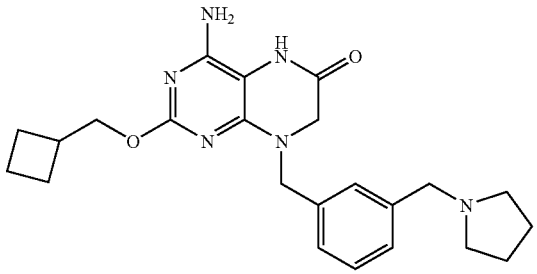

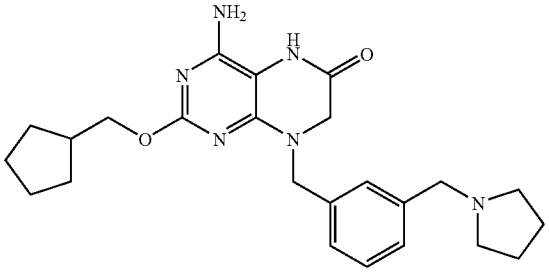

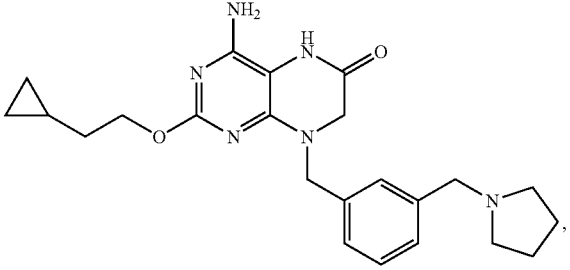

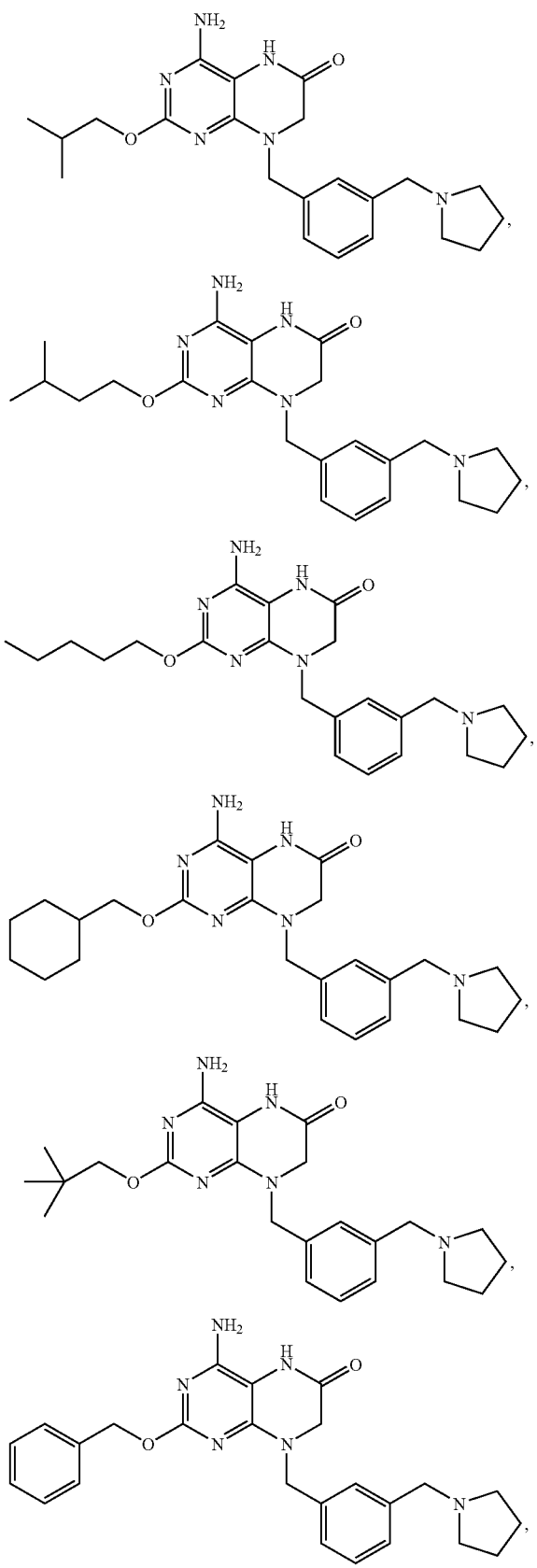
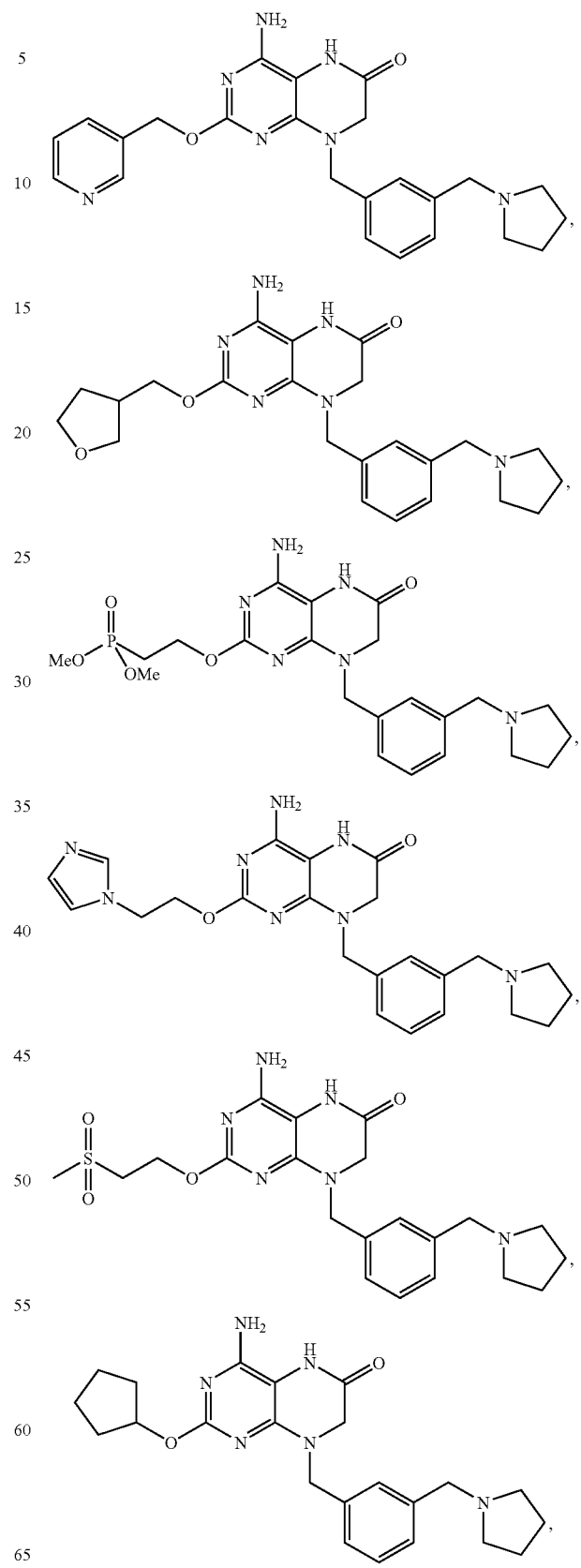

17
-continued
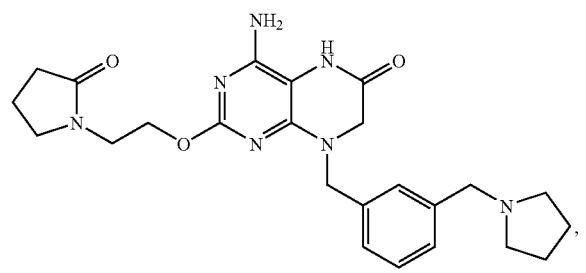
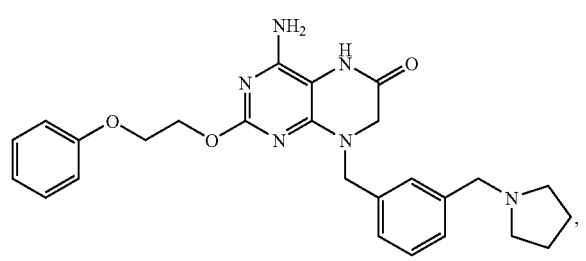
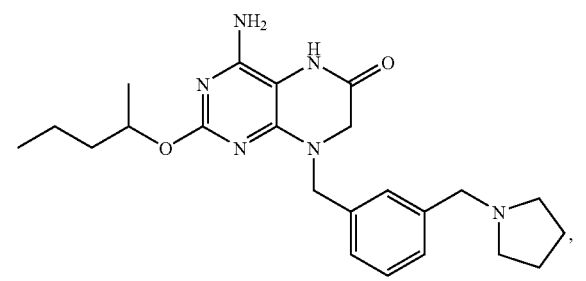
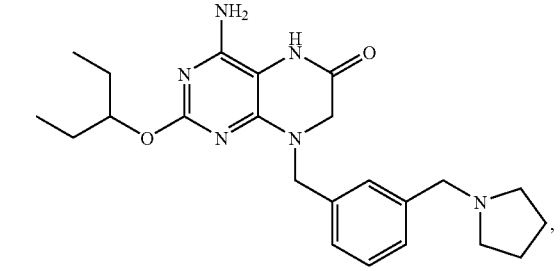
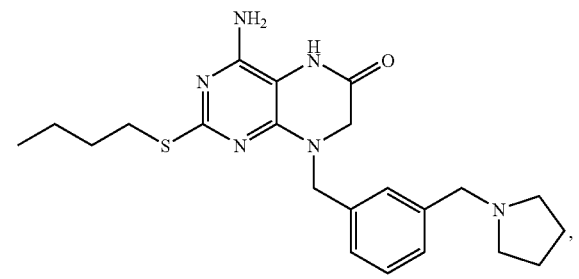
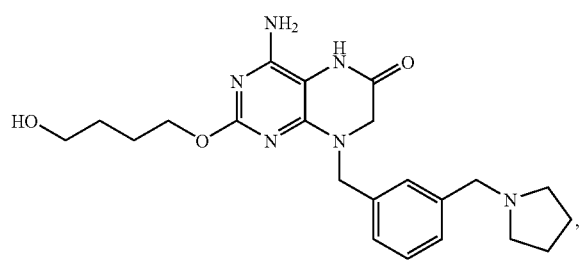
18
-continued
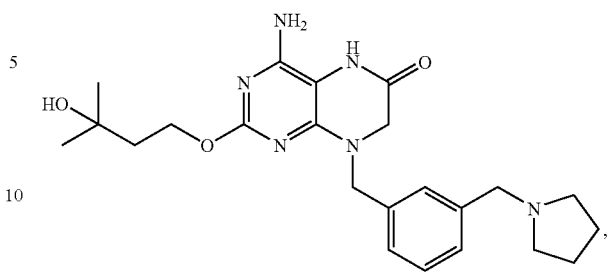
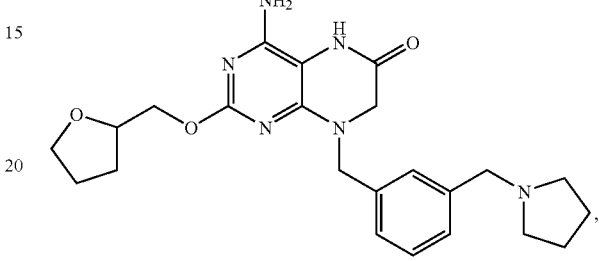
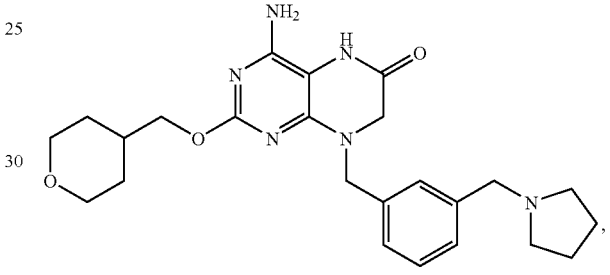
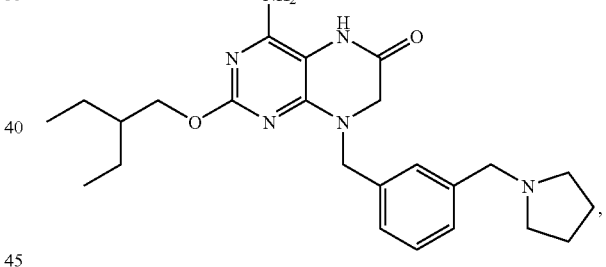
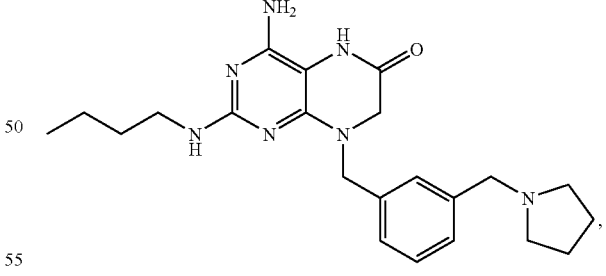
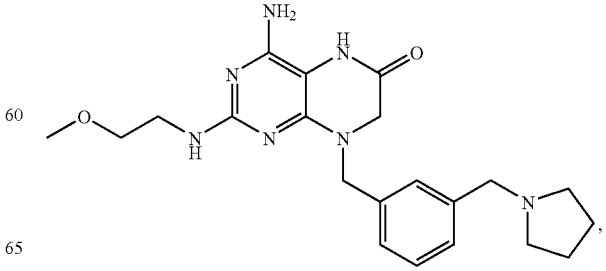

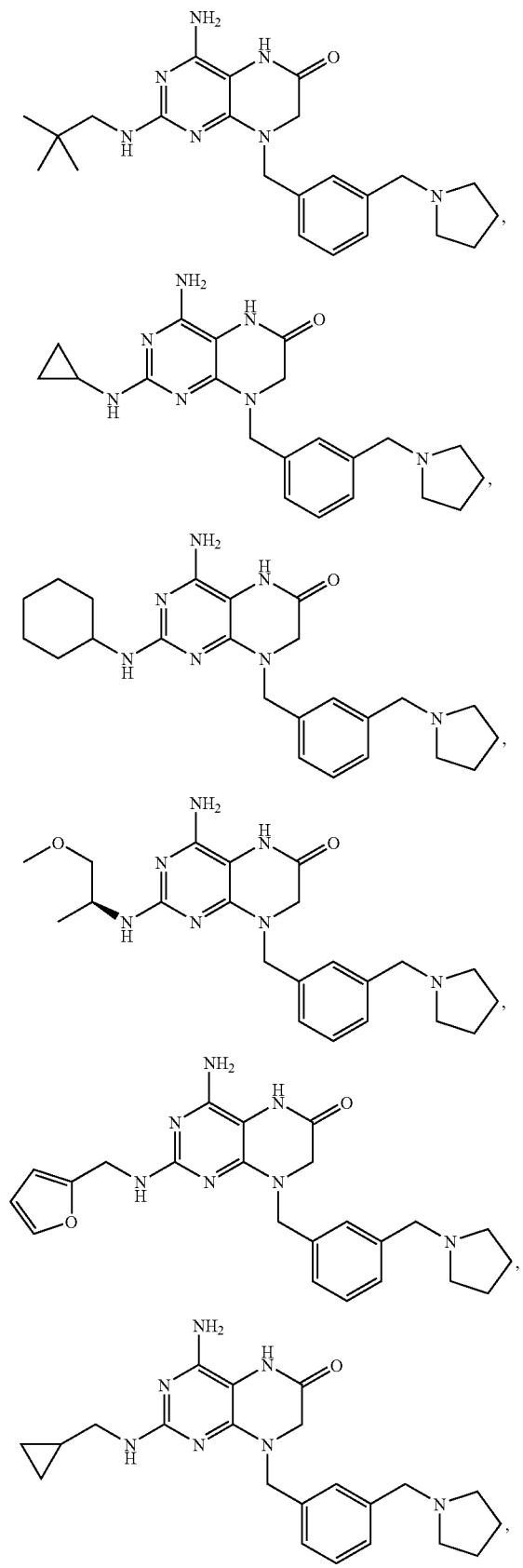
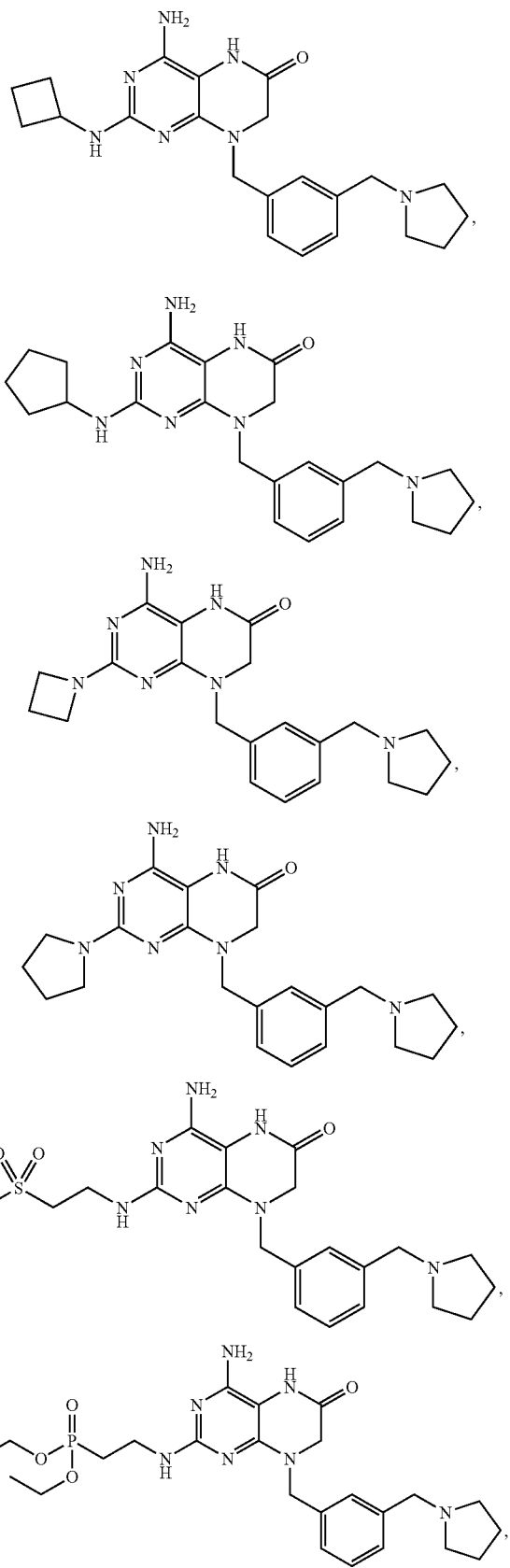

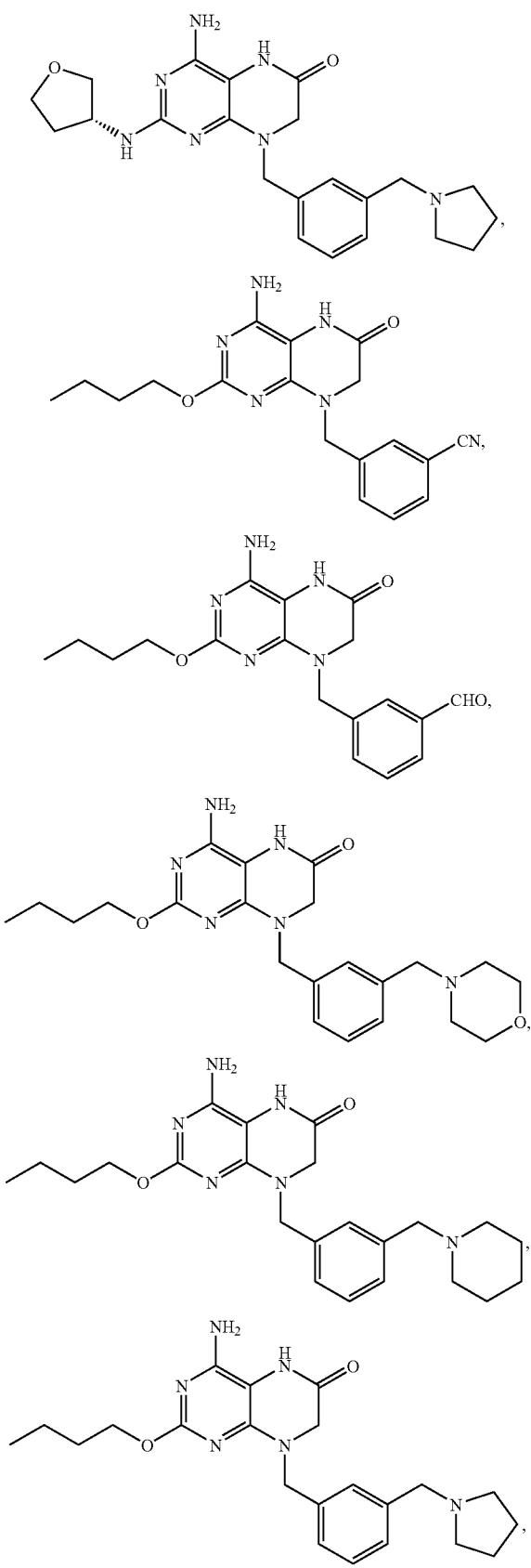
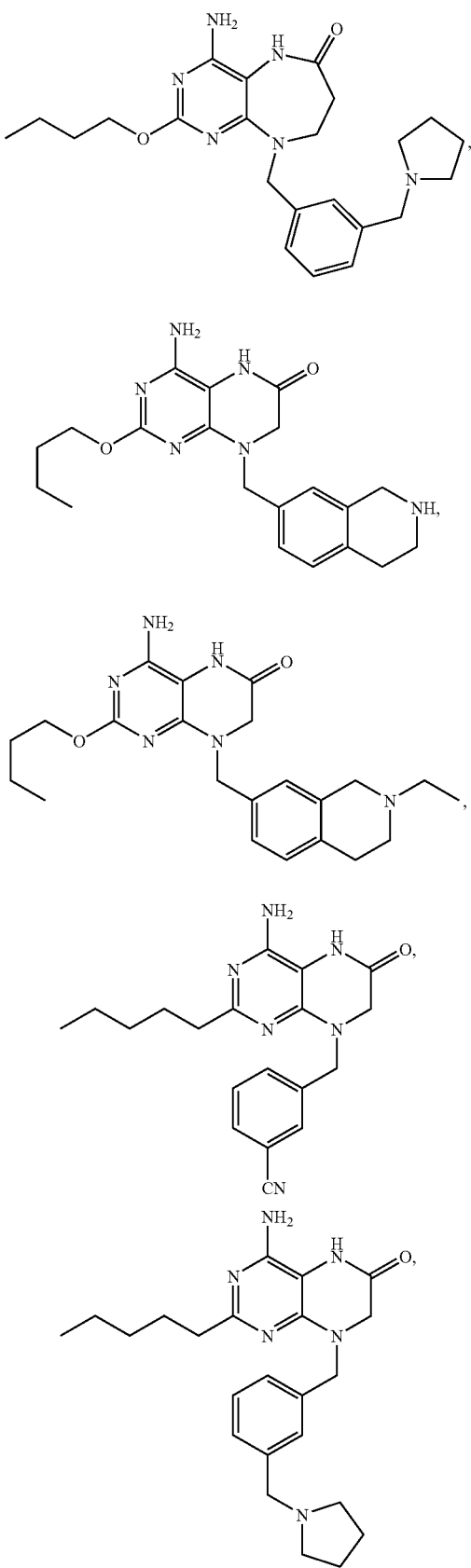

23
-continued
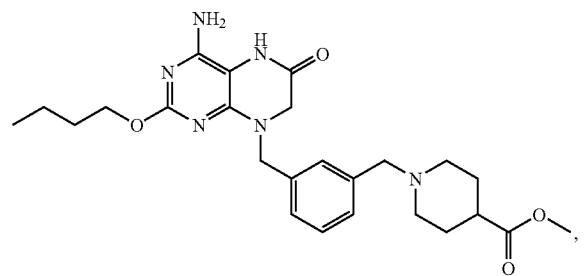
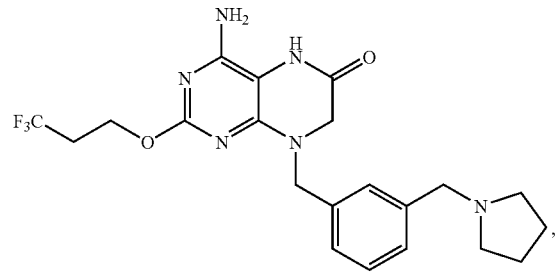
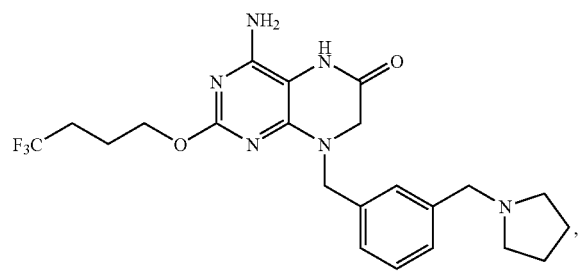
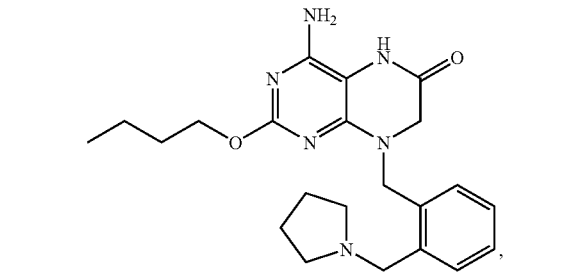
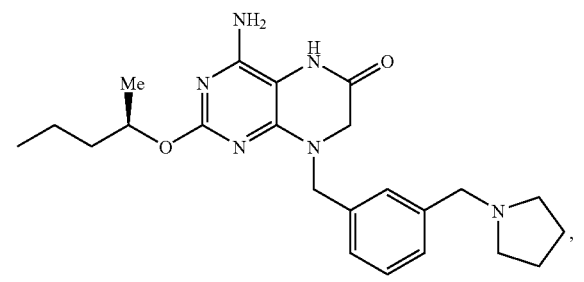
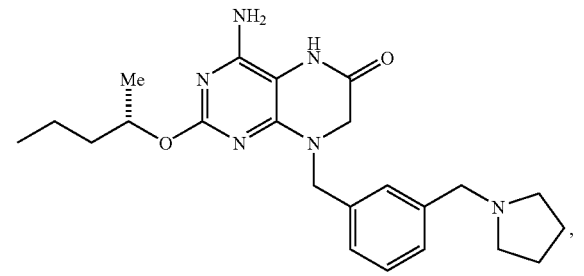
24
-continued
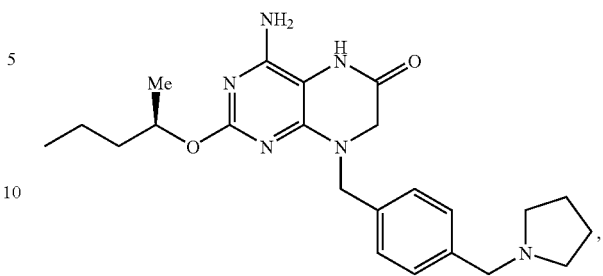
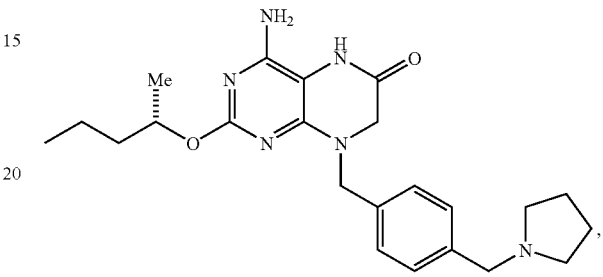
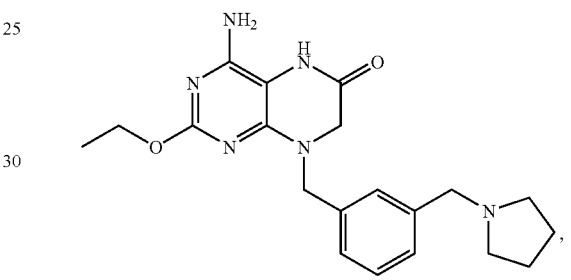
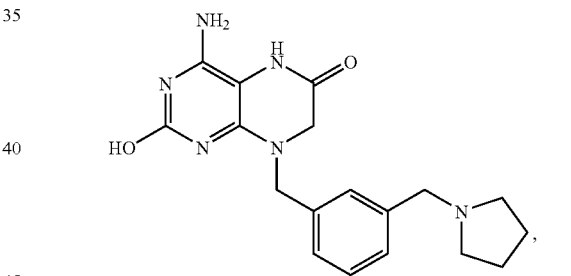
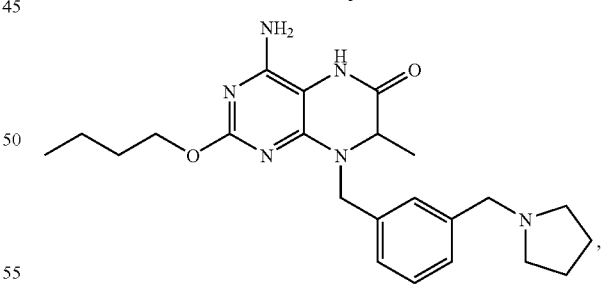
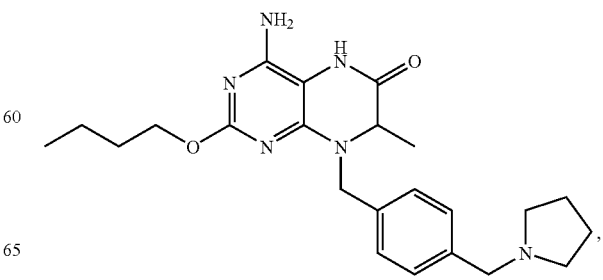

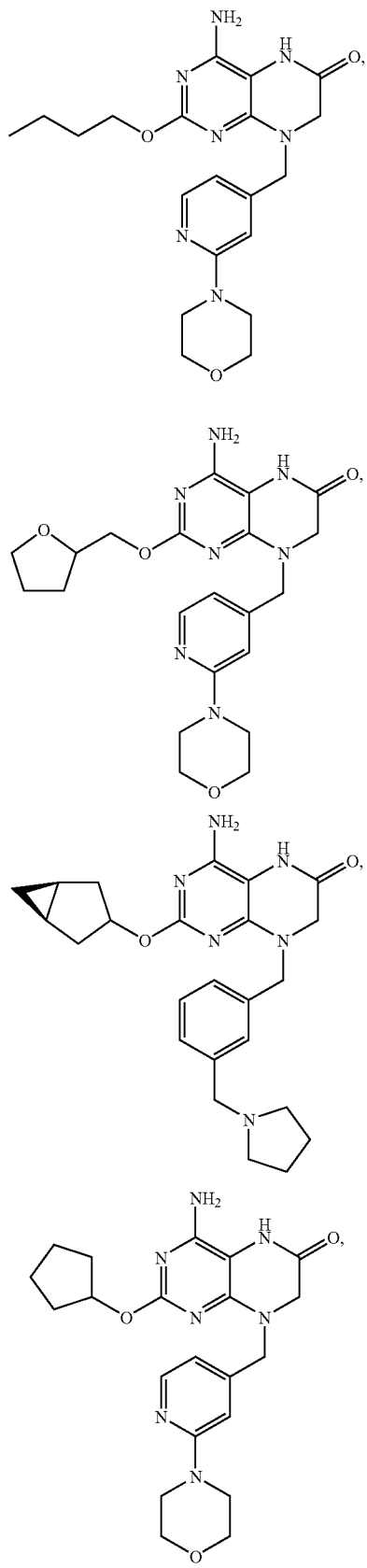
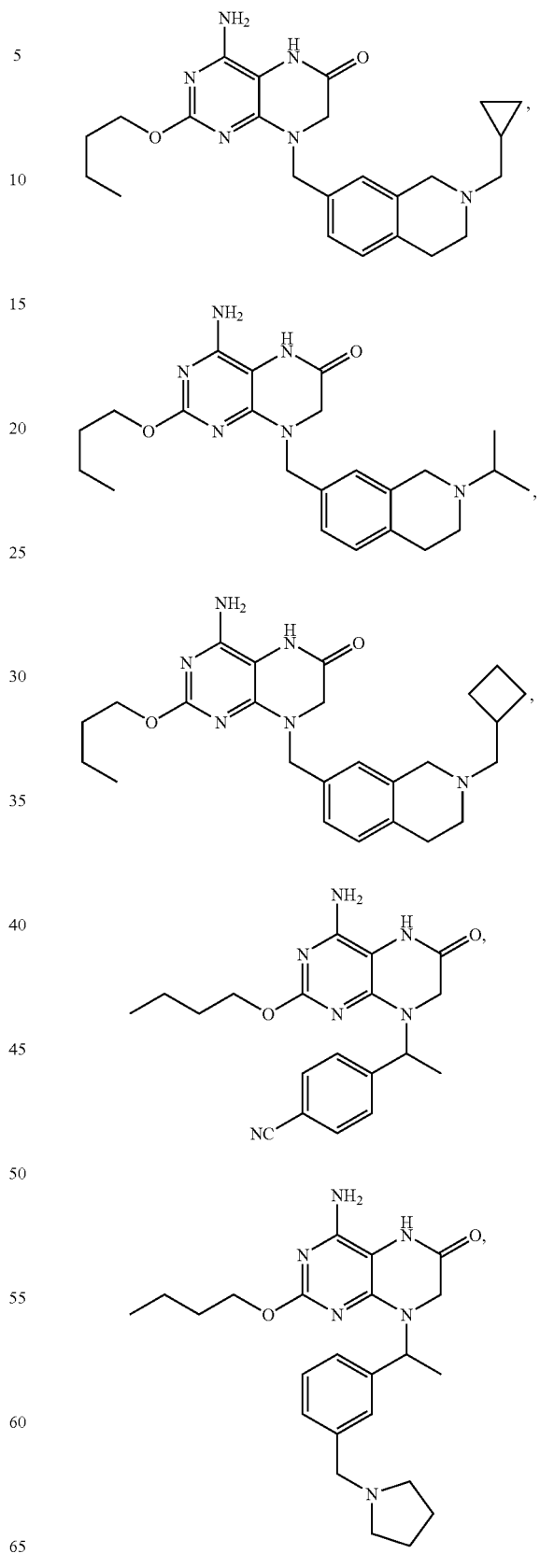

27
-continued
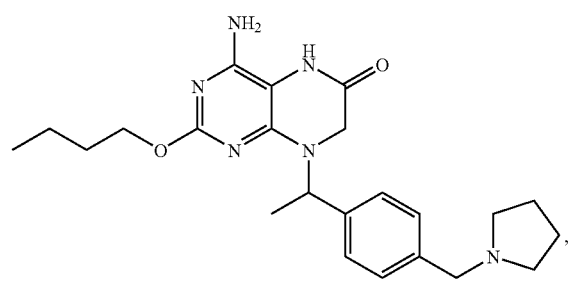
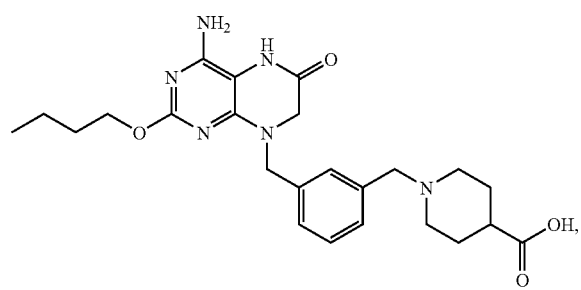
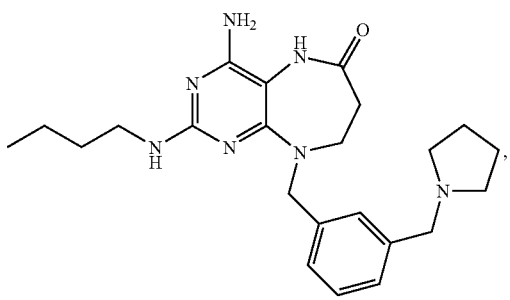
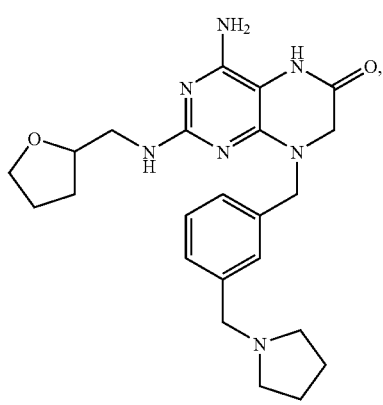
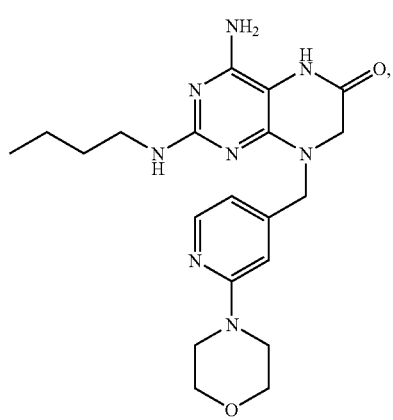
28
-continued
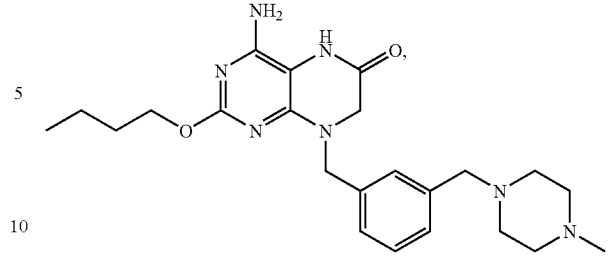
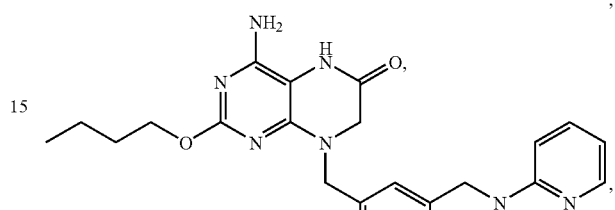
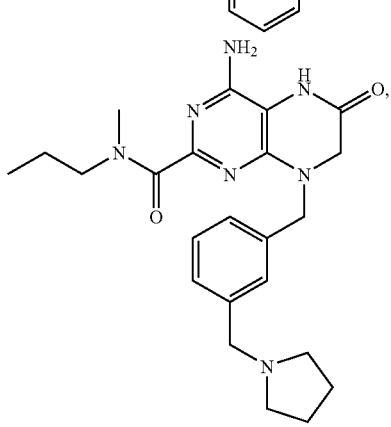
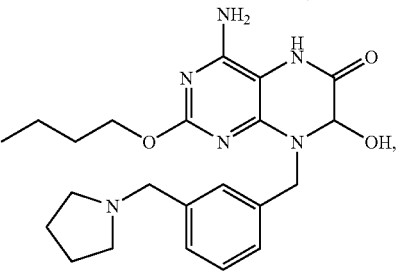
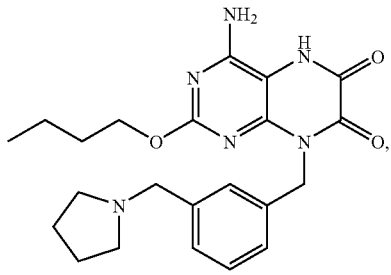
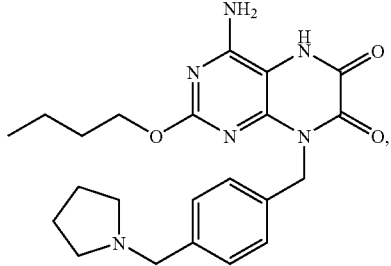

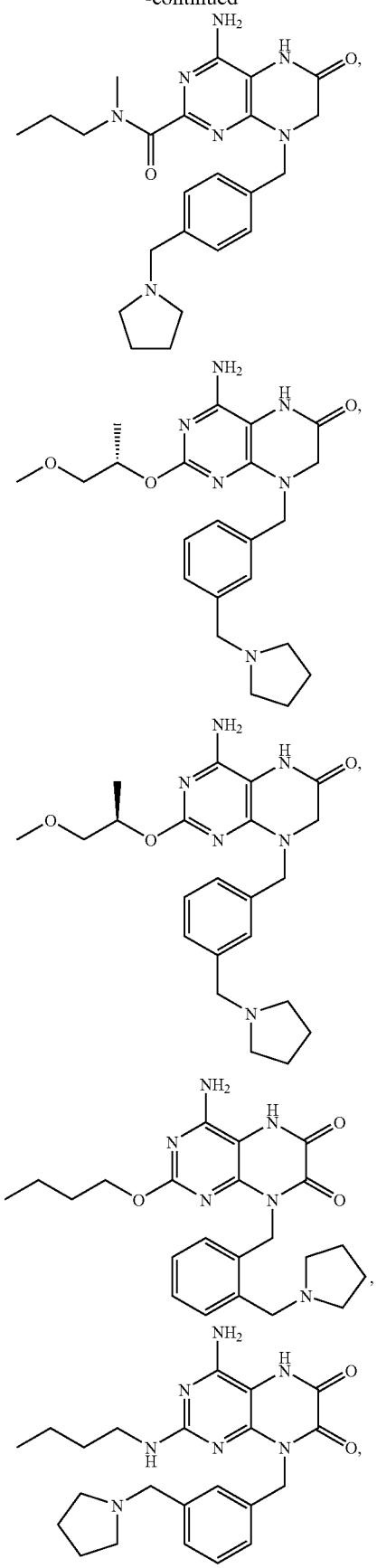
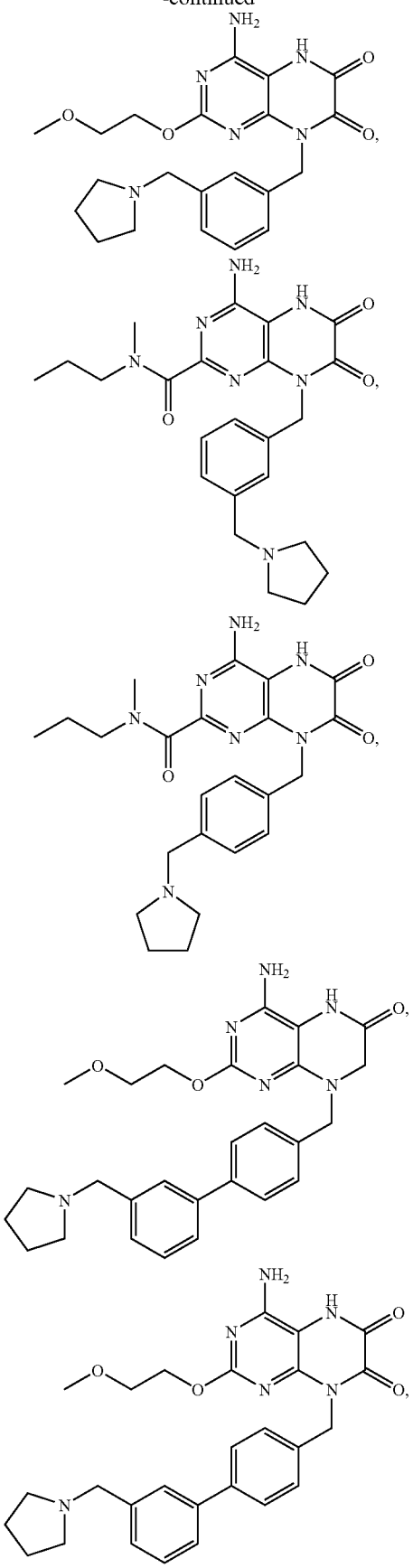

31
-continued
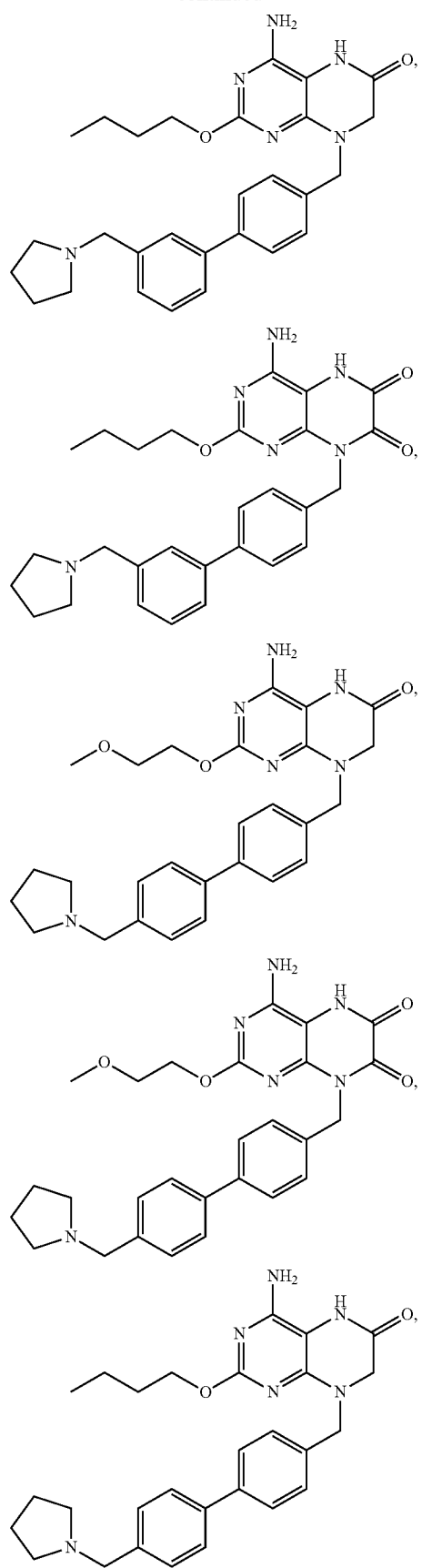
32
-continued
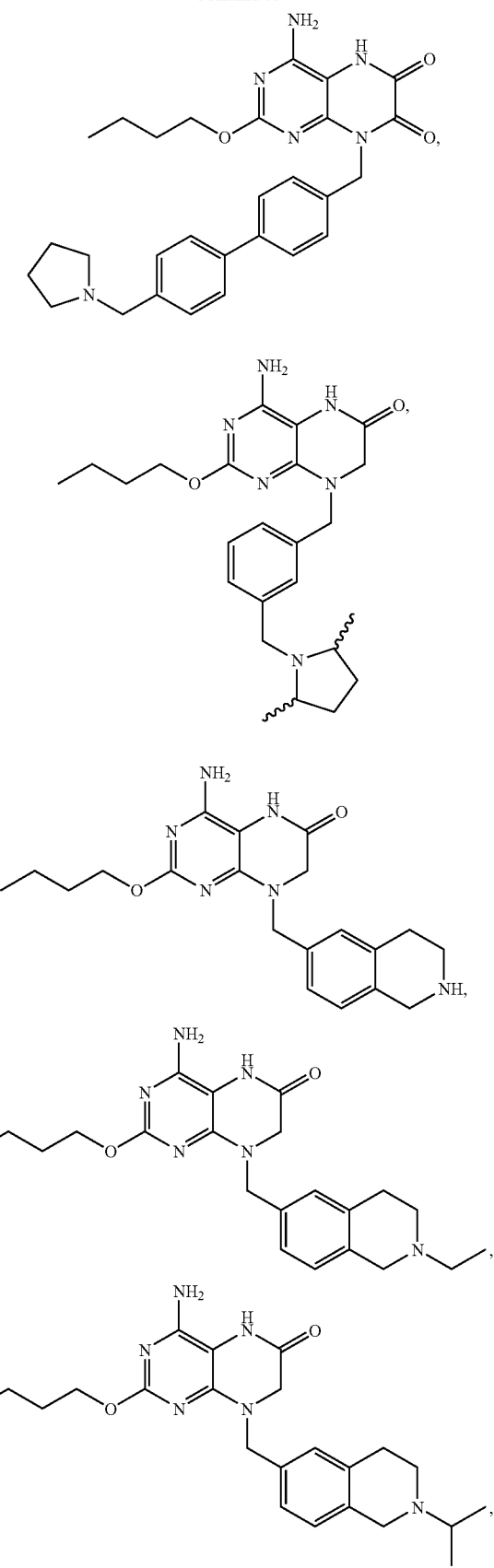

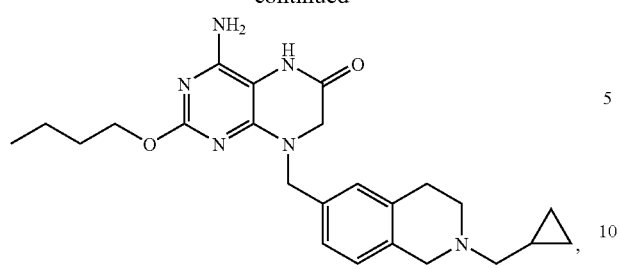
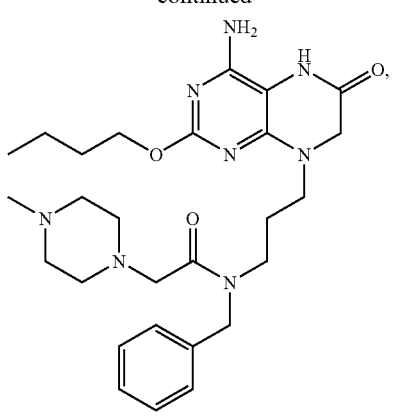
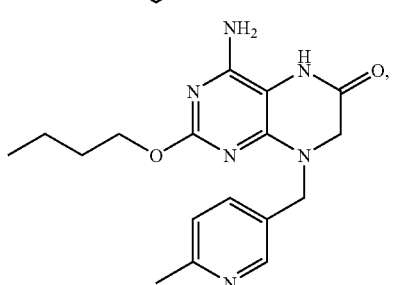
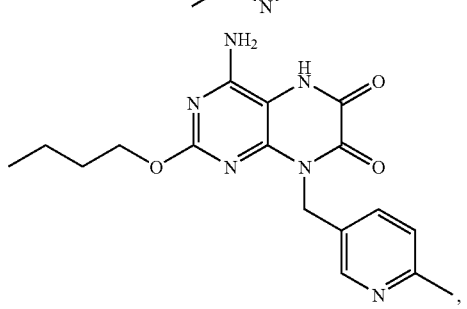
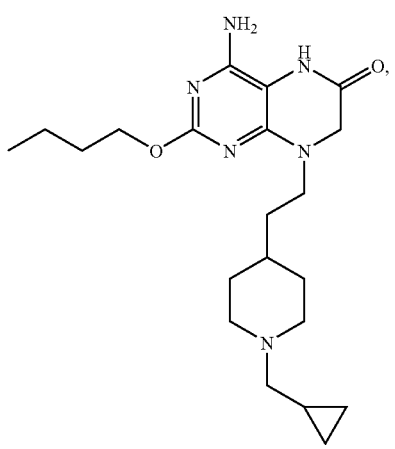
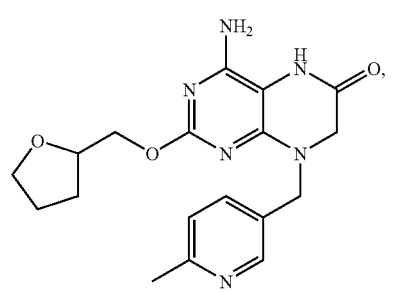

35
-continued
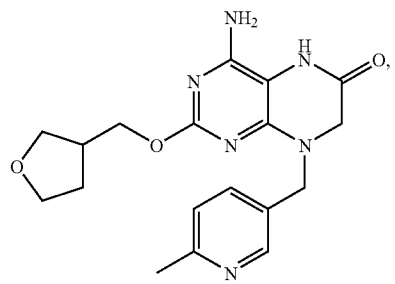
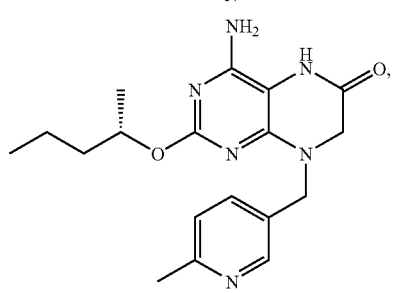
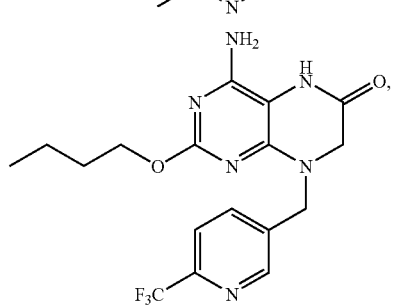
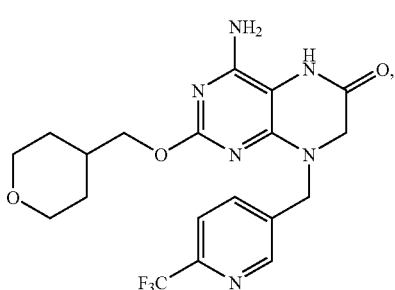
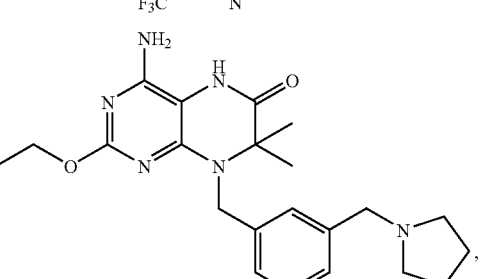
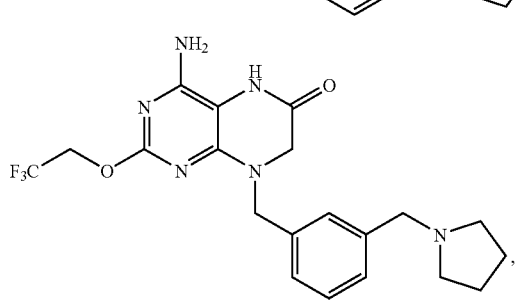
36
-continued
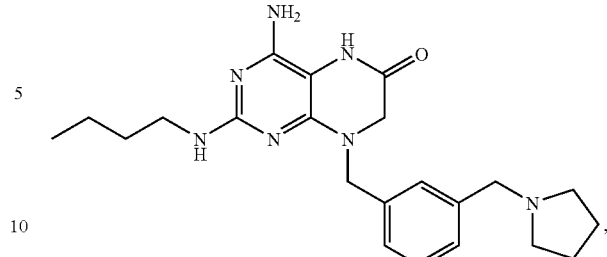
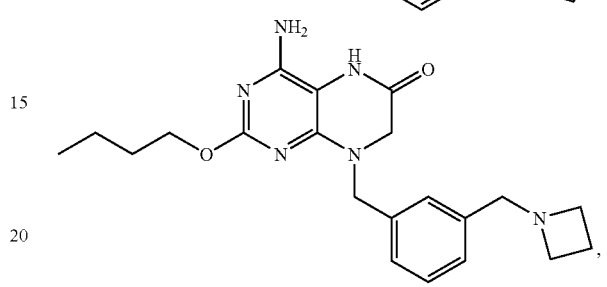
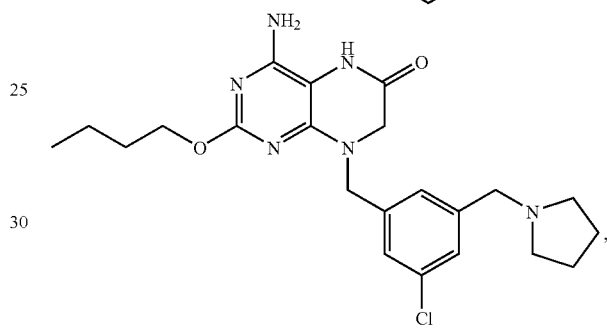
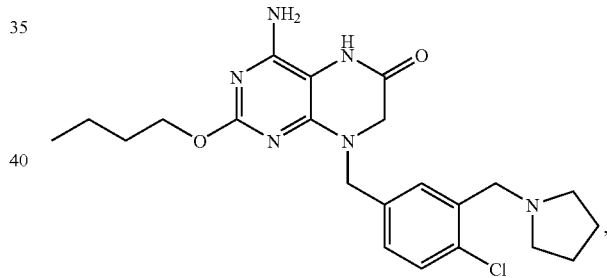
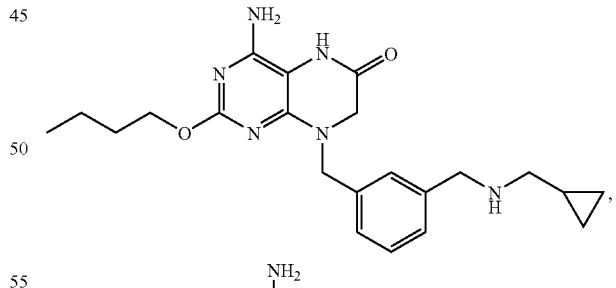
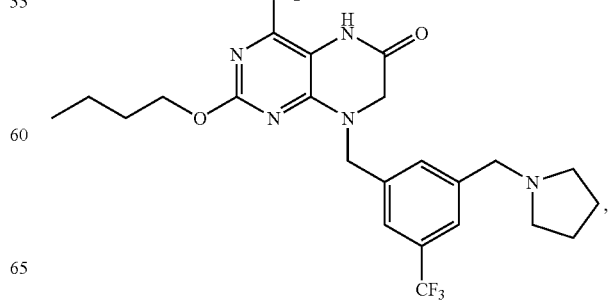

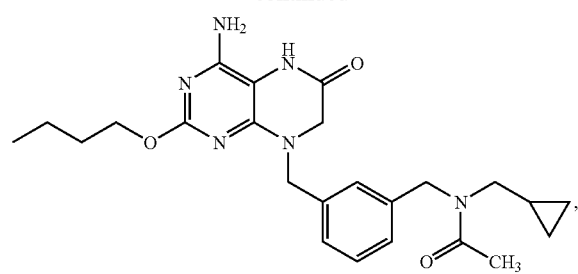
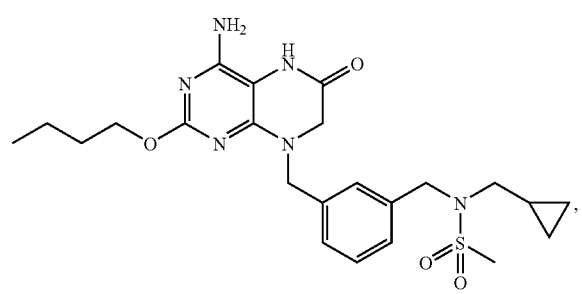
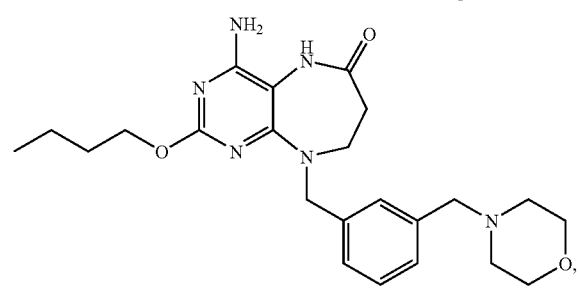
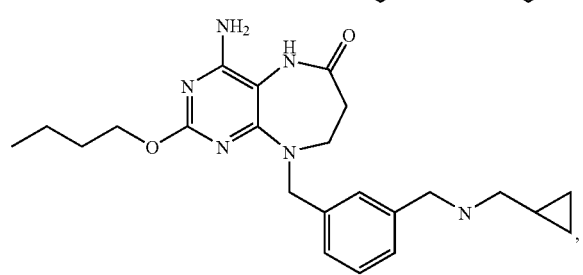
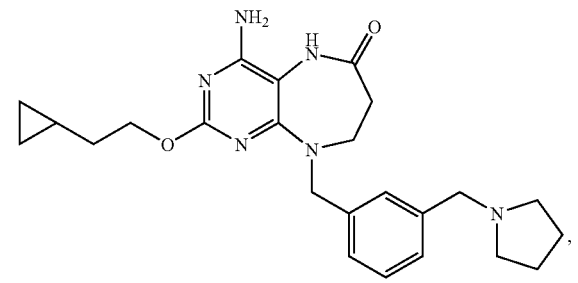
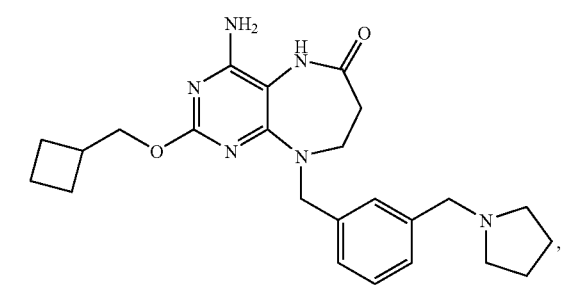
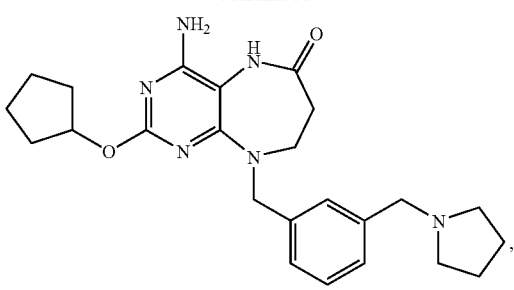
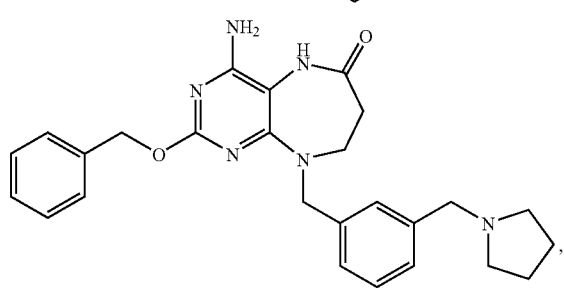
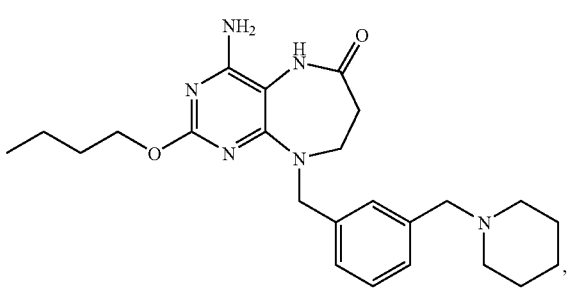
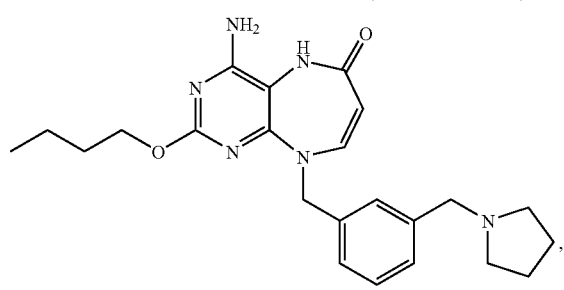
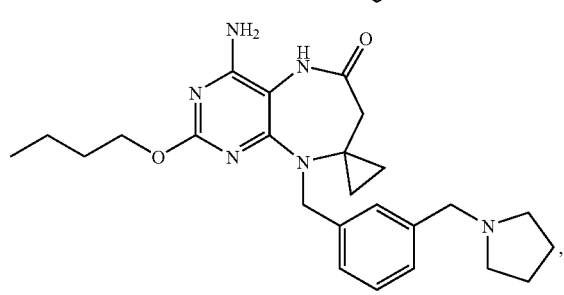

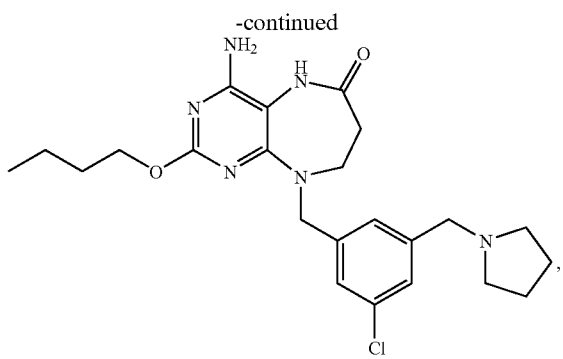

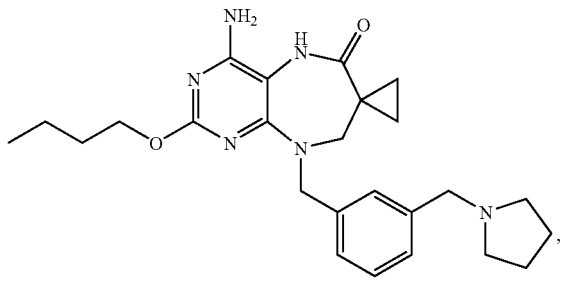

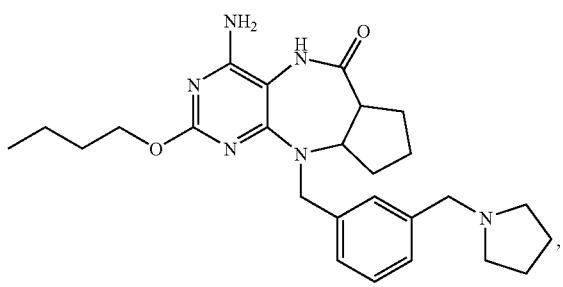

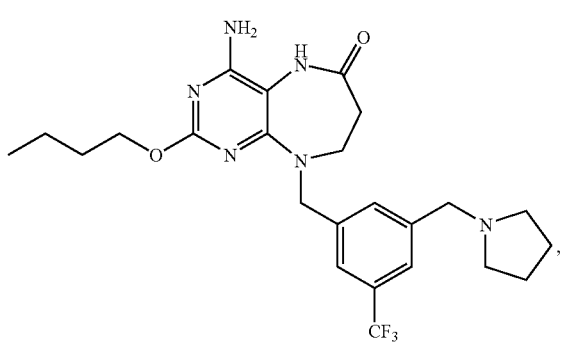

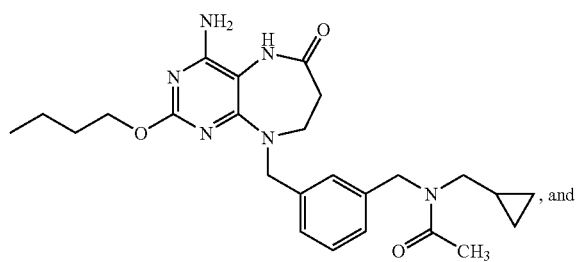

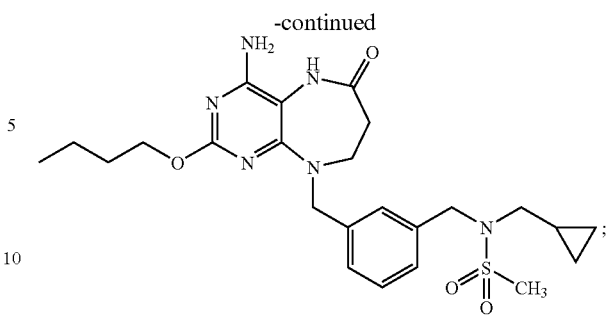

or a pharmaceutically acceptable salt or ester thereof.

DEFINITIONS

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

The term "treating", and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

As used herein, "a compound of the invention" or "a compound of formula Ia or formula II or formula IIa" means a compound of formula Ia or II or IIa, including alternative forms thereof such as, solvated forms, hydrated forms, esterified forms, or physiologically functional derivatives thereof. Compounds of the invention also include tautomeric forms thereof, e.g., tautomeric "enols" as described herein. Similarly, with respect to isolatable intermediates, the phrase "a compound of formula (number)" means a compound of that formula and alternative forms thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and octyl (—(CH$_2$)$_7$CH$_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., C$_1$-C$_{20}$ alkoxy), 1 to 12 carbon atoms (i.e., C$_1$-C$_{12}$ alkoxy), or 1 to 6 carbon atoms (i.e., C$_1$-C$_6$ alkoxy). Examples of suitable alkoxy groups include, but are not limited to, methoxy (—O—CH$_3$ or —OMe), ethoxy (—OCH$_2$CH$_3$ or —OEt), t-butoxy (—O—C(CH$_3$)$_3$ or —OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., C$_1$-C$_{20}$ haloalkyl), 1 to 12 carbon atoms (i.e., C$_1$-C$_{12}$ haloalkyl), or 1 to 6 carbon atoms (i.e., C$_1$-C$_6$, alkyl). Examples of suitable haloalkyl groups include, but are not limited to, —CF$_3$, —CHF$_2$, —CFH$_2$, —CH$_2$CF$_3$, and the like.

"Alkenyl" is a hydrocarbon containing normal, secondary, tertiary, or cyclic carbon atoms with at least one site of unsaturation, i.e. a carbon-carbon, sp2 double bond. For example, an alkenyl group can have 2 to 20 carbon atoms (i.e., C$_2$-C$_{20}$ alkenyl), 2 to 12 carbon atoms (i.e., C$_2$-C$_{12}$ alkenyl), or 2 to 6 carbon atoms (i.e., C$_2$-C$_6$ alkenyl). Examples of suitable alkenyl groups include, but are not limited to, ethylene, vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., C$_2$-C$_{20}$ alkynyl), 2 to 12 carbon atoms (i.e., C$_2$-C$_{12}$ alkyne), or 2 to 6 carbon atoms (i.e., C$_2$-C$_6$ alkynyl). Examples of suitable alkynyl groups include, but are not limited to, acetylenic (—C≡CH), propargyl (—CH$_2$≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Aminoalkyl" refers to an acyclic alkyl radical in which one of the hydrogen atoms bonded to a carbon atom, typically a terminal or sp3 carbon atom, is replaced with an amino radical.

"Amidoalkyl" refers to an acyclic alkyl radical in which one of the hydrogen atoms bonded to a carbon atom, typically a terminal or sp3 carbon atom, is replaced with a —NR$^a$COR$^b$ group where R$^a$ is hydrogen or alkyl and R$^b$ is alkyl, substituted alkyl, aryl, or substituted aryl as defined herein, e.g., —(CH$_2$)$_2$—NHC(O)CH$_3$, —(CH$_2$)$_3$—NH—C(O)—CH$_3$, and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp3 carbon atom, but also an sp2 carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp3 carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

"Halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —CF$_3$.

As used herein, the term "haloalkoxy" refers to a group —OR$^a$, where R$^a$ is a haloalkyl group as herein defined. As non-limiting examples, haloalkoxy groups include —O(CH$_2$)F, —O(CH)F$_2$, and —OCF$_3$.

The term "substituted" in reference to alkyl, aryl, arylalkyl, carbocyclyl, heterocyclyl, and other groups used herein, for example, "substituted alkyl", "substituted aryl", "substituted arylalkyl", "substituted heterocyclyl", and "substituted carbocyclyl" means a group, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O—, =O, —OR, —SR, —S—, —NR$_2$, —N(+)R$_3$, =NR, —CX$_3$, —CRX$_2$, —CR$_2$X, —CN, —OCN, —SCN, —N=C=O, —NCS, —NO, —NO$_2$, =N$_2$, —N$_3$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NR, —S(=O)R, —NRS(=O)$_2$R, —NRS(=O)$_2$NRR, —NRS(=O)$_2$OR, —OP(=O)(OR)$_2$, —P(=O)(OR)$_2$, —P(O)(OR)(O)R, —C(=O)R, —C(=S)R, —C(=O)OR, —C(=S)OR, —C(=O)SR, —C(=S)SR, —C(=O)NRR, —C(=S)NRR, —C(=NR)NRR, —NRC(=NR)NRR, where each X is independently a halogen: F, Cl, Br, or I: and each R is independently H, alkyl, cycloalkyl, aryl, arylalkyl, a heterocycle, or a protecting group or prodrug moiety. Divalent groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, and the like), or a thio-alkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, and the like), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, P or S). The terms "heterocycle" or "heterocyclyl" includes saturated rings, partially unsaturated rings, and aromatic rings (i.e., heteroaromatic rings). Heterocycles includes aromatic and non-aromatic mono-, bi-, and poly-cyclic rings, whether fused, bridged, or spiro. As used herein, the term "heterocycle" encompasses, but is not limited to "heteroaryl."

Substituted heterocyclyls include, for example, heterocyclic rings substituted with any of the substituents disclosed herein including carbonyl groups. A non-limiting example of a carbonyl substituted heterocyclyl is:

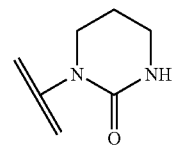

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, azetidinyl, 2-pyrrolidonyl, pyrrolinyl, tetrahydrofuranyi, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyi:

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, and the like, 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, and the like.

"Heterocyclylalkenyl" refers to an acyclic alkenyl radical in which one of the hydrogen atoms bonded to a carbon atom, typically a terminal or sp3 carbon atom, but also a sp2 carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 1 to 6 carbon atoms and the heterocyclyl moiety comprises 1 to 14 carbon atoms.

"Heterocyclylalkynyl" refers to an acyclic alkynyl radical in which one of the hydrogen atoms bonded to a carbon atom, typically a terminal or sp3 carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 2 to 20 carbon atoms, e.g., the alkynyl portion of the heterocyclyl alkynyl group comprises 1 to 6 carbon atoms and the heterocyclyl moiety comprises 1 to 14 carbon atoms.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, and the like. Heteroaryl also includes monovalent aromatic heterocyclyl comprising an aryl moiety and a heteroaryl group. Non limiting examples of these heteroaryls are:

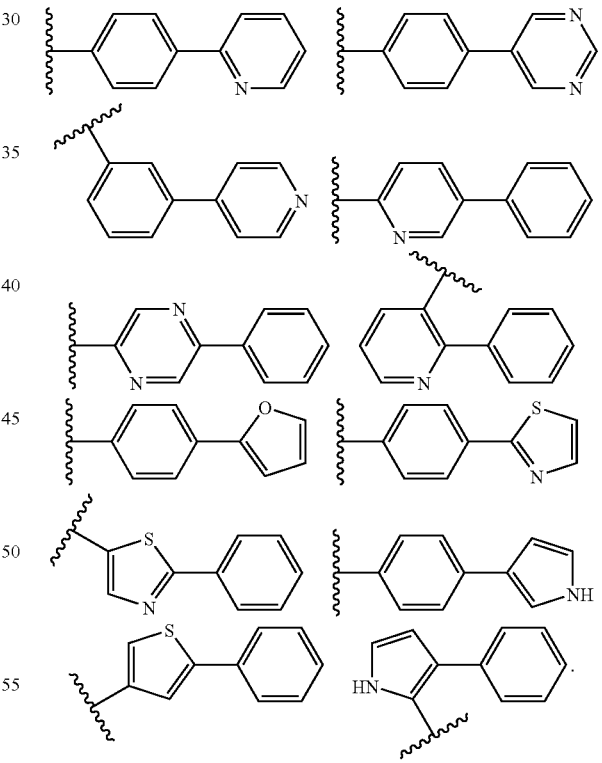

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo(4,5), (5,5), (5,6) or (6,6) system, or 9 or 10 ring atoms arranged as a bicyclo(5,6) or (6,6) system.

Carbocycles includes aromatic and non-aromatic mono-, bi-, and poly-cyclic rings, whether fused, bridged, or spiro. Non-limiting examples of monocyclic carbocycles include the cycloalkyls group such as cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl or aryl groups such as phenyl, and the like. Thus, "carbocycle," as used herein, encompasses but is not limited to "aryl", "phenyl" and "biphenyl."

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene. Thus, "carbocyclylene," as used herein, encompasses but is not limited to "arylene."

"Carbocyclylalkyl" refers to an acyclic alkyl radical in which one of the hydrogen atoms bonded to a carbon atom, typically a terminal or sp3 carbon atom, is replaced with a carbocyclyl radical as defined above. Typical carbocyclylalkyl groups include, but are not limited to the arylalkyl groups such as benzyl, 2-phenylethan-1-yl, naphthylmethyl, 2-naphthylethan-1-yl, naphthobenzyl, 2-naphthophenylethan-1-yl or the cycloalkylalkyl groups such as cyclopropylmethyl, cyclobutylethyl, cyclohexylmethyl and the like. The arylalkyl group can comprise 6 to 20 carbon atoms, e.g., the alkyl moiety is 1 to 6 carbon atoms and the aryl moiety is 6 to 14 carbon atoms. The cycloalkylalkyl group can comprise 4 to 20 carbon atoms, e.g., the alkyl moiety is 1 to 6 caron atoms and the cycloalkyl group is 3 to 14 carbon atoms.

"Arylheteroalkyl" refers to a heteroalkyl as defined herein, in which a hydrogen atom, which may be attached either to a carbon atom or a heteroatom, has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, and the like. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-thienyl, —CH$_2$-benzofuranyl, —CH$_2$-benzothiophenyl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH(CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH(CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, and the like.

The term "optionally substituted" in reference to a particular moiety of the compound of the Formulae of the invention, for example an optionally substituted aryl group, refers to a moiety having 0, 1, or more substituents.

As will be appreciated by those skilled in the art, the compounds of the present invention are capable of existing in solvated or hydrated form. The scope of the present invention includes such forms. Again, as will be appreciated by those skilled in the art, the compounds may be capable of esterification. The scope of the present invention includes esters and other physiologically functional derivatives. The scope of the present invention also includes tautomeric forms, namely, tautomeric "enols" as herein described. In addition, the scope of the present invention includes prodrug forms of the compound herein described.

"Ester" means any ester of a compound in which any of the —COON functions of the molecule is replaced by a —C(O)OR function, or in which any of the —OH functions of the molecule are replaced with a —OC(O)R function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. Esters can also include esters—as described above—of "tautomeric enols", e.g. as shown below:

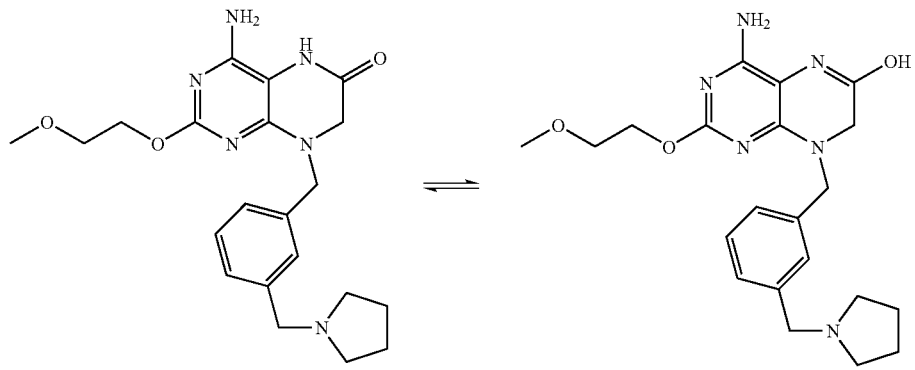 [SMILES: COCCOc1nc(N)c2c(n1)N(Cc1cccc(CN3CCCC3)c1)CC(=O)N2 ; COCCOc1nc(N)c2c(n1)N(Cc1cccc(CN3CCCC3)c1)CC(O)=N2]

The term "ester thereof" includes but is not limited to pharmaceutically acceptable esters thereof.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or II which have such stability are contemplated as falling within the scope of the present invention.

As will be appreciated by those skilled in the art, the compounds of the present invention may contain one or more chiral centers. The scope of the present invention includes such forms. Again, as will be appreciated by those skilled in the art, the compound is capable of esterification. The scope of the present invention includes esters and other physiologically functional derivatives. The scope of the present invention also includes tautomeric forms, namely, tautomeric "ends" as herein described. In addition, the scope of the present invention includes prodrug forms of the compound herein described.

A compound of Formula Ia, IIa, or II and its pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-II and their pharmaceutically acceptable salts.

A compound of Formula Ia, IIa, or II and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula Ia, IIa, or II and their pharmaceutically acceptable salts.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes the individual isomers of the compounds represented by the formulas above as mixtures with isomers thereof in which one or more chiral centers are inverted.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Ebel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The present invention includes a salt or solvate of the compounds herein described, including combinations thereof such as a solvate of a salt. The compounds of the present invention may exist in solvated, for example hydrated, as well as unsolvated forms, and the present invention encompasses all such forms.

Typically, but not absolutely, the salts of the present invention are pharmaceutically acceptable salts. Salts encompassed within the term "pharmaceutically acceptable salts" refer to non-toxic salts of the compounds of this invention.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula Ia or II or IIa

The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 µm (including particle sizes in a range between 0.1 and 500 µm in increments such as 0.5 µm, 1 µm, 30 µm, 35 µm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 10 mg/kg body weight per day, typically from about 0.001 to about 1 mg/kg body weight per day, more typically from about 0.01 to about 1 mg/kg body weight per day, even more typically from about 0.05 to about 0.5 mg/kg body weight per day. For example, the daily candidate dose for an adult human of approximately 70 kg body weight will range from about 0.05 mg to about 100 mg, or between about 0.1 mg and about 25 mg, or between about 0.4 mg and about 4 mg, and may take the form of single or multiple doses.

In yet another embodiment, the present application discloses pharmaceutical compositions comprising a compound of Formula I or H or a pharmaceutically acceptable salt thereof, and a pharmaceutically acceptable carrier or exipient.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention are used in combination with an additional active therapeutic ingredient or agent.

In one embodiment, combinations of the compounds of Formula Ia, II, or IIa and additional active agents may be selected to treat patients with a viral infection, for example, HBV, HCV, or HIV infection.

Useful active therapeutic agents for HBV include reverse transcriptase inhibitors, such as lamivudine (Epivir®), adefovir (Hepsera®), tenofovir (Viread®), telbivudine (Tyzeka®), entecavir (Baraclude®), and Clevudine®. Other useful active therapeutic agents include immunomodulators, such as interferon alpha-2b (Intron A®), pegylated interferon alpha-2a (Pegasys®), interferon alpha 2a (Roferon®), interferon alpha N1, prednisone, predinisolone, Thymalfasin®, retinoic acid receptor agonists, 4-methylumbelliferone, Alamifovir®, Metacavir®, Albuferon®, agonists of TLRs (e.g., TLR-7 agonists), and cytokines.

With regard to treatment for HCV, other active therapeutic ingredients or agents are interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, or mixtures thereof.

Combinations of the compounds are typically selected based on the condition to be treated, cross-reactivities of ingredients and pharmaco-properties of the combination. For example, when treating an infection (e.g., HCV), the compositions of the invention are combined with other active agents (such as those described herein).

Suitable active agents or ingredients which can be combined with the compounds of Formula I or II or a salt thereof, can include one or more compounds selected from the group consisting of:

(1) interferons selected from the group consisting of pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-b3 (Alferon), interferon-beta (Avonex, DL-8234), interferon-omega (omega DUROS, Biomed 510), albinterferon alpha-2b (Albuferon), IFN alpha-2b XL, BLX-883 (Locteron), DA-3021, glycosylated interferon alpha-2b (AVI-005), PEG-Infergen, PEGylated interferon lambda-1 (PEGylated IL-29), belerofon, and mixtures thereof;

(2) ribavirin and its analogs selected from the group consisting of ribavirin (Rebetol, Copegus), taribavirin (Viramidine), and mixtures thereof;

(3) HCV NS3 protease inhibitors selected from the group consisting of boceprevir (SCH-503034 SCH-7), telaprevir (VX-950), TMC435350, BI-1335, BI-1230, MK-7009, VBY-376, VX-500, BMS-790052, BMS-605339, PHX-1766, AS-101, YH-5258, YH5530, YH5531, ITMN-191, and mixtures thereof;

(4) alpha-glucosidase 1 inhibitors selected from the group consisting of celgosivir (MX-3253), Miglitol, UT-23113, and mixtures thereof;

(5) hepatoprotectants selected from the group consisting of IDN-6556, ME 3738, LB-84451, silibilin, MitoQ, and mixtures thereof;

(6) nucleoside or nucleotide inhibitors of HCV NS5B polymerase selected from the group consisting of R1626, R7128 (R4048), IDX184, IDX-102, BCX-4678, valopicitabine (NM-283), MK-0608, and mixtures thereof;

(7) non-nucleoside inhibitors of HCV NS5B polymerase selected from the group consisting of PF-868554, VCH-759, VCH-916, JTK-652, MK-3281, VBY-708, VCH-222, A848837, ANA-598, GL60667, GL59728, A-63890, A-48773, A-48547, BC-2329, VCH-796 (nesbuvir), GSK625433, BILN-1941, XTL-2125, GS-9190, and mixtures thereof;

(8) HCV NS5A inhibitors selected from the group consisting of AZD-2836 (A-831), A-689, and mixtures thereof;

(9) TLR-7 agonists selected from the group consisting of ANA-975, SM-360320, and mixtures thereof;

(10) cyciophillin inhibitors selected from the group consisting of DEBIO-025, SCY-635, NIM811, and mixtures thereof;

(11) HCV IRES inhibitors selected from the group consisting of MCI-067,

(12) pharmacokinetic enhancers selected from the group consisting of BAS-100, SPI-452, PF-4194477, TMC-41629, roxythromycin, and mixtures thereof; and

(13) other drugs for treating HCV selected from the group consisting of thymosin alpha 1 (Zadaxin), nitazoxanide (Alinea, NTZ), BIVN-401 (virostat), PYN-17 (altirex), KPE02003002, actilon (CPG-10101), KRN-7000, civacir, G1-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, VX-497 (merimepodib), and mixtures thereof.

In addition, the compounds of the invention may be employed in combination with other therapeutic agents for the treatment or prophylaxis of AIDS and/or one or more other diseases present in a human subject suffering from AIDS (e.g., bacterial and/or fungal infections, other viral infections such as hepatitis B or hepatitis C, or cancers such as Kaposi's sarcoma). The additional therapeutic agent(s) may be coformulated with one or more salts of the invention (e.g., coformulated in a tablet).

Examples of such additional therapeutic agents include agents that are effective for the treatment or prophylaxis of viral, parasitic or bacterial infections, or associated conditions, or for treatment of tumors or related conditions, include 3'-azido-3'-deoxythymidine (zidovudine, AZT), 2'-deoxy-3'-thiacytidine (3TC), 2',3'-dideoxy-2,3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chlorodeoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-arabinosyl)-5-iodocytidine (FIAC), tetrahydro-imidazo(4,5,1-jk)-(1,4)-benzodiazepin-2 (1H)-thione (TIBO), 2'-nor-cyclicGMP, 6-methoxypurine arabinoside (ara-M), 6-methoxypurine arabinoside 2'-O-valerate; cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI); acyclic nucleosides such as acyclovir, penciclovir, famciclovir, ganciclovir, HPMPC, PMEA, PMEG, PMPA, PMPDAP, FPMPA, HPMPA, HPMPDAP, (2R,5R)-9->tetrahydro-5-(phosphonomethoxy)-2-furanyladenine, (2R,5R)-1->tetrahydro-5-(phosphonomethoxy)-2-furanylthymine; other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate); antibacterial agents including bactericidal fluoroquinolones (ciprofloxacin, pefloxacin and the like); aminoglycoside bactericidal antibiotics (streptomycin, gentamicin, amicacin and the like); (3-lactamase inhibitors (cephalosporins, penicillins and the like); other antibacterials including tetracycline, isoniazid, rifampin, cefoperazone, claithromycin and azithromycin, antiparasite or antifungal agents including pentamidine (1,5-bis(4'-aminophenoxy)pentane), 9-deaza-inosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin; renal excretion inhibitors such as probenicid; nucleoside transport inhibitors such as dipyridamole, dilazep and nitrobenzylthioinosine, immunomodulators such as FK506, cyclosporin A, thymosin α-1; cytokines including TNF and TGF-β; interferons including IFN-α, IFN-β, and IFN-γ; interleukins including various interleukins, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and the like.

Examples of suitable active therapeutic agents or ingredients which can be combined with the compounds of the invention, and which have activity against HIV, include 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453, 061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+ actimmune, IFN-omega with DUROS, and albuferon, 12) ribavirin analogs, e.g., rebetol, copegus, levovirin, VX-497, and viramidine (taribavirin) 13) NS5a inhibitors, e.g., A-831 and A-689, 14) NS5b polymerase inhibitors, e.g., NM-283, valopicitabine, R1626, PSI-6130 (R1656), HIV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) non-nucleoside inhibitors of HIV, e.g., benzimidazole derivatives, benzo-1,2,4-thiadiazine derivatives, and phenylalanine derivatives, 19) other drugs for treating HIV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 19) pharmacokinetic enhancers, e.g., BAS-100 and SP1452, 20)RNAse H inhibitors, e.g., ODN-93 and ODN-112, 21) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

Again by way of example, the following list discloses exemplary HIV antivirals, with their corresponding U.S. patent numbers, incorporated by reference with regard to the preparation of such antivirals, which can be combined with the compounds of the present invention.

Exemplary HIV Antivirals and Patent Numbers
Ziagen (Abacavir sulfate, U.S. Pat. No. 5,034,394)
Epzicom (Abacavir sulfate/lamivudine, U.S. Pat. No. 5,034,394)
Hepsera (Adefovir dipivoxil, U.S. Pat. No. 4,724,233)
Agenerase (Amprenavir, U.S. Pat. No. 5,646,180)
Reyataz (Atazanavir sulfate, U.S. Pat. No. 5,849,911)
Rescriptor (Delavirdine mesilate, U.S. Pat. No. 5,563,142)
Hivid (Dideoxycytidine; Zalcitabine, U.S. Pat. No. 5,028,595)
Videx (Dideoxyinosine; Didanosine, U.S. Pat. No. 4,861,759)
Sustiva (Efavirenz, U.S. Pat. No. 5,519,021)
Emtriva (Emtricitabine, U.S. Pat. No. 6,642,245)
Lexiva (Fosamprenavir calcium, U.S. Pat. No. 6,436,989)
Virudin; Triapten; Foscavir (Foscarnet sodium, U.S. Pat. No. 6,476,009)
Crixivan (Indinavir sulfate, U.S. Pat. No. 5,413,999)
Epivir (Lamivudine, U.S. Pat. No. 5,047,407)
Combivir (Lamivudine/Zidovudine, U.S. Pat. No. 4,724,232)
Aluviran (Lopinavir)

Kaletra (Lopinavir/ritonavir, U.S. Pat. No. 5,541,206)
Viracept (Nelfinavir mesilate, U.S. Pat. No. 5,484,926)
Viramune (Nevirapine, U.S. Pat. No. 5,366,972)
Norvir (Ritonavir, U.S. Pat. No. 5,541,206)
Invirase; Fortovase (Saquinavir mesilate, U.S. Pat. No. 5,196,438)
Zerit (Stavudine, U.S. Pat. No. 4,978,655)
Truvada (Tenofovir disoproxil fumarate/emtricitabine, U.S. Pat. No. 5,210,085)
Aptivus (Tipranavir)
Retrovir (Zidovudine; Azidothymidine, U.S. Pat. No. 4,724,232)

Where the disorder is cancer, combination with at least one other anticancer therapy is envisaged. In particular, in anti-cancer therapy, combination with other anti-neoplastic agent (including chemotherapeutic, hormonal or antibody agents) is envisaged as well as combination with surgical therapy and radiotherapy. Combination therapies according to the present invention thus comprise the administration of at least one compound of formula (I) or a salt or solvate thereof, and the use of at least one other cancer treatment method. Preferably, combination therapies according to the present invention comprise the administration of at least one compound of formula (I) or a salt or solvate thereof, and at least one other pharmaceutically active agent, preferably an anti-neoplastic agent. The compound(s) of formula (I)) and the other pharmaceutically active agent(s) may be administered together or separately and, when administered separately this may occur simultaneously or sequentially in any order (including administration on different days according to the therapy regimen) and by any convenient route. The amounts of the compound(s) of formula (II) and the other pharmaceutically active agent(s) and the relative timings of administration will be selected in order to achieve the desired combined therapeutic effect.

In one embodiment, the further anti-cancer therapy is at least one additional antineoplastic agent. Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; proapoptotic agents; and cell cycle signaling inhibitors.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2a,4,7β,10β,13a-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat, Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R J. et. al, Cancer Chemotherapy Pocket Guide$_A$ 1998) related to the duration of dosing above a threshold concentration (5 OnM) (Kearns, C M. et. al., Seminars in Oncology, 3(6) p. 16-23, 1995).

Docetaxel, (2R,3S)—N-carboxy-3-phenylisoserine,N-te/f-butyl ester, 13-ester with 5β-20-epoxy-1,2a,4,7β,10β,13a-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine. Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, equation and form intra- and interstrand crosslinks with DNA causing adverse biological effects to the tumor. Examples of platinum coordination complexes include, but are not limited to, oxaliplatin, cisplatin and carboplatin. Cisplatin, cis-diamminedichloroplatinum, is commercially available as PLATINOL® as an injectable solution. Cisplatin is primarily indicated in the treatment of metastatic testicular and ovarian cancer and advanced bladder cancer. Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine. Cyclophosphamide, 2-[bis(2-chloroethyl) amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan. Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Busulfan, 1,4-butanediol dimethanesulfonate, is commercially available as MYLERAN® TABLETS. Busulfan is indicated for the palliative treatment of chronic myelogenaus leukemia. Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic anti-neoplasties are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins. Dactinomycin, also know as Actinomycin D, is commercially available in injectable form as COSMEGEN®. Dactinomycin is indicated for the treatment of Wilm's tumor and rhabdomyosarcoma. Daunorubicin, (8S-cis-)-8-acetyl-10-[(3-amino-2,3,6-trideoxy-a-L-Iyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Doxorubicin, (8S,10S)-10-[(3-amino-2,3,6-trideoxy-a-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblasts leukemia, but is also a useful component in the treatment of some solid tumors and lymphomas. Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine. 5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (I H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine. Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine. Gemcitabine, 2'-deoxy-2',2'-difluorocytidine monohydrochloride (1-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Methotrexate, N-[4[[(2,4-diamino-6-pteridinyl) methyl]methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below. Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. Topotecan HCl, (S)-10-[(dimethylamino)rnethyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5a-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C, Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed nonreceptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404. SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa,IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (1989) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imolone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancep erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic agents including non-receptorkinase angiogenesis inhibitors may alo be useful. Anti-angiogenic agents such as those which inhibit the effects of vascular edothelial growth factor, (for example the anti-vascular endothelial cell growth factor antibody bevacizumab [Avastin™], and compounds that work by other mechanisms (for example linomide, inhibitors of integrin avβ3 function, endostatin and angiostatin).

Agents used in immunotherapeutic regimens may also be useful in combination with the compounds of formula (I). Immunotherapy approaches, including for example ex-vivo and in-vivo approaches to increase the immunogenecity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using antiidiotypic antibodies.

Agents used in proapoptotic regimens (e.g., bcl-2 antisense oligonucleotides) may also be used in the combination of the present invention.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin, Ther. Patents (2000) 10(2):215-230.

For the treatment or prophylaxis of pulmonary disorders, anticholinergics of potential use in treating asthma, COPD, bronchitis, and the like, and therefore useful as an additional therapeutic agent include antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-ylester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide);

7-[3-(2-Diethylamino-acetoxy)-2-phenyl-propionyloxyl-9-ethyl-9-methyl-3-oxa-9-azonia-tricyclo[3.3.1.02,4] nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methylphenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium;
1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; beta-2 agonist used to treat broncho-constriction in asthma, CORD and bronchitis include salmeterol and albuterol; anti-inflammatory signal transduction modulators for asthma.

With regard to the pulmonary condition of asthma, those skilled in the art appreciate that asthma is a chronic inflammatory disease of the airways resulting from the infiltration of pro-inflammatory cells, mostly eosinophils and activated T-lymphocytes into the bronchial mucosa and submucosa. The secretion of potent chemical mediators, including cytokines, by these proinflammatory cells alters mucosal permeability, mucus production, and causes smooth muscle contraction. All of these factors lead to an increased reactivity of the airways to a wide variety of irritant stimuli (Kaliner, 1988). Targeting signal transduction pathways is an attractive approach to treating inflammatory diseases, as the same pathways are usually involved in several cell types and regulate several coordinated inflammatory processes, hence modulators have the prospect of a wide spectrum of beneficial effects. Multiple inflammatory signals activate a variety of cell surface receptors that activate a limited number of signal transduction pathways, most of which involve cascades of kinases. These kinases in turn may activate transcription factors that regulate multiple inflammatory genes. Applying "anti-inflammatory signal transduction modulators" (referred to in this text as AISTM), like phosphodiesterase inhibitors (e.g. PDE-4, PDE-5, or PDE-7 specific), transcription factor inhibitors (e.g. blocking NFκB through IKK inhibition), or kinase inhibitors (e.g. blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006).

Additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

Moreover, asthma is a chronic inflammatory disease of the airways produced by the infiltration of pro-inflammatory cells, mostly eosinophils and activated T-lymphocytes (Poston, Am. Rev. Respir. Dis., 145 (4 Pt 1), 918-921, 1992; Walker, J. Allergy Clin. Immunol., 88 (6), 935-42, 1991) into the bronchial mucosa and submucosa. The secretion of potent chemical mediators, including cytokines, by these proinflammatory cells alters mucosal permeability, mucus production, and causes smooth muscle contraction. All of these factors lead to an increased reactivity of the airways to a wide variety of irritant stimuli (Kaliner, "Bronchial asthma, Immunologic diseases" E. M. Samter, Boston, Little, Brown and Company: 117-118. 1988).

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation, Inhaled corticosteroids (ICS) have been developed to mitigate the severe adverse effects of oral steroids. While ICS are very effective in controlling inflammation in asthma, they too are not precisely delivered to the optimal site of action in the lungs and produce unwanted side effects in the mouth and pharynx (candidiasis, sore throat, dysphonia). Combinations of inhaled β2-adrenoreceptor agonist bronchodilators such as formoterol or salmeterol with ICS's are also used to treat both the bronchoconstriction and the inflammation associated with asthma and COPD (Symbicort® and Advair®, respectively). However, these combinations have the side effects of both the ICS's and the β2-adrenoreceptor agonist because of systemic absorption (tachycardia, ventricular dysrhythmias, hypokalemia) primarily because neither agent is delivered to the optimal sites of actions in the lungs. In consideration of all problems and disadvantages connected with the adverse side effect profile of ICS and of β2-agonists it would be highly advantageous to provide mutual steroid-β2-agonist prodrug to mask the pharmacological properties of both steroids and β2-agonists until such a prodrug reaches the lungs, thereby mitigating the oropharyngeal side effects of ICS and cardiovascular side-effects of β2-agonists. In one aspect, such a mutual steroid-β2-agonist prodrug would be effectively delivered to the endobronchial space and converted to active drugs by the action of lung enzymes, thereby delivering to the site of inflammation and bronchoconstriction a therapeutic amount of both drugs. An anti-inflammatory agent for combination therapy includes dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone propionate, ciclesonide; or a pharmaceutically acceptable salt thereof.

The immune response to certain antigens can be enhanced through the use of immune potentiators, known as vaccine adjuvants. A discussion of immunological adjuvants can be found in "Current Status of Immunological Adjuvants", *Ann. Rev. Immunol.*, 1986, 4, pp. 369-388 and "Recent Advances in Vaccine Adjuvants and Delivery Systems" by D. T. O'Hagan and N. M. Valiante. The disclosures of U.S. Pat. Nos. 4,806,352; 5,026,543; and 5,026,546 describe various vaccine adjuvants appearing in the patent literature. Each of these references is hereby incorporated by reference in their entireties.

In one embodiment of the instant invention, provided are methods of administering a vaccine by administering a compound of Formula II alone or in combination with antigens and/or other agents. In another embodiment, immune responses to vaccines using antigenic epitopes from sources such as synthetic peptides, bacterial, or viral antigens are enhanced by co-administration of the compounds of Formula II. In other embodiments, the instant invention provides immunogenic compositions comprising one or more antigens and a compound of Formula II effective to stimulate a cell mediated response to said one or more antigens.

In another embodiment, compounds of Formula II can be used in the manufacture of a medicament for enhancing the immune response to an antigen. Other embodiments provide the use of the compound of Formula II in the manufacture of a medicament for immune stimulation, and another agent, such as an antigen, for simultaneous, separate or sequential administration.

In another embodiment, provided is a pharmaceutical preparation comprising (a) a compound of Formula II and (b) an antigen, wherein (a) and (b) are either in admixture or are separate compositions. These embodiments are for simultaneous, separate or sequential administration. When in separate compositions, the compound of Formula II may be administered may be administered enterally, orally, parenterally, sublingually, intradermally, by inhalation spray, rectally, or topically in dosage unit formulations that include conventional nontoxic pharmaceutically acceptable carriers, adjuvants, and vehicles as desired. For example, suitable modes of administration include oral, subcutaneous, transdermal, transmucosal, iontophoretic, intravenous, intramuscular, intraperitoneal, intranasal, subdermal, rectal, and the like. Topical administration may also include the use of transdermal administration such as transdermal patches or ionophoresis devices. The term parenteral as used herein includes subcutaneous injections, intravenous, intramuscular, intrasternal injection, or infusion techniques. orally, topically, nasally, rectally, by inhalation or by injection.

In another embodiment, compounds of Formula II are used as polyclonal activators for the production of antigens. More particularly the invention relates to a method of preparing monoclonal antibodies with a desired antigen specificity comprising contacting a compound of Formula with immortalized memory B cells. The monoclonal antibodies produced therefrom, or fragments thereof, may be used for the treatment of disease, for the prevention of disease or for the diagnosis of disease.

Vaccines or immunogenic compositions of the instant invention comprising a compound of Formula II may be administered in conjunction with one or more immunoregulatory agents. In particular, compositions can include another adjuvant. Adjuvants for use with the invention include, but are not limited to, mineral containing compositions such as calcium or aluminium salts, for example $AlK(SO_4)_2$, $Al(OH)_3$, $AlPO_4$, or combinations thereof. Other adjuvants include oil-emulsions, particularly submicron oil-in-water emulsions such as those described in WO90/14837, U.S. Pat. No. 6,299,884 and U.S. Pat. No. 6,452,325. Other adjuvants include saponin formulations such as QS7, QS17, QS18, QS21, OH-A, QH-B and QH-C, see U.S. Pat. No. 5,057,540 and Barr, et al. *Advanced Drug Delivery Reviews* (1998), 32:247-271. Other adjuvants include virosomes and virus like particles (VLPs) (Gluck, et al., *Vaccine* (2002) 20:B10-B16, US 20090263470); bacterial or microbial derivatives, Lipid A derivatives, immunostimulatory oligonucleotides, ADP-ribosylating toxins and detoxified derivatives thereof, bioadhesives and mucoadhesives, microparticles, liposomes, polyphasphazene (PCPP), and other small molecule immunopotentiators. One or more of the above named adjuvants may be used in a vaccine combination with a compound of Formula II.

The invention is also directed to methods of administering the immunogenic compositions of the invention, wherein the immunogenic composition includes in one embodiment one or more adjuvants and antigens as described herein in combination with a compound of Formula II. in some embodiments, the immunogenic composition is administered to the subject in an amount effective to stimulate an immune response. The amount that constitutes an effective amount depends, inter alia, on the particular immunogenic composition used, the particular adjuvant compound being administered and the amount thereof, the immune response that is to be enhanced (humoral or cell mediated), the state of the immune system (e.g., suppressed, compromised, stimulated), and the desired therapeutic result. Accordingly it is not practical to set forth generally the amount that constitutes an effective amount of the immunogenic composition. Those of ordinary skill in the art, however, can readily determine the appropriate amount with due consideration of such factors.

The immunogenic compositions of the present invention can be used in the manufacture of a vaccine. Suitable vaccines include, but are not limited to, any material that raises either or both humoral or cell mediated immune response. Suitable vaccines can include live viral and bacterial antigens and inactivated viral, tumor-derived, protozoal, organism-derived, fungal, and bacterial antigens, toxoids, toxins, polysaccharides, proteins, glycoproteins, peptides, and the like.

Compositions of a compound of Formula II may be administered in conjunction with one or more antigens for use in therapeutic, prophylactic, or diagnostic methods of the instant invention. In another aspect of this embodiment, these compositions may be used to treat or prevent infections caused by pathogens. In another aspect of this embodiment, these compostions may also be combined with an adjuvant as described supra.

Antigens for use with the invention include, but are not limited to, one or more of the antigens comprising bacterial antigens, viral antigens, fungal antigens, antigens from sexually transmitted diseases (STD), respiratory antigens, pediatric vaccine antigens, antigens suitable for use in elderly or immunocompromised individuals, antigens suitable for use in adolescent vaccines, and tumor antigens.

In yet another embodiment, the present application discloses pharmaceutical compositions comprising a compound of the present invention, or a pharmaceutically acceptable salt thereof, in combination with at least one additional active agent, and a pharmaceutically acceptable carrier or excipient. In yet another embodiment, the present application provides a combination pharmaceutical agent with two or more therapeutic agents in a unitary dosage form. Thus, it is also possible to combine any compound of the invention with one or more other active agents in a unitary dosage form.

The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. in some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Methods of Treatment

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" or a "partial antagonist" is a substance that provides a level of stimulation or inhibition, respectively, to its binding partner that is not fully or completely agonistic or antagonistic, respectively. It will be recognized that stimulation, and hence, inhibition is defined intrinsically for any substance or category of substances to be defined as agonists, antagonists, or partial agonists.

As used herein, "intrinsic activity" or "efficacy" relates to some measure of biological effectiveness of the binding partner complex. With regard to receptor pharmacology, the context in which intrinsic activity or efficacy should be defined will depend on the context of the binding partner (e.g., receptor/ligand) complex and the consideration of an activity relevant to a particular biological outcome. For example, in some circumstances, intrinsic activity may vary depending on the particular second messenger system involved. Where such contextually specific evaluations are relevant, and how they might be relevant in the context of the present invention, will be apparent to one of ordinary skill in the art.

As used herein, modulation of a receptor includes agonism, partial agonism, antagonism, partial antagonism, or inverse agonism of a receptor.

As will be appreciated by those skilled in the art, when treating a viral infection such as HCV, HBV, or HIV, such treatment may be characterized in a variety of ways and measured by a variety of endpoints. The scope of the present invention is intended to encompass all such characterizations.

In one embodiment, the method can be used to induce an immune response against multiple epitopes of a viral infection in a human. Induction of an immune response against viral infection can be assessed using any technique that is known by those of skill in the art for determining whether an immune response has occurred. Suitable methods of detecting an immune response for the present invention include, among others, detecting a decrease in viral load or antigen in a subject's serum, detection of IFN-gamma-secreting peptide specific T cells, and detection of elevated levels of one or more liver enzymes, such as alanine transferase (ALT) and aspartate transferase (AST). In one embodiment, the detection of IFN-gamma-secreting peptide specific T cells is accomplished using an ELISPOT assay. Another embodiment includes reducing the viral load associated with HBV infection, including a reduction as measured by PCR testing.

In another aspect, the present invention provides methods for treating a hepatitis B viral infection or a hepatitis C viral infection, wherein each of the methods includes the step of administering to a human subject infected with hepatitis B virus or hepatitis C virus a therapeutically effective amount a compound of Formula Ia, II, or IIa or a pharmaceutically acceptable salt thereof. Typically, the human subject is suffering from a chronic hepatitis B infection or a chronic hepatitis C infection, although it is within the scope of the present invention to treat people who are acutely infected with HBV or HCV.

Treatment in accordance with the present invention typically results in the stimulation of an immune response against HBV or HCV in a human being infected with HBV or HCV, respectively, and a consequent reduction in the viral load of HBV or HCV in the infected person. Examples of immune responses include production of antibodies (e.g., IgG antibodies) and/or production of cytokines, such as interferons, that modulate the activity of the immune system. The immune system response can be a newly induced response, or can be boosting of an existing immune response. In particular, the immune system response can be seroconversion against one or more HBV or HCV antigens.

The viral bad can be determined by measuring the amount of HBV DNA or HCV DNA present in the blood. For example, blood serum HBV DNA can be quantified using the Roche COBAS Amplicor Monitor PCR assay (version 2.0; lower limit of quantification, 300 copies/mL [57 IU/mL]) and the Quantiplex bDNA assay (lower limit of quantification, 0.7 MEq/mL; Bayer Diagnostics, formerly Chiron Diagnostics, Emeryville, Calif.). The amount of antibodies against specific HBV or HCV antigens (e.g., hepatitis B surface antigen (HBsAG)) can be measured using such art-recognized techniques as enzyme-linked immunoassays and enzyme-linked immunoabsorbent assays. For example, the amount of antibodies against specific HBV or HCV antigens can be measured using the Abbott AxSYM microparticle enzyme immunoassay system (Abbott Laboratories, North Chicago, Ill.).

A compound of Formula II can be administered by any useful route and means, such as by oral or parenteral (e.g., intravenous) administration. Therapeutically effective amounts of Formula II are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

The frequency of dosage of Formula II will be determined by the needs of the individual patient and can be, for example, once per day or twice, or more times, per day. Administration of Formula II continues for as long as necessary to treat the HBV or HCV infection. For example, Formula II can be administered to a human being infected with HBV or HCV for a period of from 20 days to 180 days or, for example, for a period of from 20 days to 90 days or, for example, for a period of from 30 days to 60 days.

Administration can be intermittent, with a period of several or more days during which a patient receives a daily dose of Formula II, followed by a period of several or more days during which a patient does not receive a daily dose of Formula II. For example, a patient can receive a dose of Formula II every other day, or three times per week. Again by way of example, a patient can receive a dose of Formula II each day for a period of from 1 to 14 days, followed by a period of 7 to 21 days during which the patient does not receive a dose of Formula II, followed by a subsequent period (e.g., from 1 to 14 days) during which the patient again receives a daily dose of Formula II. Alternating periods of administration of Formula II, followed by non-administration of Formula II, can be repeated as clinically required to treat the patient.

As described more fully herein, Formula II can be administered with one or more additional therapeutic agent(s) to a human being infected with HBV or HCV. The additional therapeutic agent(s) can be administered to the infected human being at the same time as Formula II, or before or after administration of Formula II.

In another aspect, the present invention provides a method for ameliorating a symptom associated with an HBV infection or HCV infection, wherein the method comprises administering to a human subject infected with hepatitis B virus or hepatitis C virus a therapeutically effective amount of Formula II, or a pharmaceutically acceptable salt thereof, wherein the therapeutically effective amount is sufficient to ameliorate a symptom associated with the HBV infection or HCV infection. Such symptoms include the presence of HBV virus particles (or HCV virus particles) in the blood, liver inflammation, jaundice, muscle aches, weakness and tiredness.

In a further aspect, the present invention provides a method for reducing the rate of progression of a hepatitis B viral infection, or a hepatitis C virus infection, in a human being, wherein the method comprises administering to a human subject infected with hepatitis B virus or hepatitis C virus a therapeutically effective amount of Formula II, or a pharmaceutically acceptable salt thereof, wherein the therapeutically effective amount is sufficient to reduce the rate of progression of the hepatitis B viral infection or hepatitis C viral infection. The rate of progression of the infection can be followed by measuring the amount of HBV virus particles or HCV virus particles in the blood.

In another aspect, the present invention provides a method for reducing the viral load associated with HBV infection or HCV infection, wherein the method comprises administering to a human being infected with HBV or HCV a therapeutically effective amount of Formula II, or a pharmaceutically acceptable salt thereof, wherein the therapeutically effective amount is sufficient to reduce the HBV viral load or the HCV viral load in the human being.

In a further aspect, the present invention provides a method of inducing or boosting an immune response against Hepatitis B virus or Hepatitis C virus in a human being, wherein the method comprises administering a therapeutically effective amount of Formula II, or a pharmaceutically acceptable salt thereof, to the human being, wherein a new immune response against Hepatitis B virus or Hepatitis C virus is induced in the human being, or a preexisting immune response against Hepatitis B virus or Hepatitis C virus is boosted in the human being. Seroconversion with respect to HBV or HCV can be induced in the human being. Examples of immune responses include production of antibodies, such as IgG antibody molecules, and/or production of cytokine molecules that modulate the activity of one or more components of the human immune system.

Induction of seroconversion against HCV or HBV in patients chronically infected with either of these viruses is an unexpected property of Formula II. In clinical practice, an HBV patient, or HCV patient, is treated with Formula II, alone or in combination with one or more other therapeutic agents, until an immune response against HBV or HCV is induced or enhanced and the viral load of HBV or HCV is reduced. Thereafter, although the HBV or HCV virus may persist in a latent form in the patient's body, treatment with Formula II can be stopped, and the patient's own immune system is capable of suppressing further viral replication. In patients treated in accordance with the present invention and who are already receiving treatment with an antiviral agent that suppresses replication of the HBV virus or HCV virus, there may be little or no detectable viral particles in the body of the patient during treatment with the antiviral agent(s). In these patients, seroconversion will be evident when the antiviral agent(s) is no longer administered to the patient and there is no increase in the viral load of HBV or HCV.

In the practice of the present invention, an immune response is induced against one or more antigens of HBV or HCV. For example, an immune response can be induced against the HBV surface antigen (HBsAg), or against the small form of the HBV surface antigen (small S antigen), or against the medium form of the HBV surface antigen (medium S antigen), or against a combination thereof. Again by way of example, an immune response can be induced against the HBV surface antigen (HBsAg) and also against other HBV-derived antigens, such as the core polymerase or x-protein, Induction of an immune response against HCV or HBV can be assessed using any technique that is known by those of skill in the art for determining whether an immune response has occurred. Suitable methods of detecting an immune response for the present invention include, among others, detecting a decrease in viral load in a subject's serum, such as by measuring the amount of HBV DNA or HCV DNA in a subject's blood using a PCR assay, and/or by measuring the amount of anti-HBV antibodies, or anti-HCV antibodies, in the subject's blood using a method such as an ELISA.

Additionally, the compounds of this invention are useful in the treatment of cancer or tumors (including dysplasias, such as uterine dysplasia). These includes hematological malignancies, oral carcinomas (for example of the lip, tongue or pharynx), digestive organs (for example esophagus, stomach, small intestine, colon, large intestine, or rectum), liver and biliary passages, pancreas, respiratory system such as larynx or lung (small cell and non-small cell), bone, connective tissue, skin (e.g., melanoma), breast, reproductive organs (uterus, cervix, testicles, ovary, or prostate), urinary tract (e.g., bladder or kidney), brain and endocrine glands such as the thyroid. In summary, the compounds of this invention are employed to treat any neoplasm, including not only hematologic malignancies but also solid tumors of all kinds.

Hematological malignancies are broadly defined as proliferative disorders of blood cells and/or their progenitors, in which these cells proliferate in an uncontrolled manner. Anatomically, the hematologic malignancies are divided into two primary groups: lymphomas—malignant masses of lymphoid cells, primarily but not exclusively in lymph nodes, and leukemias—neoplasm derived typically from lymphoid or myeloid cells and primarily affecting the bone marrow and peripheral blood. The lymphomas can be sub-divided into Hodgkin's Disease and Non-Hodgkin's lymphoma (NHL). The later group comprises several distinct entities, which can be distinguished clinically (e.g. aggressive lymphoma, indolent lymphoma), histologically (e.g. follicular lymphoma, mantle cell lymphoma) or based on the origin of the malignant cell (e.g. B lymphocyte, T lymphocyte). Leukemias and related malignancies include acute myelogenous leukemia (AML), chronic myelogenous leukemia (CML), acute lymphoblastic leukemia (ALL) and chronic lymphocytic leukemia (CLL). Other hematological malignancies include the plasma cell dyscrasias including multiple myeloma, and the myelodysplastic syndromes.

Synthetic Examples

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac$_2$O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |

TABLE 1-continued

List of abbreviations and acronyms.

| Abbreviation | Meaning |
|---|---|
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH$^+$ | mass plus 1 |
| MH$^-$ | mass minus 1 |
| MsOH | methanesulfonic acid |
| MS or ms | mass spectrum |
| NBS | N-bromosuccinimide |
| Ph | phenyl |
| rt or r.t. | room temperature |
| TBAF | tetrabutyiammonium fluoride |
| TMSCl | chlorotrimethylsilane |
| TMSBr | bromotrimethylsilane |
| TMSI | iodotrimethylsilane |
| TMSOTf | (trimethyisilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

General Scheme Pteridinone Derivatives

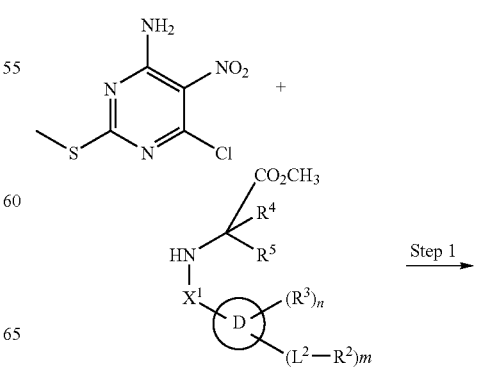

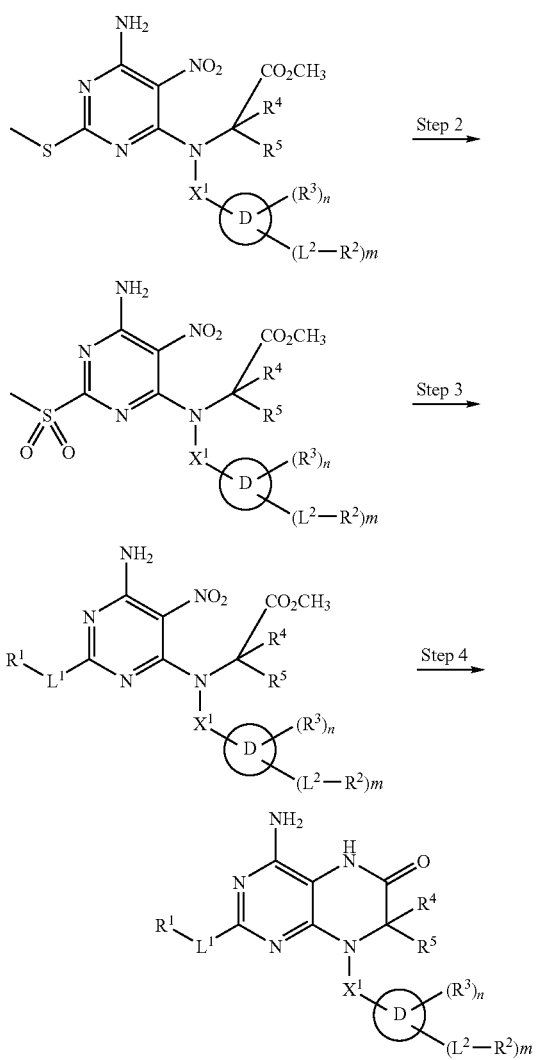

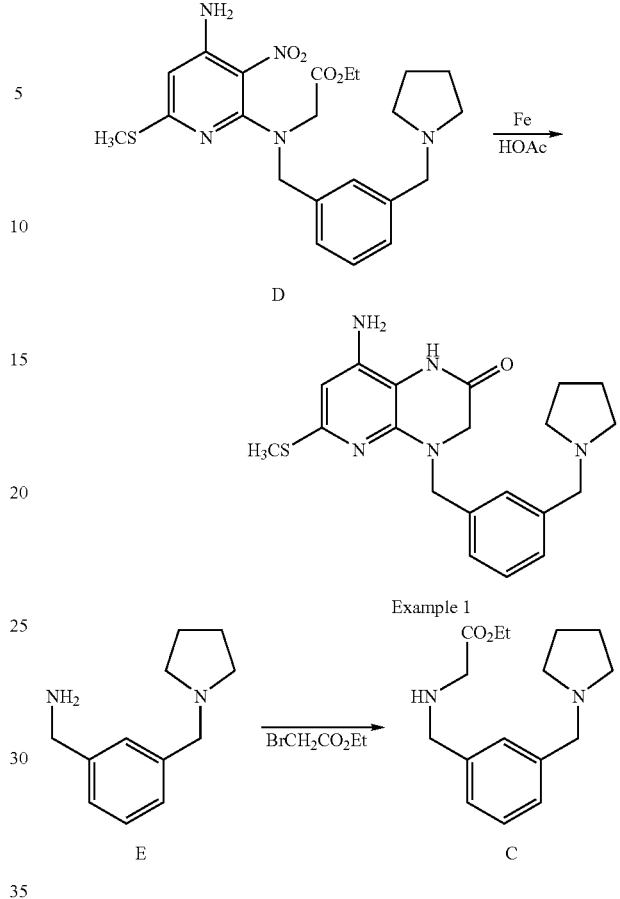

Scheme 1

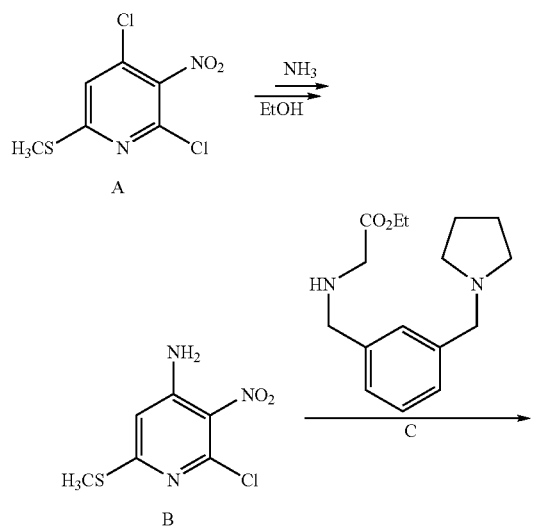

Compound B

To a solution of compound A (2.46 g, 10.2 mmol) in THF (34 mL) at −20° C. was added Et$_3$N (3.14 mL, 22.5 mmol) followed by a solution of NH$_3$ (2.0 M in MeOH, 5.4 mL, 11 mmol). The mixture was stirred while warming to 0° C. for 1.5 h (LC/MS indicated consumption of starting materials). The reaction mixture was taken forward without work-up.

Compound C

To a solution of 3-((1-pyrrolidinylmethyl)phenyl)methanamine E (1.95 g, 10.2 mmol) in THF (34 mL) at 0° C. was added Et$_3$N (3.14 mmol, 22.5 mmol) followed by methyl bromoacetate (1.04 mL, 22.3 mmol) dropwise. The reaction mixture was stirred until LC/MS indicated consumption of starting materials, approximately 2 h. The mixture was taken forward to the synthesis of compound D without work up.

Compound D

The above reaction mixture containing compound C was added to the reaction mixture containing compound B at 0° C. The reaction mixture was stirred until LC/MS indicated the consumption of compound B, approximately 45 min. A saturated solution of NH$_4$Cl (50 mL) was added. The layers were separated, and the aqueous layer was extracted with EtOAc (2×30 mL). The combined organic layers were dried over MgSO$_4$, filtered, and concentrated under vacuum. Purification by silica gel chromatography provided 2.11 g (46% from A) of compound D. $^1$H NMR (CD$_3$OD, 300 MHz): d (ppm) 7.32-7.16 (m, 4H), 4.69 (s, 2H), 4.19 (q, J=7 Hz, 2H), 4.07 (s, 2H), 3.60 (s, 2H), 2.49 (s, 4H), 2.40 (s, 3H), 1.78 (m, 4H), 1.23 (t, 3H, J=7 Hz). LCMS-ESI$^+$: calc'd for C$_{21}$H$_{29}$N$_6$O$_4$S: 461.2 (M+H$^+$); Found: 461.0 (M+H$^+$).

Example 1

A solution of compound 4 (50 mg) and Fe dust (117 mg) in AcOH (2 mL) was stirred at rt for 13 h. The reaction was filtered through Celite and purified by HPLC on a C18 column, eluting with a gradient of 2-98% acetonitrile in $H_2O$ to provide Example 1 in 13% yield. $^1$H NMR ($CD_3OD$): δ 7.40-7.22 (m, 4H), 4.82 (s, 2H), 3.93 (s, 2H), 3.73 (s, 2H), 2.70-2.60 (m, 4H), 2.41 (s, 3H), 1.90-1.78 (m, 4H); MS: 385.2 (M+H$^+$).

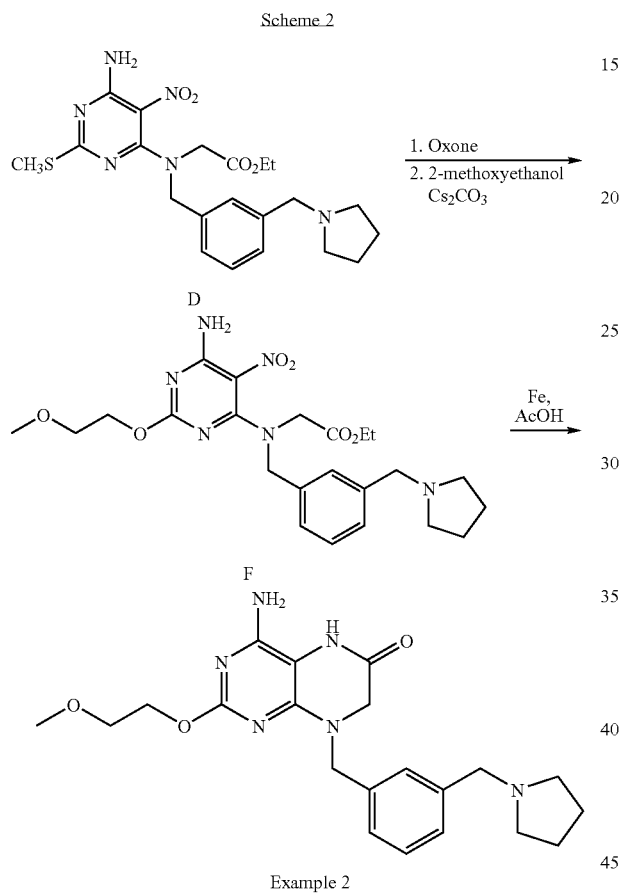

Example 2

Compound F

Compound D was dissolved in methanol (2 mL), and to this was added a solution of Oxone (1.08 g) in $H_2O$ (3 mL). The mixture was stirred for 30 min, after which the oxidation was almost complete. The mixture was added to water and extracted with $CH_2Cl_2$. The organic phase was dried over $Na_2SO_4$, filtered, and concentrated under vacuum to give the desired sulfone intermediate, which was carried on to the next step. The sulfone and $Cs_2CO_3$ (384 mg) were taken up in $CH_2Cl_2$ (4 mL) and to this was added 2-methoxyethanol (880 μL) dropwise. After stirring for one hour, some sulfone starting material remained as indicated by LC/MS, and another 200 μL of 2-methoxyethanol was added and the reaction was stirred for an additional 30 min. The reaction mixture was diluted with $CH_2Cl_2$ and washed with water. The organic layer was dried over $Na_2SO_4$, filtered, and concentrated under vacuum. The product was purified by flash chromatography on silica gel, eluting with 20% MeOH in $CH_2Cl_2$, to give compound F in 40% yield. $^1$H NMR ($CD_3OD$): δ 7.40-7.15 (m, 4H), 4.69 (br s, 2H), 4.33 (t, J=4.8 Hz, 2H), 4.17 (q, J=6.9 Hz, 2H), 4.04 (s, 2H), 3.68 (s, 2H), 3.03 (t, J=4.2 Hz, 2H), 3.68 (s, 3H), 2.60 (s, 4H), 1.81 (s, 4H), 1.24 (t, J=7.2 Hz, 3H); MS: 489.2 (M+H$^+$).

Example 2

A mixture of compound F (33 mg), iron dust (56 mg), and acetic acid (1 mL) was stirred at rt for 4 h. After this time conversion was incomplete, so another portion of iron dust (20 mg) was added and the reaction was stirred for another 6 h. A third portion of iron dust (30 mg) was added and the mixture was stirred another 12 h. The mixture was filtered through silica gel, and the solvent was removed under vacuum. The product was purified from the remaining material by preparative HPLC on a C18 column, eluting with a gradient of 2-98% acetonitrile in $H_2O$, providing Example 2. $^1$H NMR ($CD_3OD$): δ 7.62 (s, 1H), 7.50 (s, 3H), 4.95 (s, 2H), 4.60-4.53 (m, 2H), 4.39 (s, 2H), 4.15 (s, 2H), 3.95-3.67 (m, 2H), 3.60-3.42 (m, 2H), 3.68 (s, 3H), 3.25-3.12 (m, 2H), 2.23-1.95 (m, 4H); MS: 413.2 (M+H$^+$).

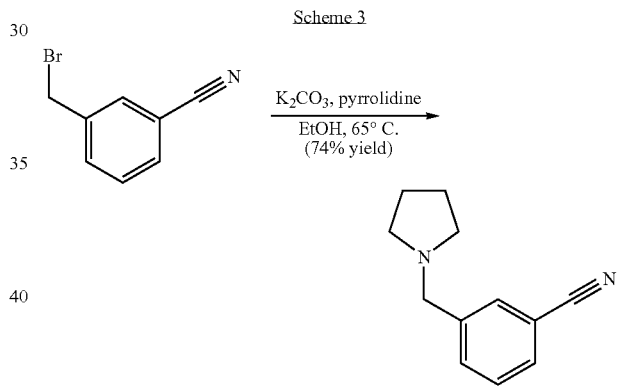

Scheme 3

Method I: 3-(pyrroldin-1'-yl)-methyl benzonitrile: To a solution of 3-(bromomethyl)-benzonitrile (30.0 g, 1.00 equiv) in absolute EtOH (600 mL) was added pyrrolidine (13.3 mL, 1.00 equiv), followed by $K_2CO_3$ (anhydrous, 63.5 g, 3.00 equiv). The reaction was stirred vigorously at 65° C. until consumption of the bromide was complete (Reaction is monitored on Merck 254 nm silica-coated TLC plates using a combination of EtOAc/hexane as eluent). The reaction (which may be orange-colored) was cooled to 23° C. and filtered over coarse glass frits, and the filtrate was concentrated. The resulting residue was partitioned between $H_2O$ and EtOAc (300 mL each) and the organic phase collected. The aqueous layer was extracted (2×200 mL EtOAc). All of the resulting organic layers were combined, dried ($Na_2SO_4$), filtered, and concentrated in vacuo, giving the title nitrile (21.1 g, 74% yield) as an orange residue. $^1$H NMR ($CDCl_3$, 300 MHz): d (ppm) 7.65 (s, 1H), 7.59 (d, J=7.7 Hz, 1H), 7.54 (d, J=7.6 Hz, 1H), 7.41 (dd, J=7.7 Hz, 7.6 Hz, 1H), 3.65 (s, 2H), 2.52 (m, 4H), 1.81 (m, 4H). LCMS-ESI$^+$: calc'd for $C_{12}H_{15}N_2$: 187.1 (M+H$^+$); Found: 187.1 (M+H$^+$).

Scheme 4

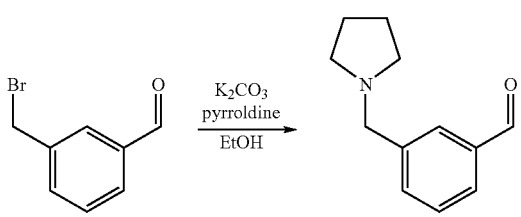

Method II: 3-(pyrroldin-1'-yl)-methyl benzaldehyde: A suspension of K₂CO₃ (2.09 g, 15.2 mmol, 3.00 equiv) in absolute ethanol (20 mL) was treated with pyrroldine (439 µL, 5.05 mmol, 1.00 equiv). 3-(bromomethyl)-benzaldehyde (1.00 g, 5.05 mmol, 1.00 equiv) was introduced, and the reaction was heated to 65° C. for 1 h. The reaction was cooled and filtered. The cake was washed with more ethanol. The filtrate was concentrated to a cloudy oil and partitioned between DCM (50 mL) and 2% w/v aq NaHCO₃ (50 mL). The organic phase was collected, and the aq layer was extracted with DCM (2×50 mL). All organic layers were combined, dried (Na₂SO₄), filtered, and concentrated, giving 3-(pyrrolidin-1-ylmethyl)-benzaldehyde (846 mg, 88% yield) as a pale yellow oil, which was used without further purification. $^1$H-NMR: 300 MHz, (CDCl₃) d: 10.00 (s, 1H), 7.84 (s, 1H), 7.76 (d, J=7.6 Hz, 1H), 7.62 (d, J=7.6 Hz, 1H), 7.47 (dd, J=7.6 Hz, 7.6 Hz, 1H), 3.69 (s, 2H), 2.52 (m, 4H), 1.79 (m, 4H). LCMS-ESI$^+$: calc'd for C₁₂H₁₆NO: 190.1 (M+H$^+$); Found: 190.1 (M+H$^+$).

Scheme 5

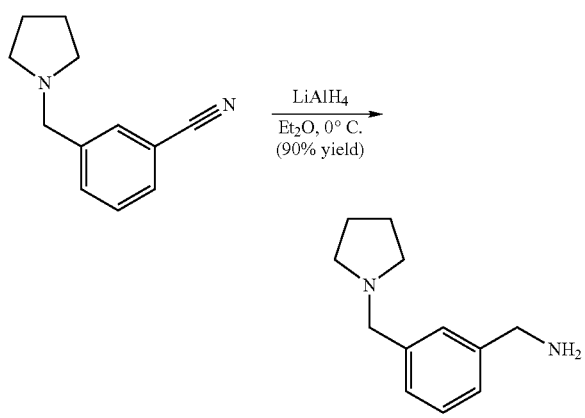

Method III: 3-(pyrrolidin-1'-yl)methyl benzylamine: A 1 Liter round-bottom flask was charged with LiAlH₄ (7.55 g) and anhydrous Et₂O (230 mL). After cooling to 0° C., 3-(pyrrolidin-1-ylmethyl)-benzonitrile (18.55 g) in THF (30 mL) was added slowly over a 5 min period. Rxn transitioned from orange to green. Once the reaction was complete (as indicated by TLC using Merck 254 nm silica-coated plates with DCM/MeOH/aq. NH₄OH eluent or by LCMS), it was slowly treated first with H₂O (7.5 mL) with sufficient time to allow gas evolution to cease, second (after a 5 min wait past the end of gas evolution) with 15% w/v aq. NaOH (7.5 mL) (again allowing gas evolution to stop, followed by a 5 min wait), and finally with more H₂O (26.5 mL). The reaction was filtered over glass frits to remove all of the solids present, and the filter cake was washed with Et₂O (100 mL). The filtrate was dried with copious MgSO₄, filtered, and concentrated, affording the title amine (17.0 g, 90% yield) as an oil. $^1$H NMR (CDCl₃, 300 MHz): d (ppm) 7.32-7.17 (m, 4H), 3.86 (s, 2H), 3.62 (s, 2H), 2.52 (m, 4H), 1.79 (m, 4H), 1.61 (s, broad, 2H). LCMS-ESI$^+$: calc'd for C₁₂H₁₉N₂: 191.1 (M+H$^+$); Found: 191.0 (M+H$^+$).

Scheme 6

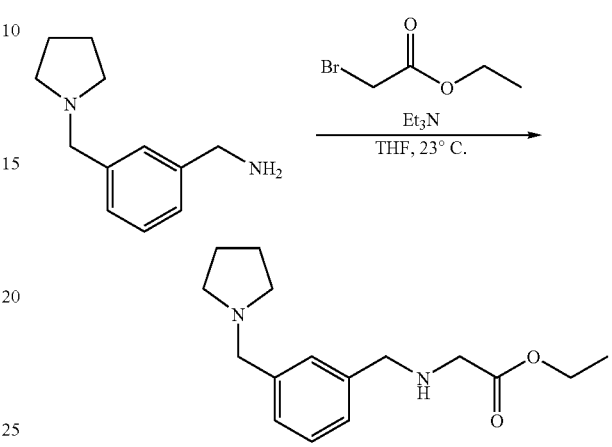

Method IV: Ethyl-N$_a$-[3-(pyrroldin-1'-ylmethyl)-benzyl]-glycinate: A solution of 3-(pyrroldin-1-ylmethyl)-benzylamine (17.0 g, 1.00 equiv) in THF (160 mL) was treated with Et₃N (27.4 mL, 2.20 equiv). Ethyl bromoacetate (9.90 mL, 1.00 equiv) was added dropwise to this solution at 23° C. over a 10 min period. After 24 hrs, the reaction was diluted with H₂O (600 mL) and extracted with EtOAc (3×150 mL). The organic layers were combined, dried (MgSO₄), filtered, and concentrated, giving the title product as a yellow oil (21.2 g, 86%). $^1$H NMR (CDCl₃, 300 MHz): d (ppm) 7.32-7.18 (m, 4H), 4.19 (q, J=7.0 Hz, 2H), 3.80 (s, 2H), 3.61 (s, 2H), 2.51 (m, 4H), 1.79 (m, 4H), 1.28 (t, J=7.0 Hz, LCMS-ESI$^+$: calc'd for C₁₆H₂₅N₂O₂: 277.2 (M+H$^+$); Found: 277.1 (M+H$^+$).

Scheme 7

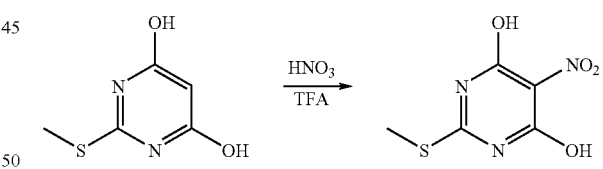

Method V: 4,6-Dihydroxy-2-methylthio-5-nitropyrimidine: A solution of 4,6-dihydroxy-2-methylthiopyrimidine (42 g, 0.257 mol) in trifluoroacetic acid (91 ml, 1.186 mol) was stirred at 23° C. and warmed until all solid had gone into solution. The reaction was stirred for five hours at 23° C. Next, fuming HNO₃ (15 ml, 350 mmol) was added portion wise to the reaction mixture over 25 minutes at 0° C. The reaction was stirred for twenty hours at 23° C., and treated with H₂O (at 23° C.) at 80% conversion (according LC-MS). The solid precipitate was captured via filteration giving 4,6-dihydroxy-2-methylthio-5-nitropyrimidine as a tan-colored solid. The crude solid was azeotroped with toluene to give 35 g of pale tan powdery solid. $^1$H-NMR: 300 MHz, (CD₃OD, 300 MHz) d (ppm) 2.63 (s, 3H). LCMS-ESI$^+$: calc'd for C₅H₄N₃O₄S: 202.0 (M−H$^-$); Found: 202.0 (M−H$^-$).

Scheme 8

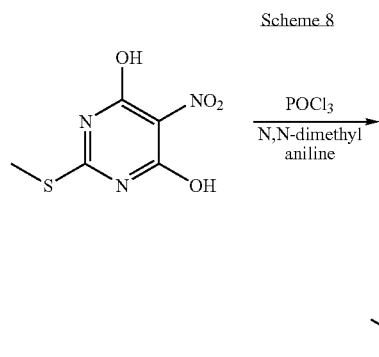

Method VI: 4,6-Dichloro-2-methylthio-5-nitropyrimidine: A 500 mL round bottom flask was charged with POCl$_3$ (89.5 mL, 0.960 mol, 5.00 equiv), and N,N-dimethylaniline (73.0 mL, 0.576 mol, 3.00 equiv). The reaction was cooled to 0° C., and 4,6-dihydroxy-2-methylthio-5-nitropyrimidine (39.0 g, 0.192 mol, 1.00 equiv) was added portionwise in a manner to control exotherm. Once the exotherm had subsided, the reaction was carefully warmed to 100° C. for 2 h. Reaction was then transferred to the upper reservoir of a continuous lower-density phase continuous extractor and extracted continuously with hot hexanes, which pooled in the lower reservoir. The lower reservoir was at 140° C. during extraction. After UV activity (254 nm) in the upper reservoir hexane phase was at its minimum, the system was cooled. The hexane phase was concentrated to an oil in vacuo. The residue was purified via silica gel chromatography (1 g residue/3 g silica) (Eluent: DCM). During loading (20 mL DCM was added to residue to aid fluidity) onto the column, there was a mild exotherm. After chromatography, crystalline 4,6-dichloro-2-methylthio-5-nitropyrimidine 34.9 g (76% yield) was obtained. $^1$H-NMR: 300 MHz, (CDCl$_3$) d (ppm): 2.62 (s, 3H). LCMS-ESI$^+$: compound does not ionize.

Scheme 9

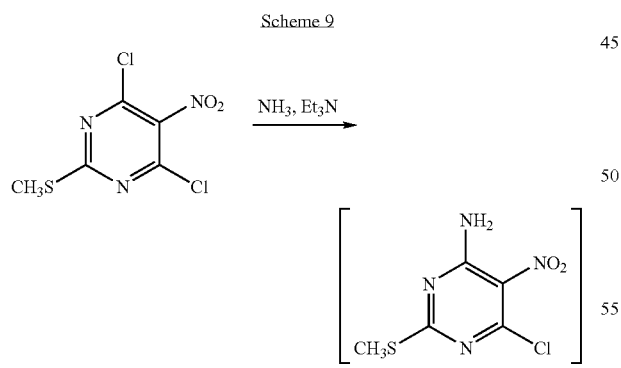

Method VII, Part 1: 4-Amino-6-chloro-2-methylthio-5-nitropyrimidine: To a solution of above dichloride (2.46 g, 10.2 mmol) in THF (34 mL) at −20° C. was added Et$_3$N (3.14 mL, 22.5 mmol) followed by a solution of NH$_3$ (2.0 M in MeOH, 5.4 mL, 11 mmol). The mixture was stirred while warming to 0° C. for 1.5 h (LC/MS indicated consumption of starting materials. Some bis-addition is observed). The reaction mixture was taken forward without work-up.

Scheme 10

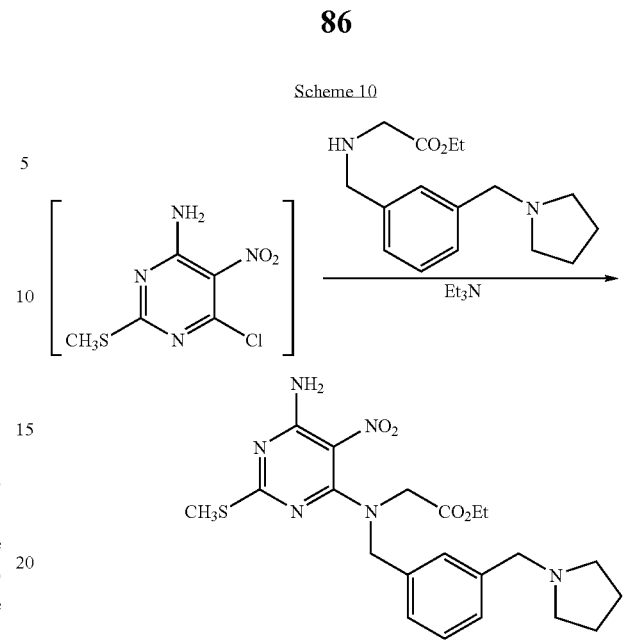

Method VII, Part 2: Ethyl-N$_a$-[4-amino-2-methylthio-5-nitropyrimidin-6-yl],N$_a$-[3'-(pyrrolidin-1''-ylmethyl)-benzyl]-glycinate: To the previous reaction mixture at 0° C. was added the secondary amine (2.82 g, 10.2 mmol) in THF (10 mL) over 5 min. The reaction mixture was stirred until LC/MS indicated the consumption of starting material, approximately 30 min. The reaction was filtered over glass frits; the filter cake was washed with EtOAc. The filtrate was concentrated and partitioned between EtOAc (30 mL) and 5% aq Na$_2$CO$_3$ (30 mL). The organic phase was collected, and the aqueous phase extracted twice more with EtOAc (30 mL each). The combined organic layers were dried over MgSO$_4$, filtered, and concentrated under vacuum. Absolute EtOH (30 mL) was added, and the material was concentrated again. The residue was taken up in a minimum of absolute EtOH at 70° C. (~12 mL), then the solution was allowed to cool gradually to 23° C. Crystals were filtered over glass frits and washed with hexane, then dried in vacuo. Product is a yellowish-green solid. $^1$H NMR (CDCl$_3$, 300 MHz): d (ppm) 7.32-7.16 (m, 4H), 4.69 (s, 2H), 4.19 (q, J=7 Hz, 2H), 4.07 (s, 2H), 3.60 (s, 2H), 2.49 (m, 4H), 2.40 (s, 3H), 1.78 (m, 4H), 1.23 (t, 3H, J=7 Hz). LCMS-ESI$^+$: calc'd for C$_{21}$H$_{29}$N$_6$O$_4$S: 461.2 (M+H$^+$); Found: 461.0 (M+H$^+$).

Scheme 11

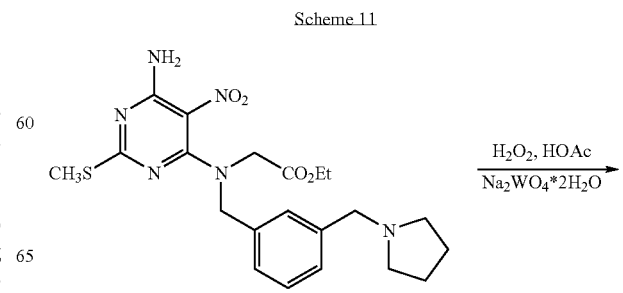

-continued

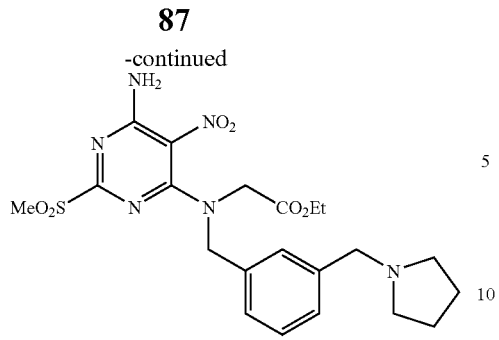

Method VIII: Ethyl-N$_a$-[4-amino-2-methanesulfonyl-5-nitropyrimidin-6-yl],N$_a$-[3'-(pyrrolidin-1''-ylmethyl)-benzyl]-glycinate: To a solution a suspension of the sulfide (3.68 g, 8.00 mmol) in EtOH (40 mL) at 0° C. was added sodium tungstate dihydrate (792 mg, 2.40 mmol), acetic acid (4.6 mL, 80 mmol), and hydrogen peroxide (3.4 mL, ~40 mmol, 35% w/w in H$_2$O) sequentially. After 3 h, additional acetic acid (4.6 mL) and hydrogen peroxide (3.4 mL) were added. The reaction was maintained at 0° C. for 16 h. A saturated solution of Na$_2$SO$_3$ (50 mL) was added carefully while at 0° C. followed by CH$_2$Cl$_2$ (75 mL). The layers were separated, and the aqueous layer was extracted with CH$_2$Cl$_2$ (4×50 mL). The combined organic layers were dried over MgSO$_4$, filtered, and concentrated under vacuum and used without further purification.

Scheme 12

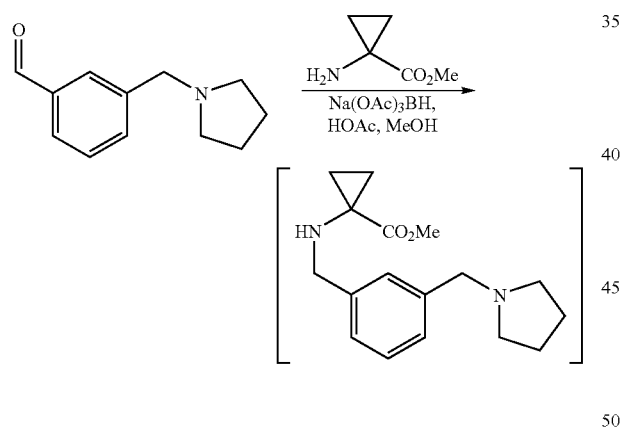

Method IX: Methyl-a,a-(1''',2'''-ethylidene),N$_a$-[3-(pyrrolidin-1'-ylmethyl)-benzyl]-glycinate: To a solution of 3-(pyrrolidin-1'-ylmethyl)-benzaldehyde (284 mg, 1.50 mmol) in MeOH (5 mL) was added acetic acid (258 µL, 4.50 mmol), sodium triacetoxyborohydride (636 mg, 3.00 mmol), and methyl 1-aminocyclopropanecarboxylate hydrochloride (250 mg, 1.65 mmol) sequentially. The reaction mixture was stirred at room temperature for 2 h and was then poured onto brine (15 mL) and CH$_2$Cl$_2$ (15 mL). The layers were separated, and the aqueous layer was extracted with CH$_2$Cl$_2$ (3×10 mL). The combined organic layers were dried (Na$_2$SO$_4$), filtered, and concentrated in vacuo and the title product was taken on without further purification as in Method XV, Parts 1 and 2 (below). LCMS-ESI$^+$: calc'd for C$_{17}$H$_{25}$N$_2$O$_2$: 289.4 (M+H$^+$); Found: 289.1 (M+H).

Scheme 13

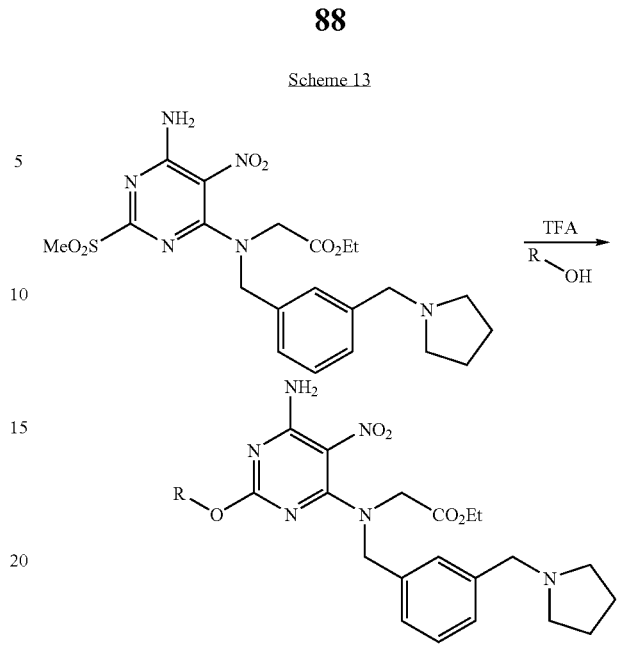

Method X: To a solution of sulfone (1.0 g, 2.0 mmol) in alcohol (R—OH) (10 mL) was added TFA (470 µL, 6.1 mmol). The reaction was stirred at 100° C. for 1 h. The reaction mixture was poured onto a saturated solution of NaHCO$_3$ (20 mL) and CH$_2$Cl$_2$ (30 mL). The layers were separated, and the aqueous layer was extracted with CH$_2$Cl$_2$ (30 mL). The combined organic layers were dried over MgSO$_4$, filtered, and concentrated under vacuum. Purification was conducted by silica gel chromatography (1 g substrate/10 g SiO$_2$) (2-15% MeOH/CH$_2$Cl$_2$).

Scheme 14

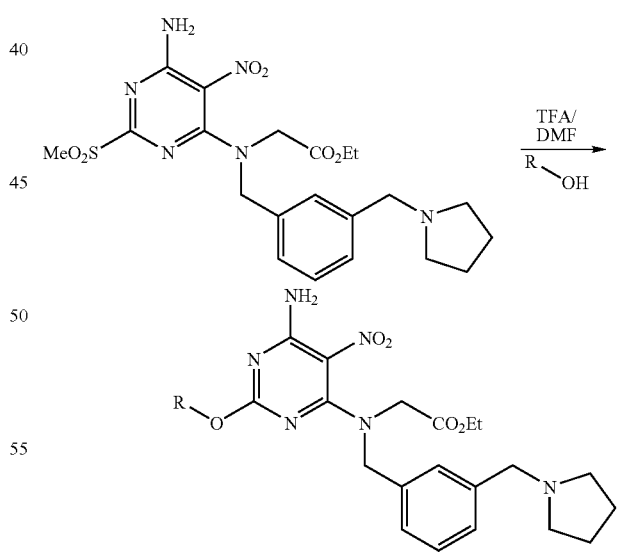

Method XI: To a solution of sulfone (1.0 g, 2.0 mmol) in alcohol (R—OH) (10 mL) was added DMF (1.0 mL) and TFA (470 µL, 6.1 mmol). The reaction was stirred at 90-100° C. for 1 h. The reaction mixture was poured onto a saturated solution of NaHCO$_3$ (20 mL) and CH$_2$Cl$_2$ (30 mL). The layers were separated, and the aqueous layer was extracted with CH$_2$Cl$_2$ (30 mL). The combined organic layers were dried over MgSO₄, filtered, and concentrated under vacuum. Purification was conducted by silica gel chromatography (1 g substrate/10 g SiO₂) (2-15% MeOH/CH₂Cl₂).

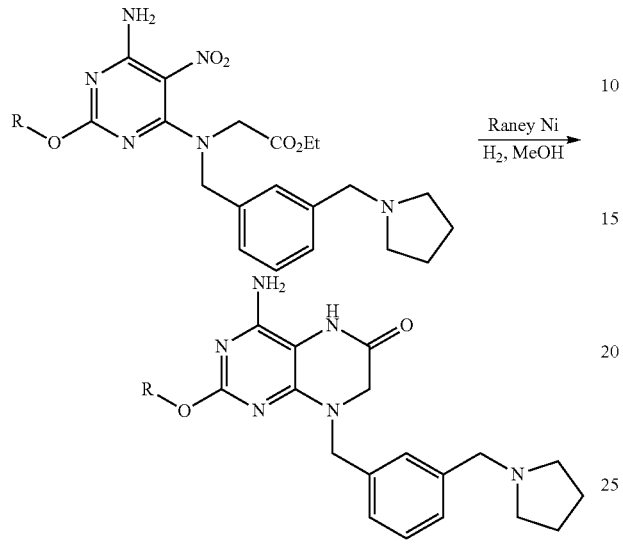

Scheme 15

Method XII: To a solution of nitro compound (730 mg, 1.5 mmol) in MeOH (10 mL) was added a Raney Nickel (~200 µL, slurry in H₂O). The reaction vessel was flushed with H₂ and then stirred under an H₂ atmosphere for 1.5 h. The mixture was filtered through celite with CH₂Cl₂ and MeOH (1:1). The filtrate was concentrated under vacuum and left on lyophilizer overnight. The title product was obtained as a free base is a white solid.

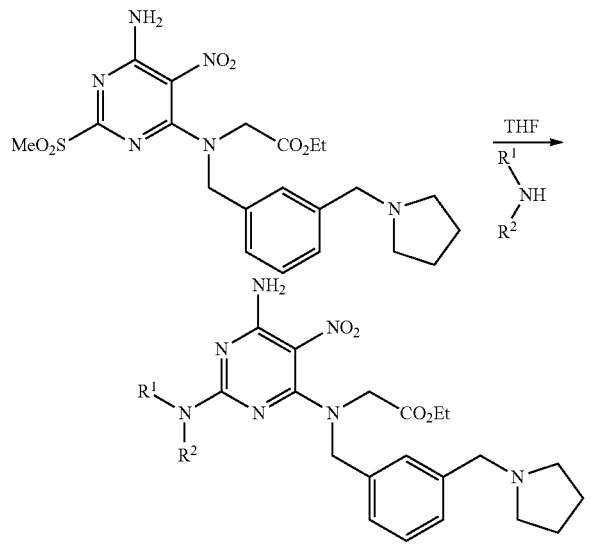

Scheme 16

Method XIII: A suspension of the sulfone (50 mg), THF (1.0 mL), and the amine (R¹R²NH) (100 µL) was heated to 60° C. for 3 h. The reaction was cooled to 23° C. and directly loaded to a C18-reversed phase column (50 mg/4 g packing material) and purified by LC (Eluent: neutral H₂O/CH₃CN 95:5→0:100→neutral CH₃CN/MeOH 100:0→50:50) to provide the product.

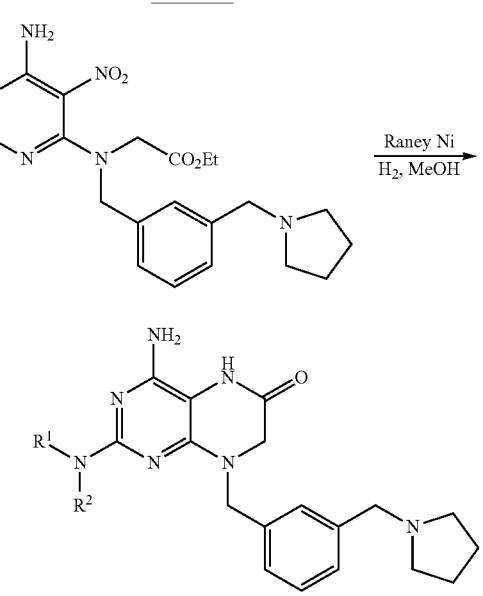

Scheme 17

Method XIV: A solution of the nitro compound (50 mg) in MeOH (4.0 mL) was treated with Raney Nickel (~200 µL, slurry in H₂O). The reaction vessel was flushed with H₂ and then stirred under an H₂ atmosphere for 1.5 h. The mixture was filtered through celite with CH₂Cl₂ and MeOH (1:1). The filtrate was concentrated and dried in vacuo, giving the product as a free base. Occasionally, 1.0 M aq HCl (200 µL) was added to the filtrate prior to concentrating. This gave an HCl salt, which usually had sharper ¹H NMR resonances.

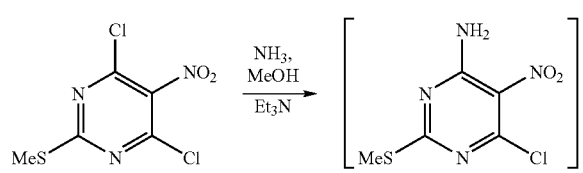

Scheme 18

Method XV, Part 1: 4-Amino-6-chloro-2-methylthio-5-nitropyrimidine: To a solution of 4,6-dichloro-2-(methylthio)-5-nitropyrimidine (327 mg, 1.36 mmol) in THF (5.4 mL) at −10° C. was added Et₃N (474 µL, 3.40 mmol) followed by a solution of NH₃ (2.0 M in MeOH, 750 µL, 1.5 mmol). The mixture was stirred while warming to 0° C. for 1.5 h (LC/MS indicated consumption of starting materials.). The reaction mixture was taken forward without work-up.

Scheme 19

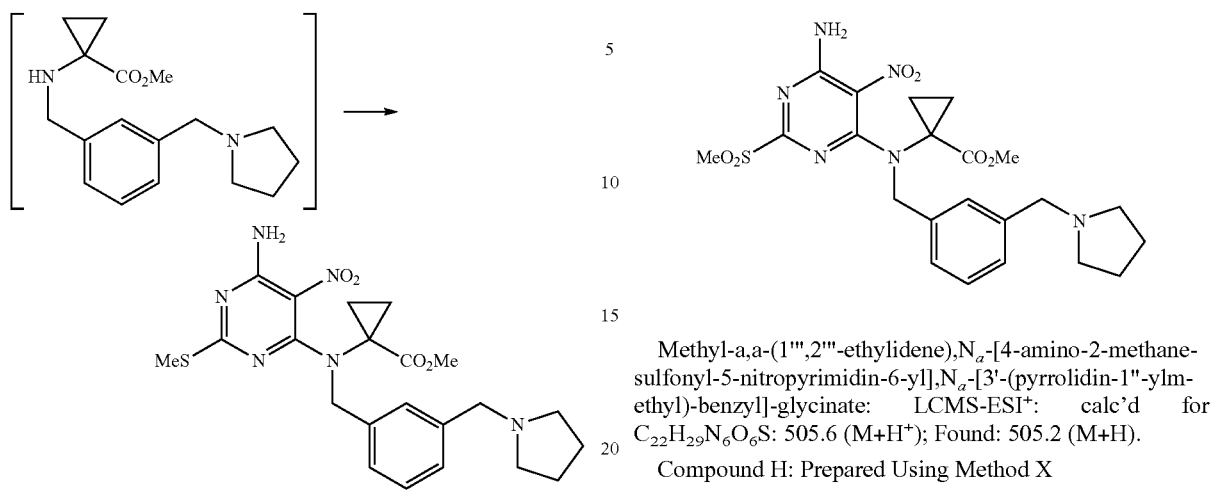

Method XV, Part 2: Methyl-a,a-(1''',2'''-ethylidene),N$_a$-[4-amino-2-methylthio-5-nitropyrimidin-6-yl],N$_a$-[3'-(pyrrolidin-1''-ylmethyl)-benzyl]-glycinate: To the previous reaction mixture at 0° C. was added the crude secondary amine (~1.5 mmol) in THF (1.5 mL). The reaction mixture was stirred at rt for 18 h then 60° C. for 6 h. A saturated solution of NH$_4$Cl (10 mL) was added. The layers were separated, and the aqueous layer was extracted with EtOAc (2×10 mL). The combined organic layers were dried over MgSO$_4$, filtered, and concentrated under vacuum. Purification by silica gel chromatography (~1 g substrate/15 g SiO$_2$) (2-20% MeOH/DCM) provided the product. LCMS-ESI$^+$: calc'd for C$_{22}$H$_{29}$N$_6$O$_4$S: 473.6 (M+H$^+$); Found: 473.1 (M+H).

Scheme 20

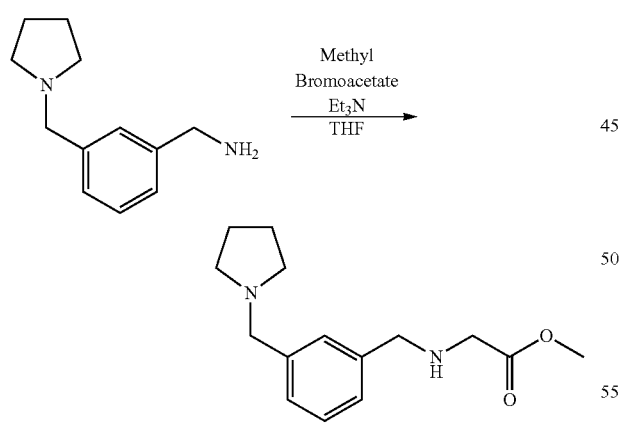

Method XVI: To a solution of 3-((1-pyrrolidinylmethyl)phenyl)methanamine (1.95 g, 10.2 mmol) in THF (34 mL) at 0° C. was added Et$_3$N (3.14 mmol, 22.5 mmol) followed by methyl bromoacetate (1.04 mL, 22.3 mmol) dropwise. The reaction mixture was stirred until LC/MS indicated consumption of starting materials, approximately 2 h. The product mixture was taken forward without work up. LCMS-ESI$^+$: calc'd for C$_{15}$H$_{23}$N$_2$O$_2$: 263.4 (M+H$^+$); Found: 263.1 (M+H).

Compound G: Prepared Using Method VIII

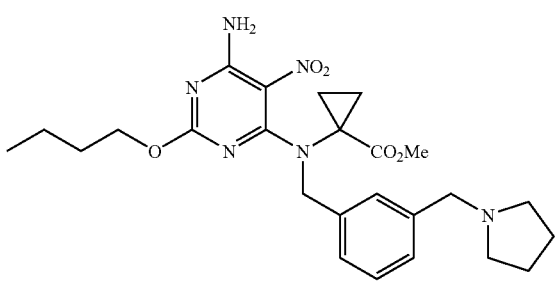 [SMILES: CCCCOc1nc(N)c([N+](=O)[O-])c(N(Cc2cccc(CN3CCCC3)c2)C2(C(=O)OC)CC2)n1]

Methyl-a,a-(1''',2'''-ethylidene),N$_a$-[4-amino-2-methanesulfonyl-5-nitropyrimidin-6-yl],N$_a$-[3'-(pyrrolidin-1''-ylmethyl)-benzyl]-glycinate: LCMS-ESI$^+$: calc'd for C$_{22}$H$_{29}$N$_6$O$_6$S: 505.6 (M+H$^+$); Found: 505.2 (M+H).

Compound H: Prepared Using Method X

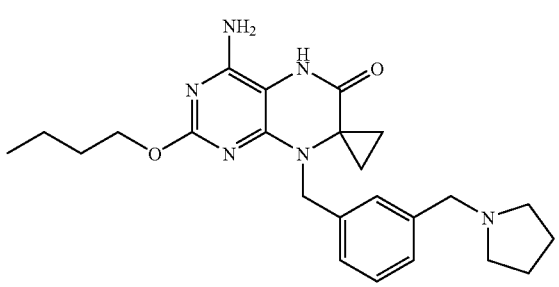 [SMILES: CCCCOc1nc(N)c2c(n1)N(Cc1cccc(CN3CCCC3)c1)C1(CC1)C(=O)N2]

Methyl-a,a-(1''',2'''-ethylidene),N$_a$-[4-amino-2-n-butoxy-5-nitropyrimidin-6-yl],N$_a$-[3'-(pyrrolidin-1''-ylmethyl)-benzyl]-glycinate: LCMS-ESI$^+$: calc'd for C$_{25}$H$_{35}$N$_6$O$_5$: 499.6 (M+H$^+$); Found: 499.2 (M+H).

Example 3

Prepared Using Method XII

4-Amino-2-n-butoxy-7-(1''',2'''-ethylidene)-8-[3'-(pyrrolidin-1''-ylmethyl)-benzyl]-5,6,7,8-tetrahydropteridine-6-one: $^1$H-NMR: 300 MHz, (CD$_3$OD) d: 7.39-7.60 (m, 4H), 4.91 (s, 2H), 4.30-4.41 (m, 4H), 3.47 (m, 2H), 3.18 (m, 2H), 2.18 (m, 2H), 2.03 (m, 2H), 1.65 (m, 2H), 1.42 (m, 2H), 0.79-0.98 (m, 7H)—[HCl salt]. LCMS-ESI$^+$: calc'd for C$_{24}$H$_{33}$N$_6$O$_2$: 437.6 (M+H$^+$); Found: 437.2 (M+H).

Compound I: Prepared Using Method XV, Parts 1 and 2

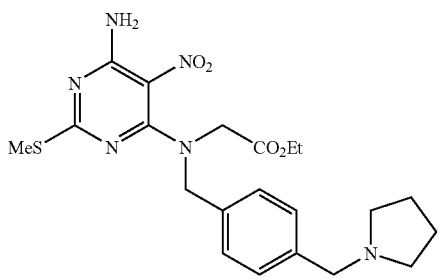 [SMILES: CCOC(=O)CN(Cc1ccc(CN2CCCC2)cc1)c1nc(SC)nc(N)c1[N+](=O)[O-]]

Ethyl-N$_a$-[4-amino-2-methylthio-5-nitropyrimidin-6-yl],N$_a$-[4'-(pyrrolidin-1"-ylmethyl)-benzyl]-glycinate: $^1$H-NMR: 300 MHz, (DMSO-d$_6$) d: 7.22-7.25 (m, 4H), 4.64 (s, 2H), 4.08 (m, 2H), 3.54 (s, 2H), 3.31 (s, 2H), 2.39 (s, 3H), 2.32 (m, 4H), 1.66 (m, 4H), 1.16 (t, J=7 Hz, 3H). LCMS-ESI$^+$: calc'd for C$_{21}$H$_{29}$N$_6$O$_4$S: 461.6 (M+H$^+$); Found: 461.2 (M+H).

Compound J: Prepared Using Method VIII

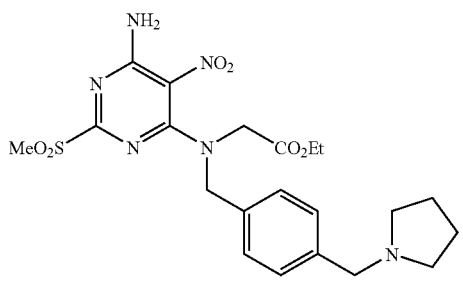 [SMILES: CCOC(=O)CN(Cc1ccc(CN2CCCC2)cc1)c1nc(S(C)(=O)=O)nc(N)c1[N+](=O)[O-]]

Ethyl-N$_a$-[4-amino-2-methanesulfonyl-5-nitropyrimidin-6-yl],N$_a$-[4'-(pyrrolidin-1"-ylmethyl)-benzyl]-glycinate: LCMS-ESI$^+$: calc'd for C$_{21}$H$_{29}$N$_6$O$_6$S 493.6 (M+H$^+$); Found: 493.2 (M+H).

Compound K: Prepared Using Method X:

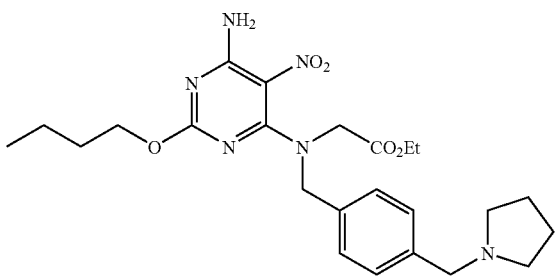 [SMILES: CCCCOc1nc(N)c([N+](=O)[O-])c(N(CC(=O)OCC)Cc2ccc(CN3CCCC3)cc2)n1]

Ethyl-N$_a$-[4-amino-2-n-butoxy-5-nitropyrimidin-6-yl],N$_a$-[4'-(pyrrolidin-1"-ylmethyl)-benzyl]-glycinate: $^1$H-NMR: 300 MHz, (CD$_3$OD) d: 7.32 (m, 4H), 4.75 (s, 2H), 4.13-4.24 (m, 6H), 3.67 (s, 2H), 2.59 (m, 4H), 1.82 (m, 4H), 1.66 (m, 2H), 1.40 (m, 2H), 1.25 (t, J=7 Hz, 3H), 0.92 (m, 3H). LCMS-ESI$^+$: calc'd for C$_{24}$H$_{35}$N$_6$O$_5$: 487.6 (M+H$^+$); Found: 487.3 (M+H).

Example 4

Prepared Using Method XII

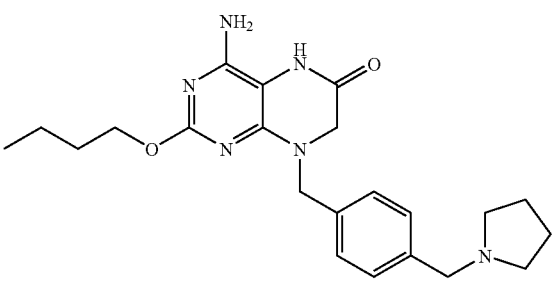 [SMILES: CCCCOc1nc(N)c2c(n1)N(Cc1ccc(CN3CCCC3)cc1)CC(=O)N2]

4-amino-2-n-butoxy-8-[4'-(pyrrolidin-1"-ylmethyl)-benzyl]-5,6,7,8-tetrahydropteridin-6-one: $^1$H-NMR: 300 MHz, (CD$_3$OD) d: 7.47-4.62 (m, 4H), 4.94 (s, 2H), 4.38-4.46 (m, 4H), 4.13 (s, 2H), 3.48 (m, 2H), 3.20 (m, 2H), 2.17 (m, 2H), 2.02 (m, 2H), 1.75 (m, 2H), 1.43 (m, 2H), 0.94 (t, J=7 Hz, 3H). LCMS-ESI$^+$: calc'd for C$_{22}$H$_{31}$N$_6$O$_2$: 411.5 (M+H$^+$); Found: 411.2 (M+H).

Compound L: Prepared Using Method X:

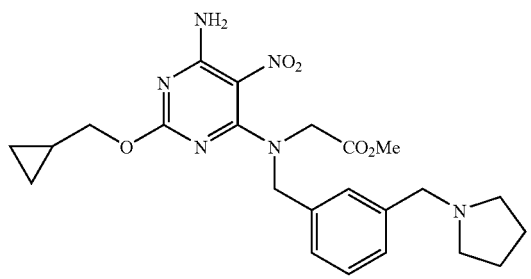 [SMILES: COC(=O)CN(Cc1cccc(CN2CCCC2)c1)c1nc(OCC2CC2)nc(N)c1[N+](=O)[O-]]

Methyl-N$_a$-[4-amino-2-{(cyclopropyl)methoxy}-5-nitropyrimidin-6-yl],N$_a$-[3'-(pyrrolidin-1"-ylmethyl)-benzyl]-glycinate: $^1$H NMR (CD$_3$OD, 300 MHz): δ 7.22-7.32 (m, 4H), 4.76 (s, 2H), 4.16 (s, 2H), 4.02 (d, J=7 Hz, 2H), 3.73 (s, 3H), 3.64 (s, 2H), 2.53 (m, 4H), 1.80 (m, 4H), 1.16 (m, 1H), 0.55 (m, 2H), 0.28 (m, 2H). LCMS-ESI⁺: calc'd for $C_{23}H_{31}N_6O_5$: 471.5 (M+H⁺); Found: 471.2 (M+H⁺).

3H), 0.48 (m, 2H), 0.39 (m, 2H). LCMS-ESI⁺: calc'd for $C_{24}H_{33}N_6O_5$: 485.6 (M+H⁺); Found: 485.2 (M+H⁺).

Example 5

Prepared Using Method XII

Example 6

Prepared Using Method XII

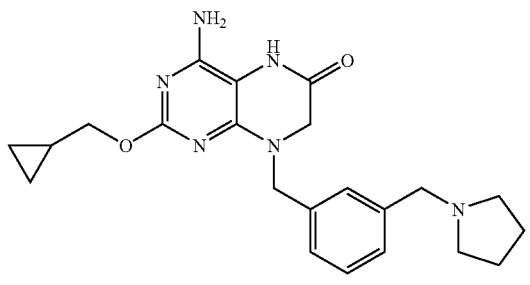 [SMILES: Nc1nc(OCC2CC2)nc2c1NC(=O)CN2Cc1cccc(CN2CCCC2)c1]

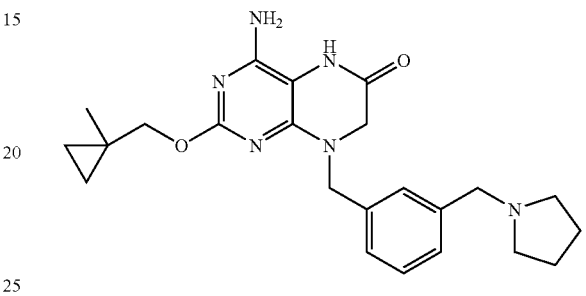

4-amino-2-{(cyclopropyl)methoxy}-8-[3'-(pyrrolidin-1"-ylmethyl)-benzyl]-5,6,7,8-tetrahydropteridin-6-one: ¹H NMR (CD₃OD, 300 MHz): δ 7.64 (s, 1H), 7.50 (m, 3H), 4.95 (s, 2H), 4.39 (s, 2H), 4.26 (d, J=7 Hz, 2H), 4.15 (s, 2H), 3.47 (m, 2H), 3.19 (m, 2H), 2.17 (m, 2H), 2.04 (m, 2H), 1.13 (m, 1H), 0.59 (m, 2H), 0.34 (m, 2H)—[HCl salt]. LCMS-ESI⁺: calc'd for $C_{22}H_{29}N_6O_2$: 409.5 (M+H⁺); Found: 409.2 (M+H⁺).

Compound M: Prepared Using Method X:

4-amino-2-{(1'''-methylcycloprop-1'''-yl)methoxy}-8-[3'-(pyrrolidin-1"-ylmethyl)-benzyl]-5,6,7,8-tetrahydropteridin-6-one: ¹H NMR (CD₃OD, 300 MHz): δ 7.63 (s, 1H), 7.51 (m, 3H), 4.94 (s, 2H), 4.39 (s, 2H), 4.24 (s, 2H), 4.14 (s, 2H), 3.48 (m, 2H), 3.18 (m, 2H), 2.17 (m, 2H), 2.04 (m, 2H), 1.19 (s, 3H), 0.56 (m, 2H), 0.43 (m, 2H)—[HCl salt]. LCMS-ESI⁺: calc'd for $C_{23}H_{30}N_6O_2$: 423.5 (M+H⁺); Found: 423.1 (M+H⁺).

Compound N: Prepared Using Method X:

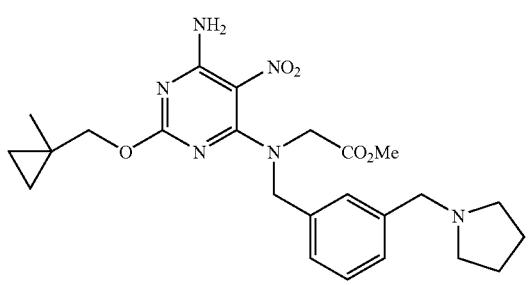 [SMILES: COC(=O)CN(Cc1cccc(CN2CCCC2)c1)c1nc(OCC2(C)CC2)nc(N)c1[N+](=O)[O-]]

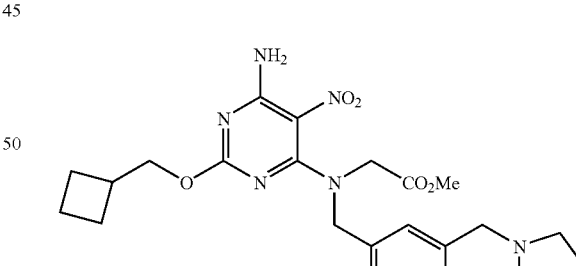

Methyl-N$_a$-[4-amino-2-{(1'''-methylcycloprop-1'''-yl)methoxy}-5-nitropyrimidin-6-yl],N$_a$-[3'-(pyrrolidin-1"-ylmethyl)-benzyl]-glycinate: ¹H NMR (CD₃OD, 300 MHz): δ 7.25-7.33 (m, 4H), 4.75 (s, 2H), 4.16 (s, 2H), 3.99 (s, 2H), 3.73 (s, 3H), 3.67 (s, 2H), 2.57 (m, 4H), 1.81 (m, 4H), 1.16 (s, Methyl-N$_a$-[4-amino-2-{(cyclobutyl)methoxy}-5-nitropyrimidin-6-yl],N$_a$-[3'-(pyrrolidin-1"-ylmethyl)-benzyl]-glycinate: ¹H NMR (CD₃OD, 300 MHz): δ 7.22-7.32 (m, 4H), 4.77 (s, 2H), 4.16 (m, 4H), 3.74 (s, 3H), 3.64 (s, 2H), 2.67

(m, 1H), 2.54 (m, 4H), 2.08 (m, 2H), 1.95 (m, 2H), 1.83 (m, 6H). LCMS-ESI$^+$: calc'd for $C_{24}H_{33}N_6O_5$: 485.6 (M+H$^+$); Found: 485.2 (M+H$^+$).

1.58 (m, 4H), 1.29 (m, 4H). LCMS-ESI$^+$: calc'd for $C_{25}H_{35}N_6O_5$: 499.6 (M+H$^+$); Found: 499.2 (M+H$^+$).

Example 7

Prepared Using Method XII

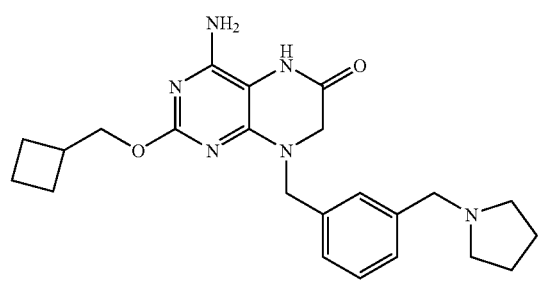 [SMILES: Nc1nc(OCC2CCC2)nc2c1NC(=O)CN2Cc1cccc(CN2CCCC2)c1]

4-amino-2-{(cyclobutyl)methoxy}-8-[3'(pyrrolidin-1"-yl-methyl)-benzyl]-5,6,7,8-tetrahydropteridin-6-one: $^1$H NMR (CD$_3$OD, 300 MHz): δ 7.63 (s, 1H), 7.50 (m, 3H), 4.96 (s, 2H), 4.39 (m, 4H), 4.16 (s, 2H), 3.47 (m, 2H), 3.19 (m, 2H), 1.85-2.17 (m, 11H)—(HCl salt). LCMS-ESI$^+$: calc'd for $C_{23}H_{31}N_6O_2$: 423.5 (M+H$^+$); Found: 423.2 (M+H$^+$).

Compound O: Prepared Using Method X:

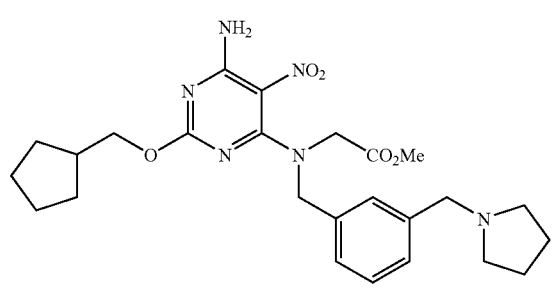 [SMILES: COC(=O)CN(Cc1cccc(CN2CCCC2)c1)c1nc(OCC2CCCC2)nc(N)c1[N+](=O)[O-]]

Methyl-N$_a$-[4-amino-2-{(cyclopentyl)methoxy}-5-nitro-pyrimidin-6-yl],N$_a$-[3'-(pyrrolidin-1"-ylmethyl)-benzyl]-glycinate: $^1$H NMR (CD$_3$OD, 300 MHz): δ 7.21-7.31 (m, 4H), 4.76 (s, 2H), 4.15 (s, 2H), 4.06 (d, J=7 Hz, 2H), 3.73 (s, 3H), 3.61 (s, 2H), 2.51 (m, 4H), 2.26 (m, 1H), 1.79 (m, 4H), Example 8

Prepared Using Method XII

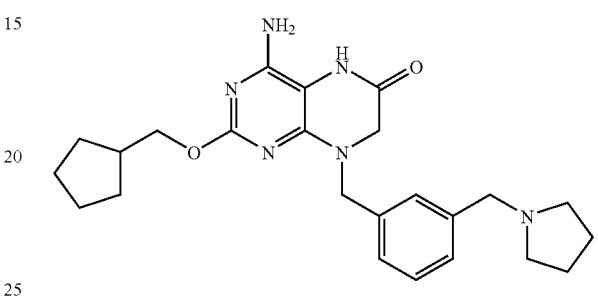

4-amino-2-{(cyclopentyl)methoxy}-8-[3'-(pyrrolidin-1"-ylmethyl)-benzyl]-5,6,7,8-tetrahydropteridin-6-one: $^1$H NMR (CD$_3$OD, 300 MHz): δ 7.65 (s, 1H), 7.50 (m, 3H), 4.95 (s, 2H), 4.39 (s, 2H), 4.31 (d, J=7 Hz, 2H), 4.16 (s, 2H), 3.47 (m, 2H), 3.19 (m, 2H), 2.33 (m, 1H), 2.17 (m, 2H), 2.03 (m, 2H), 1.77 (m, 2H), 1.60 (m, 4H), 1.33 (m, 2H)—[HCl salt]. LCMS-ESI$^+$: calc'd for $C_{24}H_{33}N_6O_2$: 437.6 (M+H$^+$); Found: 437.2 (M+H$^+$).

Compound P: Prepared Using Method X:

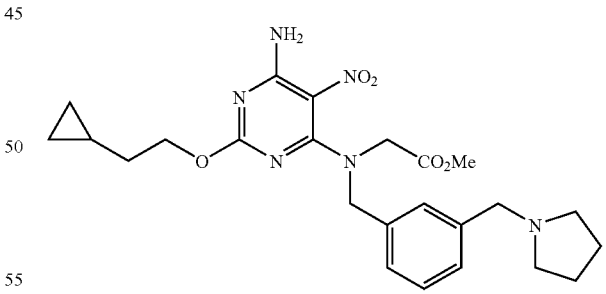

Methyl-N$_a$-[4-amino-2-{2'''-(cyclopropyl)ethoxy}-5-nitropyrimidin-6-yl],N$_a$-[3'-(pyrrolidin-1"-ylmethyl)-benzyl]-glycinate: $^1$H NMR (CD$_3$OD, 300 MHz): δ 7.21-7.31 (m, 4H), 4.76 (s, 2H), 4.26 (t, J=7 Hz, 2H), 4.16 (s, 2H), 3.73 (s, 3H), 3.62 (s, 2H), 2.50 (m, 4H), 1.79 (m, 4H), 1.56 (q, 2H, 7

Hz), 0.76 (m, 1H), 0.44 (m, 2H), 0.08 (m, 2H). LCMS-ESI⁺: calc'd for $C_{24}H_{33}N_6O_5$: 485.6 (M+H⁺); Found: 485.2 (M+H⁺).

Example 9

Prepared Using Method XII

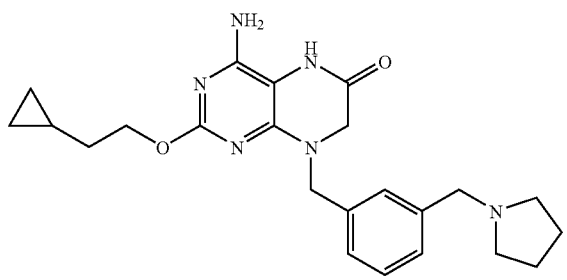 [SMILES: Nc1nc(OCCC2CC2)nc2c1NC(=O)CN2Cc1cccc(CN2CCCC2)c1]

4-amino-2-{2'''-(cyclopropyl)ethoxy}-8-[3'-(pyrrolidin-1''-ylmethyl)-benzyl]-5,6,7,8-tetrahydropteridin-6-one: ¹H NMR (CD₃OD, 300 MHz): δ 7.67 (s, 1H), 7.50 (m, 3H), 4.95 (s, 2H), 4.50 (t, J=7 Hz, 2H), 4.40 (s, 2H), 4.17 (s, 2H), 3.49 (m, 2H), 3.19 (m, 2H), 2.17 (m, 2H), 2.04 (m, 2H), 1.63 (q, J=7 Hz, 2H), 0.80 (m, 1H), 0.44 (m, 2H), 0.05 (m, 2H)—[HCl salt]. LCMS-ESI⁺: calc'd for $C_{23}H_{31}N_6O_2$: 423.5 (M+H⁺); Found: 423.2 (M+H⁺).

Compound Q: Prepared Using Method X:

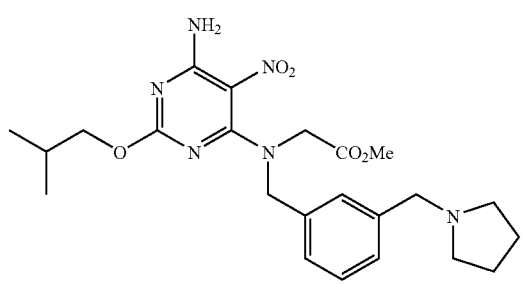 [SMILES: COC(=O)CN(Cc1cccc(CN2CCCC2)c1)c1nc(OCC(C)C)nc(N)c1[N+](=O)[O-]]

¹H NMR (CD₃OD, 300 MHz): δ 7.32-7.39 (m, 4H), 4.77 (s, 2H), 4.19 (s, 2H), 3.96 (d, J=7 Hz, 2H), 3.89 (s, 2H), 3.74 (s, 3H), 2.81 (m, 4H), 2.00 (m, 1H), 1.92 (m, 4H), 0.95 (d, 6H, J=7 Hz). LCMS-ESI⁺: calc'd for $C_{23}H_{33}N_6O_5$: 473.5 (M+H⁺); Found: 473.2 (M+H⁺).

Example 10

Prepared Using Method XII

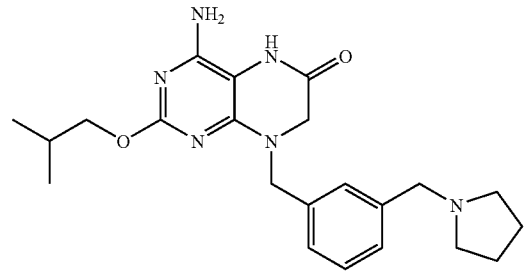 [SMILES: CC(C)COc1nc(N)c2c(n1)N(Cc1cccc(CN3CCCC3)c1)CC(=O)N2]

¹H NMR (CD₃OD, 300 MHz): δ 7.64 (s, 1H), 7.49 (m, 3H), 4.96 (s, 2H), 4.39 (s, 2H), 4.20 (d, J=7 Hz, 2H), 4.15 (s, 2H), 3.47 (m, 2H), 3.19 (m, 2H), 2.16 (m, 2H), 2.04 (m, 3H), 0.97 (d, 6H, J=6 Hz)-[HCl salt]. LCMS-ESI⁺: calc'd for $C_{22}H_{31}N_6O_2$: 411.5 (M+H⁺); Found: 411.2 (M+H⁺).

Compound R: Prepared Using Method X:

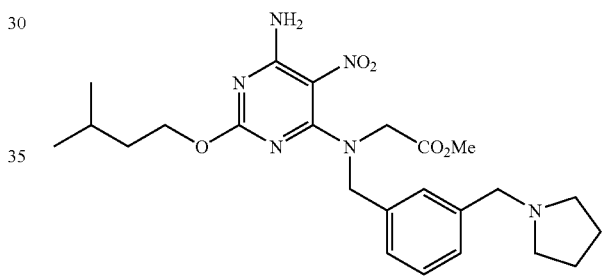

¹H NMR (CD₃OD, 300 MHz): δ 7.22-7.32 (m, 4H), 4.77 (s, 2H), 4.22 (t, J=7 Hz, 2H), 4.16 (s, 2H), 3.73 (s, 3H), 3.64 (s, 2H), 2.54 (m, 4H), 1.80 (m, 4H), 1.75 (m, 1H), 1.56 (q, J=7 Hz, 2H), 0.92 (d, 6H, J=7 Hz). LCMS-ESI⁺: calc'd for $C_{24}H_{35}N_6O_5$: 487.6 (M+H⁺); Found: 487.2 (M+H⁺).

Example 11

Prepared Using Method XII

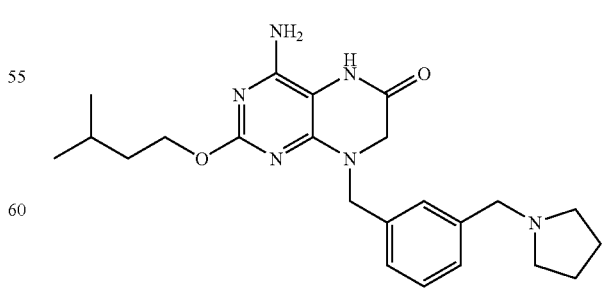

¹H NMR (CD₃OD, 300 MHz): δ 7.67 (s, 1H), 7.49 (m, 3H), 4.95 (s, 2H), 4.46 (t, J=7 Hz, 2H), 4.40 (s, 2H), 4.16 (s, 2H), 3.47 (m, 2H), 3.17 (m, 2H), 2.16 (m, 2H), 2.02 (m, 2H), 1.72

(m, 1H), 1.64 (q, J=7 Hz, 2H), 0.91 (d, 6H, J=7 Hz)-[HCl salt]. LCMS-ESI⁺: calc'd for $C_{23}H_{33}N_6O_2$: 425.5 (M+H⁺); Found: 425.3 (M+H⁺).

Compound S: Prepared Using Method X:

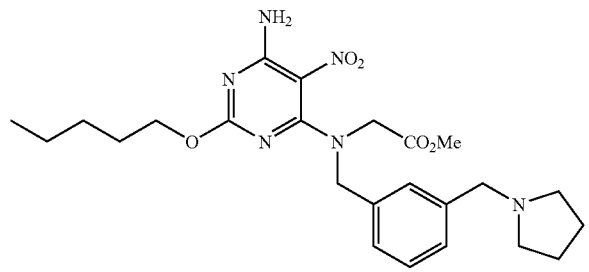 [SMILES: CCCCCOc1nc(N)c([N+](=O)[O-])c(N(CC(=O)OC)Cc2cccc(CN3CCCC3)c2)n1]

¹H NMR (CD₃OD, 300 MHz): δ 7.25-7.33 (m, 4H), 4.77 (s, 2H), 4.16-4.22 (m, 4H), 3.73 (s, 3H), 3.66 (s, 2H), 2.56 (m, 4H), 1.82 (m, 4H), 1.70 (m, 2H), 1.37 (m, 4H), 0.92 (t, J=7 Hz, 3H). LCMS-ESI⁺: calc'd for $C_{24}H_{35}N_6O_5$: 487.6 (M+H⁺); Found: 487.2 (M+H⁺).

Example 12

Prepared Using Method XII

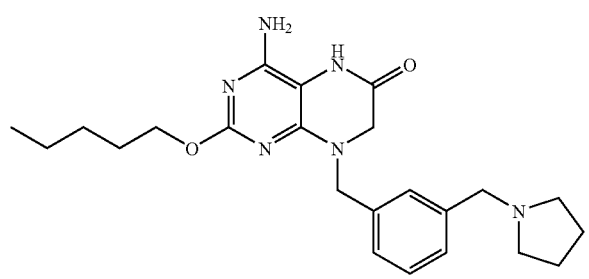 [SMILES: CCCCCOc1nc(N)c2c(n1)N(Cc1cccc(CN3CCCC3)c1)CC(=O)N2]

¹H NMR (CD₃OD, 300 MHz): δ 7.65 (s, 1H), 7.50 (m, 3H), 4.96 (s, 2H), 4.40 (m, 4H), 4.16 (s, 2H), 3.48 (m, 2H), 3.19 (m, 2H), 2.18 (m, 2H), 2.03 (m, 2H), 1.76 (m, 2H), 1.36 (m, 4H), 0.91 (t, J=7 Hz, 3H)—[HCl salt]. LCMS-ESI⁺: calc'd for $C_{23}H_{33}N_6O_2$: 425.5 (M+H⁺); Found: 425.3 (M+H⁺).

Compound T: Prepared Using Method X:

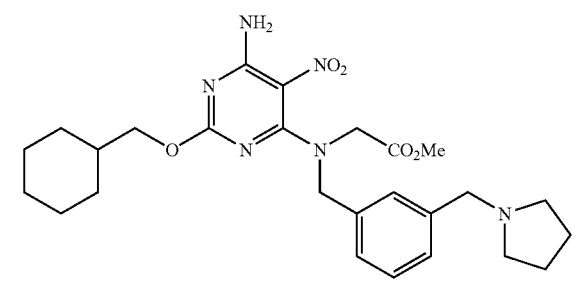 [SMILES: COC(=O)CN(Cc1cccc(CN2CCCC2)c1)c1nc(OCC2CCCCC2)nc(N)c1[N+](=O)[O-]]

¹H NMR (CD₃OD, 300 MHz): δ 7.24-7.32 (m, 4H), 4.77 (s, 2H), 4.16 (s, 2H), 3.99 (d, J=7 Hz, 2H), 3.74 (s, 3H), 3.63 (s, 2H), 2.52 (m, 4H), 1.67-1.82 (m, 9H), 1.25 (m, 4H), 1.00 (m, 2H). LCMS-ESI⁺: calc'd for $C_{26}H_{37}N_6O_5$: 513.6 (M+H⁺); Found: 513.2 (M+H⁻).

Example 13

Prepared Using Method XII

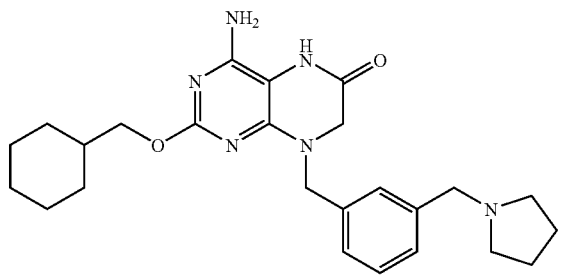 [SMILES: Nc1nc(OCC2CCCCC2)nc2c1NC(=O)CN2Cc1cccc(CN2CCCC2)c1]

¹H NMR (CD₃OD, 300 MHz): δ 7.65 (s, 1H), 7.50 (m, 3H), 4.95 (s, 2H), 4.40 (s, 2H), 4.22 (d, J=7 Hz, 2H), 4.16 (s, 2H), 3.47 (m, 2H), 3.19 (m, 2H), 2.17 (m, 2H), 2.03 (m, 2H), 1.76 (m, 5H), 1.23 (m, 4H), 1.04 (m, 2H)—[HCl salt]. LCMS-ESI⁺: calc'd for $C_{25}H_{35}N_6O_2$: 451.6 (M+H⁺); Found: 451.3 (M+H⁺).

Compound U: Prepared Using Method X:

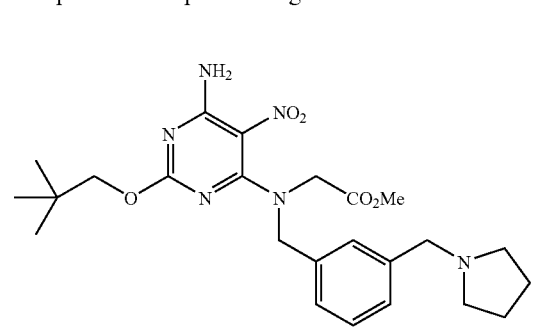

¹H NMR (CD₃OD, 300 MHz): δ 7.27-7.34 (m, 4H), 4.76 (s, 2H), 4.17 (s, 2H), 3.88 (s, 2H), 3.74 (s, 3H), 3.65 (s, 2H), 2.54 (m, 4H), 1.80 (m, 4H), 0.97 (s, 9H). LCMS-ESI⁺: calc'd for C24H34N6O5: 487.6 (M+H⁺); Found: 487.2 (M+H⁺).

Example 14

Prepared Using Method XII

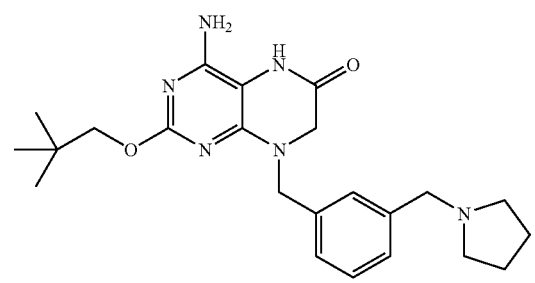 [SMILES: CC(C)(C)COc1nc(N)c2c(n1)N(Cc1cccc(CN3CCCC3)c1)CC(=O)N2]

¹H NMR (CD₃OD, 300 MHz): δ 7.65 (s, 1H), 7.50 (m, 3H), 4.96 (s, 2H), 4.39 (s, 2H), 4.16 (s, 2H), 4.11 (s, 2H), 3.48 (m, 2H), 3.19 (m, 2H), 2.17 (m, 2H), 2.04 (m, 2H), 1.00 (s,

9H)—[HCl salt]. LCMS-ESI$^+$: calc'd for C$_{23}$H$_{33}$N$_6$O$_2$: 425.5 (M+H$^+$); Found: 425.2 (M+H$^+$).

Compound V: Prepared Using Method X:

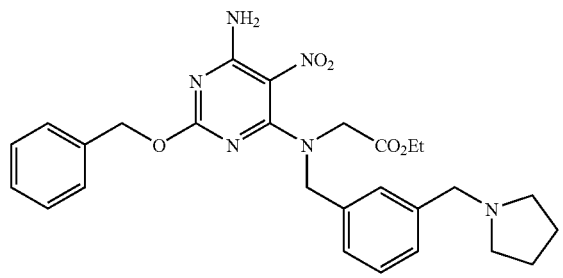 [SMILES: CCOC(=O)CN(Cc1cccc(CN2CCCC2)c1)c1nc(OCc2ccccc2)nc(N)c1[N+](=O)[O-]]

$^1$H NMR (CD$_3$OD, 300 MHz): [all resonances were rather broad] δ 7.33 (9H), 5.26 (2H), 4.78 (2H), 4.17 (4H), 3.94 (2H), 2.86 (4H), 1.90 (4H), 1.23 (3H). LCMS-ESI$^+$: calc'd for C$_{27}$H$_{33}$N$_6$O$_5$: 521.6 (M+H$^+$); Found: 521.2 (M+H$^+$).

Example 15

Prepared Using Method XII

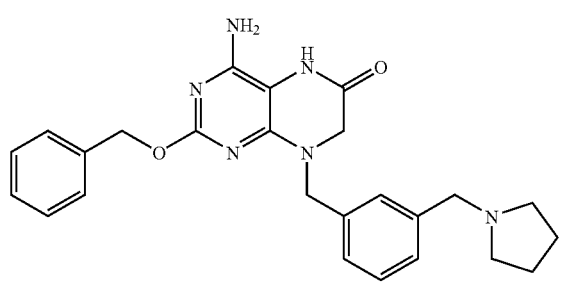 [SMILES: Nc1nc(OCc2ccccc2)nc2c1NC(=O)CN2Cc1cccc(CN2CCCC2)c1]

$^1$H NMR (CD$_3$OD, 300 MHz): δ 7.31-7.59 (m, 9H), 5.46 (s, 2H), 4.97 (s, 2H), 4.35 (s, 2H), 4.14 (s, 2H), 3.44 (m, 2H), 3.13 (m, 2H), 2.14 (m, 2H), 2.00 (m, 2H)—[HCl salt]. LCMS-ESI$^+$: calc'd for C$_{25}$H$_{29}$N$_6$O$_2$: 445.5 (M+H$^+$); Found: 445.2 (M+H$^+$).

Compound W: Prepared Using Method X:

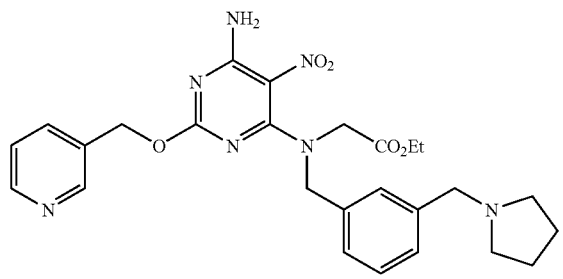 [SMILES: CCOC(=O)CN(Cc1cccc(CN2CCCC2)c1)c1nc(OCc2cccnc2)nc(N)c1[N+](=O)[O-]]

$^1$H NMR (CD$_3$OD, 300 MHz): [all resonances were rather broad] δ 8.54 (2H), 7.87 (1H), 7.43 (1H), 7.27 (4H), 5.33 (2H), 4.77 (2H), 4.15 (4H), 3.64 (2H), 2.54 (4H), 1.79 (4H), 1.23 (3H). LCMS-ESI$^+$: calc'd for C$_{26}$H$_{32}$N$_7$O$_5$: 522.6 (M+H$^+$); Found: 522.2 (M+H$^+$).

Example 16

Prepared Using Method XII

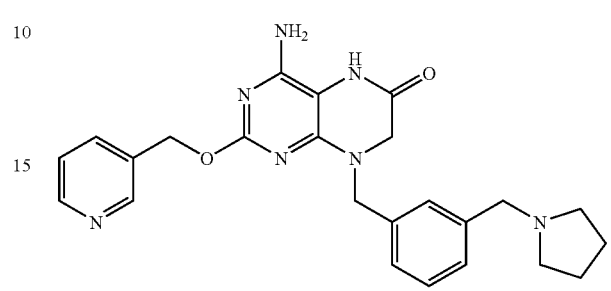

$^1$H NMR (CD$_3$OD, 300 MHz): [all resonances were rather broad] δ 9.04 (1H), 8.78 (2H), 8.06 (1H), 7.62 (1H), 7.48 (3H), 5.77 (2H), 4.91 (2H), 4.38 (2H), 4.12 (2H), 3.45 (2H), 3.16 (2H), 2.14 (2H), 2.01 (2H)—[HCl salt]. LCMS-ESI$^+$: calc'd for C$_{24}$H$_{28}$N$_7$O$_2$: 446.5 (M+H$^+$); Found: 446.2 (M+H$^+$).

Compound X: Prepared Using Method X:

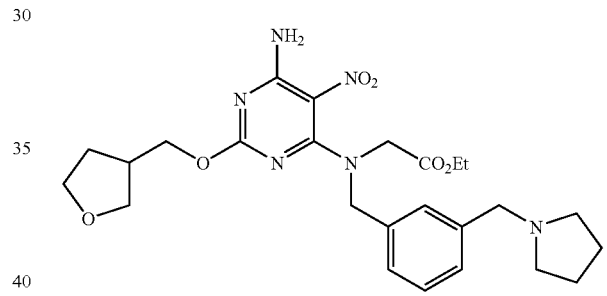

$^1$H NMR (CD$_3$OD, 300 MHz): δ 7.35 (s, 1H), 7.29 (m, 3H), 4.77 (s, 2H), 4.16 (m, 6H), 3.81 (m, 2H), 3.75 (s, 2H), 3.36 (s, 2H), 2.65 (m, 5H), 2.04 (m, 1H), 1.84 (m, 4H), 1.65 (m, 1H), 1.24 (m, 3H). LCMS-ESI$^+$: calc'd for C$_{25}$H$_{35}$N$_6$O$_6$: 515.6 (M+H$^+$); Found: 515.2 (M+H$^+$).

Example 17

Prepared Using Method XII

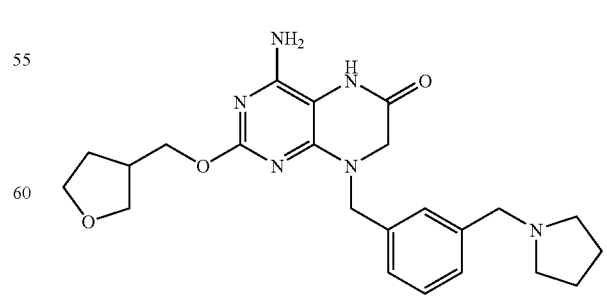

$^1$H NMR (CD$_3$OD, 300 MHz): δ 7.68 (s, 1H), 7.48 (s, 3H), 4.92 (s, 2H), 4.39 (m, 4H), 4.15 (s, 2H), 3.63-3.82 (m, 4H), 3.47 (m, 2H), 3.16 (m, 2H), 2.70 (m, 1H), 2.01-2.14 (m, 5H), 1.68 (m, 1H)—[HCl salt]. LCMS-ESI$^+$: calc'd for C$_{23}$H$_{31}$N$_6$O$_3$: 439.5 (M+H$^+$); Found: 439.3 (M+H$^+$).

Compound Y: Prepared Using Method X:

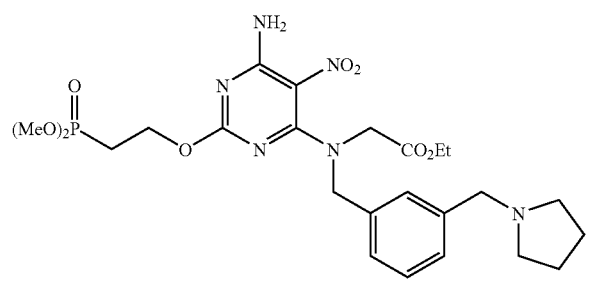

$^1$H NMR (CD$_3$OD, 300 MHz): δ 7.37 (s, 1H), 7.31 (m, 3H), 4.79 (s, 2H), 4.44 (m, 2H), 4.18 (m, 4H), 3.83 (s, 2H), 3.75 (m, 3H), 3.35 (m, 3H), 2.74 (m, 4H), 2.31 (m, 2H), 1.88 (m, 4H), 1.26 (m, 3H). LCMS-ESI$^+$: calc'd for C$_{24}$H$_{36}$N$_6$O$_8$P: 567.5 (M+H$^+$); Found: 567.2 (M+H$^+$).

Example 18

Prepared Using Method XII

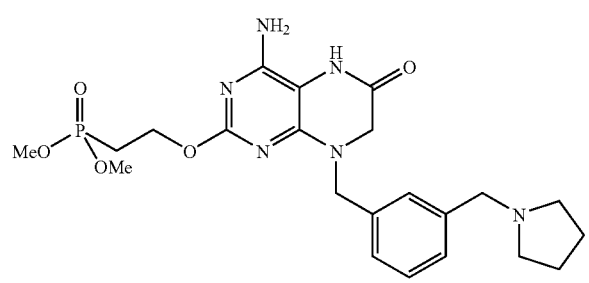 [SMILES: COP(=O)(CCOc1nc(N)c2c(n1)N(Cc1cccc(CN3CCCC3)c1)CC(=O)N2)OC]

$^1$H NMR (CD$_3$OD, 300 MHz): δ 7.69 (s, 1H), 7.49 (s, 3H), 4.96 (s, 2H), 4.66 (m, 2H), 4.40 (s, 2H), 4.17 (s, 2H), 3.71 (d, 6H, J=11 Hz), 3.48 (m, 2H), 3.16 (m, 2H), 2.42 (m, 2H), 2.16 (m, 2H), 2.03 (m, 2H)—[HCl salt]. LCMS-ESI$^+$: calc'd for C$_{22}$H$_{32}$N$_6$O$_5$P: 491.5 (M+H$^+$); Found: 491.2 (M+H$^+$).

Compound Z: Prepared Using Method X:

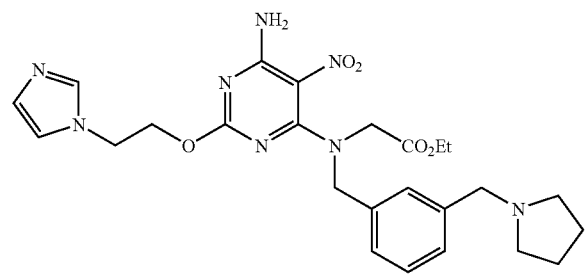 [SMILES: CCOC(=O)CN(Cc1cccc(CN2CCCC2)c1)c1nc(OCCn2ccnc2)nc(N)c1[N+](=O)[O-]]

$^1$H NMR (CD$_3$OD, 300 MHz): δ 7.66 (s, 1H), 7.32 (s, 1H), 7.27 (m, 3H), 7.16 (s, 1H), 6.96 (s, 1H), 4.77 (s, 2H), 4.47 (m, 2H), 4.32 (m, 2H), 4.18 (m, 4H), 3.72 (s, 2H), 2.61 (m, 2H), 1.82 (m, 2H), 1.24 (m, 3H). LCMS-ESI$^+$: calc'd for C$_{25}$H$_{33}$N$_8$O$_5$: 525.6 (M+H$^+$); Found: 525.2 (M+H$^+$).

Example 19

Prepared Using Method XII

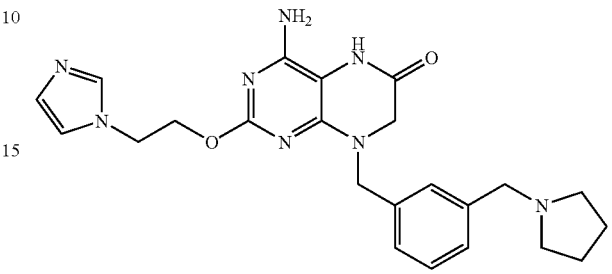

$^1$H NMR (CD$_3$OD, 300 MHz): δ 9.17 (s, broad, 1H), 7.63-7.80 (m, 3H), 7.49 (m, 3H), 4.93 (s, 2H), 4.73 (s, broad, 2H), 4.39 (m, broad, 4H), 4.15 (s, 2H), 3.47 (m, 2H), 3.18 (m, 2H), 2.17 (m, 2H), 2.02 (m, 2H)—[HCl salt]. LCMS-ESI$^+$: calc'd for C$_{23}$H$_{28}$N$_8$O$_2$: 449.5 (M+H$^+$); Found: 449.2 (M+H$^+$).

Compound AA: Prepared Using Method X:

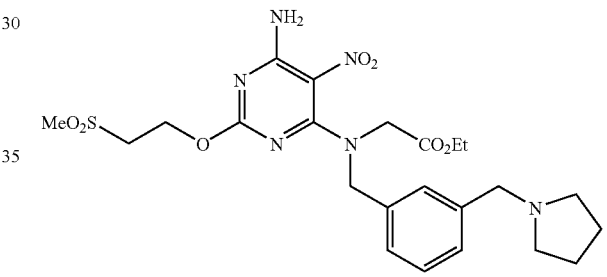

$^1$H NMR (CD$_3$OD, 300 MHz): δ 7.40-7.47 (m, 4H), 4.81 (s, broad, 2H), 4.61 (s, 2H), 4.19 (m, broad, 6H), 3.50 (s, broad, 2H), 3.12 (m, 4H), 3.02 (s, 3H), 2.01 (m, 4H), 1.26 (m, 3H). LCMS-ESI$^+$: calc'd for C$_{23}$H$_{33}$N$_6$O$_7$S: 537.6 (M+H$^+$); Found: 537.2 (M+H$^+$).

Example 20

Prepared Using Method XII

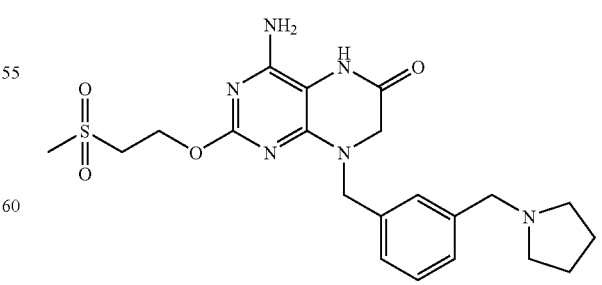

$^1$H NMR (CD$_3$OD, 300 MHz): δ 7.74 (s, 1H), 7.48 (s, 3H), 4.94 (s, 2H), 4.90 (s, 2H), 4.39 (s, 3H), 4.17 (s, 2H), 3.61 (m, broad, 2H), 3.48 (m, 2H), 3.14 (m, 2H), 3.06 (s, 3H), 2.13 (m, 2H), 2.01 (m, 2H)—[HCl salt]. LCMS-ESI⁺: calc'd for C₂₁H₂₉N₆O₄S: 461.6 (M+H⁺); Found: 461.2 (M+H⁺).

Compound AB: Prepared Using Method X:

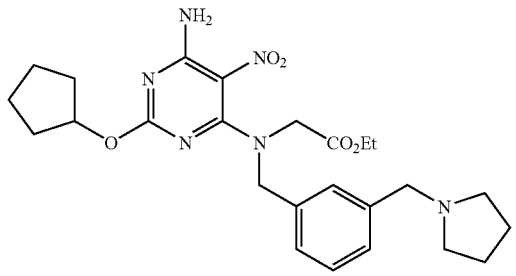 [SMILES: CCOC(=O)CN(Cc1cccc(CN2CCCC2)c1)c1nc(OC2CCCC2)nc(N)c1[N+](=O)[O-]]

¹H NMR (CD₃OD, 300 MHz): δ 7.23-7.34 (m, 4H), 5.20 (m, 1H), 4.77 (s, 2H), 4.19 (q, J=7 Hz, 2H), 4.16 (s, 2H), 3.68 (s, 2H), 2.58 (m, 4H), 1.73-1.87 (m, 10H), 1.60 (m, 2H), 1.26 (t, J=7 Hz, 3H). LCMS-ESI⁺: calc'd for C₂₅H₃₅N₆O₅: 499.6 (M+H⁺); Found: 499.2 (M+H⁺).

Example 21

Prepared Using Method XII

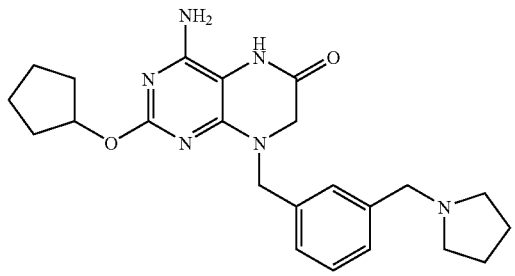 [SMILES: Nc1nc(OC2CCCC2)nc2c1NC(=O)CN2Cc1cccc(CN2CCCC2)c1]

¹H NMR (CD₃OD, 400 MHz): δ 7.60 (s, 1H), 7.47 (m, 3H), 5.40 (m, 1H), 4.93 (s, 2H), 4.32 (s, 2H), 4.03 (s, 2H), 3.45 (m, 2H), 3.16 (m, 2H), 2.15 (m, 2H), 2.00 (m, 3H), 1.86 (m, 4H), 1.62-1.75 (m, 3H)—[HCl salt]. LCMS-ESI⁺: calc'd for C₂₃H₃₁N₆O₂: 423.5 (M+H⁺); Found: 423.2 (M+H⁺).

Compound AC: Prepared Using Method X:

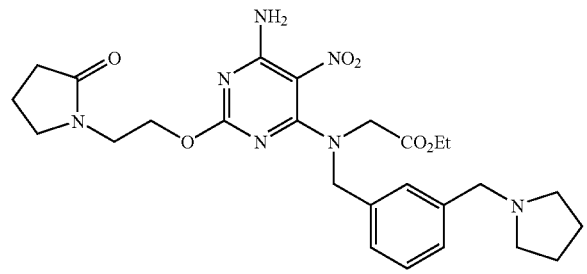 [SMILES: CCOC(=O)CN(Cc1cccc(CN2CCCC2)c1)c1nc(OCCN2CCCC2=O)nc(N)c1[N+](=O)[O-]]

¹H NMR (CD₃OD, 300 MHz): δ 7.40 (s, 2H), 7.33 (m, 3H), 4.79 (s, 2H), 4.36 (t, J=5 Hz, 2H), 4.21 (m, 4H), 3.89 (s, 2H), 3.54 (m, 4H), 2.81 (m, 4H), 2.36 (t, J=8 Hz, 2H), 2.02 (m, 2H), 1.90 (m, 4H), 1.26 (t, J=7 Hz, 3H). LCMS-ESI⁺: calc'd for C₂₆H₃₆N₇O₆: 542.6 (M+H⁻); Found: 542.2 (M+H⁺).

Example 22

Prepared Using Method XII

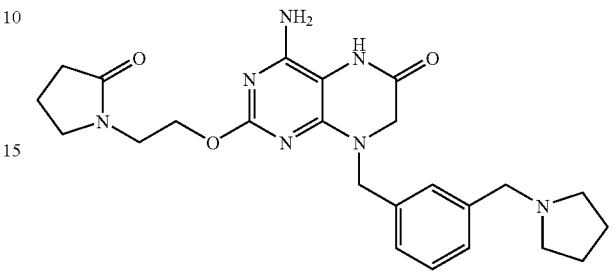

¹H NMR (CD₃OD, 400 MHz): δ 7.64 (s, 1H), 7.47 (s, 3H), 4.94 (s, 2H), 4.55 (m, 2H), 4.36 (s, 2H), 4.14 (s, 2H), 3.61 (m, 2H), 3.54 (t, 2H, J=5 Hz), 3.45 (m, 2H), 3.15 (m, 2H), 2.37 (t, J=6 Hz, 2H) 2.13 (m, 2H), 2.02 (m, 4H)—[HCl salt]. LCMS-ESI⁺: calc'd for C₂₄H₃₁N₇O₃: 466.6 (M+H⁺); Found: 466.1 (M+H⁺).

Compound AD: Prepared Using Method X:

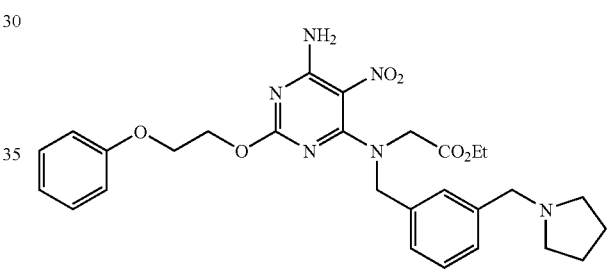

¹H NMR (CD₃OD, 300 MHz): δ 7.47 (s, 1H), 7.37 (m, 3H), 7.27 (t, 2H, J=8 Hz), 6.92 (m, 3H), 4.80 (s, 2H), 4.54 (t, J=5 Hz, 2H), 4.12-4.22 (m, 8H), 3.07 (m, 4H), 1.99 (m, 4H), 1.25 (t, J=7 Hz, 3H). LCMS-ESI⁺: calc'd for C₂₈H₃₅N₆O₆: 551.6 (M+H⁺); Found: 551.2 (M+H⁺).

Example 23

Prepared Using Method XII

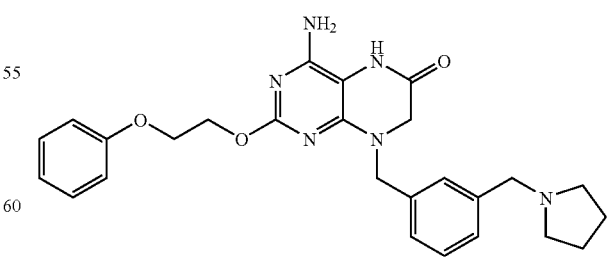

¹H NMR (CD₃OD, 300 MHz): δ 7.63 (s, 1H), 7.46 (s, 3H), 7.24 (t, 2H, J=6 Hz), 6.92 (t, J=6 Hz, 1H), 6.86 (d, J=6 Hz, 2H), 4.91 (s, 2H), 4.76 (s, broad, 2H), 4.33 (s, 2H), 4.26 (m, 2H), 4.14 (s, 2H), 3.43 (m, 2H), 3.12 (m, 2H), 2.11 (m, 2H), 1.98 (m, 2H)—[HCl salt]. LCMS-ESI⁺: calc'd for C$_{26}$H$_{30}$N$_6$O$_3$: 475.6 (M+H⁺); Found: 475.2 (M+H⁺).

Compound AE: Prepared Using Method X:

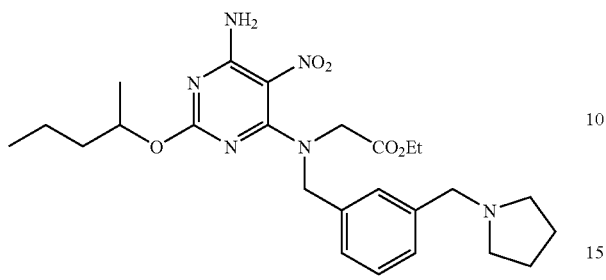

¹H NMR (CD$_3$OD, 300 MHz): δ 7.26-7.37 (m, 4H), 4.99 (m, 1H), 4.78 (s, 2H), 4.20 (m, 4H), 3.77 (s, 2H), 2.68 (m, 4H), 1.85 (m, 4H), 1.50-1.62 (m, 2H), 1.29 (m, 2H), 1.25 (m, 6H), 0.90 (t, J=7 Hz, 3H), LCMS-ESI⁺: calc'd for C$_{25}$H$_{37}$N$_6$O$_5$: 501.6 (M+H⁺); Found: 501.2 (M+H⁺).

Example 24

Prepared Using Method XII

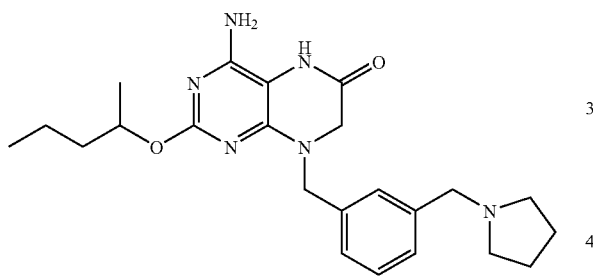

¹H NMR (CD$_3$OD, 300 MHz): δ 7.64 (s, 1H), 7.49 (m, 3H), 5.16 (m, 1H), 4.94 (s, 2H), 4.38 (s, 2H), 4.18 (s, 2H), 3.47 (m, 2H), 3.16 (m, 2H), 2.16 (m, 2H), 2.03 (m, 2H), 1.55-1.72 (m, 2H), 1.32 (m, 5H), 0.87 (t, J=7 Hz, 3H)—[HCl salt]. LCMS-ESI⁺: calc'd for C$_{23}$H$_{33}$N$_6$O$_2$: 425.5 (M+H⁺); Found: 425.2 (M+H⁺).

Compound AF: Prepared Using Method X:

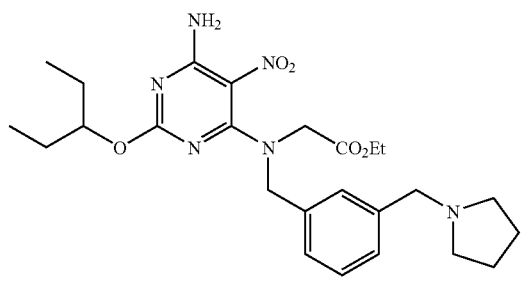 [SMILES: CCOC(=O)CN(Cc1cccc(CN2CCCC2)c1)c1nc(OC(CC)CC)nc(N)c1[N+](=O)[O-]]

¹H NMR (CD$_3$OD, 300 MHz): δ 7.29-7.37 (m, 4H), 4.83 (m, 1H), 4.78 (s, 2H), 4.19 (m, 4H), 3.77 (s, 2H), 2.67 (m, 4H), 1.85 (m, 4H), 1.62 (m, 4H), 1.27 (t, J=7 Hz, 3H), 0.88 (t, 6H, J=7 Hz). LCMS-ESI⁺: calc'd for C$_{25}$H$_{37}$N$_6$O$_5$: 501.6 (M+H⁺); Found: 501.2 (M+H⁺).

Example 25

Prepared Using Method XII

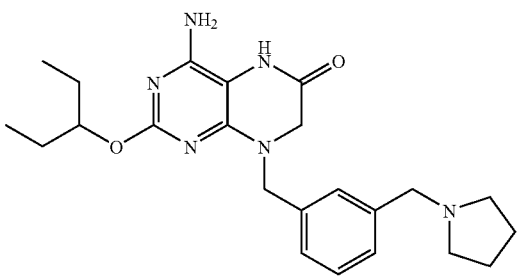 [SMILES: CCC(CC)Oc1nc(N)c2c(n1)N(Cc1cccc(CN3CCCC3)c1)CC(=O)N2]

¹H NMR (CD$_3$OD, 300 MHz): δ 7.60 (s, broad, 1H), 7.49 (m, 3H), 4.94 (s, 2H), 4.39 (s, broad, 2H), 4.20 (s, 2H), 3.48 (m, 2H), 3.17 (m, 2H), 2.17 (m, 2H) 2.04 (m, 2H), 1.70 (m, 4H), 0.89 (m, broad, 6H)—[HCl salt]. LCMS-ESI⁺: calc'd for C$_{23}$H$_{33}$N$_6$O$_2$: 425.5 (M+H⁺); Found: 425.2 (M+H⁺).

Compound AG: Prepared Using Method X (Variation Noted):

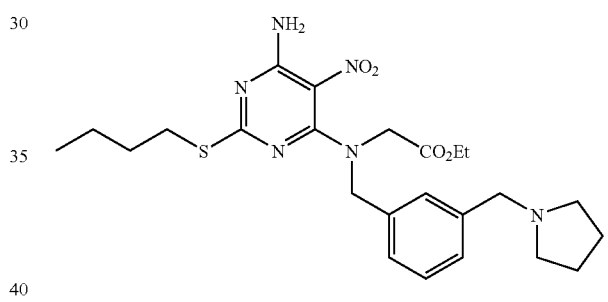

Reaction was performed in CH$_2$Cl$_2$ without TFA at 40° C. in sealed vial. ¹H NMR (CD$_3$OD, 300 MHz): δ 7.20-7.32 (m, 4H), 4.78 (s, 2H), 4.20 (q, J=7 Hz, 2H), 4.15 (s, 2H), 3.64 (s, 2H), 2.96 (t, 2H, J=7 Hz), 2.54 (m, 4H), 1.80 (m, 4H), 1.60 (m, 2H), 1.42 (m, 2H), 1.26 (t, J=7 Hz, 3H), 0.90 (t, J=7 Hz, 3H). LCMS-ESI⁺: calc'd for C$_{24}$H$_{35}$N$_6$O$_4$S: 503.6 (M+H⁺); Found: 503.2 (M+H⁺).

Example 26

Prepared Using Method XII

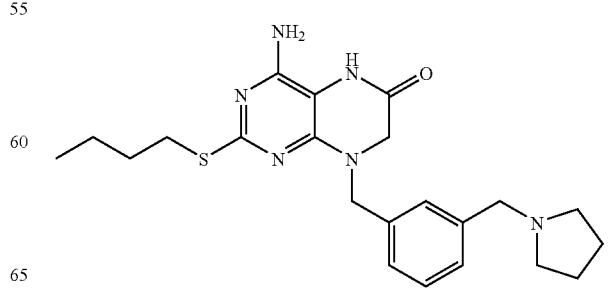

¹H NMR (CD₃OD, 300 MHz): δ 7.61 (s, 1H), 7.49 (m, 3H), 5.01 (s, 2H), 4.39 (s, 2H), 4.19 (s, 2H), 3.47 (m, 2H), 3.11 (m, 4H), 2.16 (m, 2H), 2.03 (m, 2H), 1.61 (m, 2H), 1.30 (m, 2H), 0.78 (t, J=7 Hz, 3H)—[HCl salt]. LCMS-ESI⁺: calc'd for C₂₂H₃₀N₆OS: 427.6 (M+H⁺); Found: 427.2 (M+H⁺).

Compound AH: Prepared Using Method X:

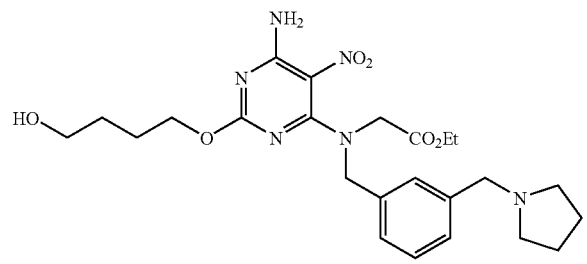 [SMILES: CCOC(=O)CN(Cc1cccc(CN2CCCC2)c1)c1nc(OCCCCO)nc(N)c1[N+](=O)[O-]]

¹H NMR (CD₃OD, 300 MHz): δ 7.29-7.36 (m, 4H), 4.77 (s, 2H), 4.16-4.25 (m, 6H), 3.77 (s, 2H), 3.57 (m, 2H), 2.68 (m, 4H), 1.85 (m, 4H), 1.75 (m, 2H), 1.58 (m, 2H), 1.26 (t, J=7 Hz, 3H). LCMS-ESI⁺: calc'd for C₂₄H₃₅N₆O₆: 503.6 (M+H⁺); Found: 503.2 (M+H⁺).

Example 27

Prepared Using Method XII

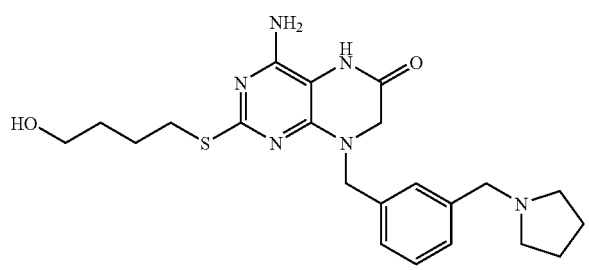 [SMILES: Nc1nc(SCCCCO)nc2c1NC(=O)CN2Cc1cccc(CN2CCCC2)c1]

¹H NMR (CD₃OD, 300 MHz): δ 7.45-7.60 (m, broad, 4H), 4.96 (s, broad, 2H), 4.44 (m, broad, 2H), 4.19 (s, broad, 2H), 3.55 (s, 2H), 3.48 (m, 2H), 3.31 (s, broad, 2H), 3.18 (m, broad, 2H), 2.15 (m, 2H), 2.03 (m, 2H), 1.81 (m, 2H), 1.58 (m, 2H)—[HCl salt]. LCMS-ESI⁺: calc'd for C₂₂H₃₁N₆O₃: 427.5 (M+H⁺); Found: 427.2 (M+H⁺).

Compound AI: Prepared Using Method X:

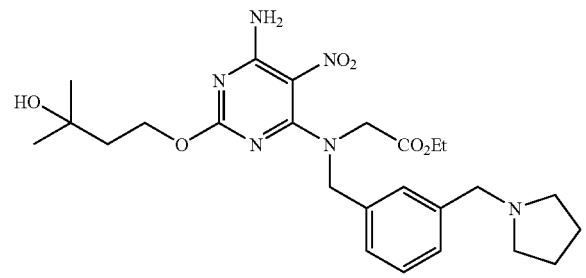 [SMILES: CCOC(=O)CN(Cc1cccc(CN2CCCC2)c1)c1nc(OCCC(C)(C)O)nc(N)c1[N+](=O)[O-]]

¹H NMR (CD₃OD, 300 MHz): δ 7.27-7.34 (m, 4H), 4.78 (s, 2H), 4.35 (t, J=7 Hz, 2H), 4.20 (q, J=7 Hz, 2H), 4.16 (s, 2H), 3.69 (s, 2H), 2.59 (m, 4H), 1.82-1.89 (m, 6H), 1.26 (t, J=7 Hz, 3H), 1.22 (s, 6H). LCMS-ESI⁺: calc'd for C₂₅H₃₇N₆O₆: 517.6 (M+H⁺); Found: 517.2 (M+H⁺).

Example 28

Prepared Using Method XII

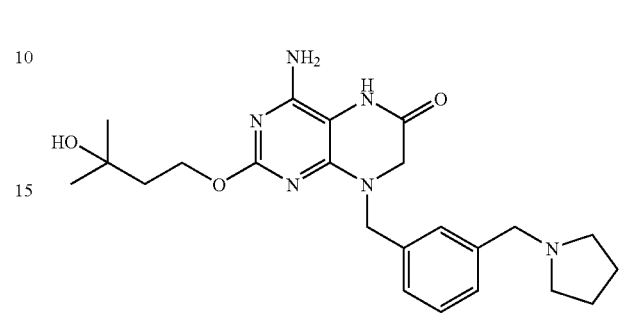

¹H NMR (CD₃OD, 300 MHz): δ 7.47-7.64 (m, broad, 4H), 4.94 (s, broad, 2H), 4.57 (m, broad, 2H), 4.41 (m, 2H), 4.19 (s, broad, 2H), 3.48 (m, 2H), 3.18 (m, 2H), 2.16 (m, 2H), 2.03 (m, 2H), 1.93 (m, 2H), 1.19 (s, 6H)—[HCl salt]. LCMS-ESI⁺: calc'd for C₂₃H₃₃N₅O₃: 441.5 (M+H⁺); Found: 441.2 (M+H⁺).

Compound AJ: Prepared Using Method X:

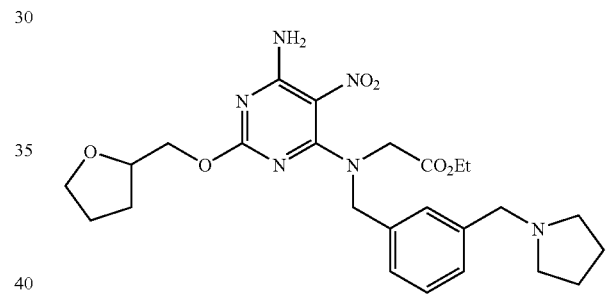

¹H NMR (CD₃OD, 300 MHz): δ 7.26-7.36 (m, 4H), 4.77 (s, 2H), 4.13-4.23 (m, 5H), 3.73-3.95 (m, 4H), 3.51 (m, 2H), 2.68 (m, 4H), 1.81-2.02 (m, 6H), 1.64 (m, 2H), 1.27 (t, J=7 Hz, 3H). LCMS-ESI⁺: calc'd for C₂₅H₃₅N₆O₆: 515.6 (M+H⁺); Found: 515.2 (M+H⁺).

Example 29

Prepared Using Method XII

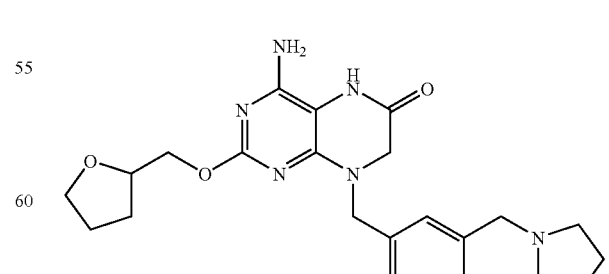

¹H NMR (CD₃OD, 300 MHz): δ 7.66 (s, 1H), 7.49 (m, 3H), 4.96 (s, 2H), 4.37-4.47 (m, 4H), 4.18 (m, 1H), 4.16 (s, 2H), 3.80 (m, 2H), 3.48 (m, 2H), 3.17 (m, 2H), 2.16 (m, 2H), 2.01 (m, 2H), 1.92 (m, 2H), 1.70 (m, 2H)—[HCl salt]. LCMS-ESI$^+$: calc'd for $C_{23}H_{31}N_6O_3$: 439.5 (M+H$^+$); Found: 439.2 (M+H$^+$).

Compound AK: Prepared Using Method X:

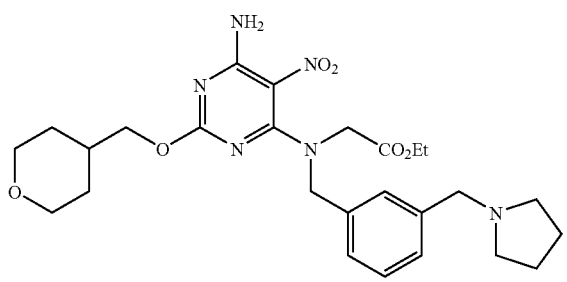 [SMILES: CCOC(=O)CN(Cc1cccc(CN2CCCC2)c1)c1nc(OCC2CCOCC2)nc(N)c1[N+](=O)[O-]]

$^1$H NMR (CD$_3$OD, 300 MHz): δ 7.24-7.34 (m, 4H), 4.77 (s, 2H), 4.19 (q, J=7 Hz, 2H), 4.16 (s, 2H), 4.05 (d, J=7 Hz, 2H), 3.94 (m, 2H), 3.71 (s, 2H), 3.39 (m, 2H), 2.61 (m, 4H), 1.95 (m, 1H), 1.83 (m, 4H), 1.65 (m, 2H), 1.24-1.36 (m, 5H). LCMS-ESI$^+$: calc'd for $C_{26}H_{37}N_6O_6$: 529.6 (M+H$^+$); Found: 529.2 (M+H$^+$).

Example 30

Prepared Using Method XII

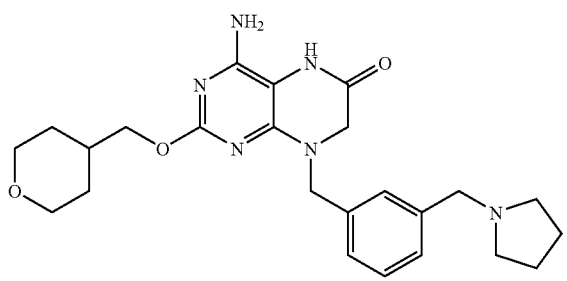 [SMILES: Nc1nc(OCC2CCOCC2)nc2c1NC(=O)CN2Cc1cccc(CN2CCCC2)c1]

$^1$H NMR (CD$_3$OD, 300 MHz): δ 7.67 (s, 1H), 7.49 (m, 3H), 4.96 (s, 2H), 4.40 (s, broad, 2H), 4.29 (d, J=6 Hz, 2H), 4.16 (s, 2H), 3.95 (m, 2H), 3.48 (m, 2H), 3.40 (m, 2H), 3.17 (m, 2H), 2.16 (m, 2H), 1.98-2.07 (m, 3H), 1.65 (m, 2H), 1.34 (m, 2H)—[HCl salt]. LCMS-ESI$^+$: calc'd for $C_{24}H_{33}N_6O_3$: 453.6 (M+H$^+$); Found: 453.2 (M+H$^+$).

Compound AL: Prepared Using Method X:

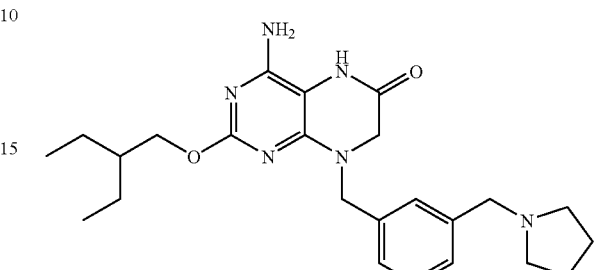

$^1$H NMR (CD$_3$OD, 300 MHz): δ 7.23-7.33 (m, 4H), 4.77 (s, 2H), 4.19 (q, 2H, J=7 Hz), 4.16 (s, 2H), 4.11 (d, J=6 Hz, 2H), 3.66 (s, 2H), 2.56 (m, 4H), 1.80 (m, 4H), 1.58 (m, 1H), 1.41 (m, 4H), 1.28 (t, J=7 Hz, 3H), 0.90 (t, J=7 Hz, 6H). LCMS-ESI$^+$: calc'd for $C_{26}H_{38}N_6O_5$: 515.6 (M+H$^+$); Found: 515.2 (M+H$^+$).

Example 31

Prepared Using Method XII

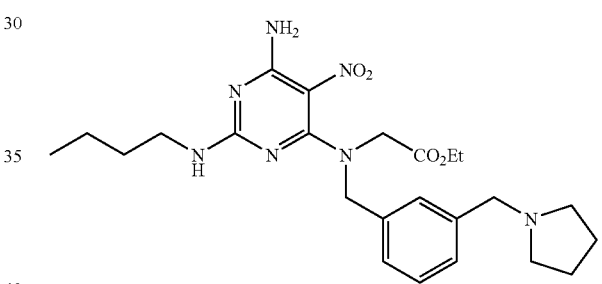

$^1$H NMR (CD$_3$OD, 300 MHz): δ 7.66 (s, 1H), 7.49 (m, 3H), 4.96 (s, 2H), 4.34-4.39 (m, 4H), 4.16 (s, 2H), 3.48 (m, 2H), 3.16 (m, 2H), 2.16 (m, 2H), 2.03 (m, 2H), 1.63 (m, 1H), 1.42 (m, 4H), 0.90 (t, J=7 Hz, 6H)—[HCl salt]. LCMS-ESI$^+$: calc'd for $C_{24}H_{34}O_2$: 439.6 (M+H$^+$); Found: 439.2 (M+H$^+$).

Compound AM: Prepared Using Method XIII:

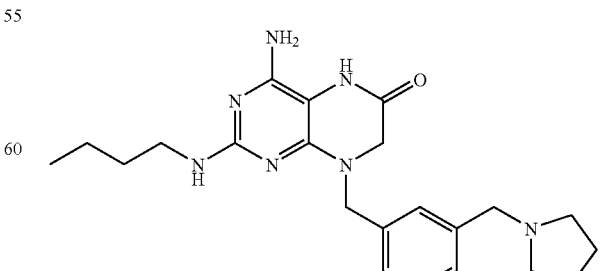

$^1$H NMR (CD$_3$OD, 300 MHz): δ 7.34-7.20 (m, 4H), 4.74 (s, 2H), 4.17 (q, J=7.0 Hz, 2H), 4.05-3.98 (m, broad, 2 lines, 2H), 3.63 (s, 2H), 3.23 (t, J=6.7 Hz, 2H), 2.54 (m, 4H), 1.79 (m, 4H), 1.56-1.34 (m, 4H), 1.24 (t, J=7.0 Hz, 3H), 0.89 (t, J=7.4 Hz, 3H). LCMS-ESI$^+$: calc'd for $C_{24}H_{35}N_7O_4$: 486.3 (M+H$^+$); Found: 486.2 (M+H$^+$), 243.7 ((M+2H$^+$)/2).

Example 32

Prepared Using Method XIV

¹H NMR (CD₃OD, 400 MHz): δ 7.56 (s, 1H), 7.46 (m, 3H), 4.90 (s, 1H), 4.37 (s, 1H), 4.08 (s, 1H), 3.46 (m, 2H), 3.32 (s, 1H) 3.29 (m, 2H), 3.16 (m, 2H), 2.14 (m, 2H), 2.01 (m, 2H), 1.51 (m, 2H), 1.32 (m, 2H), 0.86 (t, J=7 Hz, 3H)—[HCl salt]. LCMS-ESI⁺: calc'd for $C_{22}H_{32}N_7O$: 410.5 (M+H⁻); Found: 410.3 (M+H⁺).

Compound AN: Prepared Using Method XIII:

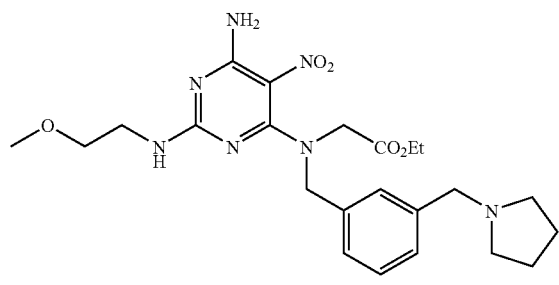 [SMILES: CCOC(=O)CN(Cc1cccc(CN2CCCC2)c1)c1nc(NCCOC)nc(N)c1[N+](=O)[O-]]

¹H NMR (CD₃OD, 300 MHz): δ 7.34-7.19 (m, 4H), 4.73 (s, 2H), 4.17 (q, J=7.0 Hz, 2H), 4.10-3.95 (m, broad, 2 lines, 2H), 3.62 (s, 2H), 3.50 (m, 2H), 3.39 (m, 2H), 3.30 (s, 3H), 2.52 (m, 4H), 1.79 (m, 4H), 1.24 (t, J=7.0 Hz, 3H). LCMS-ESI⁺: calc'd for $C_{23}H_{33}N_7O_5$: 488.3 (M+H⁺); Found: 488.0 (M+H⁺), 244.6 ((M+2H⁺)/2).

Example 33

Prepared Using Method XIV

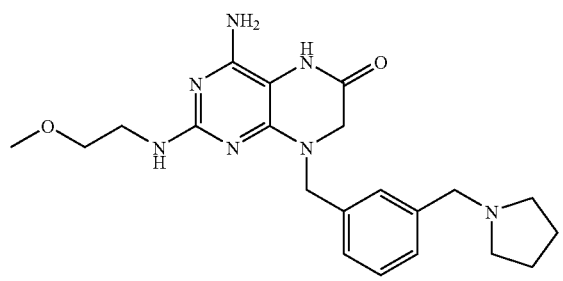 [SMILES: COCCNc1nc(N)c2c(n1)N(Cc1cccc(CN3CCCC3)c1)CC(=O)N2]

¹H NMR (CD₃OD, 400 MHz): δ 7.57 (s, 1H), 7.46 (m, 3H), 4.90 (s, 1H), 4.37 (s, 1H), 4.08 (s, 1H), 3.48 (m, 4H), 3.32 (s, 1H), 3.30 (s, 3H), 3.16 (m, 2H), 2.14 (m, 2H), 2.00 (m, 2H)—[HCl salt]. LCMS-ESI⁺: calc'd for $C_{21}H_{30}N_7O_2$: 412.5 (M+H⁺); Found: 412.2 (M+H⁺).

Compound AO: Prepared Using Method XIII:

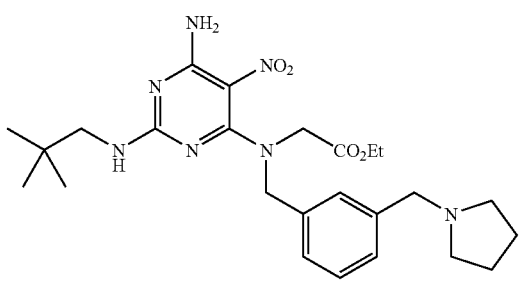 [SMILES: CCOC(=O)CN(Cc1cccc(CN2CCCC2)c1)c1nc(NCC(C)(C)C)nc(N)c1[N+](=O)[O-]]

¹H NMR (CD₃OD, 300 MHz): δ 7.34-7.19 (m, 4H), 4.73 (s, 2H), 4.17 (q, J=7.0 Hz, 2H), 4.15-3.96 (m, broad, 2 lines, 2H), 3.63 (s, 2H), 3.41-3.16 (m, broad, 2 lines, 2H), 2.53 (m, 4H), 1.79 (m, 4H), 1.25 (t, J=7.0 Hz, 3H), 0.96-0.62 (m, 2 lines, broad, 9H). LCMS-ESI⁺: calc'd for $C_{25}H_{38}N_7O_4$: 500.3 (M+H⁺); Found: 500.1 (M+H⁺), 250.7 ((M+2H⁺)/2).

Example 34

Prepared Using Method XIV

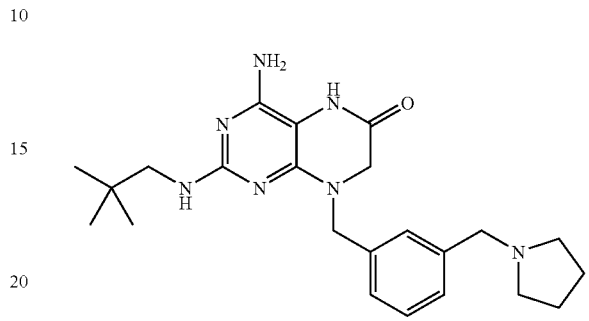

¹H NMR (CD₃OD, 400 MHz): δ 7.56 (s, 1H), 7.46 (m, 3H), 4.90 (s, 1H), 4.36 (s, 1H), 4.08 (s, 1H), 3.43 (m, 2H), 3.32 (s, 1H), 3.17 (m, 2H), 3.16 (s, 2H), 2.16 (m, 2H), 2.01 (m, 2H), 0.87 (s, 9H)—[HCl salt]. LCMS-ESI⁺: calc'd for $C_{23}H_{34}N_7O$: 424.6 (M+H⁺); Found: 424.3 (M+H⁺).

Compound AP: Prepared Using Method XIII:

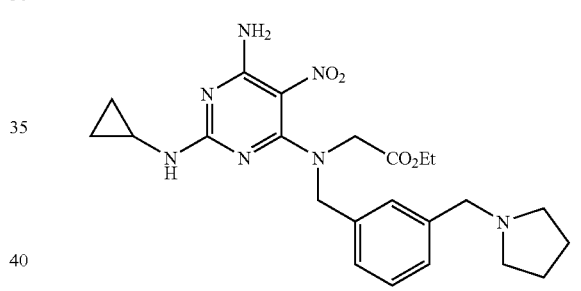

¹H NMR (CD₃OD, 300 MHz): δ 7.36-7.20 (m, 4H), 4.75 (s, 2H), 4.17 (q, J=7.0 Hz, 2H), 4.07 (app. s, broad, 2H), 3.62 (s, 2H), 2.67 (m, 1H), 2.53 (m, 4H), 1.79 (m, 4H), 1.23 (t, J=7.0 Hz, 3H), 0.67 (m, 2H), 0.48 (m, 2H). LCMS-ESI⁺: calc'd for $C_{23}H_{32}N_7O_4$: 470.3 (M+H⁺); Found: 470.0 (M+H⁺), 235.6 ((M+2H⁺)/2).

Example 35

Prepared Using Method XIV

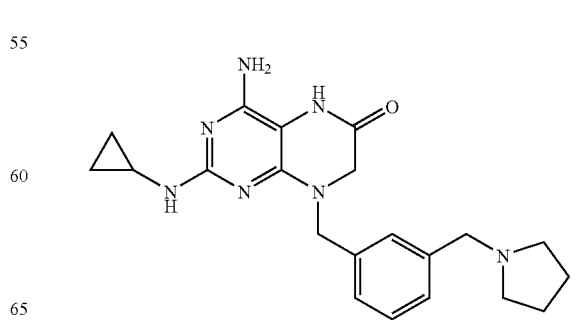

¹H NMR (CD₃OD, 400 MHz): δ 7.60 (s, 1H), 7.46 (s, 3H), 4.89 (s, 1H), 4.37 (s, 1H), 4.06 (s, 1H), 3.46 (m, 2H), 3.29 (s, 1H), 3.16 (m, 2H), 2.63 (m, 1H), 2.14 (m, 2H), 2.01 (m, 2H), 0.87 (m, 2H), 0.64 (m, 2H)—[HCl salt]. LCMS-ESI⁺: calc'd for $C_{21}H_{28}N_7O$: 394.5 (M+H⁺); Found: 394.2 (M+H⁺).

Compound AQ: Prepared Using Method XIII:

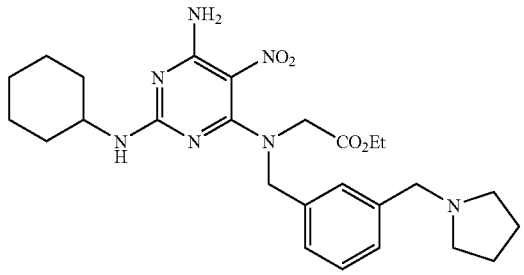 [SMILES: CCOC(=O)CN(Cc1cccc(CN2CCCC2)c1)c1nc(NC2CCCCC2)nc(N)c1[N+](=O)[O-]]

¹H NMR (CD₃OD, 300 MHz): δ 7.34-7.20 (m, 4H), 4.73 (s, 2H), 4.17 (q, J=7.0 Hz, 2H), 4.18-3.95 (m, broad, 2 lines, 2H), 3.61 (s, 2H), 2.51 (m, 5H), 1.83-1.53 (m, 6H), 1.79 (m, 4H), 1.39-1.09 (m, 7H). LCMS-ESI⁺: calc'd for $C_{26}H_{38}N_7O_4$: 512.3 (M+H⁺); Found: 512.1 (M+H⁺), 256.7 ((M+2H⁺)/2).

Compound AR: Prepared Using Method XIII:

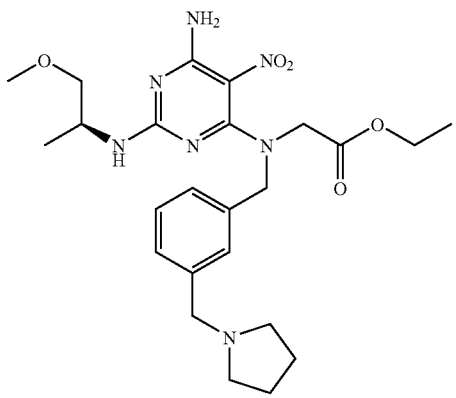

¹H NMR (CD₃OD, 300 MHz): δ 7.38-7.21 (m, 4H), 4.73 (s, 2H), 4.17 (q, J=7.0 Hz, 2H), 4.14-3.96 (m, broad, 2 lines, 2H), 3.65 (s, 2H), 3.40-3.25 (m, 3H), 3.29 (s, 3H), 2.55 (m, 4H), 1.80 (m, 4H), 1.24 (t, J=7.0 Hz, 3H), 1.09 (d, J=6.4 Hz, 3H). LCMS-ESI⁺: calc'd for $C_{24}H_{36}N_7O_5$: 502.3 (M+H⁺); Found: 502.1 (M+H⁺), 251.6 ((M+2H⁺)/2).

Example 36

Prepared Using Method XIV

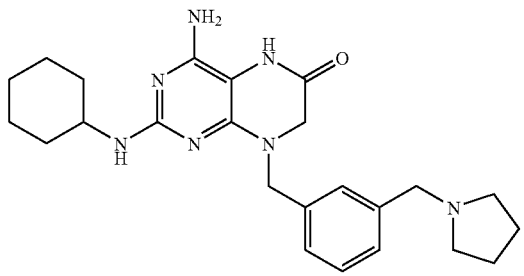 [SMILES: Nc1nc(NC2CCCCC2)nc2c1NC(=O)CN2Cc1cccc(CN2CCCC2)c1]

¹H NMR (CD₃OD, 400 MHz): δ 7.55 (s, 1H), 7.45 (m, 3H), 4.87 (s, 1H), 4.36 (s, 1H), 4.10 (s, 1H), 3.64 (m, 1H), 3.44 (m, 2H), 3.32 (s, 1H), 3.15 (m, 2H), 2.13 (m, 2H), 1.99 (m, 2H), 1.86 (m, 2H), 1.67 (m, 2H), 1.25 (m, 6H)—[HCl salt]. LCMS-ESI⁺: calc'd for $C_{24}H_{34}N_7O$: 436.6 (M+H⁺); Found: 436.3 (M+H⁺).

Example 37

Prepared Using Method XIV

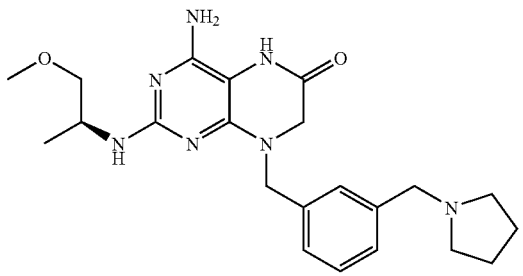 [SMILES: COC[C@H](C)Nc1nc(N)c2c(n1)N(Cc1cccc(CN3CCCC3)c1)CC(=O)N2]

¹H NMR (CD₃OD, 300 MHz): δ 7.55-7.40 (m, 4H), 4.91 (s, 1H), 4.37 (s, 1H), 4.08 (s, 1H), 3.47 (m, 2H), 3.42-3.29 (m 1H), 3.37 (d, J=4.9 Hz, 2H), 3.32 (s, 1H), 3.31 (s, 3H), 3.16 (m, 2H), 2.15 (m 2H), 2.01 (m, 2H), 1.16 (d, J=6.8 Hz, 3H)—[HCl salt]. LCMS-ESI⁺: calc'd for $C_{22}H_{32}N_7O_2$: 426.3 (M+H⁺); Found: 426.2 (M+H⁺), 213.6 ((M+2H⁺)/2).

Compound AS: Prepared Using Method XIII:

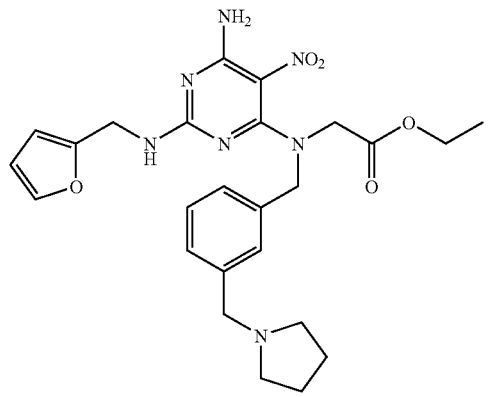 [SMILES: CCOC(=O)CN(Cc1cccc(CN2CCCC2)c1)c1nc(NCc2ccco2)nc(N)c1[N+](=O)[O-]]

¹H NMR (CD₃OD, 400 MHz): δ 7.60-7.36 (m, 4H), 6.49 (d, J=2.2 Hz, 1H), 6.44 (d, J=2.8 Hz, 1H), 6.40-6.26 (m, 1H), 4.80-4.73 (m, broad, 2 lines, 2H), 4.60-4.35 (m, 2H), 4.17 (q, J=7.0 Hz, 2H), 4.16 (s, 2H), 4.16-4.08 (m, 2H), 3.06 (m, 4H), 1.98 (m, 4H), 1.25 (t, J=7.0 Hz, 3H). LCMS-ESI⁺: calc'd for $C_{25}H_{32}N_7O_5$: 510.2 (M+H⁺); Found: 510.1 (M+H⁺) 255.6 ((M+2H⁺)/2).

Compound AT: Prepared Using Method XIII:

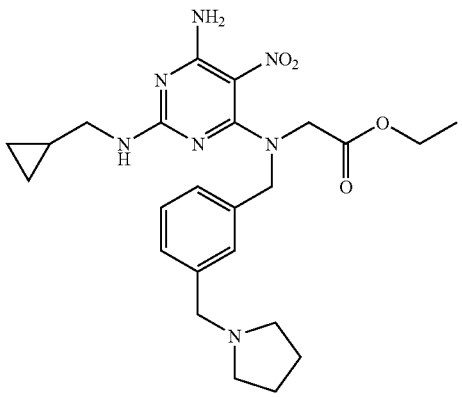

¹H NMR (CD₃OD, 400 MHz): δ 7.36-7.19 (m, 4H0, 4.71 (s, 2H), 4.17 (q, J=7.0 Hz, 2H), 4.06-3.85 (m, broad, 2 lines, 2H), 3.61 (s, 2H), 3.20-3.00 (m, 2H), 2.51 (m, 4H), 1.79 (m, 4H), 0.90 (m, 1H), 0.40 (m, 2H), 0.13 (m, 2H). LCMS-ESI⁺: calc'd for $C_{24}H_{34}N_7O_4$: 484.3 (M+H⁺); Found: 484.1 (M+H⁺), 242.7 ((M+2H⁺)/2).

Example 38

Prepared Using Method XIV

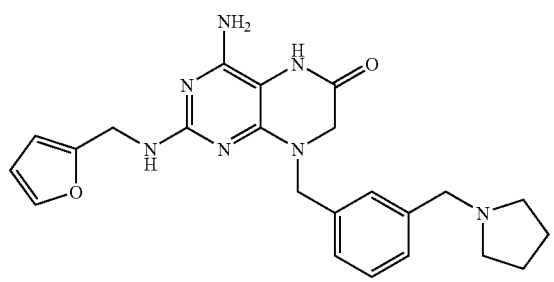 [SMILES: Nc1nc(NCc2ccco2)nc2c1NC(=O)CN2Cc1cccc(CN2CCCC2)c1]

¹H NMR (CD₃OD, 300 MHz): δ 7.60-7.40 (m, 4H), 6.40 (m, 1H), 6.26 (app. d, J=2.2 Hz, 1H), 6.15 (app. d, J=2.8 Hz, 1H), 4.91 (s, 1H), 4.49 (s, 1H), 4.36 (s, 1H), 4.34 (s, 1H), 4.07 (s, 1H), 3.56 (m, 2H), 3.32 (s, 1H), 3.15 (m, 2H), 2.14 (m, 2H), 1.98 (m, 2H)—[HCl salt]. LCMS-ESI⁺: cared for $C_{23}H_{28}N_7O_2$: 434.2 (M+H⁺); Found: 434.2 (M+H⁺), 217.5 ((M+2H⁺)/2).

Example 39

Prepared Using Method XIV

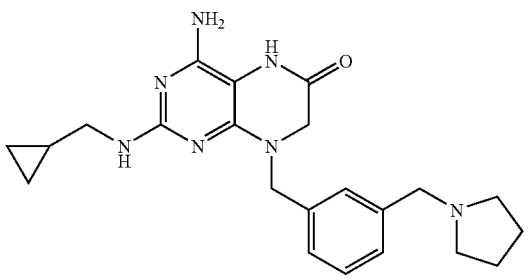 [SMILES: Nc1nc(NCC2CC2)nc2c1NC(=O)CN2Cc1cccc(CN2CCCC2)c1]

¹H NMR (CD₃OD, 300 MHz): δ 7.54-7.44 (m, 4H), 4.91 (s, 1H), 4.37 (s, 1H), 4.08 (s, 1H), 3.45 (m, 2H), 3.33 (s, 1H), 3.18 (d, J=7.0 Hz, 2H), 3.16 (m, 2H), 2.15 (m, 2H), 1.99 (m, 2H), 1.06-0.97 (m, 1H), 0.48 (app. d, J=7.6 Hz, 2H), 0.19 (app. d, J=5.5 Hz, 2H)—[HCl salt]. LCMS-ESI⁺: calc'd for $C_{22}H_{30}N_7O$: 408.3 (M+H⁺); Found: 408.2 (M+H⁺), 204.7 ((M+2H⁺)/2).

121

Compound AU: Prepared Using Method XIII:

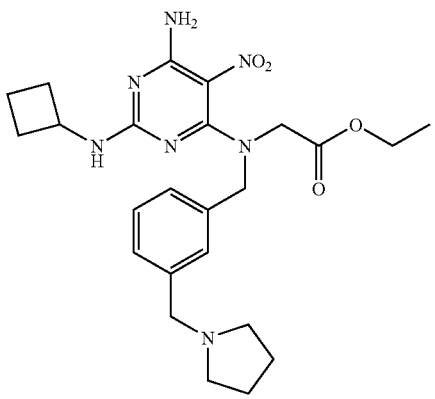 [SMILES: CCOC(=O)CN(Cc1cccc(CN2CCCC2)c1)c1nc(NC2CCC2)nc(N)c1[N+](=O)[O-]]

$^1$H NMR (CD$_3$OD, 400 MHz): δ 7.34-7.19 (m, 4H), 4.71 (s, 2H), 4.17 (q, J=7.0 Hz, 2H), 4.15-3.99 (m, broad, 2 lines, 2H), 3.62 (s, 2H), 3.50 (quintet, J=6.4 Hz, 1H), 2.53 (m, 4H), 1.79 (m, 4H), 1.64 (m, 2H), 1.57 (m, 2H), 1.40 (m, 2H), 1.23 (t, J=7.0 Hz, 3H). LCMS-ESI$^+$: calc'd for C$_{24}$H$_{34}$N$_7$O$_4$: 484.3 (M+H$^+$); Found: 484.2 (M+H$^+$), 242.7 ((M+2H$^+$)/2).

122

Compound AV: Prepared Using Method XIII:

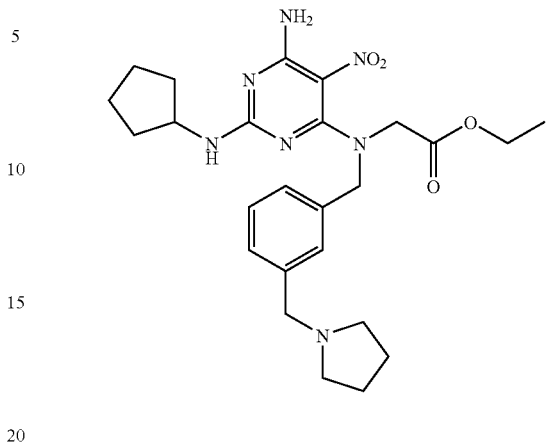

$^1$H NMR (CD$_3$OD, 400 MHz): δ 7.34-7.19 (m, 4H), 4.71 (s, 2H), 4.20 (quintet, J=5.6 Hz, 1H), 4.17 (q, J=7.0 Hz, 2H), 4.15-3.96 (m, broad, 2 lines, 2H), 3.75-3.62 (m, broad, 2 lines, 2H), 2.53 (m, 4H), 1.98-1.58 (m, 4H), 1.79 (m, 4H), 1.24 (m, 4H), 1.23 (t, J=7.0 Hz, 3H). LCMS-ESI$^+$: calc'd for C$_{25}$H$_{36}$N$_7$O$_4$: 498.3 (M+H$^+$); Found: 498.2 (M+H$^+$), 249.8 ((M+2H$^+$)/2).

Example 40

Prepared Using Method XIV

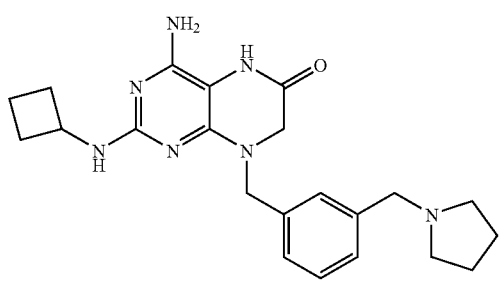 [SMILES: Nc1nc(NC2CCC2)nc2c1NC(=O)CN2Cc1cccc(CN2CCCC2)c1]

$^1$H NMR (CD$_3$OD, 300 MHz): δ 7.50-7.40 (m, 4H), 4.80 (s, 1H), 4.34 (s, 1H), 4.22 (quintet, J=8.4 Hz, 1H), 4.04 (s, 1H), 3.44 (m, 2H), 3.30 (s, 1H), 3.14 (m, 2H), 2.24 (m, 2H), 2.13 (m, 2H), 2.03-1.88 (m, 4H), 1.68 (quintet, J=8.9 Hz, 2H)—[HCl salt]. LCMS-ESI$^+$: calc'd for C$_{22}$H$_{30}$N$_7$O: 408.3 (M+H$^+$); Found: 408.2 (M+H$^+$), 204.7 ((M+2H$^+$)/2).

Example 41

Prepared Using Method XIV

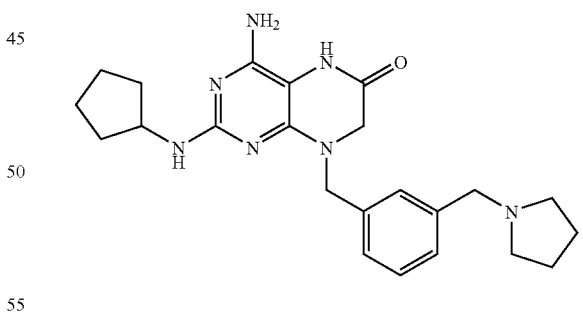

$^1$H NMR (CD$_3$OD, 300 MHz): δ 7.51-7.40 (m, 4H), 4.92 (s, 1H), 4.37 (s, 1H), 4.08 (s, 1H), 3.48 (m, 2H), 3.30 (m, 1H), 3.19 (m, 2H), 2.17 (m, 2H), 2.08-1.86 (m, 4H), 1.79-1.63 (m, 2H), 1.63-1.45 (m, 4H)—[HCl salt]. LCMS-ESI$^+$: calc'd for C$_{23}$H$_{32}$N$_7$O: 422.2 (M+H$^+$); Found: 422.2 (M+H$^+$), 211.7 ((M+2H$^+$)/2).

Compound AW: Prepared Using Method XIII:

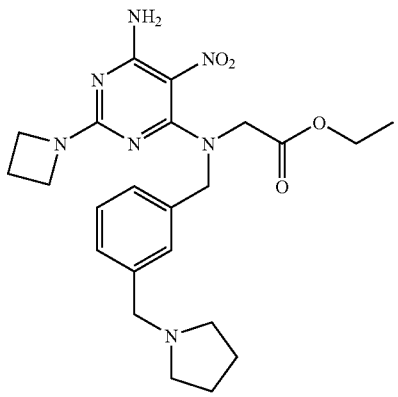 [SMILES: CCOC(=O)CN(Cc1cccc(CN2CCCC2)c1)c1nc(N2CCC2)nc(N)c1[N+](=O)[O-]]

$^1$H NMR (CD$_3$OD, 300 MHz): δ 7.40-7.20 (m, 4H), 4.76-4.71 (m, broad, 2 lines, 2H), 4.20-3.96 (m, 4H), 4.18 (q, J=7.0 Hz, 2H), 4.01 (s, 2H), 3.73-3.65 (m, broad, 2 lines, 2H), 2.57 (m, 4H), 2.30 (quintet, J=7.3 Hz, 2H), 1.81 (m, 4H), 1.25 (t, J=7.0 Hz, 3H). LCMS-ESI$^+$: calc'd for C$_{23}$H$_{31}$N$_7$O$_4$: 470.3 (M+H$^+$); Found: 470.1 (M+H$^+$), 235.6 ((M+2H$^+$)/2).

Compound AX: Prepared Using Method XIII:

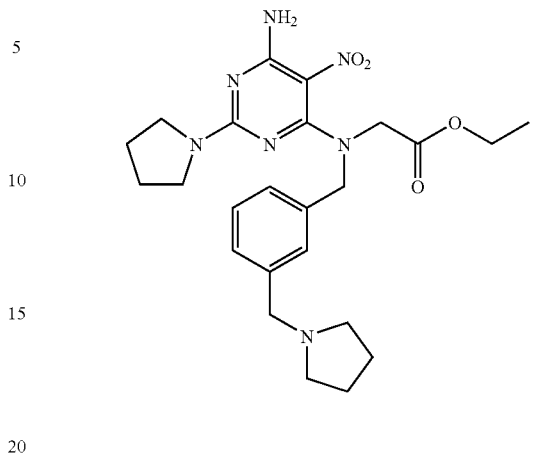

$^1$H NMR (CD$_3$OD, 300 MHz): δ 7.36-7.19 (m, 4H), 4.72 (s, 2H), 4.17 (q, J=7.0 Hz, 2H), 4.03 (s, 2H), 3.62 (s, 2H), 3.55-3.48 (m, 2H), 3.48-3.40 (m, 2H), 2.52 (m, 4H), 1.91 (m, 4H), 1.79 (m, 4H), 1.24 (t, J=7.0 Hz, 3H). LCMS-ESI$^+$: calc'd for C$_{24}$H$_{34}$N$_7$O$_4$: 484.3 (M+H$^+$); Found: 484.1 (M+H$^+$), 242.7 ((M+2H$^+$)/2).

Example 42

Prepared Using Method XIV

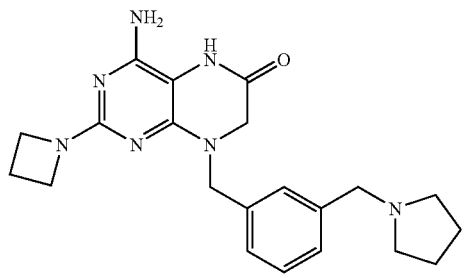 [SMILES: Nc1nc(N2CCC2)nc2c1NC(=O)CN2Cc1cccc(CN2CCCC2)c1]

$^1$H NMR (CD$_3$OD, 300 MHz): δ 7.50-7.40 (m, 4H), 4.94 (s, 0.5H), 4.37 (s, 1H), 4.21 (app. t, J=7.3 Hz, 2H), 4.09 (s, 0.5H), 4.05 (s, 1H), 3.60-3.48 (m, 3H), 3.32 (s, 1H), 3.20 (m, 2H), 2.45 (m, 1H), 2.17 (m, 2H), 1.98 (m, 2H)—[HCl salt]. LCMS-ESI$^+$: calc'd for C$_{21}$H$_{28}$N$_7$O: 394.2 (M+H$^+$); Found: 394.2 (M+H$^+$), 197.7 ((M+2H$^+$)/2).

Example 43

Prepared Using Method XIV

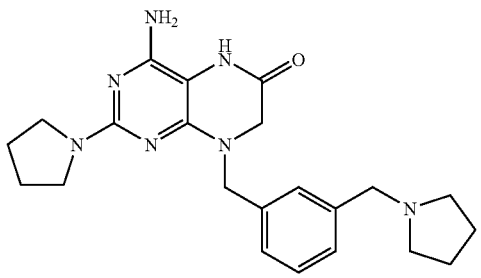 [SMILES: Nc1nc(N2CCCC2)nc2c1NC(=O)CN2Cc1cccc(CN2CCCC2)c1]

$^1$H NMR (CD$_3$OD, 300 MHz): δ 7.58-7.43 (m, 4H), 4.99 (s, 0.5H), 4.89 (s, 0.5H), 4.35 (s, 1H), 4.05 (s, 1H), 3.62-3.45 (m, 4H), 3.44 (m, 2H), 3.14 (m, 2H), 3.31 (s, 1H), 3.14 (m, 2H), 2.17 (m, 2H), 2.15-1.80 (m, 6H)—[HCl salt]. LCMS-ESI$^+$: calc'd for C$_{22}$H$_{30}$N$_7$O: 408.3 (M+H$^+$); Found: 408.2 (M+H$^+$), 204.7 ((M+2H$^+$)/2).

125

Compound AY: Prepared Using Method XIII:

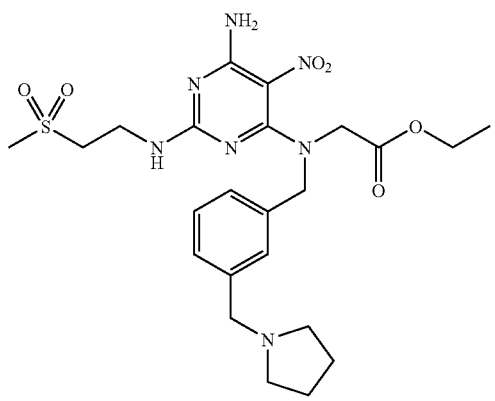 [SMILES: CCOC(=O)CN(Cc1cccc(CN2CCCC2)c1)c1nc(NCCS(C)(=O)=O)nc(N)c1[N+](=O)[O-]]

¹H NMR (CD₃OD, 300 MHz): δ 7.36-7.19 (m, 4H), 4.80-4.70 (m, broad, 2 lines, 2H), 4.17 (q, J=7.0 Hz, 2H), 4.14-3.95 (m, broad, 2 lines, 2H), 3.80-3.60 (m, 2H), 3.62 (s, broad, 2H), 3.44-3.16 (m, 2H), 3.02-2.86 (m, broad, 2 lines, 3H), 2.53 (m, 4H), 1.79 (m, 4H), 1.23 (t, J=7.0 Hz, 3H). LCMS-ESI⁺: calc'd for $C_{23}H_{34}N_7O_6S$: 536.2 (M+H⁺); Found: 536.1 (M+H⁺), 268.5 ((M+2H⁺)/2).

126

Compound AZ: Prepared Using Method XIII:

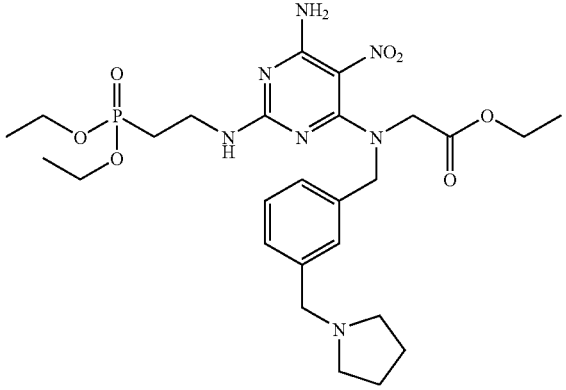

¹H NMR (CD₃OD, 300 MHz): δ 7.36-7.19 (m, 4H), 4.80-4.68 (m, broad, 2 lines, 2H), 4.17 (q, J=7.0 Hz, 2H), 4.07 (s, 2H), 4.05 (q, J=7.0 Hz, 4H), 3.62 (s, 2H), 3.52 (m, 2H), 2.52 (m, 4H), 2.20-1.93 (m, 2H), 1.79 (m, 4H), 1.26 (t, J=7.0 Hz, 6H), 1.23 (t, J=7.0 Hz, 3H). LCMS-ESI⁺: calc'd for $C_{26}H_{41}N_7O_7P$: 594.3 (M+H⁺); Found: 594.2 (M+H⁺), 297.6 ((M+2H⁺)/2).

Example 44

Prepared Using Method XIV

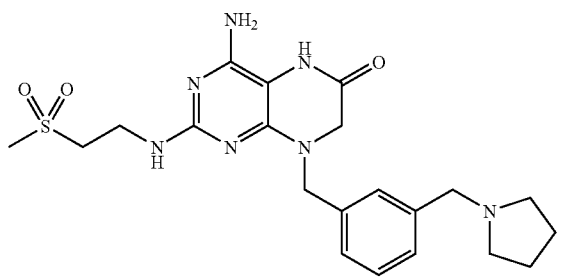 [SMILES: CS(=O)(=O)CCNc1nc(N)c2c(n1)N(Cc1cccc(CN3CCCC3)c1)CC(=O)N2]

¹H NMR (CD₃OD, 300 MHz): δ 7.60-7.40 (m, 4H), 4.92 (s, 1H), 4.36 (s, 1H), 4.12 (s, 1H), 3.81 (t, J=7.3 Hz, 2H), 3.46 (m, 2H), 3.40-3.26 (m, 2H), 3.32 (s, 1H), 3.15 (m, 2H), 2.90 (s, 3H), 2.13 (m, 2H), 1.99 (m, 2H)—[HCl salt]. LCMS-ESI⁺: calc'd for $C_{21}H_{30}N_7O_3S$: 460.2 (M+H⁺); Found: 460.2 (M+H⁺), 230.7 ((M+2H⁺)/2).

Example 45

Prepared Using Method XIV

¹H NMR (CD₃OD, 300 MHz): δ 7.60-7.40 (m, 4H), 5.03 (s, 0.5H), 4.93 (s, 0.5H), 4.36 (s, 1H), 4.08 (s, 1H), 4.07-3.92 (m, 4H), 3.62-3.50 (m, 2H), 3.45 (m, 2H), 3.32 (s, 1H), 3.16 (m, 2H), 2.30-1.90 (m, 6H), 1.34-1.19 (m, 6H)—[HCl salt]. LCMS-ESI⁺: calc'd for $C_{24}H_{37}N_7O_4P$: 518.3 (M+H⁺); Found: 518.2 (M+H⁺), 259.7 ((M+2H⁺)/2).

Compound BA: Prepared Using Method XIII:

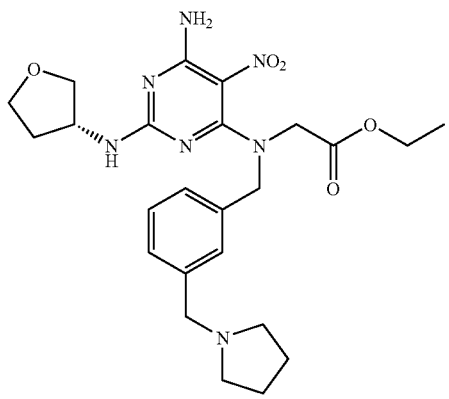 [SMILES: CCOC(=O)CN(Cc1cccc(CN2CCCC2)c1)c1nc(N[C@@H]2CCOC2)nc(N)c1[N+](=O)[O-]]

$^1$H NMR (CD$_3$OD, 300 MHz): δ 7.38-7.21 (m, 4H), 4.74 (s, 2H), 4.33 (m, 1H), 4.17 (q, J=7.0 Hz, 2H), 4.08-3.96 (m, broad, 2 lines, 2H), 3.93-3.80 (m, 2H), 3.80-3.70 (m, 2H), 3.62 (s, 2H), 3.54-3.48 (m, 1H), 2.53 (m, 4H), 2.22-2.06 (m, 1H), 1.79 (m, 4H), 1.24 (t, J=7.0 Hz, 3H). LCMS-ESI$^+$: calc'd for C$_{24}$H$_{34}$N$_7$O$_5$: 500.3 (M+H$^+$); Found: 500.1 (M+H$^+$), 250.7 ((M+2H$^+$)/2).

Example 46

Prepared Using Method XIV

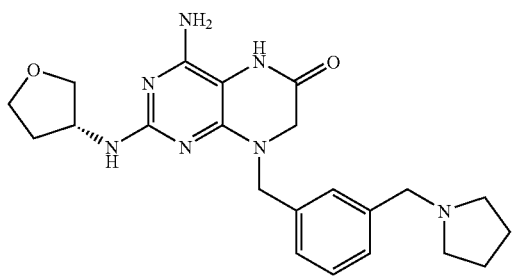 [SMILES: Nc1nc(N[C@@H]2CCOC2)nc2c1NC(=O)CN2Cc1cccc(CN2CCCC2)c1]

$^1$H NMR (CD$_3$OD, 300 MHz): δ 7.60-7.40 (m, 4H), 4.95 (s, 0.5H), 4.37 (s, 1.5H), 4.10 (s, 1.0H), 3.91 (app. q, J=7.3 Hz, 1H), 3.81-3.73 (m 2H), 3.65 (app. dd, J=7.3 Hz, 2.2 Hz, 1H), 3.46 (m, 2H), 3.33 (s, 1H), 3.20-3.08 (m, 3H), 2.25-1.85 (m, 6H)—[HCl salt]. LCMS-ESI$^+$: calc'd for C$_{22}$H$_{30}$N$_7$O$_2$: 424.2 (M+H$^+$); Found: 424.2 (M+H$^+$), 212.7 ((M+2H$^+$)/2).

Scheme 21

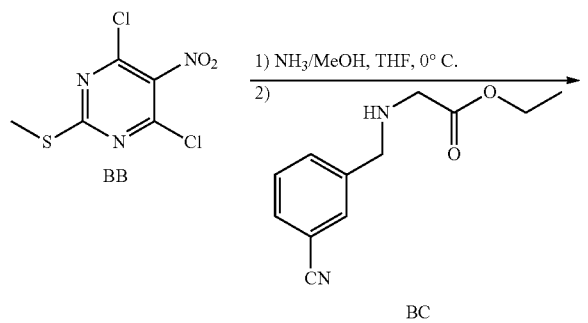

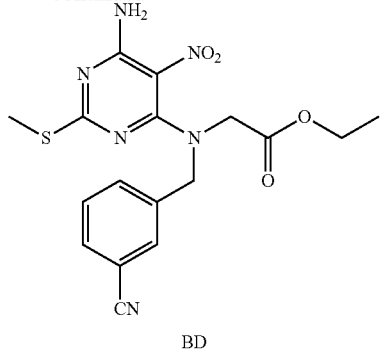

Method XVII: Dissolved BB (2.4 g, 10 mmol) in anhydrous THF (40 mL) and stirred under N$_2$(g) in an ice bath. Added 7N NH$_3$ in MeOH solution (1.6 mL, 11 mmol) dropwise over 5-10 minutes. Reaction was stirred for 60 minutes. Dissolved BC (2.2 g, 10 mmol) in anhydrous THF (4 mL) and added to the reaction in portions over 5-10 minutes. Added DIPEA (1.7 mL, 10 mmol) in portions over 5-10 minutes. Reaction mixture was then stirred for 16 hours at room temperature. Diluted reaction with EtOAc and washed with saturated NaHCO$_3$(aq) solution (2×) followed with saturated NaCl(aq). Dried organic extract over anhydrous Na$_2$SO$_4$ and concentrated under reduced pressure. Re-dissolved resultant in small amount of EtOAc and added hexanes to give solid, which was collected and dried under high vacuum to give BD (3.7 g, 9.2 mmol). $^1$H NMR: 300 MHz, (DMSO-d$_6$) d: 8.05 (s, broad, 2H), 7.78-7.52 (m, 4H), 4.73 (s, 2H), 4.17-4.08 (m, 4H), 2.28 (s, 3H), 1.17 (t, J=6.9 Hz, 3H). LCMS-ESI$^+$: calc'd for C$_{17}$H$_{18}$N$_6$O$_4$S: 403.1 (M+H$^+$); Found: 403.0 (M+H$^+$).

Scheme 22

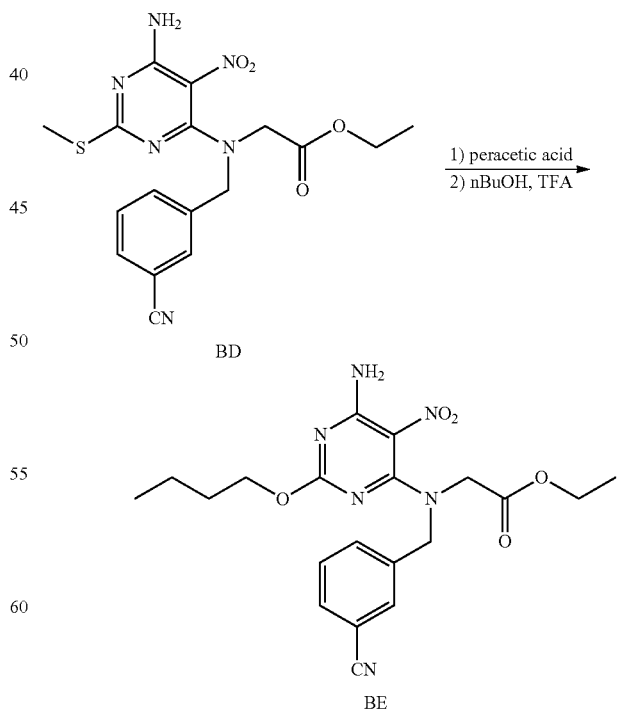

Method XVIII: Dissolved BD (1 g, 2.5 mmol) in anhydrous acetonitrile (25 mL) and stirred under N$_2$(g) in an ice bath.

Added 32% peracetic acid solution (2.1 mL, 10 mmol) dropwise over 10 minutes. Stirred for 2 hours. Added saturated Na$_2$S$_2$O$_3$(aq) solution and stirred for 5-10 minutes. Extracted with EtOAc. Organic extract was then washed with saturated NaCl(aq), dried over anhydrous Na$_2$SO$_4$ and concentrated under reduced pressure. Mixed the resultant with nBuOH (15 mL) and TFA (963 µL, 12.5 mmol) and then stirred at 100° C. for 2-3 hours. Concentrated under reduced pressure. Dissolved in EtOAc and washed with saturated NaHCO$_3$(aq) solution (2×) followed with saturated NaCl(aq). Dried organic extract over anhydrous Na$_2$SO$_4$ and concentrated under reduced pressure. Purified with Combiflash silica gel column (0-40% EtOAc in hexanes) to give BE (830 mg, 1.95 mmol). $^1$H-NMR: 300 MHz, (CDCl$_3$) d: 7.68-7.47 (m, 4H), 4.78 (s, 2H), 4.25-4.17 (m, 4H), 4.02 (s, 2H), 1.69 (m, 2H), 1.44 (m, 2H), 1.29 (t, J=6.9 Hz, 3H), 0.94 (t, J=7.5 Hz, 3H). LCMS-ESI$^+$: calc'd for C$_{20}$H$_{24}$N$_6$O$_5$: 429.2 (M+H$^+$); Found: 429.0 (M+H$^+$).

Scheme 23

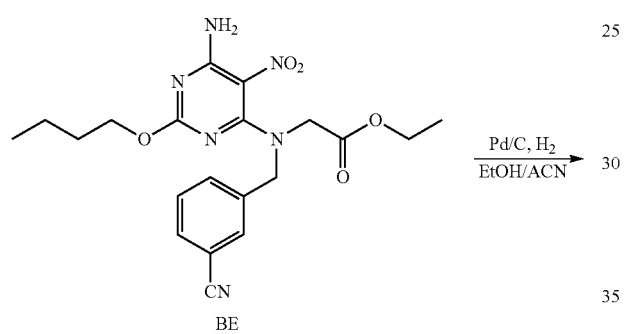

BE

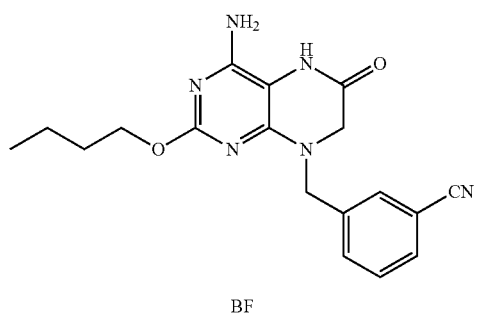

BF

Method XIX: Dissolved BE (650 mg, 4.54 mmol) in EtOH and acetonitrile. Added 10% Pd/C and stirred under atmosphere H$_2$(g) for 18 hours. Added 0.5M HCl(aq) (5 mL) and filtered through Celite. Concentrated under reduced pressure to give BF (585 mg, 1.5 mmol). Purified with prep HPLC. $^1$H-NMR: 300 MHz, (DMSO-d$_6$) d: 9.70 (s, 1H), 7.78-7.54 (m, 4H), 6.23 (s, 2H), 4.68 (s, 2H), 4.04 (t, J=6.6 Hz, 2H), 3.89 (s, 2H), 1.54 (m, 2H), 1.31 (m, 2H), 0.85 (t, J=7.5 Hz, 3H). LCMS-ESI$^+$: calc'd for C$_{18}$H$_{20}$N$_6$O$_2$: 353.2 (M+H$^+$); Found: 353.1 (M+H$^+$).

Scheme 24

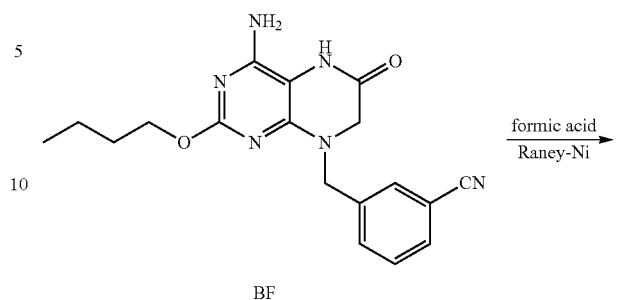

BF

BG

Method XX: Dissolved BF (176 mg, 0.5 mmol) in formic acid (2 mL). Added Raney-Ni and stirred at 80° C. for 90 minutes. Filtered through Celite and washed with formic acid. Diluted filtrate with EtOAc and washed with water (2×), saturated NaHCO$_3$(aq) solution (2×) followed with saturated NaCl(aq). Dried organic extract over anhydrous Na$_2$SO$_4$ and concentrated under reduced pressure. Purified with Combiflash silica gel column (0-10% MeOH in DCM) to give BG (40 mg, 0.11 mmol). $^1$H-NMR: 300 MHz, (DMSO-d$_6$) d: 9.99 (s, 1H), 9.71 (s, 1H), 7.84-7.57 (m, 4H), 6.23 (s, 2H), 4.74 (s, 2H), 4.07 (t, J=6.6 Hz, 2H), 3.87 (s, 2H), 1.56 (m, 2H), 1.32 (m, 2H), 0.85 (t, J=7.5 Hz, 3H). LCMS-ESI$^+$: calc'd for C$_{18}$H$_{21}$N$_5$O$_3$: 356.2 (M+H$^+$); Found: 356.0 (M+H$^+$).

Scheme 25

Example 47

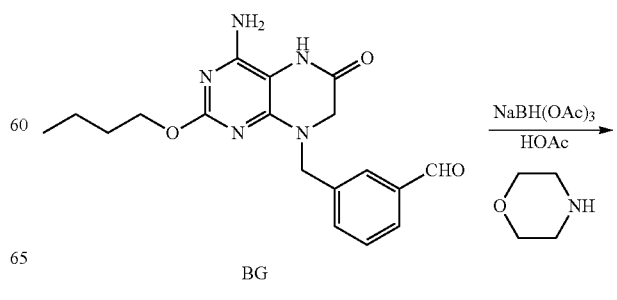

BG

-continued

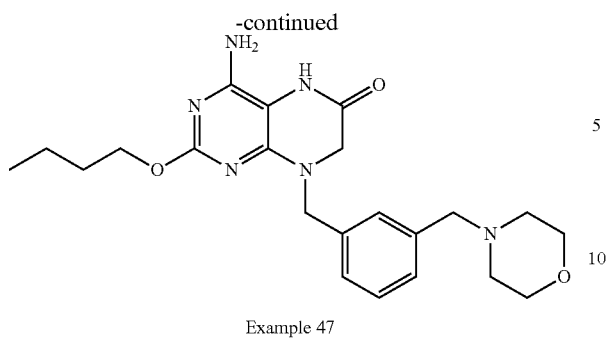

Example 47

Method XXI: Mixed BG (20 mg, 0.056 mmol) with anhydrous acetonitrile (500 µL). Added morpholine (15 µL, 0.169 mmol) and HOAc (10 µL, 0.169 mmol) and stirred for 15 minutes. Added NaBH(OAc)$_3$ (36 mg, 0.169 mmol) and stirred for 3 hours. Added more morpholine (15 µL, 0.169 mmol) and NaBH(OAc)$_3$ (36 mg, 0.169 mmol) and stirred for 16 hours. Added MeOH and stirred for 5-10 minutes. Diluted with EtOAc and washed with saturated NaHCO$_3$(aq) solution (2×) followed with saturated NaCl(aq). Dried organic extract over anhydrous Na$_2$SO$_4$ and concentrated under reduced pressure. Purified with Prep HPLC to give Example 47 (15 mg, 0.035 mmol). $^1$H-NMR: 300 MHz, (Methanol-d$_4$) d: 7.72 (s, 1H), 7.51 (m, 3H), 4.96 (s, 2H), 4.46 (t, J=6.6 Hz, 2H), 4.38 (s, 2H), 4.16 (s, 2H), 4.05-3.82 (m, 4H), 3.35-3.15 (m, 4H), 1.74 (m, 2H), 1.45 (m, 2H), 0.94 (t, J=7.2 Hz, 3H). LCMS-ESI$^+$: calc'd for C$_{22}$H$_{30}$N$_6$O$_3$: 427.2 (M+H$^+$); Found: 427.1 (M+H$^+$).

Scheme 26

Example 48

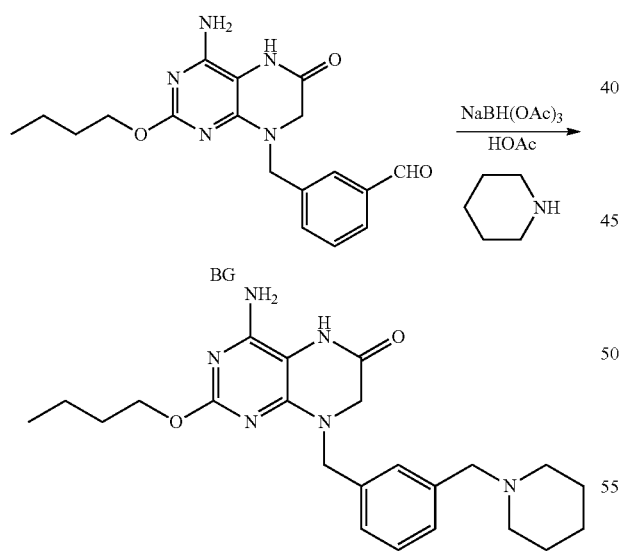

Example 48

Mixed BG (20 mg, 0.056 mmol) with anhydrous acetonitrile (5 mL). Added piperidine (55 µL, 0.56 mmol) and HOAc (16 µL, 0.28 mmol) and stirred for 15 minutes. Added NaBH(OAc)$_3$ (59 mg, 0.28 mmol) and stirred for 3 hours. Added more piperidine (55 µL, 0.56 mmol) and NaBH(OAc)$_3$ ((59 mg, 0.28 mmol) and stirred for 48 hours. Added MeOH and 0.5M HCl(aq). Concentrated under reduced pressure. Purified with Prep HPLC to give Example 48 (13.8 mg, 0.033 mmol). $^1$H-NMR: 300 MHz, (Methanol-d$_4$) d: 7.51-7.45 (m, 4H), 4.82 (s, 2H), 4.24 (s, 2H), 4.18 (t, J=6.3 Hz, 2H), 3.95 (s, 2H), 3.14 (s, broad, 4H), 1.82-1.67 (m, 8H), 1.44 (m, 2H), 0.93 (t, J=7.2 Hz, 3H). LCMS-ESI$^+$: calc'd for C$_{23}$H$_{32}$N$_6$O$_2$: 425.3 (M+H$^+$); Found: 425.2 (M+H$^+$).

Compound BH: Prepared Using Method X:

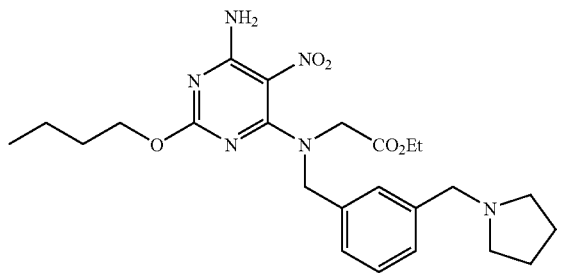

Ethyl-N$_a$-[4-amino-2-n-butoxy-5-nitropyrimidin-6-yl], N$_a$-[3'-(pyrrolidin-1"-ylmethyl)-benzyl]-glycinate: $^1$H NMR (CD$_3$OD, 300 MHz): d 7.24-7.31 (m, 4H), 4.77 (s, 2H), 4.14-4.23 (m, 6H), 3.62 (m, 2H), 2.51 (m, 4H), 1.79 (m, 4H), 1.66 (m, 2H), 1.40 (m, 2H), 1.26 (t, J=7 Hz, 3H), 0.94 (t, J=7 Hz, 3H). LCMS-ESI$^+$: calc'd for C$_{24}$H$_{35}$N$_6$O$_5$: 487.6 (M+H$^+$); Found: 487.2 (M+H$^+$).

Example 49

Prepared Using Method XII

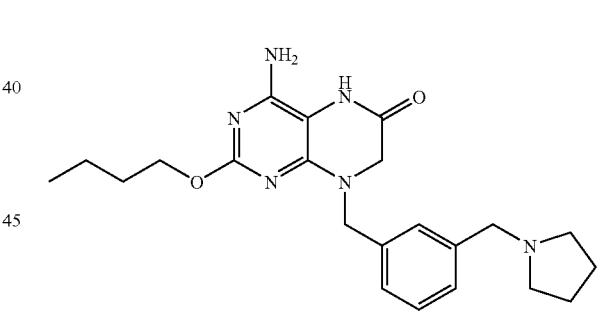

4-amino-2-n-butoxy-8-[3'-(pyrrolidin-1"-ylmethyl)-benzyl]-5,6,7,8-tetrahydropteridin-6-one: $^1$H NMR (CD$_3$OD, 300 MHz): d 7.65 (s, 1H), 7.50 (m, 3H), 4.96 (s, 2H), 4.44 (t, J=7 Hz, 2H), 4.40 (s, 2H), 4.16 (s, 2H), 3.48 (m, 2H), 3.19 (m, 2H), 2.02-2.17 (m, 4H), 1.74 (m, 2H), 1.45 (m, 2H), 0.94 (t, J=7 Hz, 3H)—[HCl salt]. LCMS-ESI$^+$: calc'd for C$_{22}$H$_{31}$N$_6$O$_2$: 411.5 (M+H$^+$); Found: 411.3 (M+H$^+$).

Scheme 27

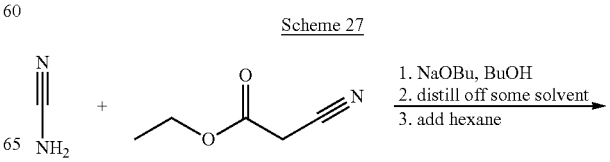

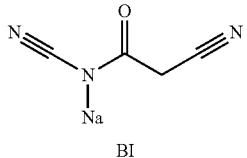

BI

Method XXII: Cyanoacetylcyanamide, Monosodium Salt (Compound BI). In a 3.0 L round bottom 1 neck flask, a solution of cyanamide (50.0 g, 1.19 mol), ethyl cyanoacetate (126.4 mL, 1.19 mol), and anhydrous n-BuOH (1.00 L mL) was treated with 20% w/w NaOBu/BuOH (571 mL, 1.19 mmol) at 23° C. The reaction was stirred vigorously and became cloudy and thick. After 12-16 hrs, the reaction was fitted with a Distillation head. The sidearm of the distillation head was fitted with a long reflux condenser (water circulated). At the end of the condenser, a Claisen Vacuum adaptor was attached and led into a receiver flask (2.0 L r.b., cooled in an ice bath). All ground glass joints were greased and clamped. A vacuum of 10 mmHg or less was applied to the system at 23° C. (some mild bumping occurred. A dry-ice/acetone trap was employed in a dewar finger trap to catch uncondensed vapors) Once bumping had become minimal, the reaction was heated externally to 45-60° C. (oil or water bath), and solvent (1.1 L) was distilled off. Vacuum was released, and while the system was still warm, hexanes (2.0 L) were added. System was allowed to cool to 23° C., and a precipitate was observed. The slurry was filtered over coarse glass frits to capture the solid. The filter cake was washed with hexanes while suction was off (2×250 mL; each time stir the cake/hexanes, then turn suction back on). The cake was then dried in a vacuum oven at 40-45° C. overnight, affording cyanoacetylcyanamide, monosodium salt (128.14 g, 82% yield) as a free-flowing, slightly hygroscopic powder. The powder was immediately placed in a glass jar and stored in a dessicator.

Scheme 28

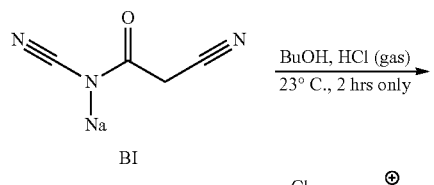

Method XXIII: N-Cyanoacetyl-butylisouronium chloride (Compound BJ). A suspension of cyanoacetylcyanamide, monosodium salt BI (20.0 g, 153 mmol) in n-BuOH (300 mL) was treated with HCl (4.0 M in dioxane, 100 mL, 400 mmol). During addition the suspension became more colloidal and there was a mild exotherm to an internal temperature of 35° C., then the reaction transitioned to a thicker consistency. After 2 h, 10% w/v aq. NaHCO$_3$ (200 mL) was added cautiously (effervescence) until the pH of the aq. phase reached 7.5. The organic layer was collected, dried (Na$_2$SO$_4$), and filtered over glass frits, then transferred into a 500 mL round bottom flask. Distillation of 330 mL of solvent away from the dried organic phase was achieved using the procedure above (step 1, pressure ~10 mmHg, 60° C. bath temp). The thick syrupy residue contains crude N-cyanoacetyl-butylisouronium chloride, BJ, which is unstable and immediately used in the next reaction.

Scheme 29

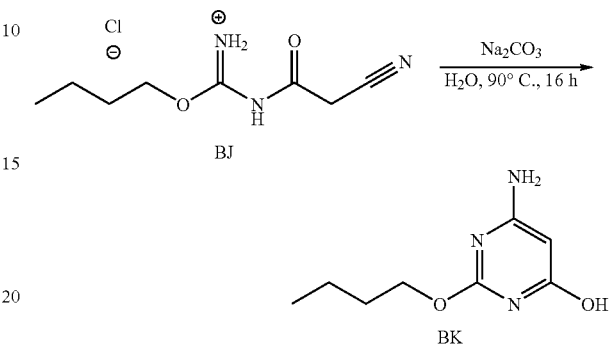

Method XXIV: 4-Amino-2-butoxy-6-hydroxypyrimidine (Compound BK). An emulsion of all of the crude N-cyanoacetyl-butylisouronium chloride BJ (33.35 g, 153 mmol) in a mixture of dioxane and n-BuOH (~70 mL) was treated with 10% w/v aq. Na$_2$CO$_3$ (200 mL) and was stirred vigorously at 90° C. for 16 h. The reaction was then allowed to cool to 23° C. over the next hour. A white semicrystalline precipitate formed. Then the system was cooled to 0° C. for 3 h, and the white-brown precipitate was collected on coarse glass frits. The filter cake was washed with hexane (2×50 mL) and dried in a vacuum oven at 40° C., giving desired product BK (14.1 g, 50% yield over 2 steps). The neutralized aqueous phase was then extracted with CH$_2$Cl$_2$ (3×50 mL). The extracts were combined, dried (MgSO$_4$), filtered, and concentrated to a brown oil. After standing at 23° C. overnight, the oil solidified. The gooey solid was triturated with hexane (50 mL) and filtered. The collected solid proved to be additional pure product (1.17 g, 4% yield). $^1$H NMR (DMSO-d$_6$, 400 MHz): δ (ppm) 11.16 (s, broad, 1H), 6.29 (s, broad, 2H), 4.73 (s, 1H), 4.23 (t, J=7 Hz, 2H), 1.70-1.60 (m, 2H), 1.43-1.33 (m, 2H), 0.92 (t, J=7 Hz, 3H).

Scheme 30

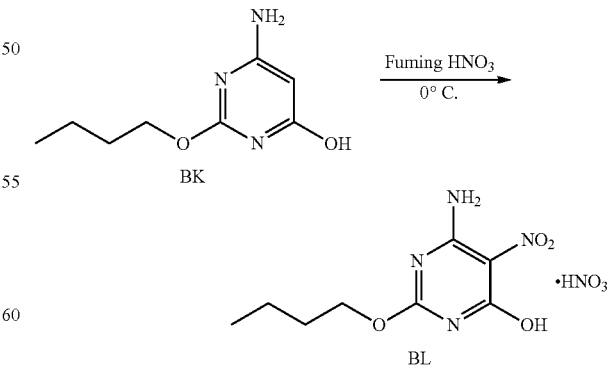

Method XXV: 4-Amino-2-butoxy-5-nitro-6-hydroxypyrimidine, BL (nitrate salt and free base). A 50 mL flask containing fuming aqueous HNO$_3$ (18 mL) at 0° C. was treated with 4-amino-2-butoxy-6-hydroxypyrimidine BK (8.00 g)

via solid addition funnel under $N_2$. The pyrimidine was added at a rate of ca. 266 mg every minute over a 30 min period. Reaction went from yellow to deep red. Once the addition was complete, the reaction was stirred at 0° C. for another 2 h. Then the reaction was added slowly to a mixture of $CH_2Cl_2$ and $H_2O$ (100 mL each) at 0° C. After addition was complete, the diluted reaction was allowed to stir for 30 min. A pink precipitate formed and was collected via vacuum filtration. LCMS analysis and $^1H$ NMR in DMSO (identical to values below) reveal that the compound is the mononitrate salt of the product (6.63 g, 52% yield). The organic layer was collected. The aq. layer was extracted exhaustively with $CH_2Cl_2$ (100 mL portions) until the aqueous layer showed no traces of product. All organic phases were combined, dried ($MgSO_4$), filtered, and concentrated. The residue was purified on silica gel by flashing (Eluent: $CH_2Cl_2$:MeOH 100/0 to 80/20, linear gradient) giving the desired product BL as a free base (2.02 g, 20% yield)(yellow powder). $^1H$ NMR (free base or nitrate salt, DMSO-$d_6$, 400 MHz): δ (ppm) 12.07 (s, broad, 1H), 8.83 (s, broad, 1H), 8.77 (s, broad, 1H), 4.36 (t, J=7 Hz, 2H), 1.73-1.63 (m, 2H), 1.44-1.34 (m, 2H), 0.94 (t, J=7 Hz, 3H).

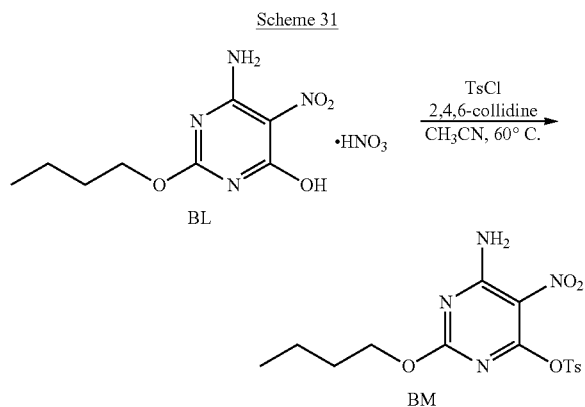

Method XXVI: 4-Amino-2-butoxy-5-nitro-6-(para-toluenesulfonyloxy)pyrimidine (BM). A solution of 4-amino-2-butoxy-5-nitro-6-hydroxypyrimidine BL (nitrate salt form, 8.00 g, 27.5 mmol, 1.00 equiv, see note below) in acetonitrile (80.0 ml) was treated with 2,4,6-collidine (distilled under vacuum from NaH, 10.90 ml, 82.4 mmol, 3.00 equiv), followed by TsCl (26.21 g, 0.138 mol, 5.00 equiv). The reaction was stirred for 4 h at 60° C. By this point, 95% conversion to the product was observed using LC-MS as the analytical method (Water/Acetonitrile (with trace AcOH) 95:5-2:98 on a C-18 gemini column). The reaction was added dropwise to a 0° C. mixture of $H_2O$ (400 mL) and $CH_2Cl_2$ (200 mL). After 10 min, the mixture was extracted (3×200 mL $CH_2Cl_2$). All organic layers were combined, dried ($Na_2SO_4$), filtered, and concentrated to a total volume of 50 mL. The crude solution of product was purified by directly loading onto a 330 g column of silica gel, followed by chromatography (Eluent hexane/EtOAc 9:1→0:100) giving semipure BM contaminated with 2,4,6-Collidine. The oily solid was taken up in hexane (50 mL) and agitated, then filtered over glass frits. The filter cake was washed with several 30 mL portions of hexane until no collidine was present, giving pure product BM (5.44 g, 52% yield). $^1H$ NMR in $CDCl_3$ was obtained, along with LCMS analysis. $^1H$ NMR ($CDCl_3$, 400 MHz): δ (ppm) 7.99 (d, J=8.2 Hz, 2H), 7.95 (s, broad, 1H), 7.39 (d, J=8.2 Hz, 2H), 6.19 (s, broad, 1H), 4.26 (t, J=7.4 Hz, 2H), 2.48 (s, 3H), 1.73 (app. quintet, J=7.4 Hz, 2H), 1.43 (app. sextet, J=7.4 Hz, 2H), 0.96 (t, J=7.4 Hz, 3H).

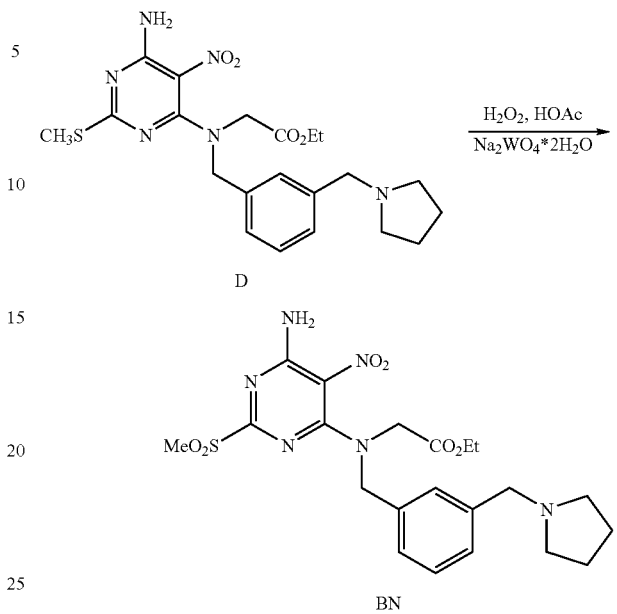

Method XXVII: Ethyl-$N_a$-[4-amino-2-methanesulfonyl-5-nitropyrimidin-6-yl],$N_a$-[3'-(pyrrolidin-1"-ylmethyl)-benzyl]-glycinate (BN). To a suspension of the sulfide D (100 mg, 0.217 mmol) in EtOH (2.0 mL) was added glacial AcOH (124 µL, 2.17 mmol) and sodium tungstate dihydrate (21.5 mg, 65.1 µmol). The reaction was cooled to 0° C., and 30% aq. hydrogen peroxide (245 µL, 2.17 mmol) was added dropwise over a 2 min period. After 9 h, the reaction was added to a 0° C. solution of 10% w/v aq. $Na_2S_2O_3$ (6 mL). After 5 min, the reaction was extracted with $CH_2Cl_2$ (7×10 mL). The combined organic layers were dried over $Na_2SO_4$, filtered, and concentrated under vacuum to a yellow powder, containing the sulfone BN and the corresponding sulfoxide as a 1:1 mixture (45.5 mg, 43% yield based on mass of sulfone). In all subsequent chemistry, both the sulfoxide and sulfone react similarly. $^1H$ NMR (sulfone, $CDCl_3$, 300 MHz): δ (ppm) 7.50-7.24 (m, 4H), 4.79 (s, 2H), 4.21 (q, J=7.0 Hz, 2H), 4.16 (s, 2H), 3.97 (s, 2H), 3.17 (s, 3H), 3.01-2.85 (m, 4H), 2.02-1.91 (m, 4H), 1.28 (t, J=7.0 Hz, 3H). LCMS-ESI$^+$: calc'd for $C_{21}H_{29}N_6O_6S$ (sulfone): 493.2 (M+H$^+$); Found: 493.1 (M+H$^+$).

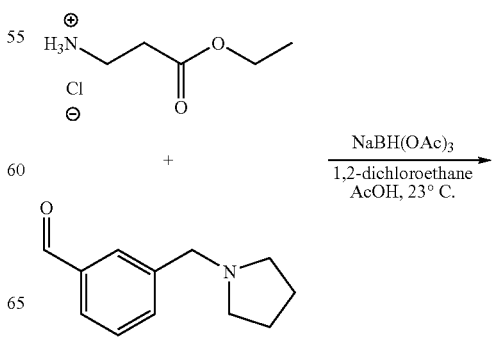

-continued

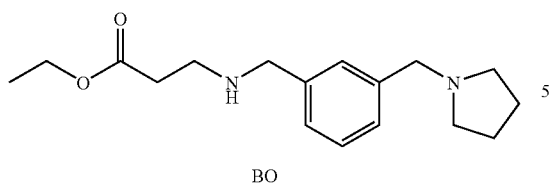

BO

Method XXVIII: Ethyl-N_β-[3-(pyrroldin-1'-ylmethyl)-benzyl]-β-alaninoate (BO). To a suspension of ethyl β-alaninoate hydrochloride (890 mg, 6.39 mmol, 1.1 equiv), 3-(pyrrolidin-1'-ylmethyl)-benzaldehyde (1.10 g, 5.81 mmol, 1.0 equiv), NaBH(OAc)$_3$ (2.46 g, 11.6 mmol, (2.0 equiv), and 1,2-dichloroethane (7.0 mL) was added glacial AcOH (830 μL, 5.81 mmol, 1.0 equiv) at 23° C. To aide fluidity, more 1,2-dichloroethane (500 μL) was added. After 75 min, the reaction was carefully quench with 0.1 M aq HCl, adjusting the pH to ~3. Then saturated aq Na$_2$CO$_3$ was added until the pH was ~8. The reaction was extracted with CH$_2$Cl$_2$ (3×150 mL). All organic layers were combined, dried (Na$_2$SO$_4$), filtered, and concentrated to a pale yellow oil BO (740 mg, 44% yield). $^1$H NMR (CDCl$_3$, 300 MHz): δ (ppm) 7.30-7.21 (m, 4H), 4.16 (q, J=7.0 Hz, 2H), 3.80 (s, 2H), 3.64 (s, 2H), 2.99 (s, broad, 1H), 2.91 (t, J=6.4 Hz, 2H), 2.58-2.48 (m, 4H), 2.53 (t, J=6.4 Hz, 2H), 1.85-1.76 (m, 4H), 1.26 (t, J=7.0 Hz, 3H). LCMS-ESI$^+$: calc'd for C$_{17}$H$_{27}$N$_2$O$_2$: 291.2 (M+H$^+$); Found: 291.1 (M+H$^+$).

Scheme 34

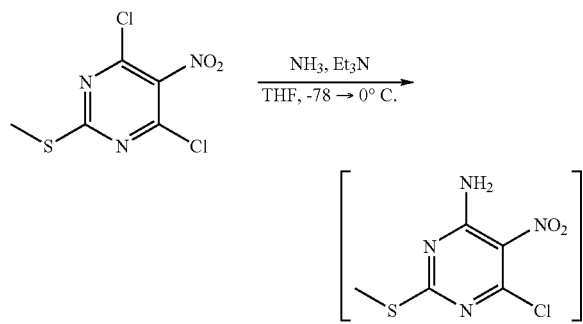

Method XXIX: 4-Amino-6-chloro-2-methylthio-5-nitropyrimidine (B). A solution of 4,6-dichloro-2-(methylthio)-5-nitropyrimidine (3.53 g, 14.7 mmol) in THF (15 mL) at −78° C. was added Et$_3$N (3.75 mL, 27.0 mmol), followed by NH$_3$ (7 N in MeOH, 1.80 mL, 12.86 mmol). The reaction was then warmed to 0° C. and stirred for 1 h. The crude solution of product B was immediately used in the next reaction (Scheme 35).

Scheme 35

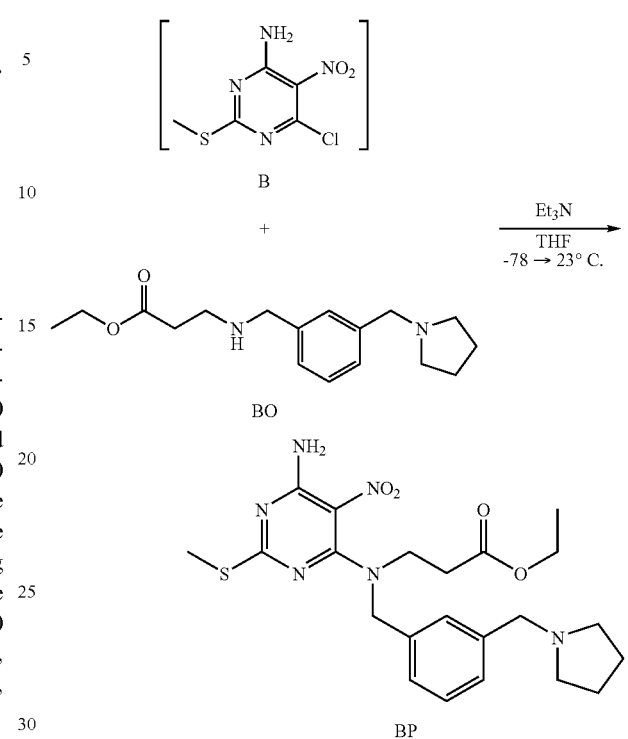

Method XXX: Compound BP. A solution of 4-amino-6-chloro-2-(methylthio)-5-nitropyrimidine (from the previous reaction above) at −78° C. was added Et$_3$N (3.75 mL, 27.0 mmol) and ethyl-N$_β$-[3-(pyrroldin-1'-ylmethyl)-benzyl]-β-alaninoate (3.56 g, 12.3 mmol). The reaction was allowed to warm to 23° C. overnight. The reaction was quenched with aq. saturated NH$_4$Cl (excess) and extracted with EtOAc (2×). All organic layers were combined, dried (Na$_2$SO$_4$), filtered, and concentrated. The residue was purified on silica gel using 20% MeOH/CH$_2$Cl$_2$ (isocratic) as the eluent, giving product BP (6.5 g, yield not determined because some solvent was present). $^1$H NMR (CDCl$_3$, 300 MHz): δ (ppm) 7.26-7.16 (m, 4H), 4.55 (s, 2H), 4.11 (q, J=7.0 Hz, 2H), 3.74 (t, J=7.0 Hz, 2H), 3.61 (s, 2H), 3.48 (s, 2H), 2.64 (t, J=7.0 Hz, 2H), 2.54-2.45 (m, 4H). 2.43 (s, 3H), 1.83-1.74 (m, 4H), 1.22 (t, J=7.0 Hz, 3H). LCMS-ESI$^+$: calc'd for C$_{22}$H$_{31}$N$_7$O$_4$S: 475.2 (M+H$^+$); Found: 475.0 (M+H$^+$).

Scheme 36

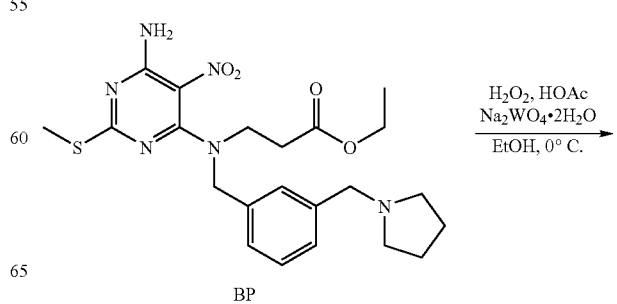

BP

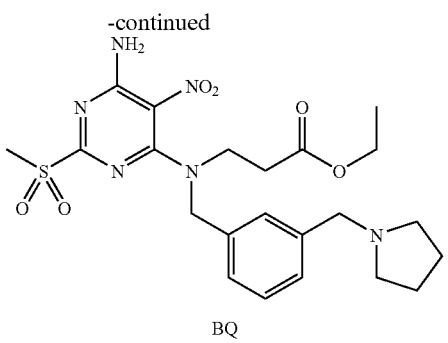

BQ

Method XXXI: Compound BP. A solution of the sulfide BP (869 mg, 1.83 mmol), in absolute EtOH (20 mL) at 0° C. was added sodium tungstate dihydrate (180 mg, 0.550 mmol), followed by glacial AcOH (590 µL, 18.3 mmol). Finally, 30% w/v aq. $H_2O_2$ (2.77 mL, 18.3 mmol) was added dropwise. Once the reaction was complete, it was added dropwise to a mixture of 10% w/v eq. $Na_2S_2O_3$ (excess relative to $H_2O_2$) and $CH_2Cl_2$. The mixture was then extracted repeatedly with $CH_2Cl_2$. All organic extracts were combined, dried ($Na_2SO_4$), filtered, and concentrated to yellow solid (3.0 g, yield not found because some glacial AcOH and $CH_2Cl_2$ are still present). The crude solid BQ was used in the next reaction without further purification. LCMS-ESI$^+$: calc'd for $C_{22}H_{31}N_6O_6S$: 507.2 (M+H$^+$); Found: 507.1 (M+H$^+$).

Scheme 37

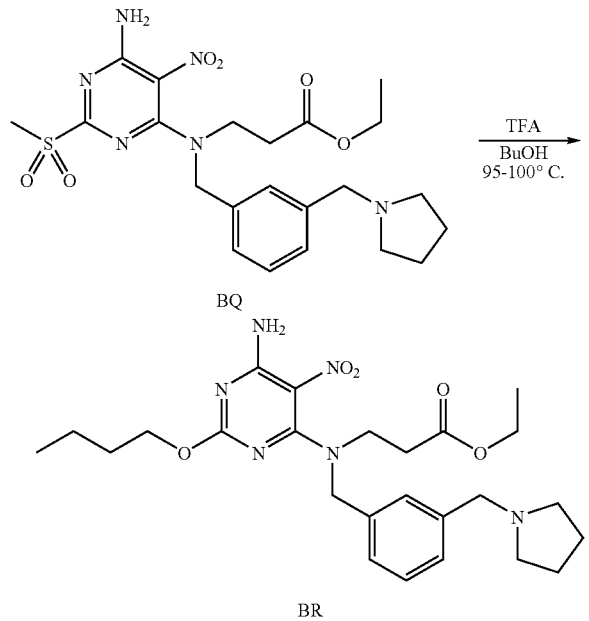

Method XXXII: Compound BR. A solution of the sulfone BQ (crude from above, 927 mg net mass) in n-butanol (15 mL) was treated with TFA (420 µL) and stirred at 95° C. More TFA (280 µL) was added after 2.5 h, and the reaction was heated to 100° C. 3 hours later, the reaction was quenched with saturated aq. $NaHCO_3$. The mixture was extracted with $CH_2Cl_2$ (8×), and all organic layers were combined, dried ($Na_2SO_4$), filtered, and concentrated. The residue was purified on silica gel using 20% MeOH in $CH_2Cl_2$ (isocratic) as the eluent. Product-containing fractions, which were semipure, were combined and purified on a C-18 reversed-phase column (first eluent: $H_2O/CH_3CN$ 100:0→0:100; second eluent $CH_3CN$/MeOH 100:0→0:100) giving pure product BR (59 mg, yield not determined). $^1$H NMR (CDCl$_3$, 300 MHz): δ (ppm) 7.26-7.06 (m, 4H), 4.53 (s, 2H), 4.24 (t, J=6.7 Hz, 2H), 4.11 (q, J=7.0 Hz, 2H), 3.71 (t, J=7.0 Hz, 2H), 3.58 (s, 2H), 3.48 (s, 2H), 2.64 (t, J=6.7 Hz, 2H), 2.52-2.43 (m, 4H), 1.81-1.74 (m, 4H), 1.74-1.56 (m, 2H), 1.50-1.33 (m, 2H), 1.22 (t, J=7.0, 3H), 0.93 (t, J=7.3 Hz, 3H). LCMS-ESI$^+$: calc'd for $C_{26}H_{37}N_6O_6$: 501.3 (M+H$^+$); Found: 501.1 (M+H$^+$).

Scheme 38: Example 50

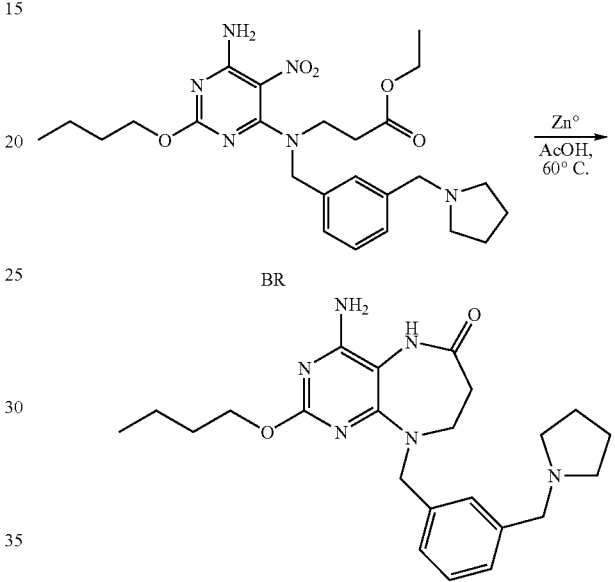

Example 50

Method XXXIII: Example 50. A suspension of the nitro compound BR (5.0 mg) and zinc powder (6.5 mg) in glacial AcOH (500 µL) was heated to 60° C. After 1 h, more zinc powder (6.5 mg) was added, and heating was continued. 2 hours later, the reaction was diluted with $H_2O$ (500 µL) and directly purified on a 4.3 g C-18 reversed-phase sep-pak column (0.05% w/v aq. HCl/CH$_3$CN 100:0→0:100) giving Example 50 (3.9 mg, 78% yield) as a di-HCl salt. $^1$H NMR (CD$_3$OD, 300 MHz): δ (ppm) 7.57-7.39 (m, 4H), 5.00 (s, 2H), 4.38 (s, 2H), 4.28 (t, J=6.5 Hz, 2H), 3.86-3.82 (m, 2H), 3.50-3.40 (m, 2H), 3.20-3.09 (m, 2H), 2.88-2.78 (m, 2H), 2.24-2.08 (m, 2H), 2.08-1.96 (m, 2H), 1.64 (app. Quintet, J=6.5 Hz, 2H), 1.34 (app. Septet, J=7.0 Hz, 2H), 0.87 (t, J=7.0 Hz, 3H). LCMS-ESI$^+$: calc'd for $C_{23}H_{33}N_6O_2$: 425.3 (M+H$^-$); Found: 425.3 (M+H$^+$).

Scheme 39

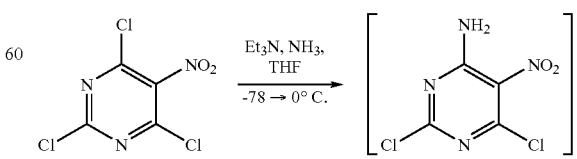

Method XXXIV, Part 1: 6-amino-2,4-dichloro-5-nitropyrimidine. A solution of 2,4,6-trichloro-5-nitropyrimidine (94 mg, 0.413 mmol) in THF (5 mL) was cooled to −78° C. and treated with Et₃N (110 µL, 0.757 mmol), followed by NH₃ (7 N in MeOH, 50 µL, 0.344 mmol). The reaction was warmed to 0° C. Once TLC indicated complete consumption of the starting material, the crude product solution was immediately used in the reaction below (Scheme 40).

Scheme 40

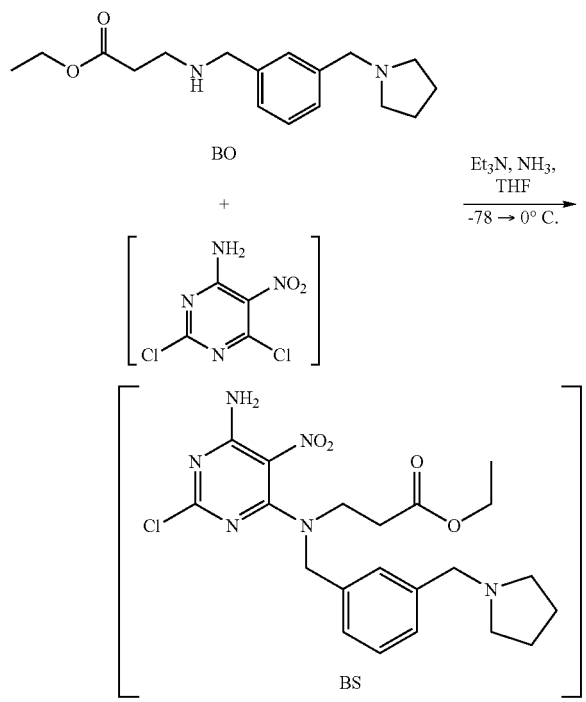

Method XXXIV, Part 2: Compound BS. A crude solution of 6-amino-2,4-dichloro-5-nitropyrimidine (from reaction above) was cooled to −78° C. and Et₃N (110 µL, 0.757 mmol) was added, followed by a solution of Ethyl-N_β-[3-(pyrroldin-1'-ylmethyl)-benzyl]-β-alaninoate (100 mg, 0.344 mmol) in THF (1.0 mL). The reaction was warmed to 0° C. After 80 min, the reaction showed complete conversion to BS. An aliquot was analyzed via LCMS. The remainder of the solution was immediately used in the next reaction below. LCMS-ESI⁺: calc'd for $C_{21}H_{28}ClN_6O_4$: 463.2 (M+H⁺); Found: 463.1 (M+H⁺ for ³⁵Cl) and 465.1 (M+H⁺ for ³⁷Cl).

Scheme 41

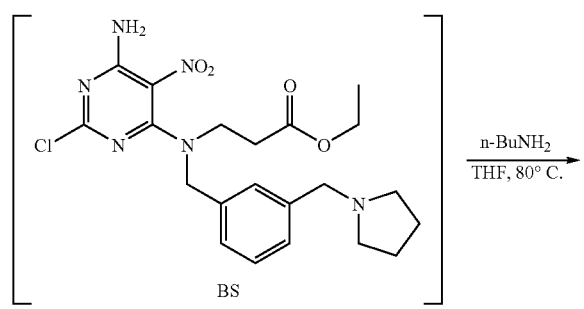

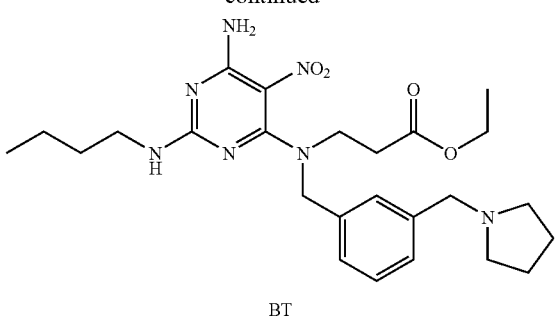

Method XXXIV, Part 3: Compound BT. A solution of the crude chloropyrimidine BS (from the reaction above) in THF was treated with n-butylamine (170 µL) and heated to 80° C. After 2.5 h, H₂O (100 µL) was added to improve fluidity, and heating was continued. The completed reaction was loaded directly onto a C-18 reversed-phase column and chromatographed (eluent: 0.1% w/v aq. TFA/CH₃CN 100:0→0:100), giving pure product BT (23.5 mg, 14% yield over 3 steps). ¹H NMR (CD₃OD, 300 MHz): δ (ppm) 7.32-7.14 (m, 4H), 4.64-4.61 (app. d, broad, J=5.5 Hz, 2H), 4.07 (q, J=7.0 Hz, 2H), 3.72-3.61 (m, 2H), 3.62 (s, 2H), 3.30 (s, 2H), 2.72-2.60 (m, 2H), 2.58-2.46 (m, 4H), 1.84-1.73 (m, 4H), 1.69-1.24 (m, 4H), 1.20 (t, J=7.0 Hz, 3H). LCMS-ESI⁺: calc'd for $C_{25}H_{38}N_7O_4$: 500.3 (M+H⁺); Found: 500.1 (M+H⁺).

Scheme 42

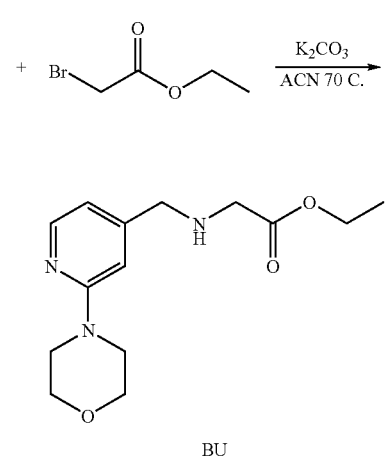

Method XXXV: Compound BU. (2-Morpholinopyridin-4-yl)methylamine (900 mg, 4.657 mmol) was dissolved in acetonitrile and combined with solid potassium carbonate (2.52 g, 18.23 mmol) followed by heating to 70° C. Ethyl-2-bromoacetate (566 µL, 5.114 mmol) was then added over 10-15 minutes and the mixture was continued to stir at 70° C. for 45 min wherein the consumption of SM was observed by HPLC analysis. The mixture was removed from heat source, allowed to cool to RT and was diluted with EtOAc (100 mL) and H₂O. The reaction was washed with brine (3×) and dried with Na₂SO₄, filtered, and concentrated. Desired product BU was obtained in 84.4% yield and used without purification.

Scheme 43

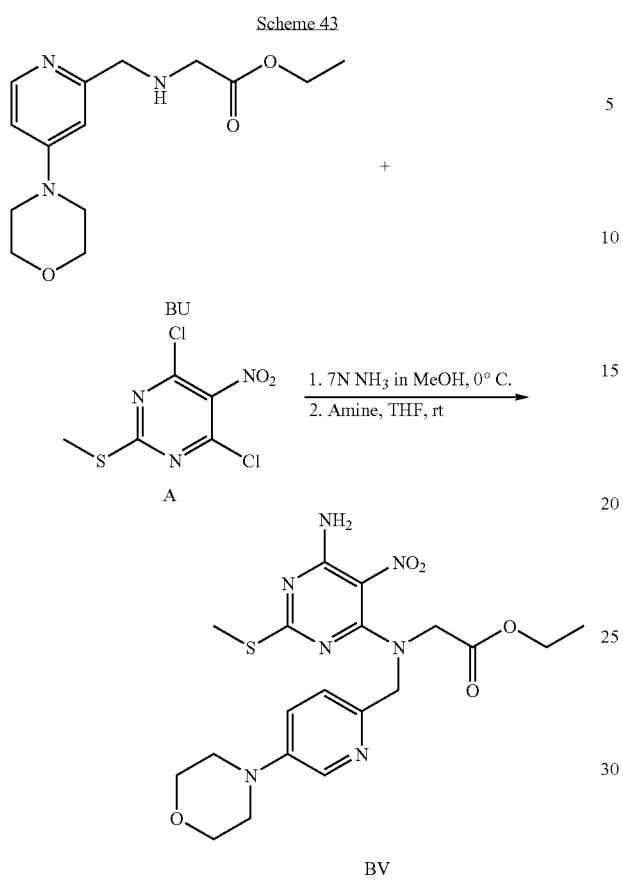

Method XXXVI: Compound BV. Dichloropyrimidine A (1.0715 g, 4.502 mmol) was dissolved in 25 mL THF and cooled to 0° C. NH$_3$ was added (3.5 Equiv) and the mixture was allowed to stir cold for 1 h. Aminoester (1.22 g, 4.37 mmol) was then added dropwise as a solution in 10 mL THF over 10-15 minutes, and the resulting mixture was allowed to warm to room temperature. After 3 h, the reaction was quenched with the addition of water, diluted with EtOAc and the pH was adjusted to =8 using solid K$_2$CO$_3$. The mixture was washed with water, washed with brine then dried with sodium sulfate and concentrated in vacuo. The crude product was then chromatographed on silica with a CH$_2$Cl$_2$ and 20% MeOH/CH$_2$Cl$_2$ gradient over 10-15 column volumes to give BV.

Scheme 44

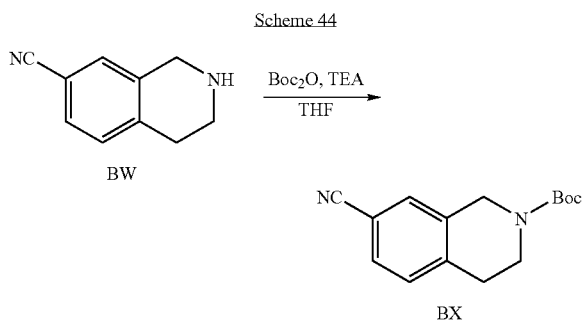

Method XXXVII: Compound BX. Compound BW (500 mg, 3.16 mmol) was added to THF (15 mL). To this was added triethylamine (659 μL, 4.74 mmol). A solution of Boc anhydride (759 mg, 3.48 mmol) in THF was added in portions. The mixture was stirred for 2 hours. After this, the reaction was diluted with EtOAc and washed with saturated NaHCO$_3$(aq) (2×) followed with 5% citric acid(aq) and then saturated NaCl(aq). The organic extract was dried over anhydrous Na$_2$SO$_4$ and concentrated under reduced pressure. The product was purified with silica gel chromatography (0-20% EtOAc in hexanes) to give BX (751 mg, 2.9 mmol). $^1$H NMR: (CDCl$_3$, 300 MHz): δ 7.44-7.25 (m, 3H), 4.60 (s, 2H), 3.67 (t, J=5.7 Hz, 2H), 2.89 (t, J=6.0 Hz, 2H), 1.50 (s, 9H).

Scheme 45

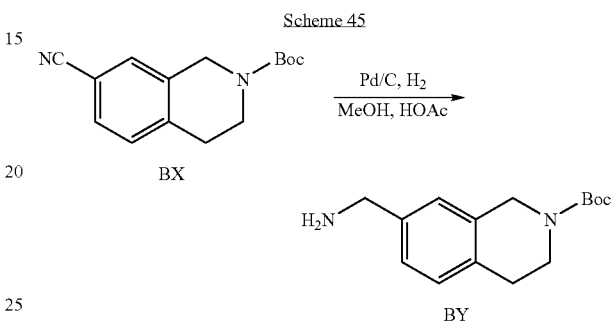

Method XXXVIII: Compound BY. Compound BX (751 mg, 2.9 mmol) was dissolved in MeOH. To this was added HOAc (300 μL) and 10% Pd/C. The mixture was stirred under 1 atm H$_2$ for 6 hours. The mixture was filtered through Celite and the filtrate was concentrated under reduced pressure. The residue was dissolved in EtOAc and washed with saturated NaHCO$_3$(aq) (2×) followed with saturated NaCl(aq). The organic extract was dried over anhydrous Na$_2$SO$_4$ and concentrated under reduced pressure to give BY (474 mg, 1.47 mmol). $^1$H NMR: (CDCl$_3$, 300 MHz): δ 7.13 (m, 3H), 4.56 (s, 2H), 3.87 (s, 2H), 3.63 (s, 2H), 2.80 (m, 2H), 1.49 (s, 9H). LCMS-ESI$^+$: calc'd for C$_{11}$H$_{15}$N$_2$O$_2$: 206.1 (M–tBu+H$^+$); Found: 206.8 (M–tBu+H$^+$)

Scheme 46

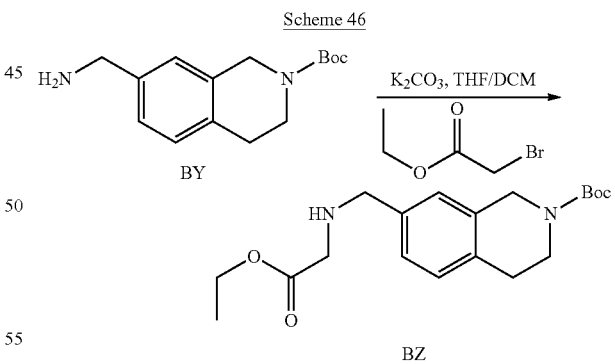

Method XXXIX: Compound BZ. Compound BY (474 mg, 1.47 mmol) was added to anhydrous THF (15 mL). To this was added potassium carbonate and the reaction was stirred under N$_2$ in an ice bath. A solution of ethyl bromoacetate in anhydrous THF was added dropwise. To this was added anhydrous CH$_2$Cl$_2$ (5 mL) and the mixture was stirred for 48 hours. The reaction was diluted with EtOAc and washed with saturated NaHCO$_3$(aq) (2×) followed with saturated NaCl (aq). The organic extract was dried over anhydrous Na$_2$SO$_4$ and concentrated under reduced pressure. The product was purified with Prep HPLC to give BZ (180 mg, 0.52 mmol). $^1$H NMR: (CDCl$_3$, 300 MHz): δ 7.12 (m, 3H), 4.57 (s, 2H), 4.22 (m, 2H), 3.77 (s, 2H), 3.64 (m, 2H), 3.41 (s, 2H), 2.82 (m, 2H), 1.50 (s, 9H), 1.29 (t, J=7.2 Hz, 3H). LCMS-ESI$^+$: calc'd for C$_{19}$H$_{28}$N$_2$O$_4$: 349.2 (M+H$^+$); Found: 348.9 (M+H$^+$)

Scheme 47: Example 51

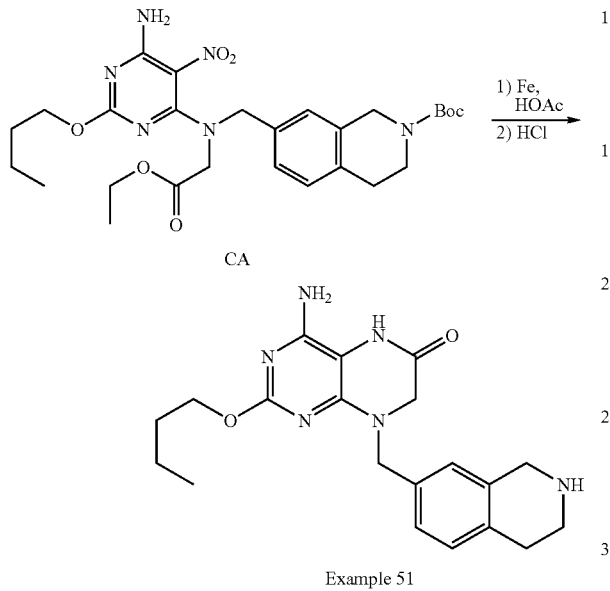

Example 51

Method XL: Example 51. Compound CA was dissolved in HOAc (6 mL). To this was added iron powder and the reaction was stirred at 60° C. for 3 hours. The mixture was filtered and washed with HOAc. The mixture was concentrated under reduced pressure. The Boc protected lactam intermediate was purified with silica gel chromatography (0-5% MeOH in CH$_2$Cl$_2$). The material was then dissolved in MeOH to this was added 4N HCl in dioxane. The mixture was stirred for 30-60 minutes, concentrated under reduced pressure, and then purified with Prep HPLC Phenomenex Gemini 5u C$_{18}$ column and eluted with a linear gradient of 5-100% Acetonitrile containing 0.1% TFA to give Example 51 (109 mg, 0.28 mmol). $^1$H NMR: (CD$_3$OD, 300 MHz): δ 7.30-7.22 (m, 4.88 (s, 2H), 4.45 (t, J=6.3 Hz, 2H), 4.37 (s, 2H), 4.09 (s, 2H), 3.51 (t, J=6.3 Hz, 2H), 3.12 (m, 2H), 1.76 (m, 2H), 1.47 (m, 2H), 0.96 (t, J=7.5 Hz, 3H). LCMS-ESI$^+$: calc'd for C$_{20}$H$_{27}$N$_6$O$_2$: 383.2 (M+H$^+$); Found: 383.0 (M+H$^+$).

Scheme 48: Example 52

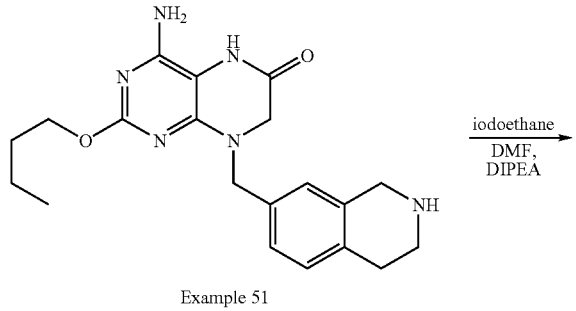

Example 51

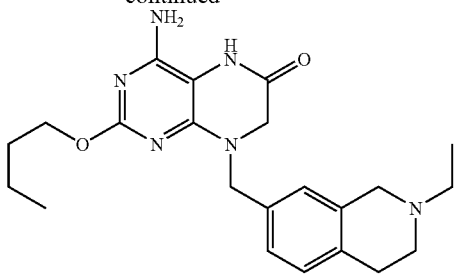

Example 52

Method XLI: Example 52. Example 51 (20 mg, 0.0417 mmol) was dissolved in anhydrous DMF (1 mL). To this was added iodoethane 3.7 µL, 0.0459 mmol) and DIPEA (16 µL, 0.0917 mmol). The mixture was stirred for 14 hours. The product was purified with Prep HPLC Phenomenex Gemini 5u C$_{18}$ column and eluted with a linear gradient of 5-100% Acetonitrile containing 0.1% TFA to give Example 52 (6.4 mg, 0.0156 mmol). $^1$H NMR: (CD$_3$OD, 300 MHz): δ 7.32-7.25 (m, 3H), 4.65 (m, 1H), 4.46 (t, J=6.9 Hz, 2H), 4.35 (m, 1H), 4.10 (s, 2H), 3.80 (m, 1H), 3.39-3.19 (m, 8H), 1.75 (m, 2H), 1.46 (m, 5H), 0.97 (t, J=7.5 Hz, 3H). LCMS-ESI$^+$: calc'd for C$_{22}$H$_{31}$N$_6$O$_2$: 411.2 (M+H$^+$); Found: 411.1 (M+H$^+$).

Scheme 49

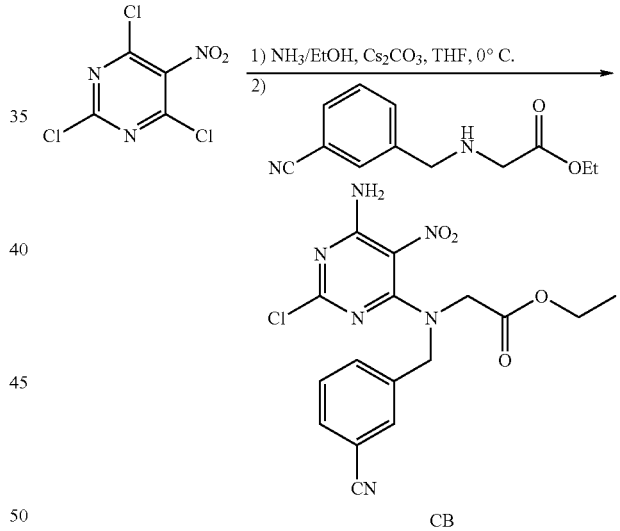

CB

Method XLII: Compound CB. To a solution of 2,4,6-trichloro-5-nitropyrimidine (200 mg, 0.38 mmol) in THF (3 ml) at 0° C. was added Cs$_2$CO$_3$ (286 mg, 0.88 mmol) and NH$_3$ in EtOH (2 M, 540 µL, 1.08 mmol) dropwise. The reaction mixture was stirred for 30 min. After 2,4,6-trichloro-5-nitropyrimidine was consumed, a solution of 3-((2-ethoxy-2-oxo-ethylamino)methyl)benzonitrile (190 mg, 0.88 mmol) in THF (2 ml) was added to the reaction mixture at 0° C. Then the reaction mixture was allowed to rise to room temperature and stirred for 2 h. The reaction mixture was washed with saturated NaHCO$_3$ (aq) and extracted with CH$_2$Cl$_2$ (×3). The organic phase was combined, dried over Na$_2$SO$_4$, filtered and concentrated. The residue was purified by silica gel column (0-50% EtOAc in hexanes) to give CB. $^1$H NMR: (CDCl$_3$, 300 MHz): δ 7.65-7.43 (m, 4H), 4.75 (s, 2H), 4.23-4.19 (m, 2H), 4.03 (s, 2H), 1.28 (t, J=6.9 Hz, 3H). LCMS-ESI⁺: calc'd for $C_{16}H_{16}ClN_6O_4$: 391.8 (M+H⁺); Found: 391.0 (M+H⁺).

Scheme 50

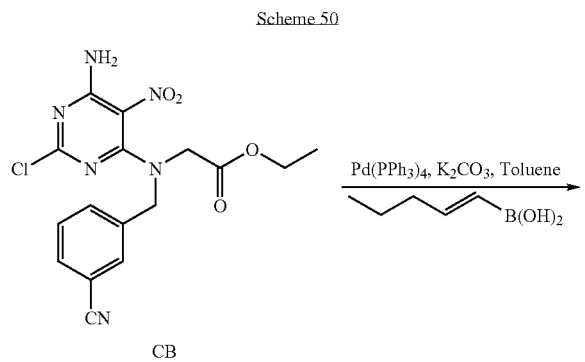

Method XLIII: Compound CC. To a solution of CB in toluene was added pent-1-enylboronic acid (420 mg, 3.04 mmol), $K_2CO_3$ (350 mg, 3.07 mmol) and tetrakis(triphenylphosphine)palladium (353 mg, 0.30 mmol). The reaction mixture was reacted at 100° C. for 4 h. The reaction was cooled down, washed with saturated $NaHCO_3$ (aq) and extracted with $CH_2Cl_2$ (×3). The organic phase was combined, dried over $Na_2SO_4$ and filtered. The filtrate was concentrated down and purified by silica gel column (0-50% EtOAc in hexanes) to give CC. ¹H NMR: (CDCl₃, 300 MHz): δ 7.70-7.44 (m, 4H), 7.14-6.99 (m, 1H), 6.18 (d, J=15.3 Hz, 1H), 4.78 (s 2H), 4.27-4.19 (m, 2H), 4.05 (s, 2H), 2.28-2.15 (m, 2H), 1.59-1.14 (m, 2H), 1.28 (t, J=7.5 Hz, 3H), 0.98-0.91 (m, 3H). LCMS-ESI⁺: calc'd for $C_{21}H_{25}N_6O_4$: 425.5 (M+H⁺); Found: 425.1 (M+H⁺).

Scheme 51

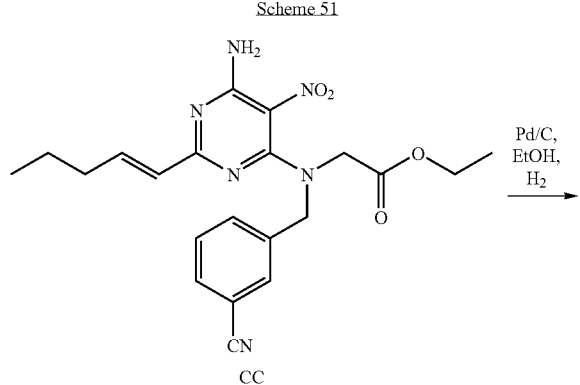

-continued

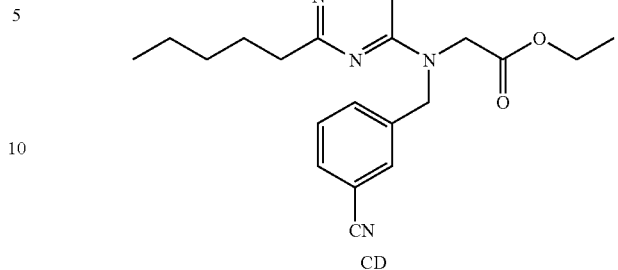

Method XLIV: Compound CD. To a solution of CC (200 mg, 0.47 mmol) in EtOH (5 ml) was added Pd/C (100 mg). The reaction vessel was flushed with $H_2$ and then stirred under an $H_2$ atmosphere for 20 min. Then more Pd/C (30 mg) was added and stirred for another 10 min. The reaction mixture was filtered over Celite and was concentrated to give CD, which was used without purification. LCMS-ESI⁻: calc'd for $C_{21}H_{27}N_6O_4$: 427.5 (M+H⁺); Found: 427.2 (M+H⁺).

Scheme 52

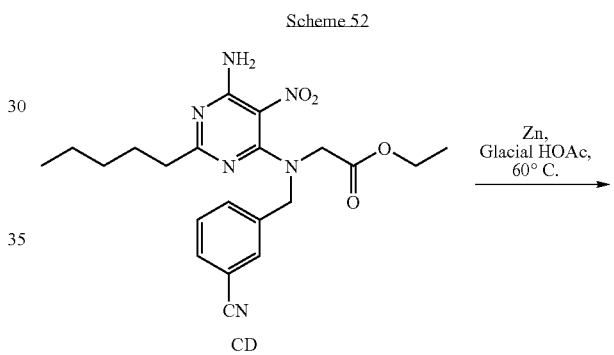

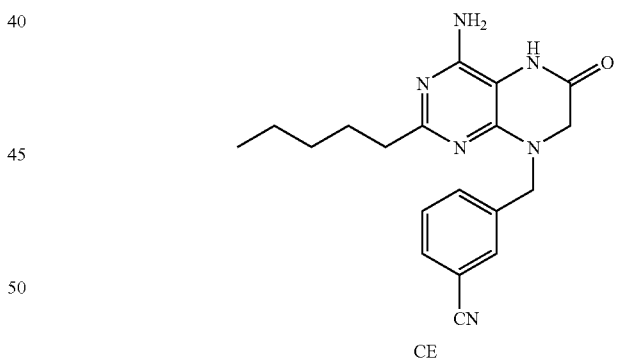

Method XLV: Compound CE. To a solution of CD (120 mg, 0.28 mmol) in glacial acetic acid (3 ml) was added zinc powder (370 mg, 5.7 mmol). The reaction mixture was stirred at 60° C. for 3 h. The solvent was removed to dryness under reduced pressure. The residue was washed with saturated $NaHCO_3$ (aq) solution and extracted with $CH_2Cl_2$ (×3). The organic phase was combined, dried over $Na_2SO_4$ and filtered. The filtrate was concentrated down and purified by silica gel column (0-100% EtOAc in hexanes) to give CE. ¹H NMR (CD₃OD, 300 MHz): δ 7.80-7.52 (m, 4H), 4.79 (s, 2H), 3.98 (s, 2H), 3.35 (s, 2H), 1.69-1.29 (m, 6H), 0.90-0.86 (m, 3H). LCMS-ESI⁻: calc'd for $C_{19}H_{23}N_6O$: 351.4 (M+H⁺); Found: 351.2 (M+H⁺).

Scheme 53: Example 53

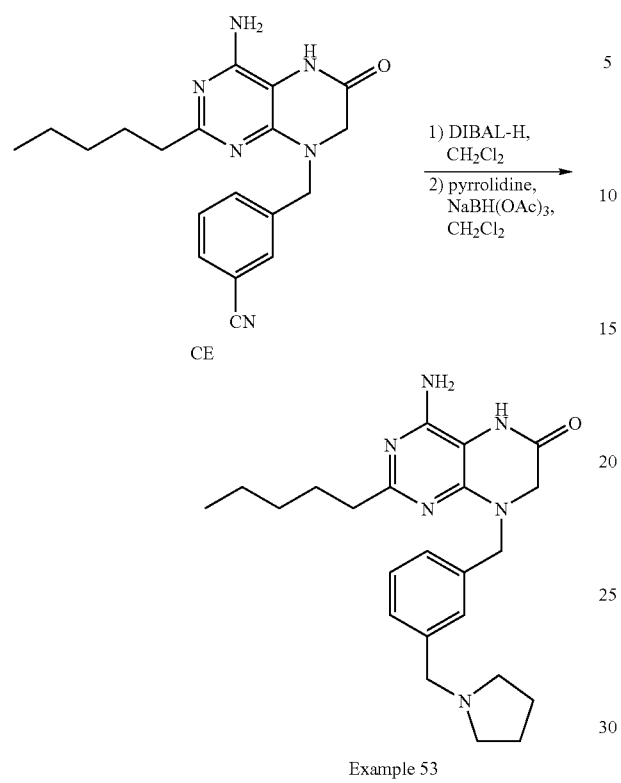

Method XLVI: Example 53.

To a solution of CE (50 mg, 0.14 mmol) in CH$_2$Cl$_2$ (2 ml) at 0° C. was added DIBAL-H (1M in toluene, 710 μL, 0.71 mmol) dropwise. The reaction mixture was stirred at 0° C. for 15 min. The reaction was quenched by water. The mixture was extracted with CH$_2$Cl$_2$ (×3). The organic phase was combined, dried over Na$_2$SO$_4$ and filtered. The filtrate was concentrated down. The residue was dissolved in CH$_2$Cl$_2$/MeOH(1:1, 2 ml) and to this was added pyrrolidine (60 μL, 0.72 mmol), sodium triacetoxyborohydride (75 mg, 0.35 mmol) at 0° C. The reaction mixture was stirred at room temperature for 1 h. The reaction was quenched by adding drops of 1N HCl, filtered and purified by reverse phase HPLC (5-100% Acetonitrile in H$_2$O) to give Example 53. $^1$H-NMR (300 MHz, methanol-d$_4$): δ 7.49-7.47 (m, 4H), 4.82 (s, 2H), 4.99 (s, 2H), 4.38 (s, 2H), 4.14 (s, 2H), 3.47-3.42 (m, 2H), 3.22-3.18 (m, 2H), 2.72 (t, J=7.2 Hz, 2H), 2.20-2.16 (m, 2H), 2.03-2.00 (m, 2H), 1.36-1.34 (m, 4H), 0.90 (t, J=6.6 Hz, 3H). LCMS-ESI$^+$: calc'd for C$_{23}$H$_{33}$N$_6$O: 409.5 (M+H$^+$); Found: 409.1 (M+H$^+$).

Scheme 54: Example 54

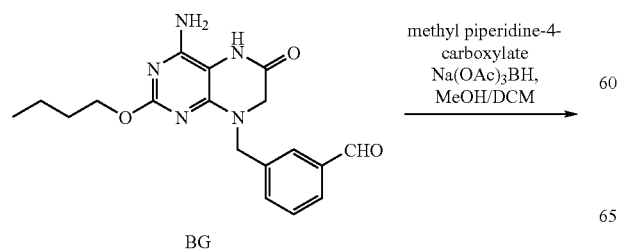

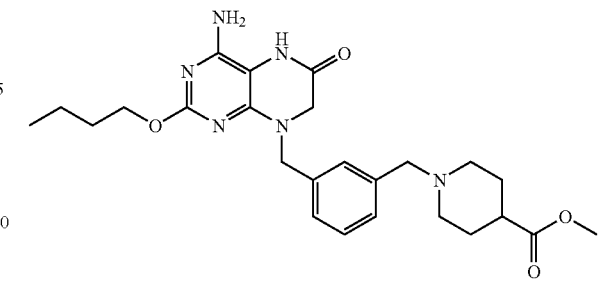

Method XLVII: Example 54.

To a solution of the aldehyde BG (20 mg, 0.056 mmol) in MeOH/CH$_2$Cl$_2$ (1:1, 3 ml) was added methyl piperidine-4-carboxylate (40 mg, 0.28 mmol) and sodium triacetoxyborohydride (30 mg, 0.14 mmol) at 0° C. The reaction mixture was stirred at room temperature for 2 days. The reaction was quenched by adding drops of 1N HCl, filtered and purified by reverse phase HPLC (5-100% acetonitrile in H$_2$O) to give Example 54. $^1$H NMR (CD$_3$OD, 300 MHz): δ 7.53-7.48 (m, 4H), 4.92 (s, 2H), 4.39-4.33 (m, 4H), 4.09 (s, 2H), 3.70 (s, 3H), 3.55-3.51 (m, 2H), 3.08-2.99 (m, 2H), 2.70-2.66 (m, 1H), 2.25-2.20 (m, 2H), 1.87-1.82 (m, 2H), 1.75-1.67 (m, 2H), 1.48-1.40 (m, 2H), 0.94 (t, J=7.8 Hz, 3H). LCMS-ESI$^+$: calc'd for C$_{25}$H$_{35}$N$_6$O$_4$: 483.6 (M+H$^+$); Found: 483.3 (M+H$^+$).

Compound CF, Prepared Using Method XI:

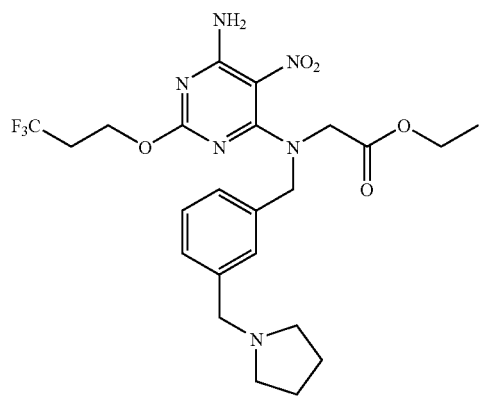 [SMILES: CCOC(=O)CN(Cc1cccc(CN2CCCC2)c1)c1nc(OCCC(F)(F)F)nc(N)c1[N+](=O)[O-]]

$^1$H NMR (CD$_3$OD, 300 MHz): δ 7.52-7.36 (m, 4H), 4.78 (s, 1H), 4.39 (t, J=6.3 Hz, 2H), 4.20 (s, 1H), 4.17 (q, J=7.0 Hz, 2H), 4.08 (s, 1H), 3.36 (s, 1H), 3.06 (m, 4H), 2.60 (qt, J$_{FH}$=8.5 Hz, J$_{HH}$=6.3 Hz, 2H), 1.98 (m, 4H), 1.25 (t, J=7.0 Hz, 3H).

$^{19}$F NMR (CD$_3$OD, 282 MHz): δ −66.8 (t, J$_{FH}$=8.5 Hz, 3F). LCMS-ESI$^+$: calc'd for C$_{23}$H$_{30}$F$_3$N$_6$O$_6$: 527.2 (M+H$^+$); Found: 527.2 (M+H$^+$).

Example 55

Prepared Using Method XII

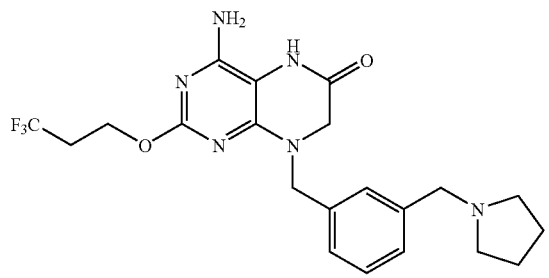 [SMILES: Nc1nc(OCCC(F)(F)F)nc2c1NC(=O)CN2Cc1cccc(CN2CCCC2)c1]

$^1$H NMR (CD$_3$OD, 300 MHz): δ 7.40-7.20 (m, 4H), 4.77 (s, 1H), 4.40 (t, J=6.3 Hz, 2H), 4.39 (s, 1H), 3.92 (s, 1H), 3.31 (s, 1H), 2.50 (m, 4H), 2.11-1.95 (m, 2H), 1.78 (m, 4H) [free base]. $^{19}$F NMR (CD$_3$OD, 282 MHz): δ −66.8 (m, 3F). LCMS-ESI$^+$: calc'd for C$_{21}$H$_{26}$F$_3$N$_6$O$_2$: 451.2 (M+H$^+$); Found: 451.2 (M+H$^+$).

Compound BI, Prepared Using Method XI:

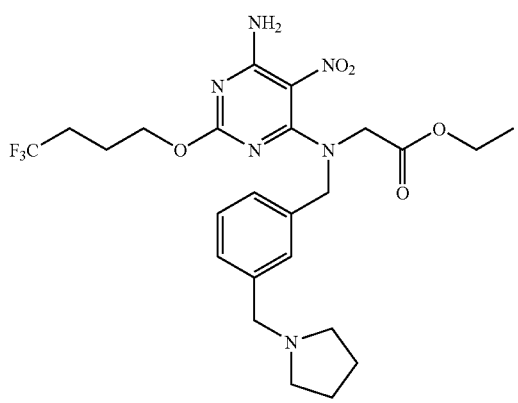 [SMILES: CCOC(=O)CN(Cc1cccc(CN2CCCC2)c1)c1nc(OCCCC(F)(F)F)nc(N)c1[N+](=O)[O-]]

$^1$H NMR (CD$_3$OD, 300 MHz): δ 7.40-7.25 (m, 4H), 4.76 (s, 1H), 4.26 (t, J=6.3 Hz, 2H), 4.17 (q, J=7.0 Hz, 2H), 4.16 (s, 1H), 3.72 (s, 1H), 3.32 (s, 1H), 2.63 (m, 4H), 2.28 (qt, J$_{FH}$=11.4 Hz, J$_{HH}$=6.3 Hz, 2H), 1.95-1.75 (m, 2H), 1.83 (m, 4H), 1.25 (t, J=7.0 Hz, 3H). $^{19}$F NMR (CD$_3$OD, 282 MHz): δ −68.5 (t, J$_{FH}$=11.4 Hz, 3F). LCMS-ESI$^+$: calc'd for C$_{24}$H$_{32}$F$_3$N$_6$O$_5$: 541.2 (M+H$^+$); Found: 541.2 (M+H$^+$).

Example 56

Prepared Using Method XII

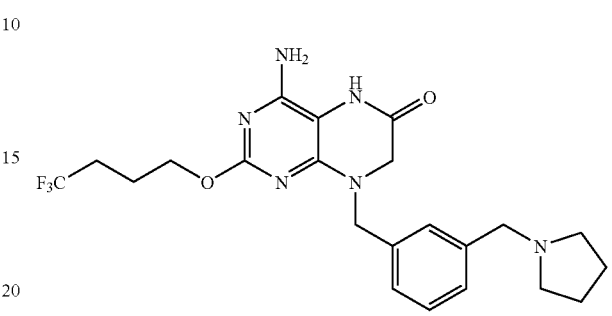

$^1$H NMR (CD$_3$OD, 300 MHz): δ 7.40-7.20 (m, 4H), 4.79 (s, 1H), 4.27 (t, J=6.3 Hz, 2H), 4.27 (s, 1H), 3.91 (s, 1H), 3.34 (s, 1H), 2.69 (m, 4H), 2.34-2.18 (m, 2H), 1.96-1.82 (m, 2H), 1.85 (m, 4H) [free base]. $^{19}$F NMR (CD$_3$OD, 282 MHz): δ −68.5 (m, 3F). LCMS-ESI$^+$: calc'd for C$_{21}$H$_{28}$F$_3$N$_6$O$_2$: 465.2 (M+H$^+$); Found: 465.2 (M+H$^+$).

Compound CG, Prepared Using Method XV Parts 1 and 2:

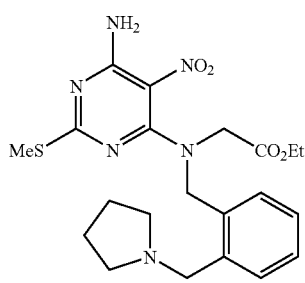 [SMILES: CCOC(=O)CN(Cc1ccccc1CN1CCCC1)c1nc(SC)nc(N)c1[N+](=O)[O-]]

$^1$H NMR (CD$_3$OD, 300 MHz): δ 7.25-7.37 (m, 2H), 4.75 (s, 2H), 4.12 (m, 4H), 3.52 (s, 2H), 2.38 (s, 3H), 2.35 (m, 4H), 1.73 (m, 4H), 1.20 (t, J=7 Hz, 3H). LCMS-ESI$^+$: calc'd for C$_{21}$H$_{29}$N$_6$O$_4$S: 461.6 (M+H$^+$); Found: 461.2 (M+H).

Compound CH, Prepared Using Method VIII:

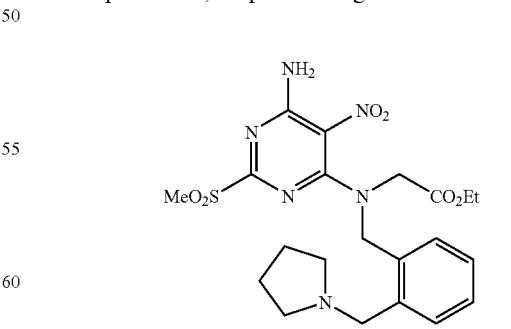

Ethyl-N$_a$-[4-amino-2-methanesulfonyl-5-nitropyrimidin-6-yl],N$_a$-[2'-(pyrrolidin-1"-ylmethyl)-benzyl]-glycinate: LCMS-ESI$^+$: calc'd for C$_{21}$H$_{29}$N$_6$O$_6$S; 493.6 (M+H$^+$); Found: 493.2 (M+H).

Compound CI, Prepared Using Method X:

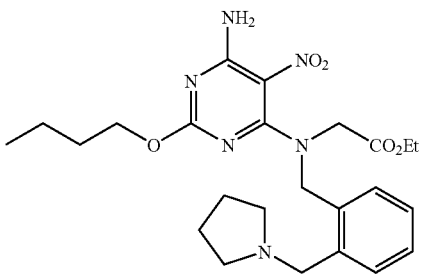 [SMILES: CCCCOc1nc(N)c([N+](=O)[O-])c(N(CC(=O)OCC)Cc2ccccc2CN2CCCC2)n1]

¹H NMR (CD₃OD, 300 MHz): δ 7.26-7.34 (m, 4H), 4.77 (s, 2H), 4.07-4.23 (m, 6H), 3.53 (s, 2H), 2.36 (m, 4H), 1.73 (m, 4H), 1.64 (m, 2H), 1.41 (m, 2H), 1.22 (t, J=7 Hz, 3H), 0.94 (t, J=7 Hz, 3H). LCMS-ESI⁺: calc'd for $C_{24}H_{35}N_6O_5$: 487.6 (M+H⁺); Found: 487.2 (M+H⁺).

Example 57

Prepared Using Method XII

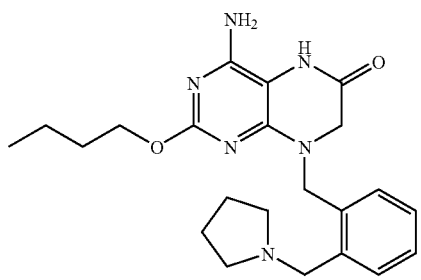 [SMILES: CCCCOc1nc(N)c2c(n1)N(Cc1ccccc1CN1CCCC1)CC(=O)N2]

¹H NMR (CD₃OD, 300 MHz): δ 7.37-7.67 (m, 4H), 5.20 (s, 2H), 4.58 (s, 2H), 4.39 (t, J=7 Hz, 2H), 4.16 (s, 2H), 3.61 (m, 2H), 3.31 (m, 2H), 2.21 (m, 2H), 2.09 (m, 2H), 1.67 (m, 2H), 1.42 (m, 2H), 0.90 (t, J=7 Hz)-[HCl salt]. LCMS-ESI⁺: calc'd for $C_{22}H_{31}N_6O_2$: 411.5 (M+H⁺); Found: 411.2 (M+H⁺).

Compound CJ, Prepared Using Method XI:

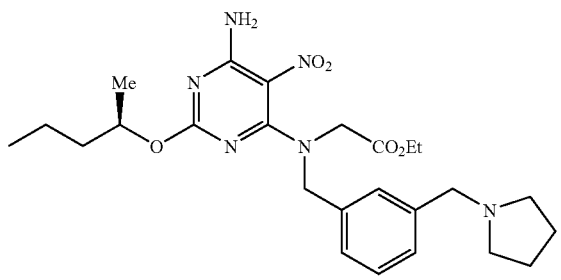 [SMILES: CCC[C@@H](C)Oc1nc(N)c([N+](=O)[O-])c(N(CC(=O)OCC)Cc2cccc(CN3CCCC3)c2)n1]

¹H NMR (CD₃OD, 300 MHz): δ 7.26-7.37 (m, 4H), 4.99 (m, 1H), 4.78 (s, 2H), 4.20 (m, 4H), 3.77 (s, 2H), 2.68 (m, 4H), 1.85 (m, 4H), 1.50-1.62 (m, 2H), 1.29 (m, 2H), 1.25 (m, 6H), 0.90 (t, J=7 Hz, 3H). LCMS-ESI⁺: calc'd for $C_{25}H_{37}N_6O_5$: 501.6 (M+H⁺); Found: 501.2 (M+H⁺).

Example 58

Prepared Using Method XII

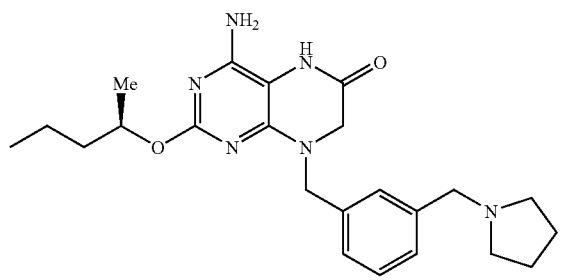 [SMILES: CCC[C@@H](C)Oc1nc(N)c2c(n1)N(Cc1cccc(CN3CCCC3)c1)CC(=O)N2]

¹H NMR (CD₃OD, 300 MHz): δ 7.64 (s, 1H), 7.49 (m, 3H), 5.16 (m, 1H), 4.94 (s, 2H), 4.38 (s, 2H), 4.18 (s, 2H), 3.47 (m, 2H), 3.16 (m, 2H), 2.16 (m, 2H), 2.03 (m, 2H), 1.55-1.72 (m, 2H), 1.32 (m, 5H), 0.87 (t, J=7 Hz, 3H)—[HCl salt]. LCMS-ESI⁺: calc'd for $C_{23}H_{33}N_6O_2$: 425.5 (M+H⁺); Found: 425.2 (M+H⁺), Compound CK, Prepared Using Method XI:

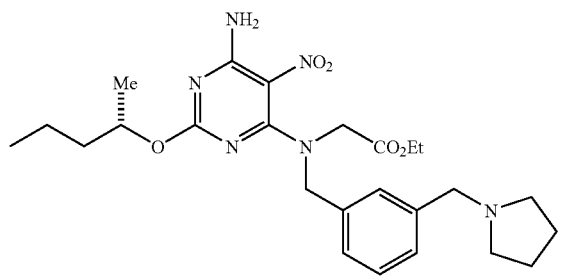 [SMILES: CCC[C@H](C)Oc1nc(N)c([N+](=O)[O-])c(N(CC(=O)OCC)Cc2cccc(CN3CCCC3)c2)n1]

¹H NMR (CD₃OD, 300 MHz): δ 7.26-7.37 (m, 4H), 4.99 (m, 1H), 4.78 (s, 2H), 4.20 (m, 4H), 3.77 (s, 2H), 2.68 (m, 4H), 1.85 (m, 4H), 1.50-1.62 (m, 2H), 1.29 (m, 2H), 1.25 (m, 6H), 0.90 (t, J=7 Hz, 3H). LCMS-ESI⁺: calc'd for $C_{25}H_{37}N_6O_5$: 501.6 (M+H⁺); Found: 501.2 (M+H⁺).

Example 59

Prepared Using Method XII

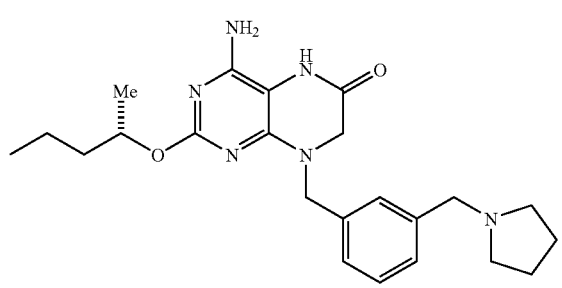 [SMILES: CCC[C@H](C)Oc1nc(N)c2c(n1)N(Cc1cccc(CN3CCCC3)c1)CC(=O)N2]

¹H NMR (CD₃OD, 300 MHz): δ 7.64 (s, 1H), 7.49 (m, 3H), 5.16 (m, 1H), 4.94 (s, 2H), 4.38 (s, 2H), 4.18 (s, 2H), 3.47 (m,

2H), 3.16 (m, 2H), 2.16 (m, 2H), 2.03 (m, 2H), 1.55-1.72 (m, 2H), 1.32 (m, 5H), 0.87 (t, J=7 Hz, 3H)—[HCl salt]. LCMS-ESI$^+$: calc'd for C$_{23}$H$_{33}$N$_6$O$_2$: 425.5 (M+H$^+$); Found: 425.2 (M+H$^+$).

Compound CL, Prepared Using Method XI:

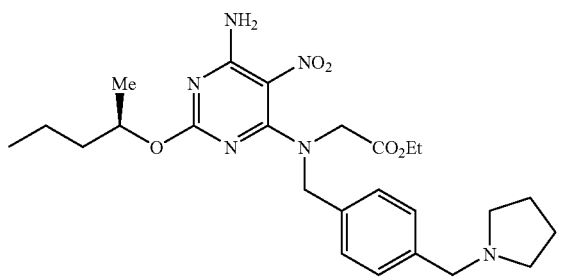 [SMILES: CCC[C@@H](C)Oc1nc(N)c([N+](=O)[O-])c(N(CC(=O)OCC)Cc2ccc(CN3CCCC3)cc2)n1]

$^1$H NMR (CD$_3$OD, 300 MHz): δ 7.31 (m, 4H), 5.00 (m, 1H), 4.76 (s, 2H), 4.19 (q, J=7 Hz, 2H), 4.13 (s, 2H), 3.64 (s, 2H), 2.56 (m, 4H), 1.82 (m, 4H), 1.62 (m, 2H), 1.40 (m, 2H), 1.25 (m, 6H), 0.90 (t, J=7 Hz, 3H). LCMS-ESI$^+$: calc'd for C$_{25}$H$_{37}$N$_6$O$_5$: 501.6 (M+H$^+$); Found: 501.2 (M+H$^+$).

Example 60

Prepared Using Method XII

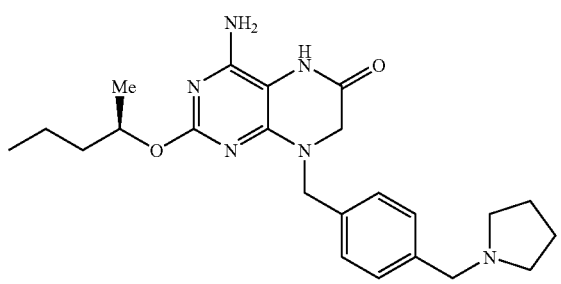 [SMILES: CCC[C@@H](C)Oc1nc(N)c2c(n1)N(Cc1ccc(CN3CCCC3)cc1)CC(=O)N2]

$^1$H NMR (CD$_3$OD, 300 MHz): δ 7.47-7.58 (m, 4H), 5.12 (m, 1H), 4.94 (s, 2H), 4.39 (s, 2H), 4.14 (s, 2H), 3.47 (m, 2H), 3.19 (m, 2H), 2.12 (m, 2H), 2.03 (m, 2H), 1.55-1.72 (m, 2H), 1.36 (m, 5H), 0.87 (t, J=7 Hz, 3H)—[HCl salt]. LCMS-ESI$^+$: calc'd for C$_{23}$H$_{33}$N$_6$O$_2$: 425.5 (M+H$^+$); Found: 425.2 (M+H$^+$).

Compound CM, Prepared Using Method XI:

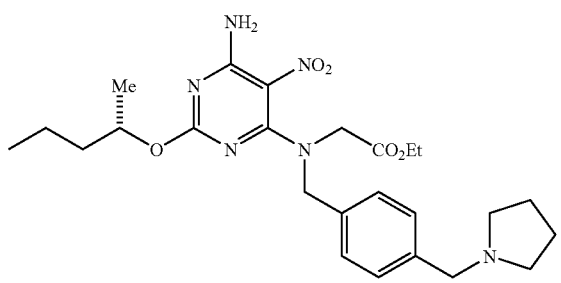 [SMILES: CCC[C@H](C)Oc1nc(N)c([N+](=O)[O-])c(N(CC(=O)OCC)Cc2ccc(CN3CCCC3)cc2)n1]

$^1$H NMR (CD$_3$OD, 300 MHz): δ 7.31 (m, 4H), 5.00 (m, 1H), 4.76 (s, 2H), 4.19 (q, J=7 Hz, 2H), 4.13 (s, 2H), 3.64 (s, 2H), 2.56 (m, 4H), 1.82 (m, 4H), 1.62 (m, 2H), 1.40 (m, 2H), 1.25 (m, 6H), 0.90 (t, J=7 Hz, 3H). LCMS-ESI$^+$: calc'd for C$_{25}$H$_{37}$N$_6$O$_5$: 501.6 (M+H$^+$); Found: 501.2 (M+H$^+$).

Example 61

Prepared Using Method XII

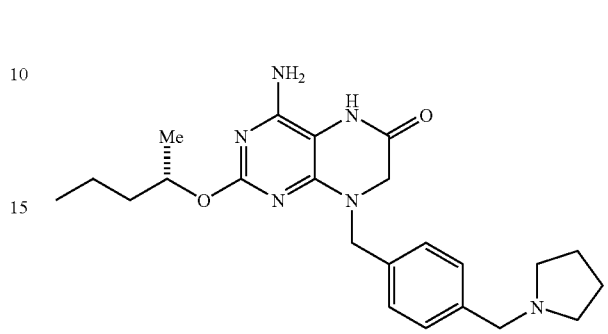

$^1$H NMR (CD$_3$OD, 300 MHz): δ 7.47-7.58 (m, 4H), 5.12 (m, 1H), 4.94 (s, 2H), 4.39 (s, 2H), 4.14 (s, 2H), 3.47 (m, 2H), 3.19 (m, 2H), 2.12 (m, 2H), 2.03 (m, 2H), 1.55-1.72 (m, 2H), 1.36 (m, 5H), 0.87 (t, J=7 Hz, 3H)—[HCl salt]. LCMS-ESI$^+$: calc'd for C$_{23}$H$_{33}$H$_6$O$_2$: 425.5 (M+H$^+$); Found: 425.2 (M+H$^+$).

Compound CN, Prepared Using Method X:

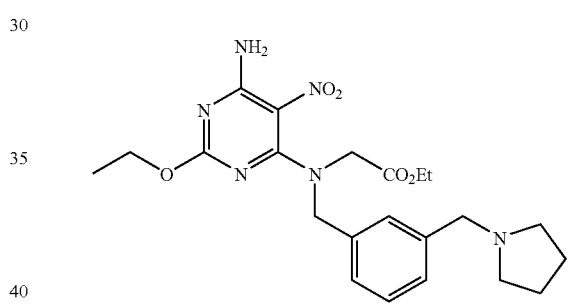

$^1$H NMR (CD$_3$OD, 300 MHz): δ 7.22-7.32 (m, 4H), 4.76 (s, 2H), 4.14-4.29 (m, 6H), 3.63 (s, 2H), 2.53 (m, 4H), 1.80 (m, 4H), 1.28 (m, 6H). LCMS-ESI$^+$: calc'd for C$_{22}$H$_{31}$N$_6$O$_3$: 459.5 (M+H$^+$); Found: 459.2 (M+H$^+$).

Example 62

Prepared Using Method XII

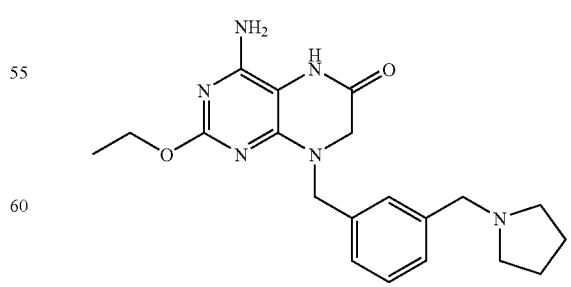

$^1$H NMR (CD$_3$OD, 300 MHz): δ 7.68 (s, 1H), 7.49 (m, 3H), 4.96 (s, 2H), 4.48 (q, J=7 Hz, 2H), 4.41 (s, 2H), 4.15 (s, 2H), 3.47 (m, 2H), 3.18 (m, 2H), 2.17 (m, 2H), 2.03 (m, 2H), 1.37

(t, J=7 Hz, 3H). LCMS-ESI⁺: calc'd for C₂₀H₂₇N₆O₂: 383.5 (M+H⁺); Found: 383.1 (M+H⁺).

Compound CM, Prepared Using Method X:

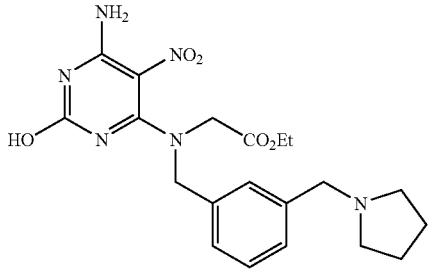 [SMILES: CCOC(=O)CN(Cc1cccc(CN2CCCC2)c1)c1nc(O)nc(N)c1[N+](=O)[O-]]

¹H NMR (CD₃OD, 300 MHz): δ 7.42-7.56 (m, 4H), 4.81 (s, 2H), 4.40 (s, 2H), 4.21 (q, J=7 Hz, 2H), 4.12 (s, 2H), 3.50 (m, 2H), 3.17 (m, 2H), 2.17 (m, 2H), 2.00 (m, 2H), 1.25 (t, J=7 Hz, 3H). LCMS-ESI⁺: calc'd for C₂₀H₂₇N₆O₅: 431.5 (M+H⁺); Found: 431.2 (M+H⁺).

Example 63

Prepared Using Method XII

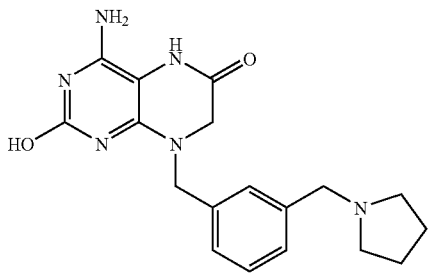 [SMILES: Nc1nc(O)nc2c1NC(=O)CN2Cc1cccc(CN2CCCC2)c1]

¹H NMR (CD₃OD, 300 MHz): δ 7.64 (s, 1H), 7.45-7.53 (m, 3H), 4.85 (s, 2H), 4.40 (s, 2H), 4.08 (s, 2H), 3.48 (m, 2H), 3.18 (m, 2H), 2.14 (m, 2H), 2.01 (m, 2H). LCMS-ESI⁺: calc'd for C₁₈H₂₃N₆O₂: 355.4 (M+H⁺); Found: 355.1 (M+H⁺).

Compound CN, Prepared Using Method IV and Method VII Parts 1 and 2:

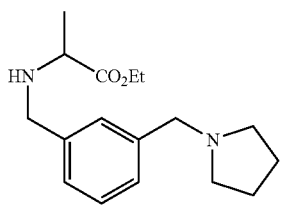

LCMS-ESI⁺: calc'd for C₁₂H₂₇N₂O₂: 291.4 (M+H⁺); Found: 291.2 (M+H).

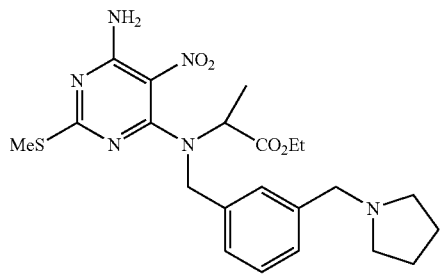 [SMILES: CCOC(=O)C(C)N(Cc1cccc(CN2CCCC2)c1)c1nc(SC)nc(N)c1[N+](=O)[O-]]

¹H NMR (CD₃OD, 300 MHz): δ 7.27 (s, 1H), 7.20 (m, 3H), 4.78 (d, J=16 Hz, 1H), 4.63 (q, J=7 Hz, 1H), 4.55 (d, J=16 Hz, 1H), 4.20 (m, 2H), 3.56 (m, 2H), 2.44 (m, 2H), 2.36 (s, 3H), 1.76 (m, 4H), 1.63 (d, J=7 Hz, 3H), 1.25 (t, J=7 Hz, 3H). LCMS-ESI⁺: calc'd for C₂₂H₃₁N₆O₄S: 475.6 (M+H⁺); Found: 475.2 (M+H).

Compound CO, Prepared Using Method VIII:

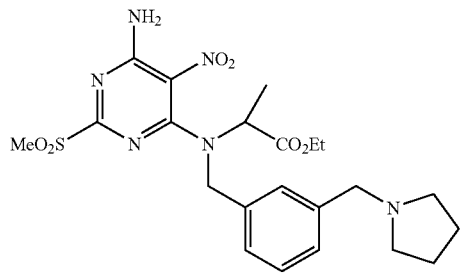 [SMILES: CCOC(=O)C(C)N(Cc1cccc(CN2CCCC2)c1)c1nc(S(C)(=O)=O)nc(N)c1[N+](=O)[O-]]

LCMS-ESI⁺: calc'd for C₂₂H₃₁N₆O₆S: 507.6 (M+H⁺); Found: 507.2 (M+H).

Compound CP, Prepared Using Method X:

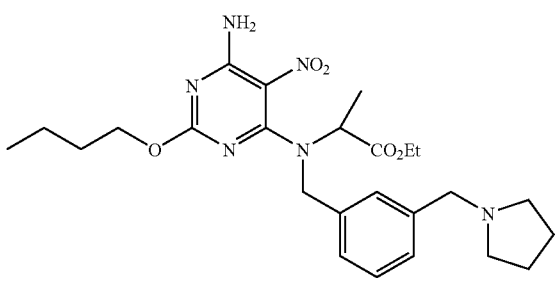 [SMILES: CCCCOc1nc(N)c([N+](=O)[O-])c(N(Cc2cccc(CN3CCCC3)c2)C(C)C(=O)OCC)n1]

¹H NMR (CD₃OD, 300 MHz): δ 7.30 (s, 1H), 7.22 (m, 3H), 4.80 (d, J=16 Hz, 1H), 4.57 (m, 2H), 4.12-4.25 (m, 4H), 3.58 (m, 2H), 2.46 (m, 4H), 1.76 (m, 4H), 1.62 (m, 5H), 1.44 (m,

2H), 1.24 (t, J=7 Hz, 3H), 0.96 (t, J=7 Hz). LCMS-ESI⁺: calc'd for $C_{25}H_{37}N_6O_5$: 501.6 (M+H⁺); Found: 501.2 (M+H).

Example 64

Prepared Using Method XII

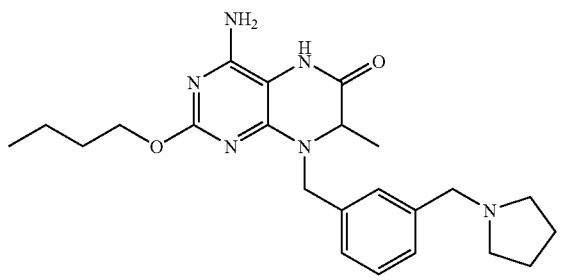 [SMILES: CCCCOc1nc(N)c2c(n1)N(Cc1cccc(CN3CCCC3)c1)C(C)C(=O)N2]

¹H NMR (CD₃OD, 300 MHz): δ 7.66 (s, 1H), 7.49 (m, 3H), 5.34 (d, J=16 Hz, 1H), 4.64 (d, J=16 Hz, 1H), 4.40 (m, 4H), 4.22 (q, J=7 Hz, 1H), 3.46 (m, 2H), 3.18 (m, 2H), 2.17 (m, 2H), 2.03 (m, 2H), 1.70 (m, 2H), 1.44 (m, 5H), 0.93 (t, J=7 Hz, 3H). LCMS-ESI⁺: calc'd for $C_{23}H_{33}N_6O_2$: 425.5 (M+H⁺); Found: 425.2 (M+H).

Compound CQ: Prepared Via Method IV:

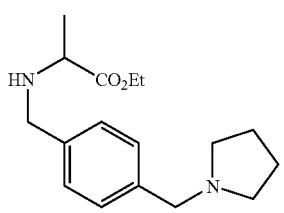 [SMILES: CCOC(=O)C(C)NCc1ccc(CN2CCCC2)cc1]

LCMS-ESI⁺: calc'd for $C_{12}H_{27}N_2O_2$: 291.4 (M+H⁺); Found: 291.1 (M+H).

Compound CR, Prepared Using Method VII Parts 1 and 2:

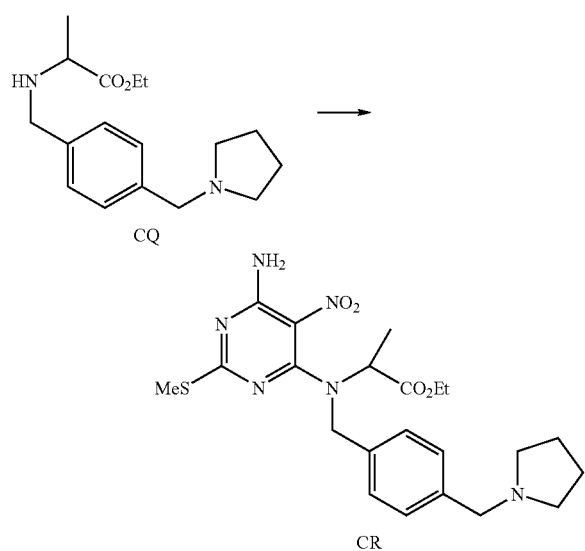

¹H NMR (CD₃OD, 300 MHz): δ 7.21-7.30 (m, 4H), 4.76 (d, J=16 Hz, 1H), 4.57 (m, 2H), 4.20 (m, 2H), 3.58 (s, 2H), 2.50 (m, 4H), 2.36 (s, 3H), 1.78 (m, 4H), 1.62 (d, J=7 Hz, 3H), 1.25 (t, J=7 Hz, 3H). LCMS-ESI⁺: calc'd for $C_{22}H_{31}N_6O_4S$: 475.6 (M+H⁺); Found: 475.2 (M+H).

Compound CS, Prepared Using Method VIII:

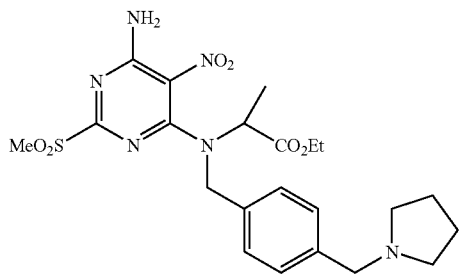 [SMILES: CCOC(=O)C(C)N(Cc1ccc(CN2CCCC2)cc1)c1nc(S(C)(=O)=O)nc(N)c1[N+](=O)[O-]]

LCMS-ESI⁺: calc'd for $C_{22}H_{31}N_6O_6S$: 507.6 (M+H⁺); Found: 507.2 (M+H).

Compound CT, Prepared Using Method X:

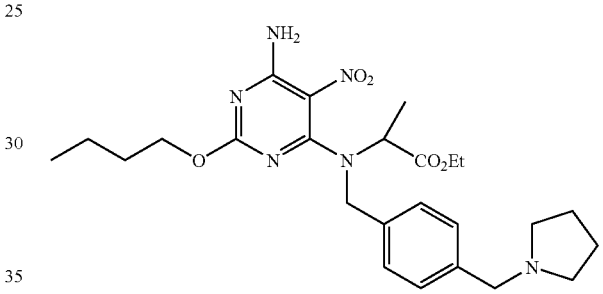

¹H NMR (CD₃OD, 300 MHz): δ 7.23-7.31 (m, 4H), 4.78 (d, J=16 Hz, 1H), 4.54 (m, 2H), 4.11-4.22 (m, 4H), 3.59 (m, 2H), 2.51 (m, 4H), 1.79 (m, 4H), 1.62 (m, 5H), 1.43 (m, 2H), 1.25 (t, J=7 Hz, 3H), 0.95 (t, J=7 Hz). LCMS-ESI⁺: calc'd for $C_{25}H_{37}N_6O_5$: 501.6 (M+H⁺); Found: 501.2 (M+H).

Example 65

Prepared Using Method XII

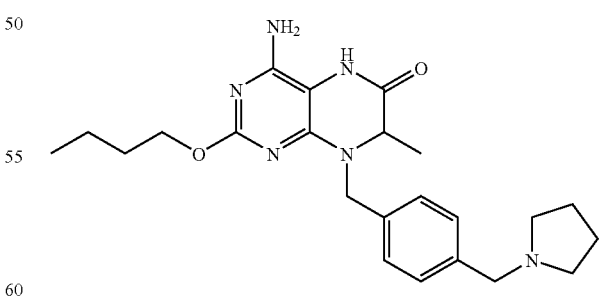

¹H NMR (CD₃OD, 300 MHz): δ 7.61 (d, J=8 Hz, 2H), 7.49 (d, J=8 Hz, 2H), 5.32 (d, J=16 Hz, 1H), 4.65 (d, J=16 Hz, 1H), 4.40 (m, 4H), 4.22 (q, J=7 Hz, 1H), 3.48 (m, 2H), 3.19 (m, 2H), 2.17 (m, 2H), 2.03 (m, 2H), 1.70 (m, 2H), 1.45 (m, 5H), 0.94 (t, J=7 Hz, 3H). LCMS-ESI⁺: calc'd for $C_{23}H_{33}N_6O_2$: 425.5 (M+H⁺); Found: 425.2 (M+H).

Scheme 55: Example 66, Method VIII followed by Method X followed by Method XII

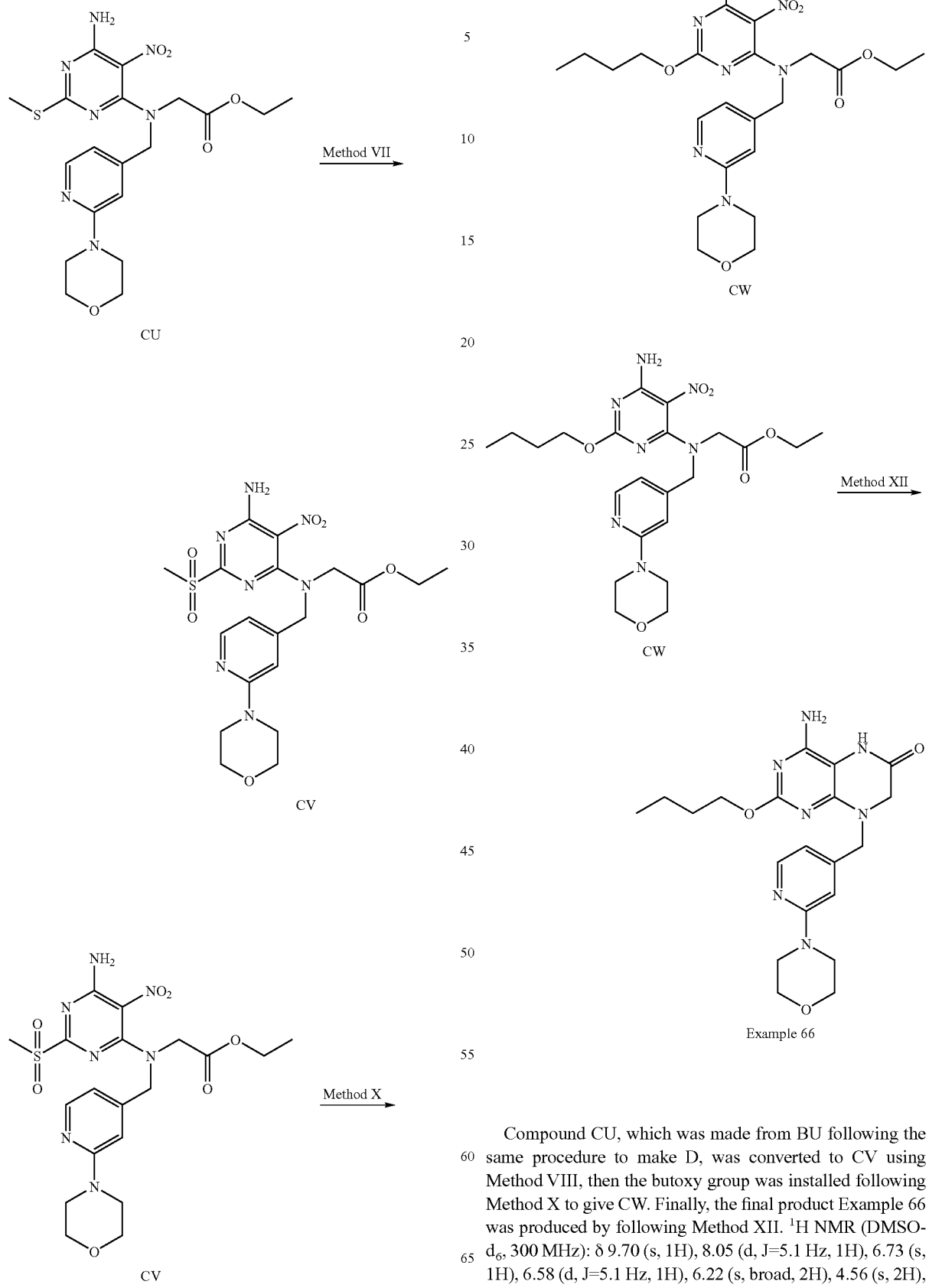

Example 66

Compound CU, which was made from BU following the same procedure to make D, was converted to CV using Method VIII, then the butoxy group was installed following Method X to give CW. Finally, the final product Example 66 was produced by following Method XII. $^1$H NMR (DMSO-$d_6$, 300 MHz): δ 9.70 (s, 1H), 8.05 (d, J=5.1 Hz, 1H), 6.73 (s, 1H), 6.58 (d, J=5.1 Hz, 1H), 6.22 (s, broad, 2H), 4.56 (s, 2H), 4.06-4.02 (m, 2H), 3.86 (s, 2H), 3.67-3.66 (m, 4H), 3.41-3.37

(m, 4H), 1.57-1.50 (m, 2H), 1.35-1.17 (m, 2H), 0.88-0.83 (m, 3H). LCMS-ESI⁺: calc'd for C₂₀H₂₈N₇O₃: 413.47 (M+H⁺); Found: 414.1 (M+H⁺).

Example 67

Method X Followed by Method XII

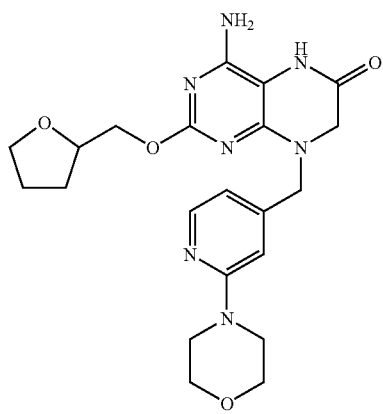 [SMILES: Nc1nc(OCC2CCCO2)nc2c1NC(=O)CN2Cc1ccnc(N2CCOCC2)c1]

From the corresponding sulfone/sulfoxide, this compound was made following Method X using tetrahydrofurfurol as the alcohol. Method XII was then employed to achieve the final product. ¹H NMR (DMSO-d₆, 300 MHz): δ 9.71 (s, broad, 1H), 8.05 (d, J=5.1 Hz, 1H), 6.73 (s, 1H), 6.54 (d, J=4.8 Hz, 1H), 6.23 (s, broad, 2H), 4.56 (s, 2H), 4.01 (s, 2H), 3.87 (s, 2H), 3.71-3.58 (m, 7H), 3.46-3.39 (m, 4H), 1.93-1.75 (m, 4H). LCMS-ESI⁺: calc'd for C₂₁H₂₈N₇O₄: 441.48 (M+H⁺); Found: 442.1 (M+H⁺).

Scheme 56: Prepared Via Method XI

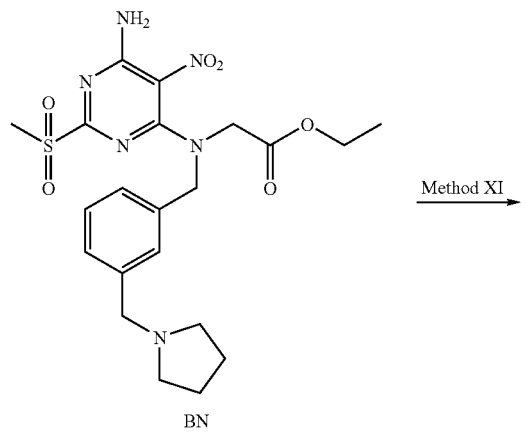

BN

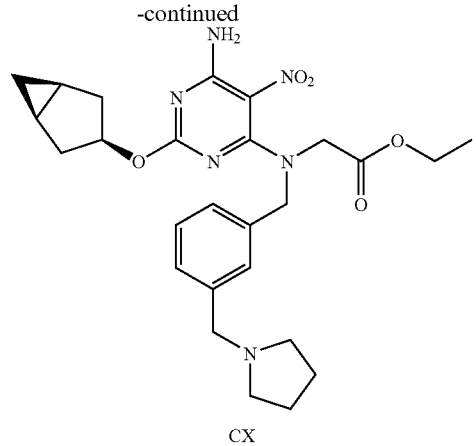

CX

Compound CX was made following Method XI using the corresponding sulfone BN (125 mg) and (1S,3R,5R)-bicyclo[3.1.0]hexan-3-ol (440 mg) with 2.5 mL of DMF as cosolvent and 4 drops of TFA at 102° C. over 2 h. The mixture was quenched with water, diluted with EtOAc, and the pH was adjusted to =8 using solid K₂CO₃. The mixture was partitioned into EtOAc, and the organic layer was dried with Na₂SO₄, filtered, and concentrated in vacuo. Chromatography on silica gel using CH₂Cl₂ and MeOH/CH₂Cl₂ as eluent afforded 23 mg of desired compound CX. LCMS-ESI⁺: calc'd for C₂₆H₃₅N₆O₅: 510.59 (M+H⁺); Found: 511.1 (M+H⁺).

Scheme 57: Example 68, Method XII

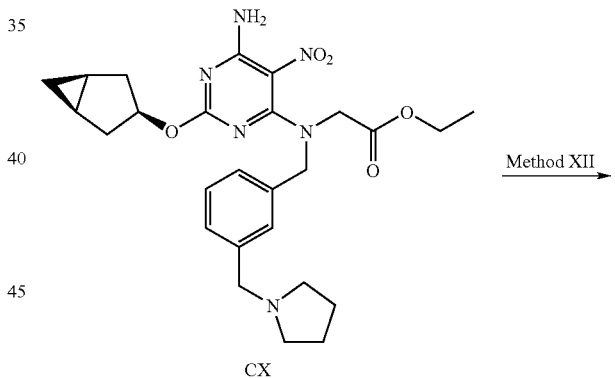

CX

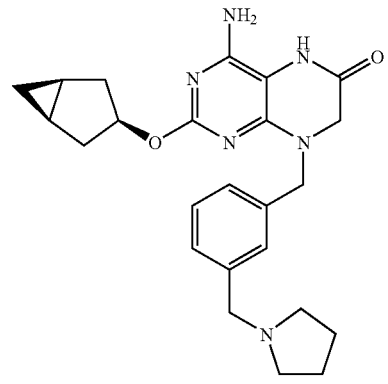

Example 68

The unpurified CX from before was carried forward following: Method XII in MeOH and stirred 3 h until starting material consumed by HPLC/LCMS. The mixture was diluted with CH$_2$Cl$_2$, filtered through short plug of Celite, and the Celite was washed with copious methanol:CH$_2$Cl$_2$ (50-50), and the filtrate was concentrated. The residue was re-dissolved in acetonitrile, and filtered through a 0.2 micron filter to remove any residual Celite. Water was added, the mixture was frozen and lyophilized. 4.7 mg of Example 68 was obtained. $^1$H NMR (DMSO-d$_6$, 300 MHz): δ 11.37 (s, broad, 1H), 10.23-10.17 (m, 1H), 7.54-7.39 (m, 4H), 5.35-5.25 (m, 1H), 4.76 (m, 2H), 4.29-4.28 (m, 2H), 4.05 (m, 3H), 3.28 (s, broad, 2H), 2.98 (s, broad, 2H), 2.14-1.46 (m, 9H), 1.38-1.16 (m, 3H). LCMS-ESI$^+$: calc'd for C$_{24}$H$_{31}$N$_6$O$_2$: 434.53 (M+H$^+$); Found: 435.1 (M+H$^+$).

Scheme 58: Example 69, Method X followed by Method XII

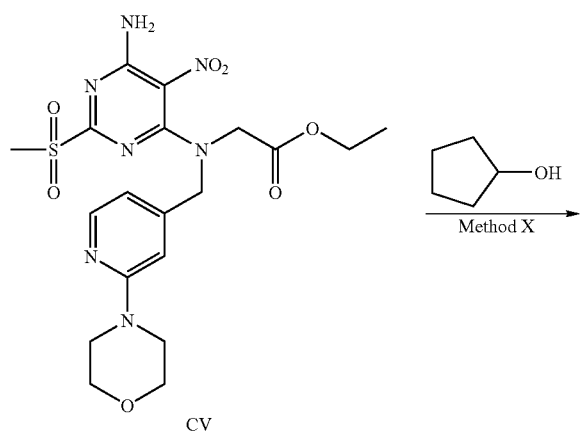

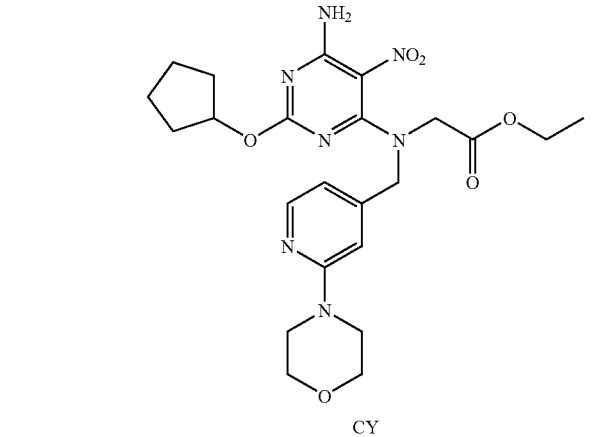

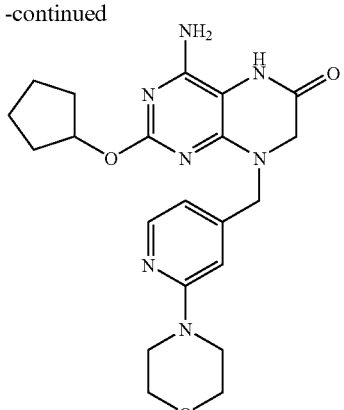

Example 69

Starting from CV, Method X was employed to install the cyclopentoxy functionality on the pyrimidine ring and give CY. This intermediate was then advanced into Method XII to give rise to Example 69. $^1$H NMR: (DMSO-d$_6$, 300 MHz): δ 9.70 (s, broad, 1H), 8.04 (s, 1H), 6.77 (s, 1H), 6.58 (s, 1H), 6.19 (s, broad, 2H), 5.08 (s, broad, 2H), 4.55 (s, broad, 2H), 3.85 (s, broad, 1H), 3.66 (s, broad, 4H), 3.38 (s, broad, 4H), 1.78-1.22 (m, broad, 8H). LCMS-ESI$^+$: calc'd for C$_{21}$H$_{28}$N$_7$O$_3$: 425.48 (M+H$^+$); Found: 426.1 (M+H$^+$).

Scheme 59: Prepared Via Method XVII:

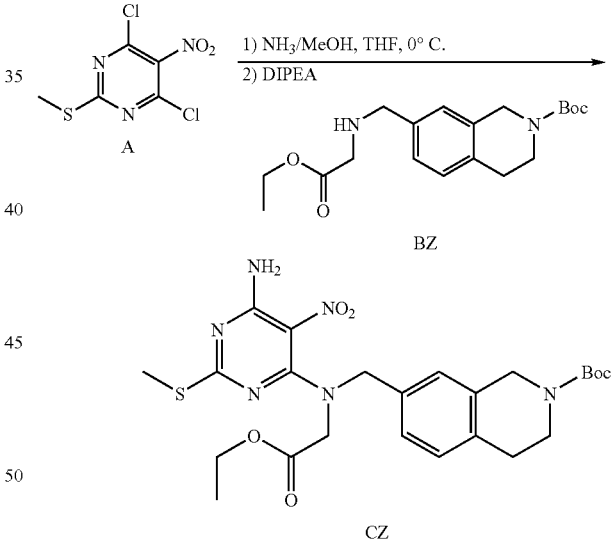

Compound A (224 mg, 0.844 mmol) was dissolved in anhydrous THF (10 mL) and the mixture was stirred under N$_2$(g) in an ice bath. A 7 N NH$_3$ in MeOH solution (131 μL, 0.92 mmol) in THF (1 mL) was added dropwise over 3 minutes. The reaction was stirred for 30 minutes, after which more 7 N NH$_3$ in MeOH solution (40 μL, 0.36 mmol) was added, and the mixture was stirred for 30 more minutes. A solution of BZ (267 mg, 0.767 mmol) in anhydrous THF (2 mL) was added to the reaction, followed by DIPEA (267 μL, 1.53 mmol). The reaction mixture was then stirred for 2 hours at room temperature, diluted reaction with EtOAc and washed with saturated NaHCO$_3$(aq) solution (2×) followed with saturated NaCl(aq). The organic extract was dried over anhydrous Na₂SO₄, filtered, and concentrated under reduced pressure. Purification with silica gel chromatography (0-30% EtOAc in hexanes) gave CZ (353 mg, 0.663 mmol). ¹H NMR (CDCl₃, 300 MHz): δ 7.11-7.04 (m, 3H), 4.66 (s, 2H), 4.55 (s, 2H), 4.21 (m, 2H), 4.05 (s, 2H), 3.64 (m, 2H), 2.82 (m, 2H), 2.42 (s, 3H), 1.50 (s, 9H), 1.27 (t, J=7.2 Hz, 3H).

Scheme 60: Compound CA Prepared Via Method XVIII:

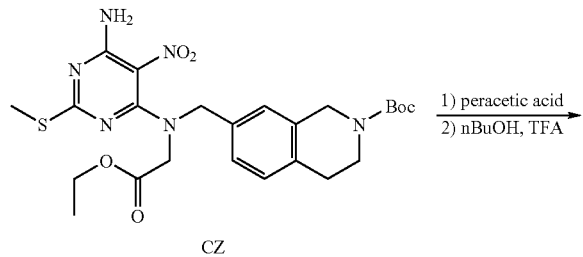

CZ

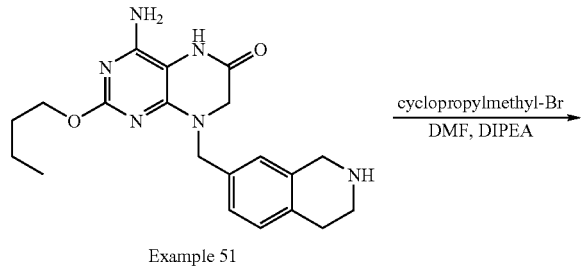

CA

Compound CZ (353 mg, 0.663 mmol) was dissolved in anhydrous acetonitrile (13 mL) and stirred under N₂(g) in an ice bath. A 32% peracetic acid solution (700 µL, 3.22 mmol) was added and the mixture was stirred for 4-5 hours. To this was added saturated Na₂S₂O₃(aq) solution and EtOAc and the mixture was stirred for 5 minutes. The organic extract was then washed with NaHCO₃(aq) solution followed with saturated NaCl(aq), dried over anhydrous Na₂SO₄, filtered, and concentrated under reduced pressure. The intermediate was added to n-BuOH (10 mL) and TFA (204 µL, 2.65 mmol) and then stirred at 100° C. for 7 hours. The mixture was concentrated under reduced pressure to give Compound CA that was used without purification.

Scheme 61: Example 70, Method XLVIII

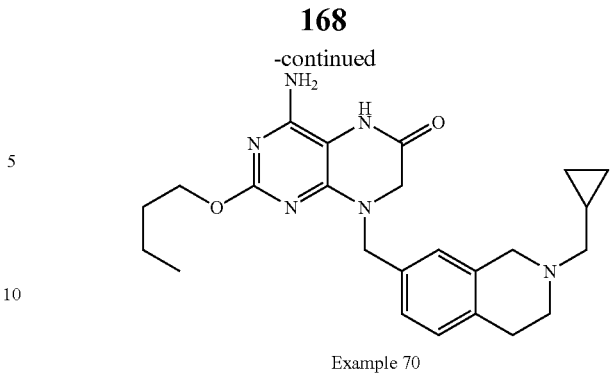

Example 70

Example 51 (20 mg, 0.0417 mmol) was dissolved in anhydrous DMF (1 mL). To this was added bromomethylcyclopropane (4.5 µL, 0.0459 mmol) and DIPEA (16 µL, 0.0917 mmol), and the mixture was stirred for 14 hours. Purification with Prep HPLC Phenomenex Gemini 5u C₁₈ column and eluted with a linear gradient of 5-100% Acetonitrile containing 0.1% TFA to gave Example 70 (8.2 mg, 0.0188 mmol). ¹H NMR (CD₃OD, 300 MHz): δ 7.32-7.26 (m, 3H), 4.73 (m, 1H), 4.42 (m, 3H), 4.11 (s, 2H), 3.87 (m, 1H), 3.43-3.19 (m, 8H), 1.77 (m, 2H), 1.48 (m, 2H), 1.26 (m, 1H), 0.96 (t, J=7.5 Hz, 3H), 0.83 (d, J=7.2 Hz, 2H), 0.52 (d, J=4.5 Hz, 2H). LCMS-ESI⁺: calc'd for C₂₂H₃₁N₆O₂: 437.3 (M+H⁺); Found: 437.2 (M+H⁺).

Scheme 62: Example 71, Method XLVIII:

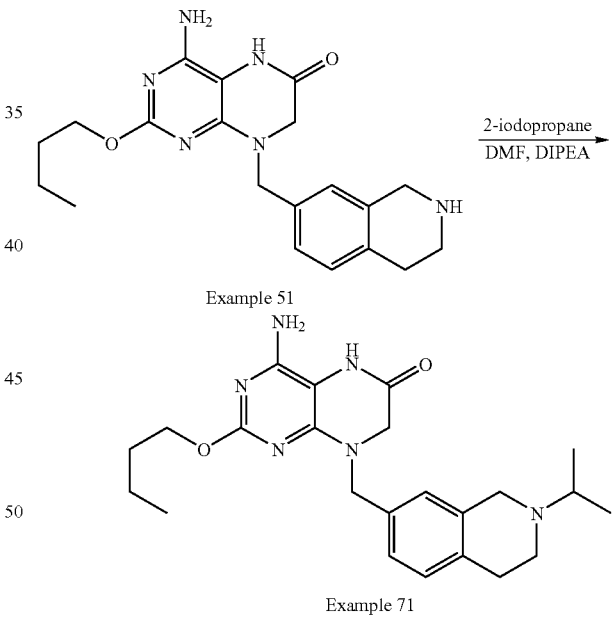

Example 71

Example 51 (20 mg, 0.0417 mmol) was dissolved in anhydrous DMF (1 mL). To this was added 2-iodopropane (4.6 µL, 0.0459 mmol) and DIPEA (16 µL, 0.0917 mmol), and the mixture was stirred for 14 hours. Purification with Prep HPLC Phenomenex Gemini 5u C₁₈ column and eluted with a linear gradient of 5-100% Acetonitrile containing 0.1% TFA to gave Example 71 (5.5 mg, 0.0130 mmol). ¹H NMR (CD₃OD, 300 MHz): δ 7.30-7.28 (m, 3H), 5.52 (m, 1H), 4.68 (m, 1H), 4.45 (m, 4H), 3.78 (m, 2H), 3.38-3.15 (m, 6H), 1.75 (m, 2H), 1.47 (m, 8H), 0.97 (t, J=7.5 Hz, 3H). LCMS-ESI⁺: calc'd for C₂₃H₃₃N₆O₂: 425.3 (M+H⁺); Found: 425.2 (M+H⁺).

Scheme 63: Example 72, Method XLVIII:

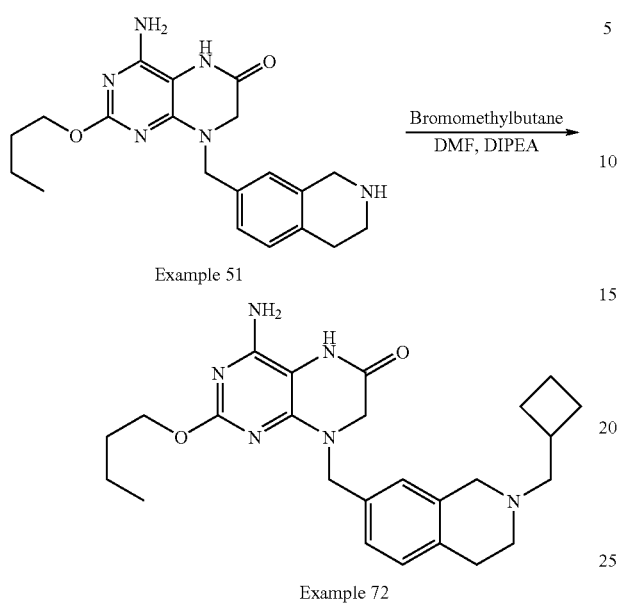

Example 51 (20 mg, 0.0417 mmol) was dissolved in anhydrous DMF (1 mL). To this was added bromomethylbutane (5.2 µL, 0.0459 mmol) and DIPEA (16 µL, 0.0917 mmol), and the mixture was stirred for 14 hours. Purification with Prep HPLC Phenomenex Gemini 5u $C_{18}$ column and eluted with a linear gradient of 5-100% Acetonitrile containing 0.1% TFA to gave Example 72 (8.4 mg, 0.0186 mmol). NMR (CD$_3$OD, 300 MHz): δ 7.35-7.20 (m, 3H), 5.43 (m, 1H), 4.41 (m, 4H), 3.70 (m, 1H), 3.32-3.22 (m, 7H), 3.13 (m, 1H), 2.89 (m, 1H), 2.22 (m, 2H), 1.99 (m, 4H), 1.73 (m, 2H), 1.45 (m, 2H), 0.94 (t, J=7.5 Hz, 3H). LCMS-ESI$^+$: calc'd for $C_{25}H_{35}N_6O_2$: 451.3 (M+H$^+$); Found: 451.2 (M+H$^+$).

Compound DC, Method VII Followed by Method VIII Followed by Method X

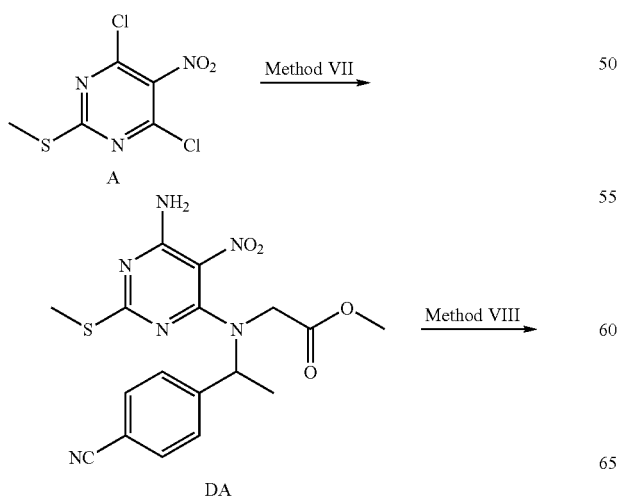

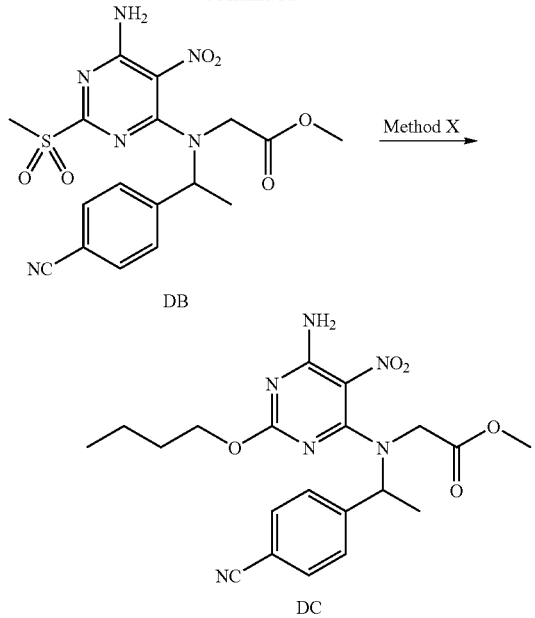

Prepared by using Method VII Compound DA: LCMS-ESI$^+$: calc'd for $C_{18}H_{20}N_6O_4S$: 417.4 (M+H$^+$); Found: 417.0 (M+H$^+$). After Method VIII: Compound DB: LCMS-ESI$^+$: calc'd for $C_{18}H_{20}N_6O_6S$: 449.4 (M+H$^+$); Found: 448.8 (M+H$^+$). After Method X: Compound DC: $^1$H NMR (CDCl$_3$, 300 MHz): δ 7.68-7.48 (m, 4H), 5.10-4.90 (m, 1H), 4.22-4.09 (m, 4H), 3.91 (d, J=4.8 Hz, 2H), 1.72-1.65 (m, 2H), 1.52-1.40 (m, 2H), 1.29-1.19 (m, 6H), 0.95 (t, J=7.5 Hz, 3H). LCMS-ESI$^+$: calc'd for $C_{21}H_{27}N_6O_5$: 443.5 (M+H$^+$); Found: 443.1 (M+H$^+$).

Scheme 64: Compound DD Prepared Via Method XXXIII:

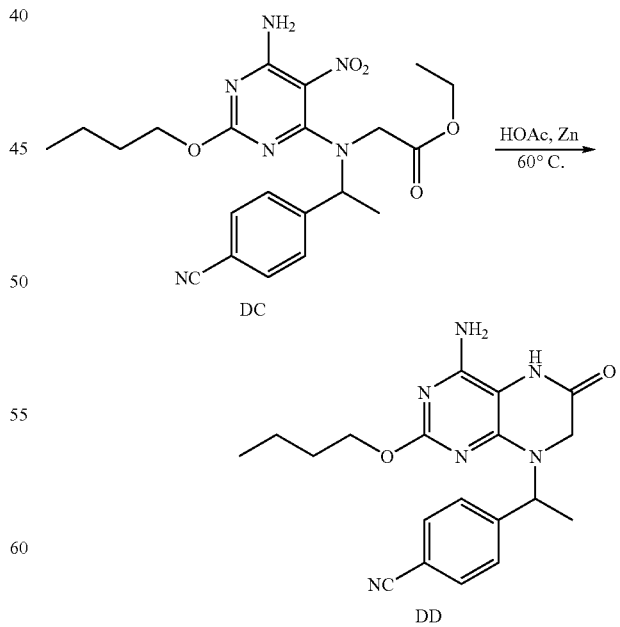

Compound DD was made by a similar method to that used to make compound CE. LCMS-ESI$^+$: calc'd for $C_{19}H_{23}N_6O_2$: 367.4 (M+H$^+$); Found: 367.1 (M+H$^+$).

Scheme 65: Example 73, Method XLIX:

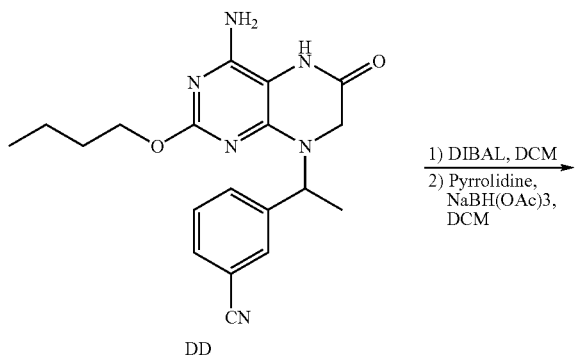

Example 73

¹H NMR (CD₃OD, 300 MHz): δ 7.60-7.50 (m, 4H), 4.22-4.17 (m, 1H), 4.50-4.41 (m, 4H), 4.13 (d, J=16.8 Hz, 1H), 3.60 (d, J=17.1 Hz, 1H), 3.49-3.42 (m, 2H), 3.20-3.17 (m, 2H), 2.20-2.16 (m, 2H), 2.03-2.00 (m, 2H), 1.80-1.68 (m, 5H), 1.52-1.42 (m, 2H), 0.98 (t, J=7.5 Hz, 3H). LCMS-ESI⁺: calc'd for $C_{23}H_{33}N_6O_2$: 425.5 (M+H⁺); Found: 425.3 (M+H⁺).

Example 74

Method XXXIII Followed by Method XLIX

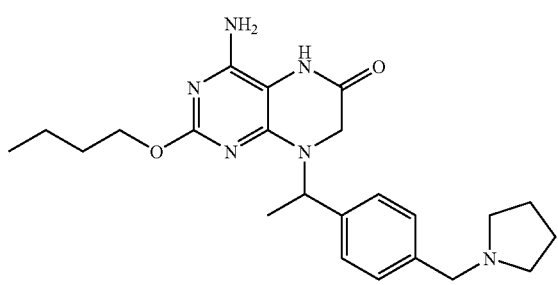 [SMILES: CCCCOc1nc(N)c2c(n1)N(C(C)c1ccc(CN3CCCC3)cc1)CC(=O)N2]

¹H NMR (CD₃OD, 300 MHz): δ 7.58-7.48 (m, 4H), 6.22-6.18 (m, 1H), 4.45-4.35 (m, 4H), 4.12 (d, J=17.1 Hz, 1H), 3.58 (d, J=16.8 Hz, 1H), 3.49-3.42 (m, 2H), 3.22-3.18 (m, 2H), 2.20-2.16 (m, 2H), 2.03-2.00 (m, 2H), 1.80-1.45 (m, 7H), 0.98 (t, J=7.5 Hz, 3H). LCMS-ESI⁺: calc'd for $C_{23}H_{33}N_6O_2$: 425.5 (M+H⁺); Found: 425.2 (M+H⁺).

Scheme 66: Example 75, Method L:

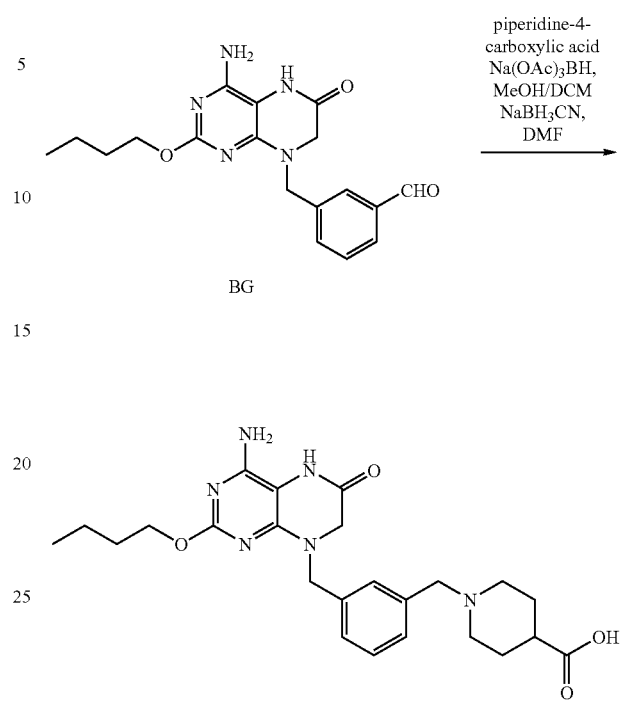

Example 75

To a solution of BG (20 mg, 0.056 mmol) in MeOH/CH₂Cl₂ (1:1, 3 mL) was added piperidine-4-carboxylic acid (33 mg, 0.25 mmol) and sodium triacetoxyborohydride (30 mg, 0.14 mmol) at 0° C. The reaction mixture was stirred at room temperature for 2 days. Then the solvent was removed and the residue was redissolved in DMF (2 mL). To the mixture was added sodium cyanoborohydride (15 mg, 0.24 mmol). The reaction mixture was stirred at room temperature for 1 day. The reaction was quenched with 1N HCl, the mixture was diluted by MeOH, filtered and purified by reverse phase HPLC (5-100% acetonitrile in H₂O) to give Example 75. ¹H NMR (CD₃OD, 300 MHz): δ 7.53-7.49 (m, 4H), 4.93 (s, 2H), 4.39-4.33 (m, 4H), 4.10 (s, 2H), 3.55-3.51 (m, 2H), 3.08-2.99 (m, 2H), 2.63-2.60 (m, 1H), 2.26-2.21 (m, 2H), 1.87-1.83 (m, 2H), 1.73-1.68 (m, 2H), 1.50-1.38 (m, 2H), 0.94 (t, J=7.5 Hz, 3H). LCMS-ESI⁺: calc'd for $C_{24}H_{33}N_6O_4$: 469.5 (M+H⁺); Found: 469.2 (M+H⁺).

Scheme 67: Example 76, Prepared using Method XIV:

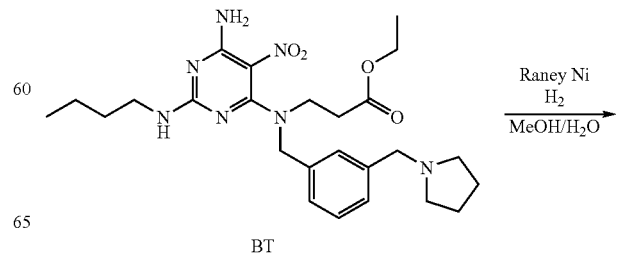

BT

-continued

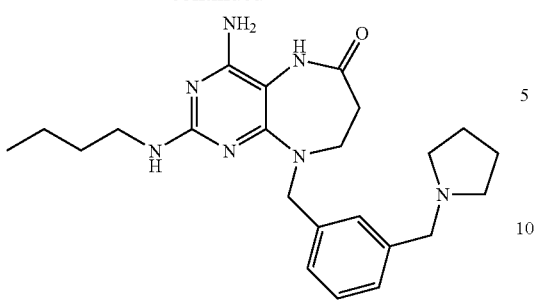

Example 76

Example 76

A flask containing a solution of BT (23.0 mg) in MeOH (4.0 mL) was treated with a slurry of 50% w/v aq. Raney Nickel (1 mL). The system was purged/backfilled with H$_2$/vacuum several times, then stirred vigorously under a balloon of H$_2$ at 23° C. for 4 days. The reaction was filtered over Celite with the aide of MeOH/CH$_2$Cl$_2$. The filtrate was concentrated, giving Example 76 as a yellow solid (20 mg, 99% yield). $^1$H NMR (CD$_3$OD, 300 MHz): δ (ppm) 7.31-7.17 (m, 4H), 4.77 (s, 2H), 3.65-3.58 (m, 2H), 3.61 (s, 2H), 3.17 (t, J=7.0 Hz, 2H), 2.63-2.56 (m, 2H), 2.54-2.47 (m, 4H), 1.83-1.74 (m, 4H), 1.47-1.38 (m, 2H), 1.38-1.18 (m, 2H), 0.83 (t, J=7.0 Hz, 3H). LCMS-ESI$^+$: calc'd for C$_{23}$H$_{34}$N$_7$O: 424.3 (M+H$^+$); Found: 424.2 (M+H$^+$).

Scheme 68: Compound DE Prepared Via Method XIII

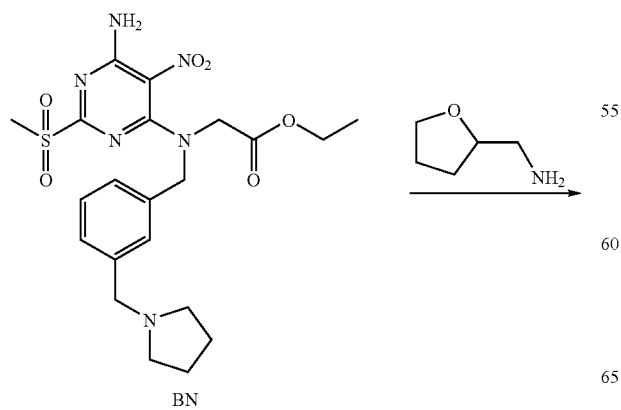

-continued

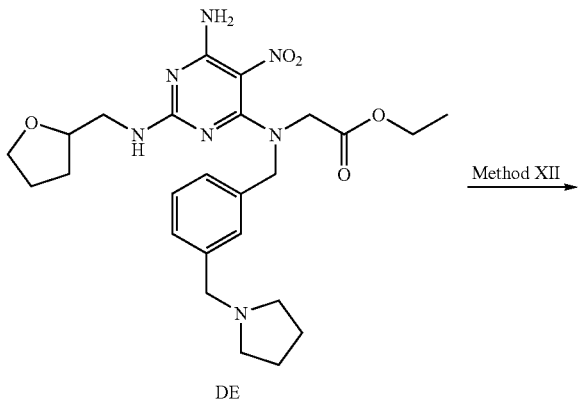

DE

The sulfone BN, (74.3 mg) was dissolved in 1.5 mL THF, and 300 μL of tetrahydrofurfuryl amine was added. The mixture was heated to 60° C. for one hour, then quenched by the addition of water, and diluted with EtOAc. After washing organic layer with water, then brine, the organic extracts were dried with sodium sulfate, filtered, and concentrated in vacuo. The product DE was purified with silica gel chromatography, eluting with MeOH/CH$_2$Cl$_2$ to give 35.3 mg. LCMS-ESI$^+$: calc'd for C$_{25}$H$_{35}$N$_7$O$_5$: 513.59 (M+H$^+$); Found: 514.0 (M+H$^+$), 257.6 (M+2H$^+$/2).

Scheme 69: Example 77, Method XII

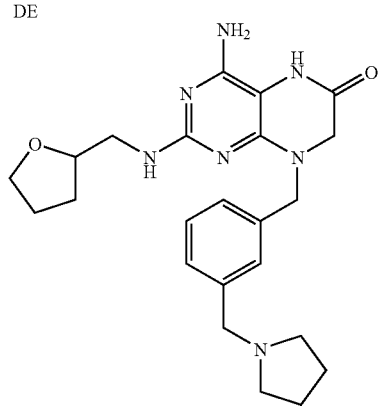

Example 77

Compound DE was advanced by Method XII to give rise to give Example 77. $^1$H NMR (DMSO-d$_6$, 300 MHz): δ 9.52 (s, broad, 1H), 7.27-7.21 (m, 4H), 5.85 (s, broad, 2H), 4.67 (s, 2H), 3.96-3.86 (m, 1H), 3.70 (m, 3H), 3.64-3.45 (m, 3H), 3.35-3.08 (m, 3H), 2.49 (s, broad, 4H), 1.89-1.64 (m, 6H), 1.58-1.41 (m, 2H). LCMS-ESI[30] : calc'd for $C_{23}H_{32}N_7O_2$: 437.54 (M+H$^+$); Found: 438.2 (M+H$^+$).

Scheme 70: Compound DF Prepared Via Method XIII

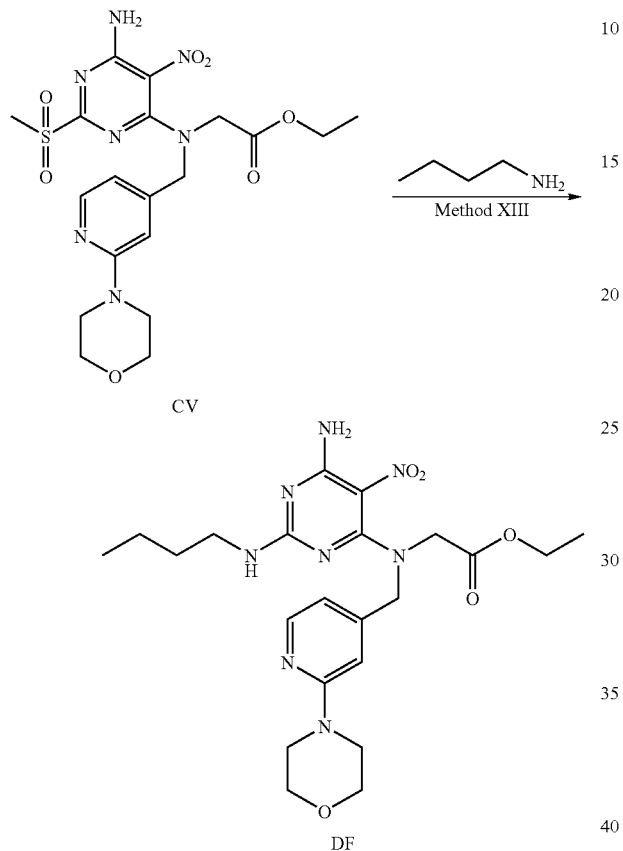

Starting from CV, Method XIII was employed with butylamine. After purification on silica gel eluting with $CH_2Cl_2$ and a 20% MeOH/$CH_2Cl_2$ gradient, Compound DF was obtained. LCMS-ESI$^+$: calc'd for $C_{23}H_{32}N_7O_2$: 488.54 (M+H$^+$); Found: 489.1 (M+H$^+$), 245.0 ((M+2H$^+$)/2).

Scheme 71: Example 78, Method XII

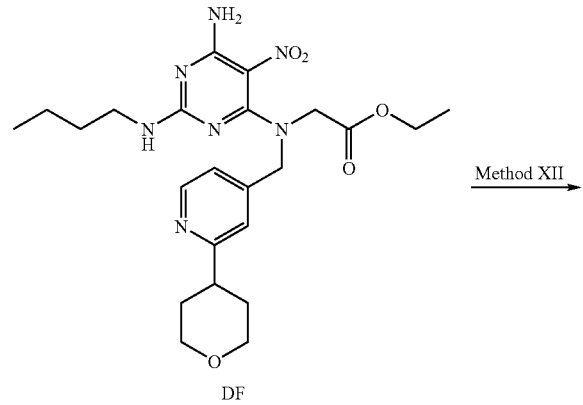

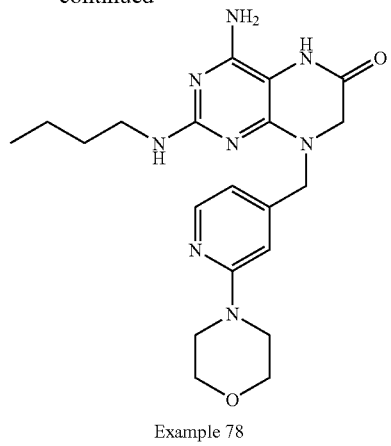

Example 78

Compound DF was advanced using Method XII to give rise to Example 78. $^1$H NMR (DMSO-d$_6$, 300 MHz): δ 10.05 (s, 1H), 7.80 (s, broad, 1H), 7.51 (d, broad, J=5.7 Hz, 1H), 7.39 (s, broad, 2H), 7.03 (s, 1H), 6.81 (s, 1H), 4.71 (s, 2H), 4.10 (s, 2H), 3.72 (s, broad, 4H), 3.58 (s, broad, 4H), 3.16-3.14 (m, 2H), 1.38-1.16 (m, 4H), 0.78 (t, J=7 Hz, 3H). LCMS-ESI$^+$: calc'd for $C_{20}H_{29}N_8O_2$: 412.49 (M+H$^+$); Found: 413.2 (M+H$^+$).

Scheme 72: Example 79, Made Using Method XXI:

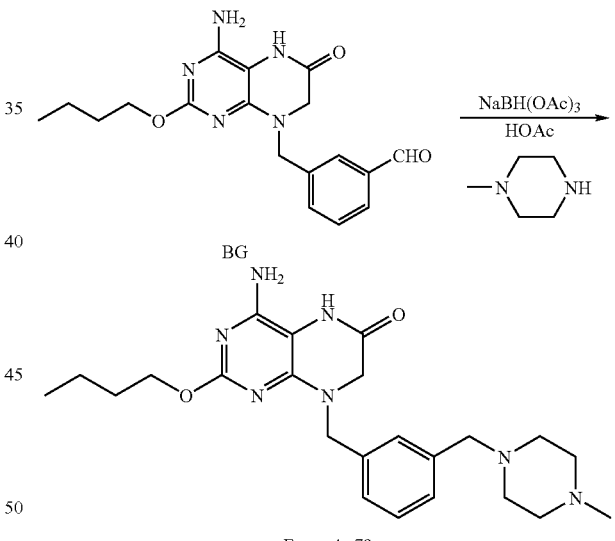

Example 79

Compound BG (23 mg, 0.066 mmol) was added to anhydrous NMP (1 mL). To this was added methyl piperazine (73 μL, 0.66 mmol) and HOAc (19 μL, 0.33 mmol) and the mixture was stirred for 5 minutes. To this was added NaBH(OAc)$_3$ (140 mg, 0.66 mmol) and the mixture was stirred for 16 hours. The mixture was diluted with MeOH and purified with Prep HPLC Phenomenex Gemini 5u C$_{18}$ column and eluted with a linear gradient of 5-100% Acetonitrile containing 0.1% TFA to give Example 79 (16 mg, 0.036 mmol). $^1$H NMR (CD$_3$OD, 300 MHz): δ 7.48-7.45 (m, 4H), 4.44 (m, 2H), 4.19 (s, 2H), 4.11 (s, 2H), 3.52 (bs, 4H), 3.32 (bs, 3H), 1.75 (m, 2H), 1.46 (m, 2H), 0.95 (t, J=7.2 Hz, 3H). LCMS-ESI$^+$: calc'd for $C_{23}H_{34}N_7O_2$: 440.3 (M+H$^+$); Found: 440.2 (M+H$^+$).

Scheme 73: Example 80, Made Using XXI:

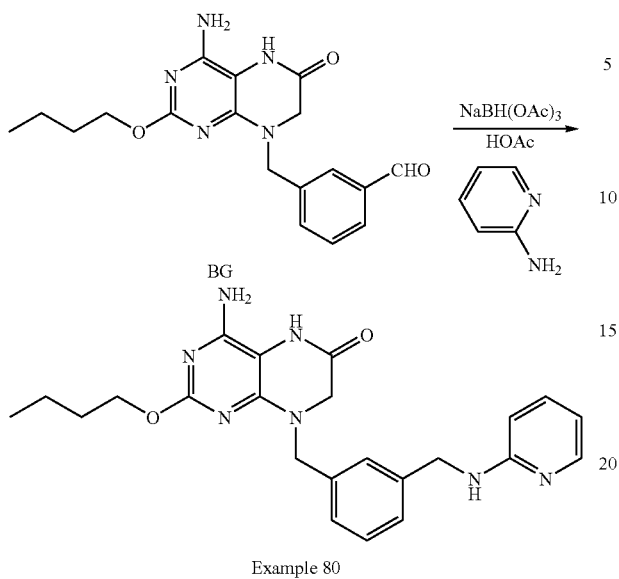

Example 80

Compound BG (23 mg, 0.066 mmol) was added to anhydrous NMP (1 mL). To this was added 2-amino pyridine (62 mg, 0.66 mmol) and HOAc (19 µL, 0.33 mmol) and the mixture was stirred for 5 minutes. To this was then added NaBH(OAc)$_3$ (140 mg, 0.66 mmol) and the mixure was stirred for 16 hours. The mixture was diluted with MeOH and purified with Prep HPLC Phenomenex Gemini 5u C$_{18}$ column and eluted with a linear gradient of 5-100% Acetonitrile containing 0.1% TFA to give Example 80 (6 mg, 0.014 mmol). $^1$H NMR (CD$_3$OD, 300 MHz): δ 7.93 (m, 2H), 7.43-7.37 (m, 4H), 7.09 (d, J=8.7 Hz, 1H), 6.93 (m, 1H), 4.62 (s, 2H), 4.39 (t, J=6.3 Hz, 2H), 4.07 (s, 2H), 1.74 (m, 2H), 1.44 (m, 2H), 0.94 (t, J=7.2 Hz, 3H). LCMS-ESI$^+$: calc'd for C$_{23}$H$_{28}$N$_7$O$_2$: 434.2 (M+H$^+$); Found: 434.1 (M+H$^+$).

Scheme 74

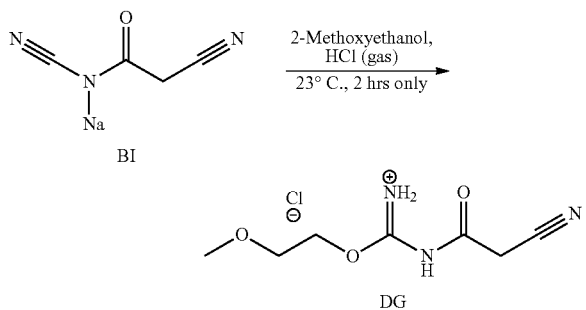

Method LI: N-Cyanoacetyl-(2-methoxyethoxyl)-isouronium chloride (Compound DG). A suspension of cyanoacetylcyanamide, monosodium salt BI (20.0 g, 153 mmol) in 2-Mwthoxyethanol (100 mL) was treated with HCl (4.0 M in dioxane, 100 mL, 400 mmol). During addition the suspension became more colloidal and there was a mild exotherm to an internal temperature of 52° C. After 3 h, 10% w/v aq. NaHCO$_3$ (140 mL) was added cautiously (effervescence) until the pH of the aq. phase reached 8.0. The organic layer was collected, and the aqueous phase was extracted (2×100 mL EtOAc). All organic layers were combined, dried (Na$_2$SO$_4$), and filtered over glass frits, and concentrated to a volume of ~10 mL. The thick syrupy residue contains crude N-cyanoacetyl-(2-methoxyethoxyl)-isouronium chloride, DG, which is unstable and immediately used in the next reaction. LCMS-ESI$^+$: calc'd for C$_7$H$_{12}$N$_3$O$_3$: 186.1 (M+H$^+$); Found: 186.0 (M+H$^+$).

Scheme 75

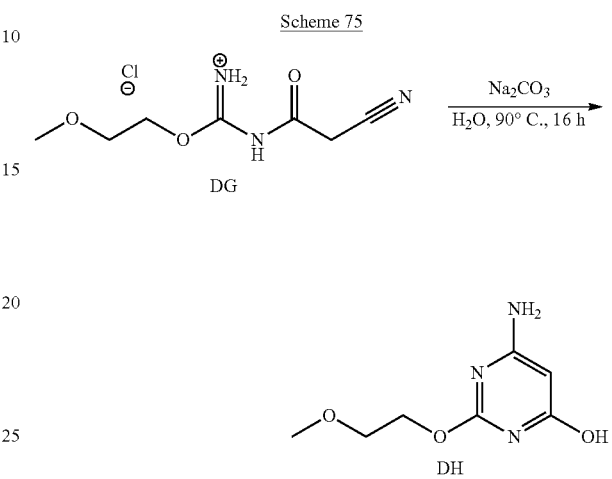

Method LII: 4-Amino-2-(2'-Methoxyethoxyl)-6-hydroxypyrimidine (Compound DH). An emulsion of all of the crude N-cyanoacetyl-butylisouronium chloride DG (28.4 g, 153 mmol) in a mixture of dioxane and 2-methoxyethanol (~10 mL) was treated with 10% w/v aq. Na$_2$CO$_3$ (120 mL) and was stirred vigorously at 90° C. for 18 h. The reaction was then allowed to cool to 23° C. over the next hour. The reaction was extracted with several portions of EtOAc. The aqueous layer was neutralized to pH=7.0 with conc. aq. HCl and concentrated to a semisolid. The organic layers and aqueous-derived semisolid were combined, and triturated with hot MeOH/EtOAc. The system was cooled to 23° C. and filtered. The filtrate was concentrated and the residue purified via flash chromatography on silica gel (Eluent: DCM/MeOH 100:0→80:20), giving semipure product Compound DH as an oily solid. The solid was was triturated with DCM, and the white crystals of pure Compound DH were obtained via filtration (584 mg, 2% yield over 2 steps). $^1$H NMR (DMSO-d$_6$, 300 MHz): δ (ppm) 11.22 (s, broad, 1H), 10.43 (s, broad, 1H), 7.40 (s, broad, 1H), 6.39 (s, 1H), 4.36 (t, J=4.6 Hz, 2H), 3.61 (t, J=4.6 Hz, 2H), 3.30 (s, 3H). LCMS-ESI$^+$: calc'd for C$_7$H$_{12}$N$_3$O$_3$: 186.1 (M+H$^+$); Found: 186.0 (M+H$^+$).

Scheme 76

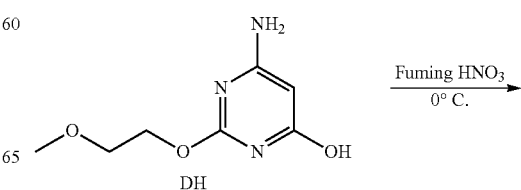

-continued

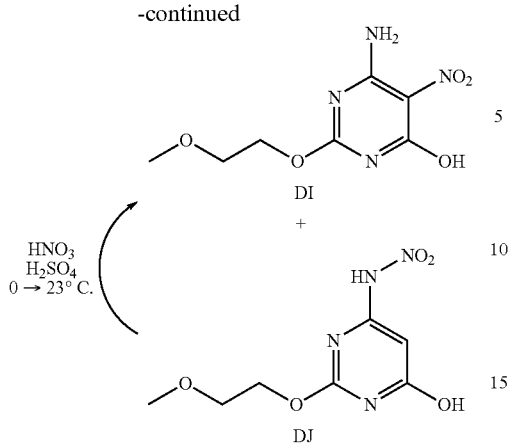

-continued

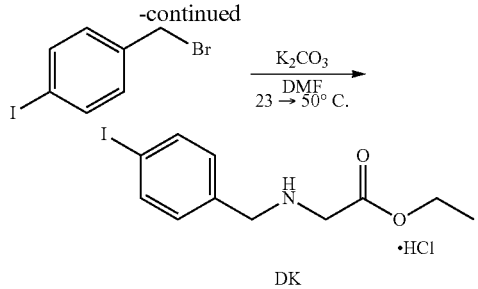

Method LIV: Ethyl N$_a$-(4'-Iodobenzyl)-glycinate, hydrochloride, compound DK. A suspension of ethyl glycinate hydrochloride (944 mg) in DMF (6.0 mL) was stirred for 5 min. p-Iodobenzyl bromide (2.00 g) was added. The heterogeneous system was warmed to 50° C. and stirred for 5 min, during which time, most solids dissolved. K$_2$CO$_3$ (2.80 g, granular) was added steadily over 5 min. After 2 h, the reaction was cooled to 23° C. Conc. eq. HCl (3.3 mL) was added, followed by H$_2$O (7.0 mL). The heterogeneous mix was stirred for 15 min and filtered (the cake was washed with CH$_3$CN (4×5 mL)). The net filtrate was concentrated until no CH$_3$CN remained. The crude product solution was filtered through a 0.45 micron Teflon filter and loaded directly onto a Teledyne Isco 'gold' 100 gram column and flashed (Eluent: 0.05% w/v aq. HCl/CH$_3$CN 95:5→0:100), giving DK (688 mg, 29% yield) as an HCl salt. $^1$H NMR (DMSO-d$_6$, 300 MHz): δ (ppm) 9.78 (s, 2H), 7.84 (d, J=7.8 Hz, 2H), 7.36 (d, J=7.8 Hz, 2H), 4.23 (q, J=7.0 Hz, 2H), 4.15 (s, 2H), 3.95 (s, 2H), 1.25 (t, J=7.0 Hz, 3H). LCMS-ESI$^+$: calc'd for C$_{11}$H$_{15}$INO$_2$: 320.0 (M+H$^+$); Found: 319.9 (M+H$^+$).

Method LIII: 4-Amino-2-(2'-methoxyethoxyl)-5-nitro-6-hydroxypyrimidine, DJ. A flask containing fuming aqueous HNO$_3$ (1.0 mL) at 0° C. was treated with 4-amino-2-(2'-methoxyethoxy)-6-hydroxypyrimidine DH (500 mg) in portions over a 10 min period. The maroon reaction was treated with additional fuming HNO$_3$ (200 μL). After 2 h, the reaction was added dropwise to H$_2$O (10 mL) at 0° C. pH was adjusted to 11.0 via portionwise addition of solid Na$_2$CO$_3$ at 0° C. Then 1.0 M eq HCl was added dropwise until the pH reached 3.0. The pink solid that precipitated was removed via filtration, and the filtrate was allowed to stand open to the air overnight. The solution went from purple to yellow. The filtrate was then directly loaded onto a C18 Teledyne Isco 'gold' 50 gram column and flashed (Eluent: 0.05% w/v aq. HCl/CH$_3$CN 95:5→0:100) giving a mixture of DI and DJ. This mixture was dissolved in a minimum of DMSO and directly loaded onto a Teledyne Isco 'gold' 15 gram column and flashed (Eluent: 0.05% w/v aq. HCl/CH$_3$CN 95:5→0:100), giving separated products DI (higher polarity product) (175 mg, 28% yield) and DJ (lower polarity product)(44.2 mg, 7% yield). Data for DI (high polarity product): $^1$H NMR (DMSO-d$_6$, 300 MHz): δ (ppm) 12.15 (s, 1H), 8.83 (s, 1H), 8.79 (s, 1H), 4.50 (t, J=4.6 Hz, 2H), 3.66 (t, J=4.6 Hz, 2H), 3.31 (s, 3H). LCMS-ESI$^+$: calc'd for C$_7$H$_{11}$N$_4$O$_5$: 231.1 (M+H$^+$); Found: 230.9 (M+H$^+$). Data for DJ (high polarity product): $^1$H NMR (DMSO-d$_6$, 300 MHz): δ (ppm) 12.40 (s, broad, 1H), 6.38 (s, 1H), 4.43 (t, J=4.6 Hz, 2H), 3.66 (t, J=4.6 Hz, 2H), 3.31 (s, 3H). LCMS-ESI$^+$: calc'd for C$_7$H$_{11}$N$_4$O$_5$: 231.1 (M+H$^+$); Found: 230.8 (M+H$^+$).

An analytically pure sample of DI (36.3 mg) was treated with fuming HNO$_3$ (500 μL) at 0° C. Then conc. aq. H$_2$SO$_4$ (500 μL) was introduced dropwise over a 3 min period. After 5 min, the reaction was added to an ice-cold suspension of NaHCO$_3$ (2.52 g) in H$_2$O (10 mL) in a dropwise fashion. The reaction was allowed to warm to 23° C. The homogeneous solution was directly loaded onto a Teledyne Isco 'gold' 15 gram column and flashed (Eluent: 0.05% w/v aq. HCl/CH$_3$CN 95:5→0:100), giving DJ (16.2 mg, 45% yield) having analytical data as detailed above.

Scheme 78

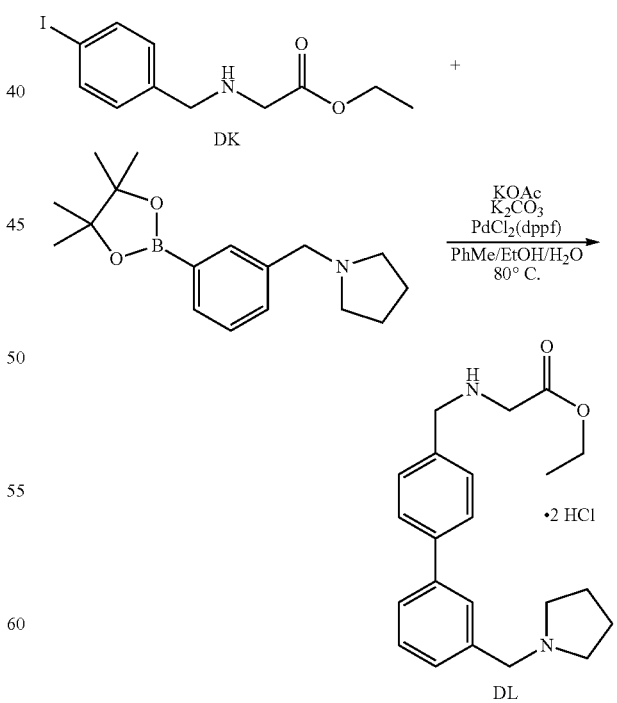

Scheme 77

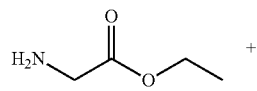

+

Method LV: Compound DL. A suspension of ethyl N$_a$-(4'-Iodobenzyl)-glycinate, hydrochloride (DK)(200 mg), 3-(pyrrolidin-1'-ylmethyl) benzeneboronic acid pinacolate diester (162 mg), KOAc (166 mg), H₂O (1.0 mL), absolute EtOH (1.0 mL), and PhMe (2.0 mL) was degassed with argon via needle for 5 min. PdCl₂(dppf) (12 mg) was added and the reaction was heated to 80° C. After 12 h, no conversion was achieved, so K₂CO₃ (233 mg) was added, followed after 2 h, by additional PdCl₂(dppf) (12 mg). After the reaction was complete, it was cooled to 23° C. and partitioned between 10% Na₂CO₃ and EtOAc. The organic phase was collected, dried (Na₂SO₄), filtered, and concentrated. The residue was treated with 1.0 M aq. HCl and CH₃CN (minimum to achieve solution) and directly loaded onto a Teledyne Isco 'gold' 50 gram column and flashed (Eluent: 0.05% w/v aq. HCl/CH₃CN 95:5→0:100), giving DL (185.2 mg, 77% yield) as a white solid (in the dihydrochloride form). ¹H NMR (CD₃OD, 300 MHz): δ (ppm) 7.96 (s, 1H), 7.85 (d, J=8.3 Hz, 2H), 7.85-7.76 (m, 1H), 7.65 (d, J=8.3 Hz, 2H), 7.64-7.58 (m, 2H), 4.49 (s, 2H), 4.35 (s, 2H), 4.33 (q, J=7.0 hz, 2H), 4.03 (s, 2H), 3.60-3.48 (m, 2H), 3.31-3.27 (m, 2H), 2.23-2.13 (m, 2H), 2.12-2.00 (m, 2H), 1.33 (t, J=7.0 Hz, 3H). LCMS-ESI⁺: calc'd for C₂₂H₂₉N₂O₂: 353.2 (M+H⁺); Found: 353.1 (M+H⁺).

(minimum needed for salvation). The solution was loaded onto a Teledyne Isco 'gold' 50 gram column and flashed (Eluent: 0.05% w/v aq. HCl/CH₃CN 95:5→0:100), giving DM (187 mg, 78% yield) as a white solid (in the dihydrochloride form). ¹H NMR (CD₃OD, 300 MHz): δ (ppm) 7.891 (d, J=7.6 Hz, 2H), 7.890 (d, J=7.6 Hz, 2H), 7.67 (d, J=7.6 Hz, 2H), 7.62 (d, J=7.6 Hz, 2H), 4.44 (s, 2H), 4.33 (s, 2H), 4.32 (q, J=7.0 Hz, 2H), 4.02 (s, 2H), 3.58-3.48 (m, 2H), 3.30-3.18 (m, 2H), 2.24-2.11 (m, 2H), 2.10-1.96 (m, 2H), 1.32 (t, J=7.0 Hz, 3H). LCMS-ESI⁺: calc'd for C₂₂H₂₉N₂O₂: 353.2 (M+H⁺); Found: 353.0 (M+H⁺).

Scheme 80

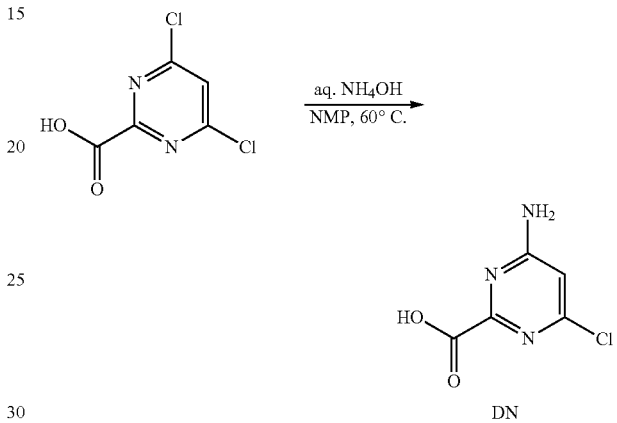

Scheme 79

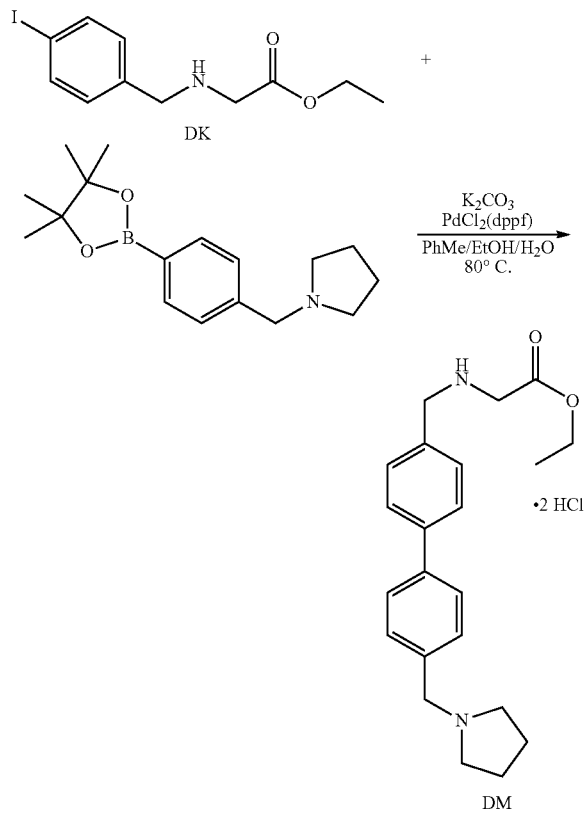

Method LVI: Compound DM. A suspension of ethyl N_α-(4'-Iodobenzyl)-glycinate, hydrochloride (DK)(200 mg), 4-(pyrrolidin-1'-ylmethyl) benzeneboronic acid pinacolate diester (162 mg), PdCl₂(dPPf) (24 mg) and K₂CO₃ (233 mg) in PhMe (2.0 mL), absolute EtOH (1.0 mL), and H₂O (1.0 mL) was degassed with argon from a needle for 2 min. Then the reaction was heated to 80° C. for 16 h. The reaction was cooled to 23° C., and the pH was adjusted to 1.0 using 1.0 M aq HCl (~4.0 mL). The reaction was concentrated to remove PhMe and EtOH, and H₂O was added along with CH₃CN Method LVII: Compound DN. A solution of 2-carboxy-4,6-dichloropyrimidine (1.00 g) in NMP (10 mL) at 23° C. was treated dropwise with conc. aq. NH₄OH (2.0 mL). Once effervescence ceased, the reaction was slowly warmed to 60° C., and held at this temperature for 4 h. The reaction was cooled to 23° C., and H₂O (10 mL) was added, giving a milky suspension. Conc. aq. HCl (2.0 mL) was added dropwise. After 30 min, the suspension was filtered, and the filter cake was dried in a vacuum oven at 45° C., giving DN (537 mg, 61%) as a white solid. ¹H NMR (DMSO-d₆, 300 MHz): δ (ppm) 13.40 (s, broad, 1H), 7.58 (app. s, broad, 2H), 6.58 (s, 1H). LCMS-ESI: compound does not ionize.

Scheme 81:

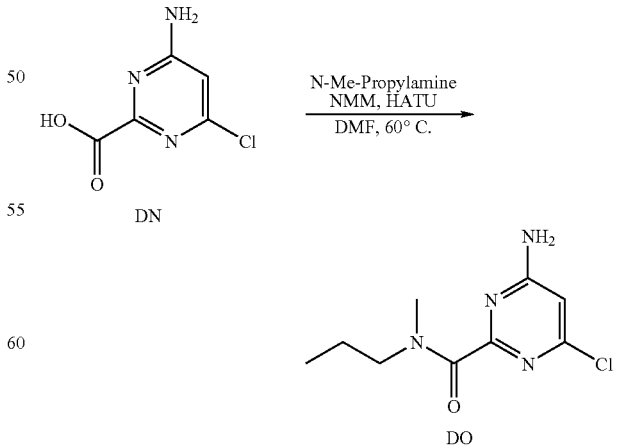

Method LVIII: Compound DO: A suspension of 4-amino-2-carboxy-6-chloropyrimidine (535 mg), DMF (3.0 mL), and N-Methyl Morpholine (1.72 mL) was heated to 60° C. N-Methyl-Propylamine (642 μL) was added, along with more DMF (1.0 mL, to aide fluidity). Then HATU (1.19 g) was introduced. After the reaction was complete, it was concentrated at 60° C. to remove volatile amines. The reaction was cooled to 23° C., and 1.0 M aq HCl (2.0 mL) was added. The solution was directly loaded onto a Teledyne Isco 'gold' 50 gram column and flashed (Eluent: 0.05% w/v aq. HCl/CH$_3$CN 95:5→0:100), giving DO (618 mg, 87%) as an orange oil, which solidified upon standing. $^1$H NMR (DMSO-d$_6$, 300 MHz)(compound exists as a mixture of two amide rotamers at 23° C. with some associated protons having distinct resonances): δ (ppm) 7.50 (app. s, broad, 2H), 6.49 (s, 1H), 3.36 (t, J=7.6 Hz, 1.5H, one rotamer), 3.06 (t, J=7.6 Hz, 1.5H, one rotamer), 2.93 (s, 1.5H, one rotamer), 2.80 (s, 1.5H, one rotamer), 1.56 (app. qt, J=7.6 Hz, 7.6 Hz, 2H, both rotamers), 0.91 (t, J=7.6 Hz, 1.5H, one rotamer), 0.76 (t, J=7.6 Hz, 1.5H, one rotamer). LCMS-ESI$^+$: calc'd for C$_9$H$_{14}$ClN$_4$O: 229.1 (M+H$^+$) and 231.1 (M+2+H$^+$); Found: 229.1 (M+H$^+$) and 231.1 (M+2+H$^+$).

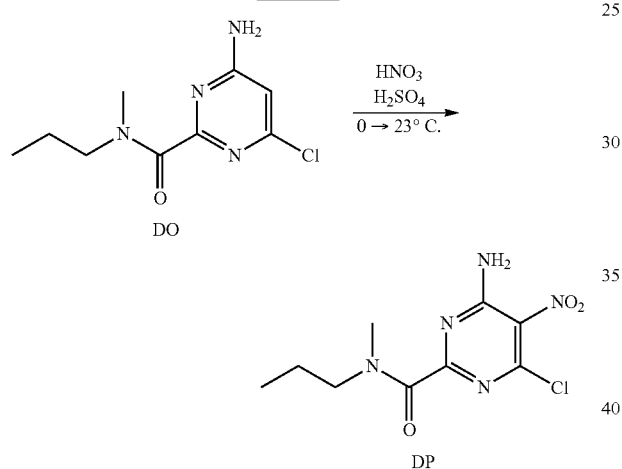

Scheme 82

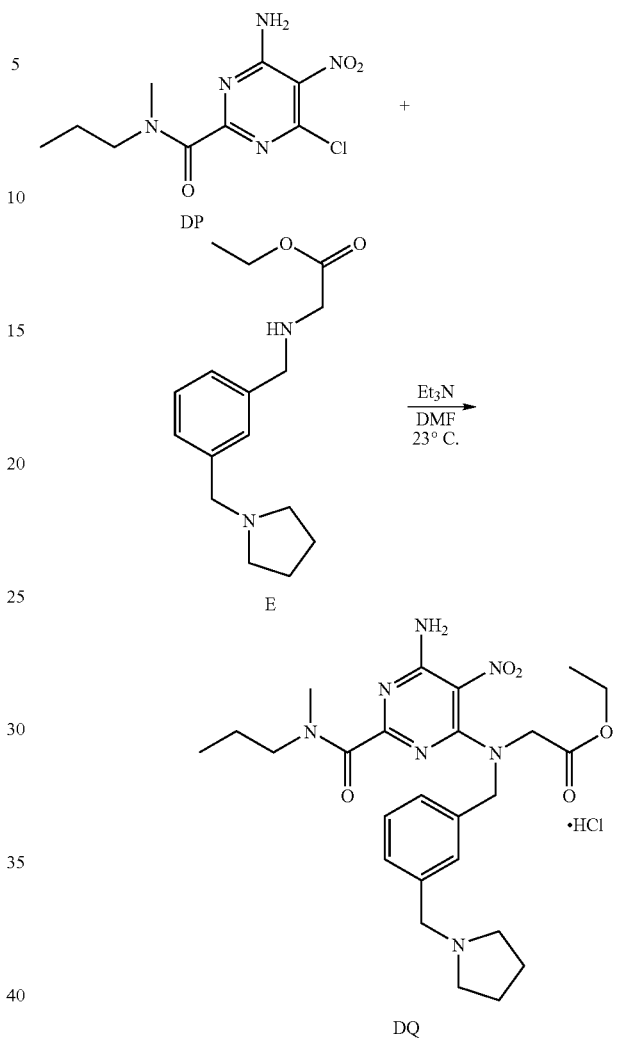

Scheme 83:

Method LIX: Compound DP. A flask containing the pyrimidine DO (538 mg) was cooled to 0° C. Fuming HNO$_3$ (1.0 mL) was added. After the initial exotherm had subsided, conc. aq. H$_2$SO$_4$ (1.0 mL) was introduced over a 3 min period. The reaction was then allowed to warm to 23° C. After 45 h, the reaction was added dropwise to an ice-cold suspension of NaKCO$_3$ (5.0 g) in H$_2$O (20 mL). A yellow precipitate formed. The quenched reaction was then treated with CH$_3$CN (4.5 mL) and DMF (1.5 mL). The now homogeneous solution was directly loaded onto a Teledyne Isco 'gold' 50 gram column and flashed (Eluent: 0.05% w/v aq. HCl/CH$_3$CN 95:5→0:100), giving DP (180.4 mg, 28% yield) as a colorless oil. $^1$H NMR (CDCl$_3$, 300 MHz)(compound exists as a mixture of two amide rotamers at 23° C. with some associated protons having distinct resonances): δ (ppm) 7.91 (app. s, broad, 2H), 3.50 (t, J=7.6 Hz, 1H, single rotamer), 3.17 (t, J=7.6 Hz, 1H, single amide rotamer), 3.10 (s, 1.5H, single rotamer), 2.98 (s, 1.5H, single rotamer), 1.68 (app. qt, J=7.6 Hz, 7.6 Hz, 2H, both rotamers), 0.97 (t, J=7.6, 1.5H, single rotamer), 0.85 (t, J=7.6 Hz, 1.5H, single rotamer). LCMS-ESI$^+$: calc'd for C$_9$H$_{13}$ClN$_5$O$_3$: 274.1 (M+H$^+$) and 276.1 (M+2+H$^+$); Found: 274.0 (M+H$^+$) and 276.0 (M+2+H$^+$).

Method LX: Compound DQ. A solution of E (30 mg) in DMF (500 μL) was added to a vial containing the pyrimidine DP (30 mg). Finally, Et$_3$N (31 μL) was added at 23° C. After 2 h, the reaction was complete. 1.0 M aq. HCl (300 μL) and CH$_3$CN (50 μL). The reaction was loaded directly onto a Teledyne Isco 'gold' 5.5 gram column and flashed (Eluent: 0.05% w/v aq. HCl/CH$_3$CN 95:5→0:100), giving DQ (16.4 mg, 27% yield) as a monohydrochloride salt. $^1$H NMR (CDCl$_3$, 300 MHz)(compound exists as a mixture of two amide rotamers at 23° C. with some associated protons having distinct resonances): δ (ppm) 12.65 (s, broad, 1H), 7.71 (app. s, broad, 2H), 7.44-7.26 (m, 4H), 4.83 (s, 2H), 4.30-4.02 (m, 4H), 3.63-3.57 (m, 2H), 3.43 (t, J=7.6 Hz, 1H, single rotamer), 3.17 (t, J=7.6 Hz, 1H, single rotamer), 3.02 (s, 1.5H, single rotamer), 3.01-2.79 (m, 4H), 2.92 (s, 1.5H, single rotamer), 2.30-2.20 (m, 2H), 2.20-2.10 (m, 2H), 1.61 (app. qt, J=7.6 Hz, 7.6 Hz, 2H, both rotamers), 1.27 (t, J=6.8 Hz, 3H), 0.93 (t, J=7.6 Hz, 1.5H, single rotamer), 0.85 (t, J=7.6 Hz, 1.5H, single rotamer). LCMS-ESI$^+$: calc'd for C$_{25}$H$_{36}$N$_7$O$_5$: 514.3 (M+H$^+$); Found: 514.2 (M+H$^+$).

Scheme 84: Example 81

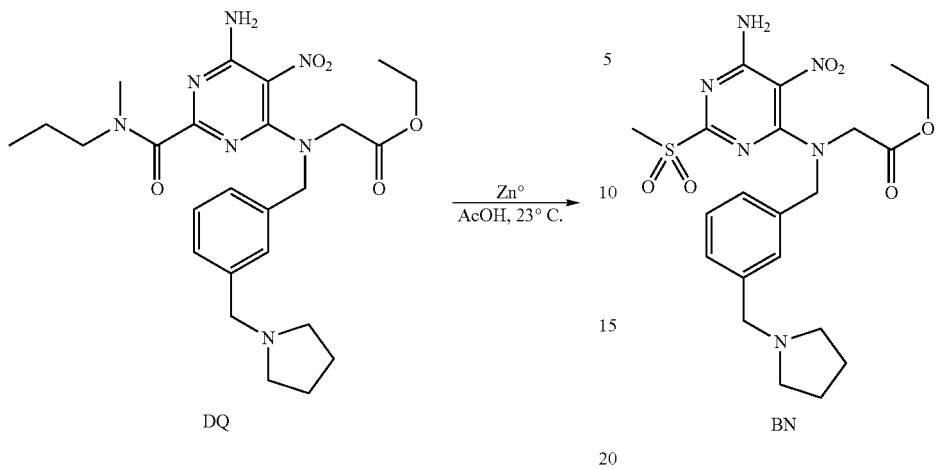

DQ

Example 81

Scheme 85

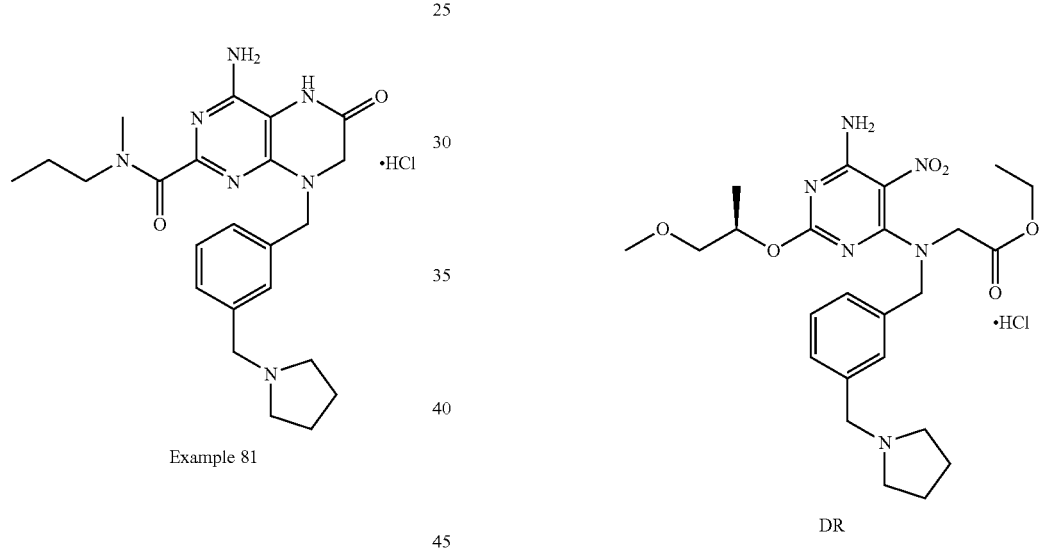

BN

DR

Method LXI: Example 81. A solution of the amide DQ (16.4 mg) in glacial AcOH (1.64 mL) was treated with zinc powder (48 mg) at 23° C. After the reaction was complete (3 h), it was diluted with $H_2O$ (300 μL) and loaded onto a Teledyne Isco 'gold' 5.5 gram column and flashed (Eluent: 0.05% w/v aq. $HCl/CH_3CN$ 95:5→0:100), giving Example 81 (1.8 mg, 14% yield) as a white solid in monohydrochloride form. $^1H$ NMR ($CD_3OD$, 300 MHz)(compound exists as a mixture of two amide rotamers at 23° C. with some associated protons having distinct resonances): δ (ppm) 7.60-7.42 (m, 4H), 5.50 (s, 2H), 4.94 (s, 2H), 4.38 (s, 2H), 4.18 (app. s, 1H, single rotamer), 4.16 (app. s, 1H, single rotamer), 3.55-3.41 (m, 2H), 3.40-3.25 (m, 2H), 3.14 (s, 1.5H, single rotamer), 3.07 (s, 1.5H, single rotamer), 2.22-2.08 (m, 2H), 2.08-1.99 (m, 2H), 1.68-1.64 (m, 2H, both rotamers), 0.97 (t, J=7.6 Hz, 1.5H, single rotamer), 0.75 (t, J=7.6 Hz, 1.5H), single rotamer). LCMS-ESI$^+$: calc'd for $C_{23}H_{32}N_7O_2$: 438.3 (M+H$^+$); Found: 438.2 (M+H$^+$) and 219.7 ((M+2H$^+$)/2).

Method LXII: Compound ZZ. A suspension of the sulfone (BN)(15.8 mg), (R)-1-methoxy-2-propanol (300 μL), and TFA (10 μL) was heated to 100° C. for 17.5 h. The reaction was cooled to 23° C., diluted with $H_2O$ (600 μL) and loaded directly onto a Teledyne Isco 'gold' 5.5 gram column and flashed (Eluent: 0.05% w/v aq. $HCl/CH_3CN$ 95:5→0:100), giving DR (13 mg, 76% yield) as a monohydrochloride salt. $^1H$ NMR (CDCl$_3$, 300 MHz): δ (ppm) 12.64 (s, 1H), 9.68 (s, 1H), 8.36 (s, 1H), 7.93 (s, 1H), 7.49-7.20 (m, 4H), 5.27 (s, broad, 2H), 4.87 (s, 2H), 4.40-4.08 (m, 5H), 3.67-3.30 (m, 4H), 3.34 (s, 3H), 2.85-2.70 (m, 2H), 2.30-2.20 (m, 2H), 2.20-2.10 (m, 2H), 1.35-1.18 (m, 6H). LCMS-ESI$^+$: calc'd for $C_{24}H_{35}N_6O_6$: 503.3 (M+H$^+$); Found: 503.2 (M+H$^+$).

Scheme 86

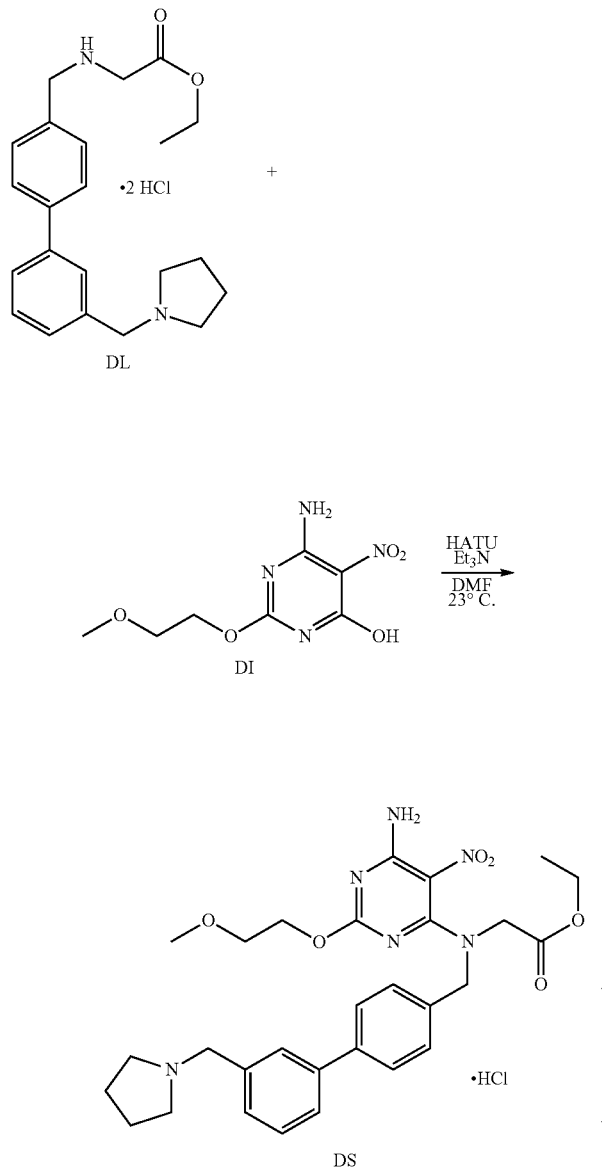

Scheme 87

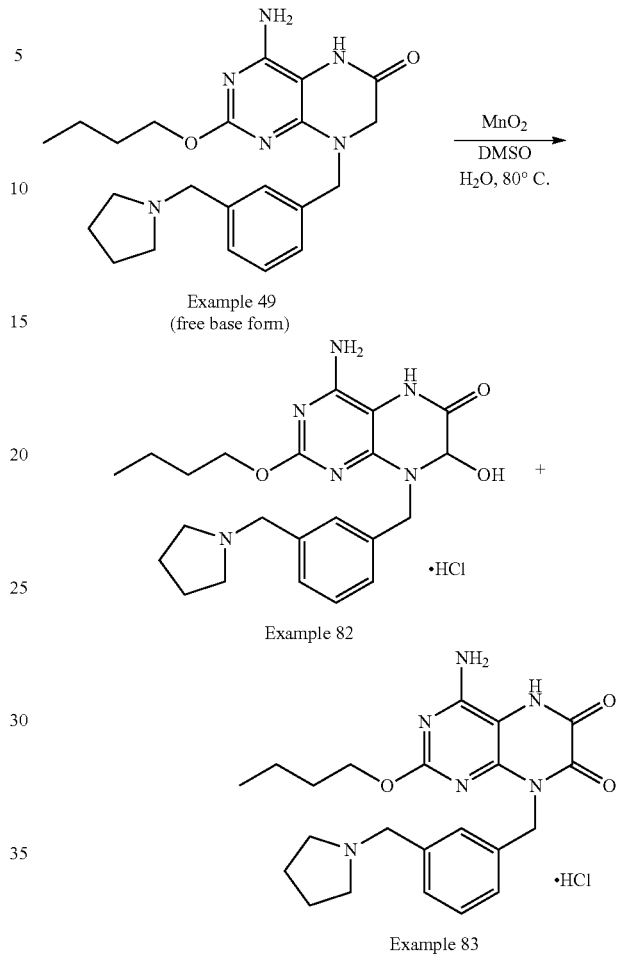

Method LXIII: Compound DS. A suspension of nitropyrimidine (DI)(15.3 mg), amino acid ester (DL)(31.4 mg), and DMF (589 μL) was treated with Et$_3$N (37 μL). HATU (33 mg) was introduced, followed by more DMF (589 μL) to aide fluidity. After 1 h, the completed reaction was treated with 1.0 M aq. HCl (300 μL) followed by CH$_3$CN (100 μL). The reaction was directly loaded onto a Teledyne Isco 'gold' 15 gram column and flashed (Eluent: 0.05% w/v aq. HCl/CH$_3$CN 95:5→0:100), giving DS (31.1 mg, 78% yield) as a monohydrochloride salt. $^1$H NMR (CDCl$_3$, 300 MHz): δ (ppm) 12.74 (s, broad, 1H), 8.96 (s, broad, 1H), 8.24 (s, broad, 1H), 8.07 (s, 1H), 7.72-7.40 (m, 5H), 7.35 (d, J=7.0 Hz, 2H), 4.82 (s, 2H), 4.47 (s, 2H), 4.30-4.10 (m, 6H), 3.62-3.51 (m, 4H), 3.35 (s, 3H), 2.94-2.70 (m, 2H), 2.29-2.12 (m, 2H), 2.11-2.00 (m, 2H), 1.27 (t, J=7.0 Hz, 3H). LCMS-ESI$^+$: calc'd for C$_{29}$H$_{37}$N$_6$O$_6$: 565.3 (M+H$^+$); Found: 565.3 (M+H$^+$).

Method LXIV: Examples 82 and 83: A solution of Example 49 (free base, 10.2 mg) in DMSO (800 μL) and H$_2$O (200 μL) was heated to 80° C. and treated with MnO$_2$ (85%, activated, from Sigma-Aldrich, 21 mg). After 45 min, the reaction was quickly cooled to 23° C. and filtered through a 0.45 micron Teflon filter. The filtrate was directly loaded onto a Teledyne Isco 'gold' 5.5 gram column and flashed (Eluent: 0.05% w/v aq. HCl/CH$_3$CN 95:5→0:100), giving Example 82 (1.0 mg, 8.7% yield, higher-polarity product) as a monohydrochloride salt. $^1$H NMR (CD$_3$OD, 300 MHz): δ (ppm) 7.60-7.39 (m, 4H), 5.48 (app. s, 1H), 5.38 (app. d, J=15.2 Hz, 1H), 5.05 (s, 1H), 4.36 (s, 2H), 4.36-4.34 (m, 2H), 3.60-3.40 (m, 2H), 3.32-3.10 (m, 2H), 2.20-2.05 (m, 4H), 1.69 (tt, J=7.6 Hz, 2H), 1.41 (qt, 7.6 Hz, 7.6 Hz, 2H), 0.93 (t, J=7.0 Hz, 3H). LCMS-ESI$^+$: calc'd for C$_{22}$H$_{31}$N$_6$O$_3$: 427.2 (M+H$^+$) and calc'd for C$_{22}$H$_{29}$N$_6$O$_2$: 409.2 (M–OH)$^+$; Found: 409.1 (M–OH)$^+$. In addition, Example 83 (5.7 mg, 50% yield, lower-polarity product) was obtained as a monohydrochloride salt. $^1$H NMR (CD$_3$OD, 300 MHz): δ (ppm) 7.60-7.39 (m, 4H), 5.50 (s, 2H), 4.34 (q, J=7.0 Hz, 2H), 4.33 (s, 2H), 3.48-3.39 (m, 2H), 3.20-3.04 (m, 2H), 2.20-2.05 (m, 2H), 2.05-1.90 (m, 2H), 1.70 (tt, J=7.6 Hz, 7.6 Hz, 2H), 1.42 (qt, J=7.6 Hz, 7.6 Hz, 2H), 0.93 (t, J=7.6 Hz, 3H). LCMS-ESI$^+$: calc'd for C$_{22}$H$_{29}$N$_6$O$_3$: 425.2 (M+H$^+$); Found: 425.2 (M+H$^+$).

Scheme 88:

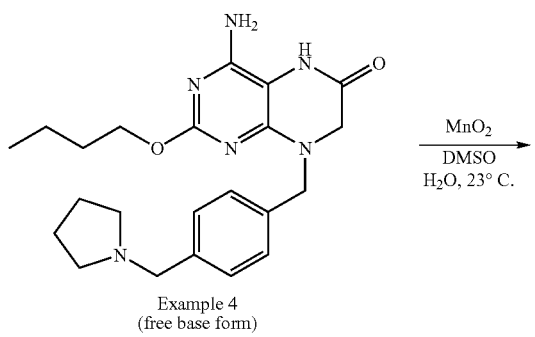

Example 4
(free base form)

-continued

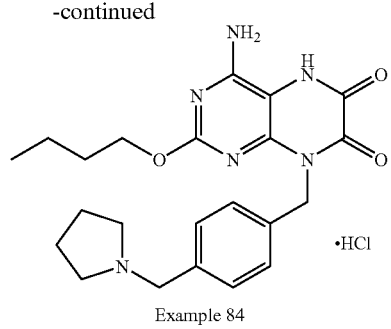

Example 84

Method LXV: Example 84 A solution of Example 4 (free base form, 9.9 mg) in DMSO (2.4 mL) was treated with H₂O (600 μL) followed by MnO₂ (85%, activated, from Sigma-Aldrich, 104 mg) at 23° C. Once the reaction was complete, it was filtered through a 0.45 micron Teflon filter. The filtrate was directly loaded onto a Teledyne Isco 'gold' 5.5 gram column and flashed (Eluent: 0.05% w/v aq. HCl/CH₃CN 95:5→0:100), giving Example 84 (3.0 mg, 27% yield) as a monohydrochloride salt. $^1$H NMR (CD₃OD, 300 MHz): δ (ppm) 7.53 (d, J=7.8 Hz, 2H), 7.46 (d, J=7.8 Hz, 2H), 5.50 (s, 2H), 4.34 (s, 2H), 4.32 (t, J=7.6 Hz, 2H), 3.50-3.38 (m, 2H), 3.21-3.09 (m, 2H), 2.25-2.18 (m, 2H), 2.17-1.99 (m, 2H), 1.70 (tt, J=7.6 Hz, 7.6 Hz, 2H), 1.45 (qt, J=7.6 Hz, 7.6 Hz, 2H), 0.94 (t, J=7.6 Hz, 3H). LCMS-ESI⁺: calc'd for C₂₂H₂₉N₆O₃: 425.2 (M+H⁺); Found: 425.1 (M+H⁺).

Scheme 89:

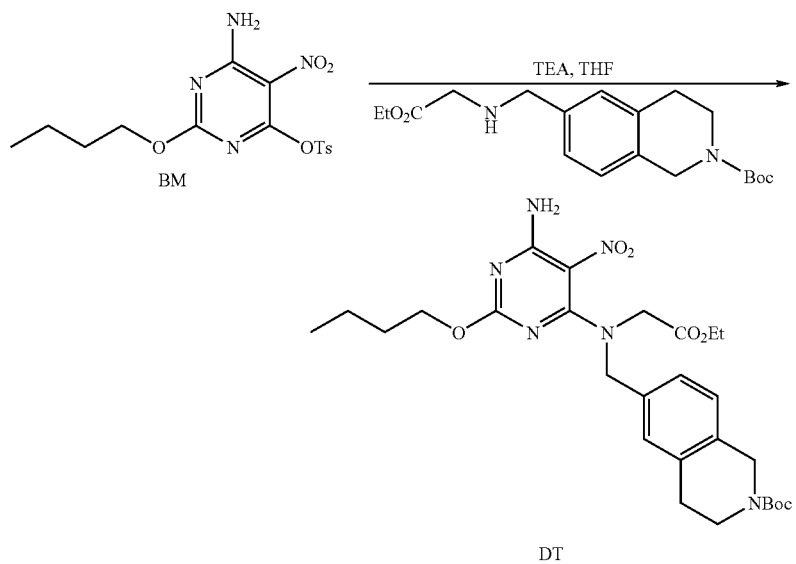

Method LXVI: Compound DT: To a solution of compound BM (220 mg, 0.57 mmol) in THF, was added triethyl amine (160 μL, 1.14 mmol), tert-butyl 6-((2-ethoxy-2-oxoethylamino)methyl)-3,4-dihydroisoquinoline-2(1H)-carboxylate (200 mg, 0.57 mmol). The reaction mixture was stirred at room temperature for 2 h. After reaction finished, the reaction mixture was diluted with EtOAc, treated with saturated aq. NaHCO₃, and extracted by EtOAc (3×). The organic layer was combined, dried over MgSO₄, filtered, concentrated, and purified on a silica gel column. (Eluent: 0→100% EtOAc in Hexanes), giving Compound DT. $^1$H NMR (CDCl₃, 300 MHz): d (ppm) 7.30-7.06 (m, 3H), 4.66 (s, 2H), 4.54 (s, 2H), 4.21-4.10 (m, 4H), 4.03 (s, 2H), 3.62-3.34 (m, 2H), 2.81-2.79 (m, 2H), 1.69-1.65 (m, 2H), 1.50 (s, 9H), 1.48-1.43 (m, 2H), 1.28-1.22 (m, 3H), 0.96-0.89 (m, 3H).

Compound DU: Prepared by Method I:

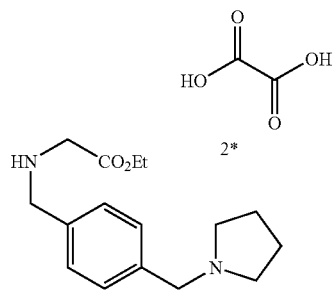

Compound DU was prepared according to Method I: (Free base form of DU was converted to dioxalic acid salt by slurrying with 2.0 equiv. of oxalic acid in warm absolute EtOH. Precipitate was dried in a vacuum oven after filtration). $^1$H NMR (D$_2$O, 300 MHz): d 7.46 (s, 4H), 4.29 (s, 2H), 4.25 (s, 2H), 4.16 (q, J=7.0 Hz, 2H), 3.90 (s, 2H), 3.39 (m, 2H), 3.06 (m, 2H), 2.04 (m, 2H), 1.84 (m, 2H), 1.15 (t, J=7.0 Hz, 3H). LCMS-ESI$^+$: calc'd for C$_{16}$H$_{25}$N$_2$O$_2$: 277.4 (M+H$^+$); Found: 277.1 (M+H$^+$).

Compound DV, Method LX

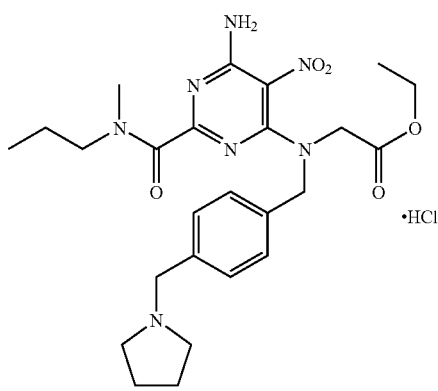

Compound DV was prepared from Compound DU and Compound DP according to Method LX: 11% yield; compound is a monohydrochloride salt. $^1$H NMR (CDCl$_3$, 300 MHz)(compound exists as a mixture of two amide rotamers at 23° C. with some associated protons having distinct resonances): δ (ppm) 12.75 (s, 1H), 7.66 (app. s, broad, 2H), 7.38 (app. s, broad, 21-1), 4.76 (s, 2H), 4.33-4.27 (m, 4H), 3.62 (s, 2H), 3.16 (t, J=7.6 Hz, 1H, single rotamer), 3.02 (t, J=7.6 Hz, 1H, single rotamer), 2.91 (s, 1.5H, single rotamer), 2.90-2.80 (m, 2H), 2.84 (s, 1.5H, single rotamer), 2.80-2.65 (m, 2H), 2.30-2.18 (m, 2H), 2.18-2.06 (m, 2H), 1.64 (app. qt, J=7.6 Hz, 7.6 Hz, 2H, both rotamers), 1.24 (t, J=6.8 Hz, 3H), 0.97 (t, J=7.6 Hz, 1.5H, single rotamer), 0.87 (t, J=7.6 Hz, 1.5H, single rotamer). LCMS-ESI$^+$: calc'd for C$_{25}$H$_{36}$N$_7$O$_5$: 514.3 (M+H$^+$); Found: 514.2 (M+H$^+$).

Example 85

Prepared by Method LXI

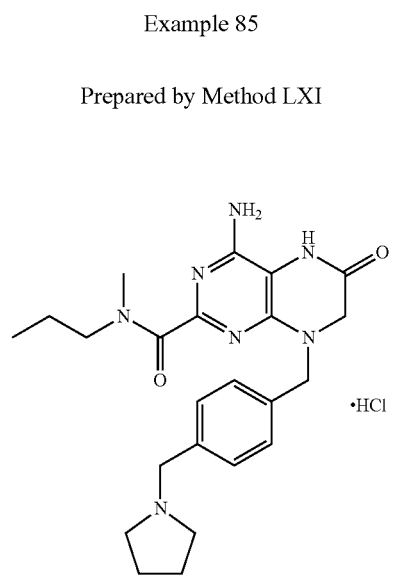

Example 85

Example 85 was obtained in 20% yield as a white solid in the form of a monohydrochloride salt. $^1$H NMR (CD$_3$OD, 300 MHz)(compound exists as a mixture of two amide rotamers at 23° C. with some associated protons having distinct resonances): δ (ppm) 7.62-7.53 (m, 2H), 7.50-7.45 (m, 2H), 5.50 (s, 2H), 4.97 (s, 2H), 4.40 (s, 2H), 4.19 (app. s, 1H, single rotamer), 4.15 (app. s, 1H, single rotamer), 3.55-3.40 (m, 2H), 3.40-3.25 (m, 2H), 3.20 (s, 1.5H, single rotamer), 3.09 (s, 1.5H, single rotamer), 2.30-1.95 (m, 4H), 1.69-1.65 (m, 2H, both rotamers), 0.96 (t, J=7.6 Hz, 1.5H, single rotamer), 0.76 (t, J=7.6 Hz, 1.5H, single rotamer). LCMS-ESI$^+$: calc'd for C$_{23}$H$_{32}$N$_7$O$_2$: 438.3 (M+H$^+$); Found: 438.2 (M+H$^+$) and 219.7 ((M+2H$^+$)/2).

Compound 86: Prepared by Method LXII:

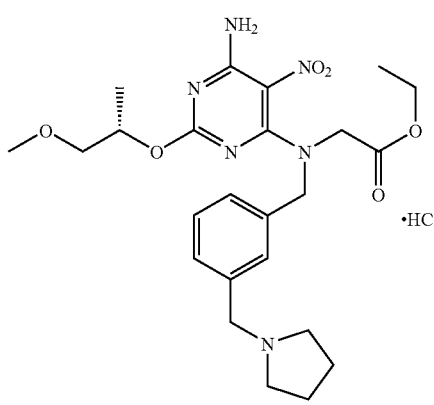

Compound DW was prepared in 38% yield as a monohydrochloride salt. $^1$H NMR (CDCl$_3$, 300 MHz): δ (ppm) 12.63 (s, 1H), 7.75-7.30 (m, 4H), 5.24-5.06 (m, 2H), 4.79 (s, 2H), 4.32-4.16 (m, 5H), 3.66-3.35 (m, 4H), 3.34 (s, 3H), 2.85-2.70

(m, 2H), 2.30-2.20 (m, 2H), 2.20-2.10 (m, 2H), 1.34-1.20 (m, 6H). LCMS-ESI⁺: calc'd for $C_{24}H_{35}N_6O_6$: 503.3 (M+H⁺); Found: 503.2 (M+H⁺).

Example 87

Prepared by Method LXI

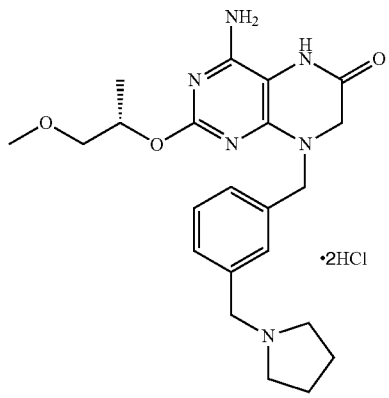

Example 87

Example 87 was obtained in 43% yield as a dihydrochloride salt. ¹H NMR (CD₃OD, 300 MHz): δ (ppm) 7.56 (s, 1H), 7.54-7.50 (m, 3H), 5.38-5.30 (m, 1H), 4.94 (s, 2H), 4.39 (s, 2H), 4.17 (s, 2H), 3.60-3.48 (m, 4H), 3.34 (s, 3H), 3.26-3.17 (m, 2.22-2.12 (m, 2H), 2.11-1.99 (m, 2H), 1.32 (d, J=6.4 Hz, 3H). LCMS-ESI⁺: calc'd for $C_{22}H_{31}N_6O_3$: 427.2 (M+H⁺); Found: 427.2 (M+H⁺), 214.2 ((M+2H⁺)/2).

Example 88

Prepared by Method LXI

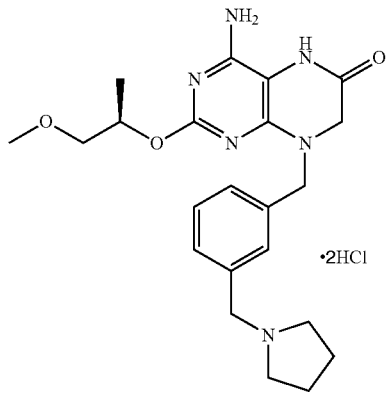

Example 88

Example 88 was obtained in 18% yield as a dihydrochloride salt. ¹H NMR (CD₃OD, 300 MHz): δ (ppm) 7.54 (s, 1H), 7.53-7.50 (m, 3H), 5.37-5.29 (m, 1H), 4.94 (s, 2H), 4.39 (s, 2H), 4.14 (s, 2H), 3.58-3.45 (m, 4H), 3.34 (s, 3H), 3.22-3.18 (m, 2H), 2.27-1.96 (m, 4H), 1.31 (d, J=6.4 Hz, 3H). LCMS-ESI⁺: calc'd for $C_{22}H_{31}N_6O_3$: 427.2 (M+H⁺); Found 472.2 (M+H⁺), 214.2 ((M+2H⁺)/2).

Compound DX: Prepared by Method LXIII:

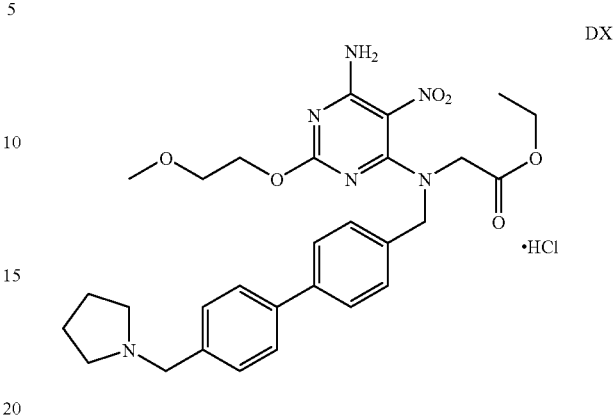

Compound DX was prepared in 54% yield as a monohydrochloride salt. ¹H NMR (CD₃OD, 300 MHz): δ (ppm) 7.76 (d, J=7.6 Hz, 2H), 7.66 (d, J=7.6 Hz, 2H), 7.63 (d, J=7.6 Hz, 2H), 7.48 (d, J=7.6 Hz, 2H), 4.91 (s, 2H), 4.48 (t, J=4.4 Hz, 2H), 4.44 (s, 2H), 4.30 (s, 2H), 4.23 (q, J=7.0 Hz, 2H), 3.65 (t, J=4.4 Hz, 2H), 3.60-3.48 (m, 2H), 3.35 (s, 3H), 3.30-3.17 (m, 2H), 2.25-2.15 (m, 2H), 2.10-1.99 (m, 2H), 1.27 (t, J=7.0 Hz, 3H). LCMS-ESI⁺: calc'd for $C_{29}H_{37}N_6O_6$: 565.3 (M+H⁺); Found 565.1 (M+H⁺).

Compound DY: Prepared by Method LXIII:

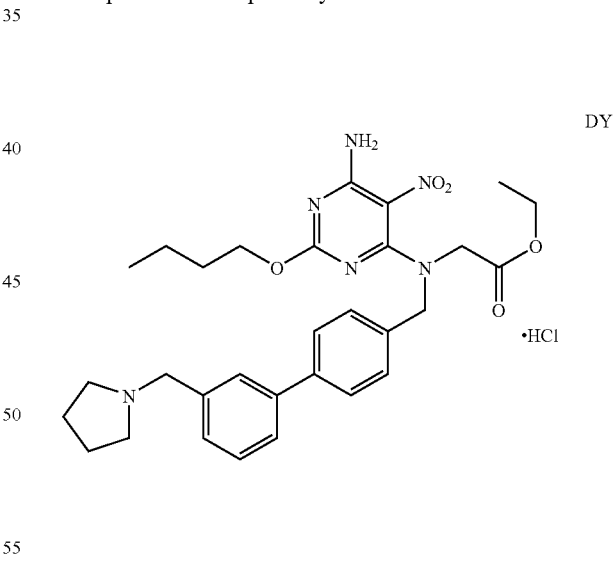

Compound DY was prepared in 75% yield as a monohydrochloride salt. ¹H NMR (CDCl₃, 300 MHz): δ (ppm) 12.76 (s, broad, 1H), 8.85 (s, broad, 1H), 8.21 (s, broad, 1H), 8.07 (s, 1H), 7.72-7.40 (m, 7.40-7.33 (m, 2H), 4.80 (s, 2H), 4.37-4.10 (m, 6H), 3.73-3.59 (m, 2H), 2.94-2.79 (m, 2H), 2.30-2.15 (m, 2H), 2.14-1.96 (m, 2H), 1.75-1.62 (m, 2H), 1.43-1.30 (m, 2H), 1.27 (t, J=7.0 Hz, 3H), 0.91 (t, J=7.3 Hz, 3H). LCMS-ESI⁺: calc'd for $C_{30}H_{39}N_6O_5$: 563.3 (M+H⁺); Found: 563.3 (M+H⁺).

Compound DZ: Prepared by Method LXIII:

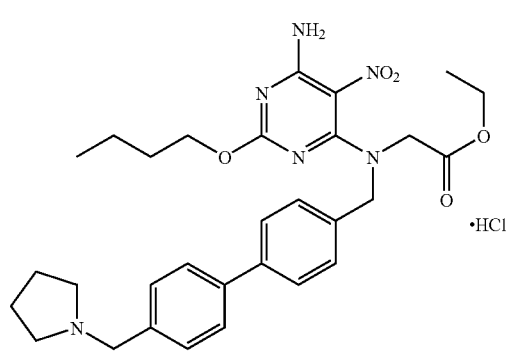

DZ

Compound DZ was prepared in 54% yield as a monohydrochloride salt. $^1$H NMR (CD$_3$OD, 300 MHz): δ (ppm) 7.75 (d, J=7.9 Hz, 2H), 7.66 (d, J=7.9 Hz, 2H), 7.63 (d, J=7.9 Hz, 2H), 7.47 (d, J=8.3 Hz, 2H), 4.94 (s, 2H), 4.43 (s, 2H), 4.39 (t, J=6.7 Hz, 2H), 4.35 (s, 2H), 4.22 (q, J=7.0 Hz, 2H), 3.58-3.48 (m, 2H), 3.30-3.16 (m, 2H), 2.25-2.10 (m, 2H), 2.10-1.96 (m, 2H), 1.71 (tt, J=7.6 Hz, 7.6 Hz, 2H), 1.45 (qt, J=7.6 Hz, 7.6 Hz, 2H), 1.27 (t, J=7.0 Hz, 3H), 0.93 (t, J=7.6 Hz, 3H). LCMS-ESI$^+$: calc'd for C$_{30}$H$_{39}$N$_6$O$_5$: 563.3 (M+H$^+$); Found: 563.2 (M+H$^+$).

Example 89

Prepared by Method LXV

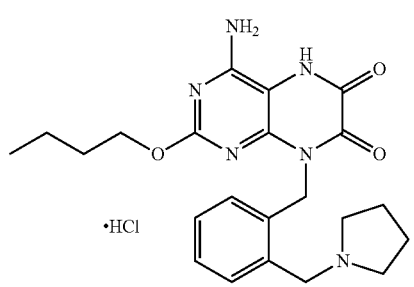

Example 89

Example 89 was obtained in 35% yield as a monohydrochloride salt. $^1$H NMR (CD$_3$OD, 300 MHz): δ (ppm) 7.55-7.38 (m, 4H), 5.58 (s, 2H), 4.73 (s, 2H), 4.31 (t, J=7.6 Hz, 2H), 3.72-3.59 (m, 2H), 3.42-3.30 (m, 2H), 2.32-2.20 (m, 2H), 2.20-2.02 (m, 2H), 1.71 (tt, J=7.6 Hz, 7.6 Hz, 2H), 1.42 (qt, J=7.6 Hz, 7.6 Hz, 2H), 0.94 (t, J=7.6 Hz, 3H). LCMS-ESI$^+$: calc'd for C$_{22}$H$_{29}$N$_6$O$_3$: 425.2 (M+H$^+$); Found: 425.2 (M+H$^+$).

Example 90

Prepared by Method LXV

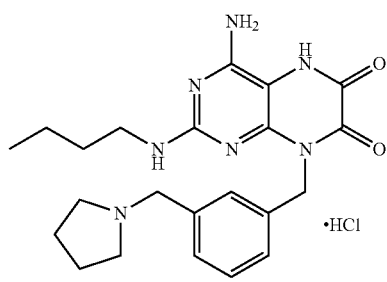

Example 90

Example 90 was obtained in 14% yield as a monohydrochloride salt. $^1$H NMR (CD$_3$OD, 300 MHz): δ (ppm) 7.70-7.40 (m, 4H), 4.36 (q, J=7.6, 2H), 3.60-3.20 (m, 4H), 2.25-1.95 (m, 4H), 1.60-1.20 (m, 4H), 0.94 (t, J=7.6 Hz, 2H); other resonances were too broad or poorly resolved to be labeled definitively. LCMS-ESI$^+$: calc'd for C$_{22}$H$_{30}$N$_7$O$_2$: 424.2 (M+H$^+$); Found: 424.2 (M+H$^+$).

Example 91

Prepared by Method LXV

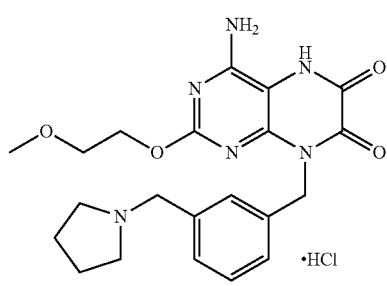

Example 91

Example 91 was obtained in 80% yield as a monohydrochloride salt. $^1$H NMR (CD$_3$OD, 300 MHz): δ (ppm) 7.60-7.35 (m, 4H), 5.52 (s, 2H), 4.40-4.36 (m, 2H), 4.34 (s, 2H), 3.69-3.65 (m, 2H), 3.60-3.23 (m, 4H), 3.38 (s, 3H), 2.30-2.20

(m, 2H), 2.20-2.10 (m, 2H). LCMS-ESI⁺: calc'd for C$_{21}$H$_{27}$N$_6$O$_4$: 427.2 (M+H⁺); Found: 427.2 (M+H⁺).

Example 92

Prepared by Method LXV

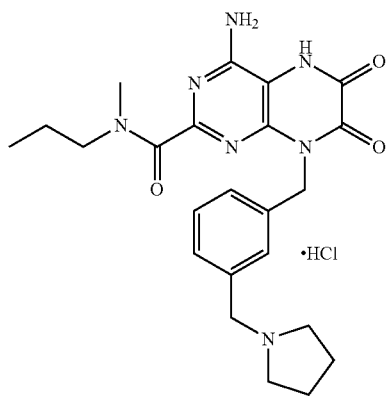

Example 92

Example 92 was obtained in 9% yield as a monohydrochloride salt. To reach complete conversion, an extra 100 equiv of MnO$_2$ was implemented. ¹H NMR (CD$_3$OD, 300 MHz)(compound exists as a mixture of two amide rotamers at 23° C. with some associated protons having distinct resonances): δ (ppm) 7.60-7.40 (m, 4H), 5.52 (s, 2H), 4.38 (s, 2H), 3.80-3.25 (m, 6H), 3.08 (s, 1.5H, single rotamer), 2.93 (s, 1.5H, single rotamer), 2.25-2.10 (m, 2H), 2.10-1.95 (m, 2H), 1.47 (app. t, J=8.4 Hz, 1H, single rotamer), 1.05 (app, t, J=8.4 Hz, 1H, single rotamer), 0.98-0.86 (m, 1.5H, single rotamer), 0.85-0.78 (m, 1.5H, single rotamer). LCMS-ESI⁺: calc'd for C$_{23}$H$_{30}$N$_7$O$_3$: 452.2 (M+H⁺); Found: 452.2 (M+H⁺).

Example 93

Prepared by Method LXV

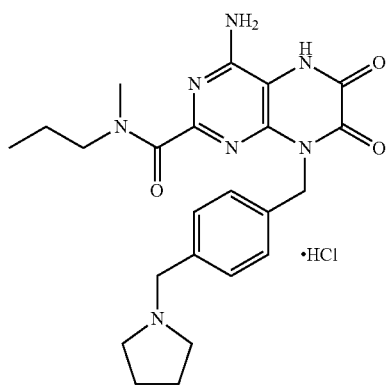

Example 93

Example 93 was obtained in 16% yield as a monohydrochloride salt. To reach complete conversion, an extra 100 equiv of MnO$_2$ was implemented. ¹H NMR (CD$_3$OD, 300 MHz)(compound exists as a mixture of two amide rotamers at 23° C. with some associated protons having distinct resonances): δ (ppm) 7.60-7.40 (m, 4H), 5.52 (s, 2H), 4.34 (s, 2H), 3.80-3.25 (m, 6H), 3.05 (s, 1.5H, single rotamer), 2.88 (s, 1.5H, single rotamer), 2.21-2.10 (m, 2H), 2.10-1.96 (m, 2H), 1.47 (app. t, J=8.4 Hz, 1H, single rotamer), 0.95 (app. t, J=8.4 Hz, 1H, single rotamer), 0.92-0.86 (m, 1.5H, single rotamer), 0.82-0.70 (m, 1.5H, single rotamer). LCMS-ESI⁺: calc'd for C$_{23}$H$_{30}$N$_7$O$_3$: 452.2 (M+H⁺); Found: 452.2 (M+H⁺).

Example 94

Prepared by Method LXI

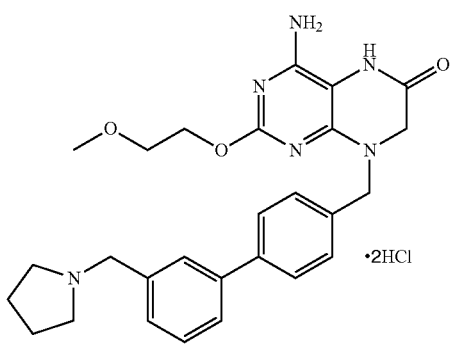

Example 94

Example 94 was obtained in 87% yield as a dihydrochloride salt. ¹H NMR (CD$_3$OD, 300 MHz): δ (ppm) 7.89 (s, 1H), 7.79-7.70 (m, 3H), 7.61-7.43 (m, 4H), 4.96 (s, 2H), 4.61 (t, J=4.7, 2H), 4.47 (s, 2H), 4.16 (s, 2H), 3.73 (t, J=4.7 Hz, 2H), 3.60-3.43 (m, 2H), 3.38 (s, 3H), 3.30-3.18 (m, 2H), 2.25-2.13 (m, 2H), 2.11-1.96 (m, 2H). LCMS-ESI⁺: calc'd for C$_{27}$H$_{33}$N$_6$O$_3$: 489.3 (M+H⁺); Found: 489.2 (M+H⁺), 245.2 ((M+2H⁺)/2).

Example 95

Prepared by Method LXV

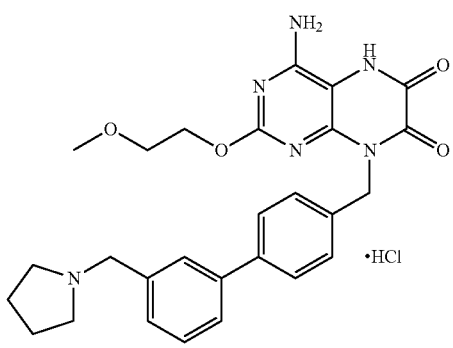

Example 95

Example 95 was obtained in 97% yield as a monohydrochloride salt. ¹H NMR (CD$_3$OD, 300 MHz): δ (ppm) 7.80-

7.46 (m, 8H), 5.53 (s, 2H), 4.46 (t, J=4.5 Hz, 2H), 4.45 (s, 2H), 3.68 (t, J=4.5 Hz, 2H), 3.58-3.42 (m, 2H), 3.36 (s, 3H), 3.35-3.21 (m, 2H), 2.28-2.10 (m, 2H), 2.10-1.99 (m, 2H). LCMS-ESI$^+$: calc'd for $C_{27}H_{31}N_5O_4$: 503.2 (M+H$^+$); Found: 503.2 (M+H$^+$).

Example 96

Prepared by Method LXI

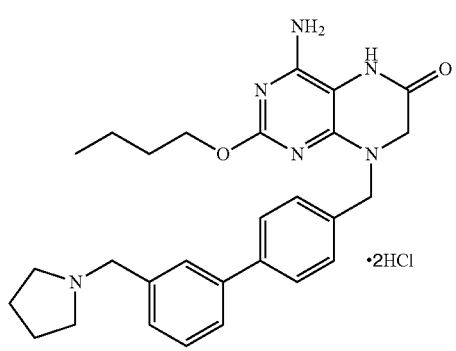

Example 96

Example 96 was obtained in 87% yield as a dihydrochloride salt. $^1$H NMR (CD$_3$OD, 300 MHz): δ (ppm) 7.89 (s, 1H), 7.76-7.70 (m, 3H), 7.61-7.44 (m, 4H), 4.97 (s, 2H), 4.49 (t, J=7.6 Hz, 2H), 4.47 (s, 2H), 4.17 (s, 2H), 3.58-3.51 (m, 2H), 3.31-3.19 (m, 2H), 2.23-2.11 (m, 2H), 2.10-1.99 (m, 2H), 1.77 (tt, J=7.6 Hz, 7.6 Hz, 2H), 1.48 (qt, J=7.6 Hz, 7.6 Hz, 2H), 0.95 (t, J=7.6 Hz, 3H). LCMS-ESI$^+$: calc'd for $C_{28}H_{35}N_6O_2$: 487.3 (M+H$^+$); Found: 487.2 (M+H$^+$) and 244.2 ((M+2H$^+$)/2).

Example 97

Prepared by Method LXV

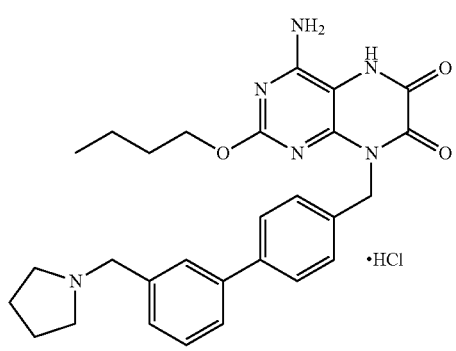

Example 97

Example 97 was obtained in 21% yield as a monohydrochloride salt. $^1$H NMR (CD$_3$OD, 300 MHz): δ (ppm) 7.80-7.43 (m, 8H), 5.54 (s, 2H), 4.45 (s, 2H), 4.32 (t, J=7.6 Hz, 2H), 3.58-3.47 (m, 2H), 3.45-3.38 (m, 2H), 2.21-1.87 (m, 4H), 1.76 (tt, J=7.6 Hz, 7.6 Hz, 2H), 1.47 (qt, J=7.6 Hz, 7.6 Hz, 2H), 0.95 (t, J=7.6 Hz, 3H). LCMS-ESI$^+$: calc'd for $C_{28}H_{33}N_6O_3$: 501.3 (M+H$^+$); Found: 501.2 (M+H$^+$).

Example 98

Prepared by Method LXI

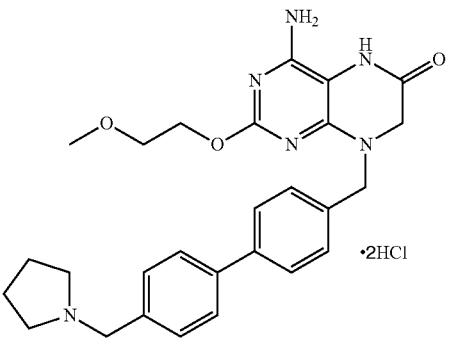

Example 98

Example 98 was obtained in quantitative yield as a dihydrochloride salt. $^1$H NMR (CD$_3$OD, 300 MHz): δ (ppm) 7.77 (d, J=7.8 Hz, 2H), 7.71 (d, J=7.8 Hz, 2H), 7.64 (d, J=7.8 Hz, 2H), 7.50 (d, J=7.8 Hz, 2H), 4.97 (s, 2H), 4.62 (t, J=4.4 Hz, 2H), 4.45 (s, 2H), 4.18 (s, 2H), 3.72 (t, J=4.4 Hz, 2H), 3.58-3.49 (m, 2H), 3.38 (s, 3H), 3.30-3.17 (m, 2H), 2.26-2.12 (m, 2H), 2.11-1.99 (m, 2H). LCMS-ESI$^+$: calc'd for $C_{27}H_{33}N_6O_3$: 489.3 (M+H$^+$); Found: 489.1 (M+H$^+$) and 245.2 ((M+2H$^+$)/2).

Example 99

Prepared by Method LXV

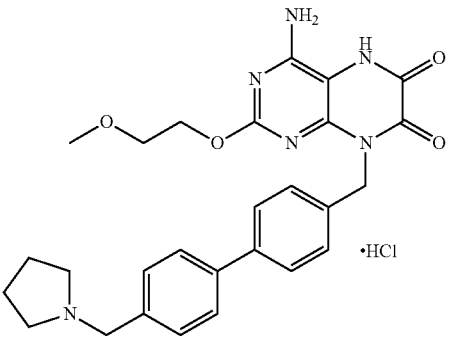

Example 99

Example 99 was obtained in 20% yield as a monohydrochloride salt. $^1$H NMR (CD$_3$OD, 300 MHz): δ (ppm) 7.74 (d, J=7.8 Hz, 2H), 7.62-7.50 (m, 6H), 5.53 (s, 2H), 4.43 (t, J=4.4 Hz, 2H), 4.42 (s, 2H), 3.66 (t, J=4.4 Hz, 2H), 3.58-3.44 (m, 2H), 3.42-3.30 (m, 2H), 2.25-2.10 (m, 2H), 2.10-1.99 (m, 2H). LCMS-ESI⁺: calc'd for C₂₇H₃₁N₆O₄: 503.2 (M+H⁺); Found: 503.1 (M+H⁺).

Example 100

Prepared by Method LXI

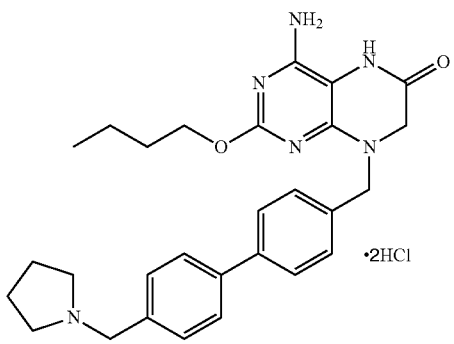

Example 100

Example 100 was obtained in 86% yield as a dihydrochloride salt. ¹H NMR (CD₃OD, 300 MHz): δ (ppm) 7.77 (d, J=7.8 Hz, 2H), 7.70 (d, J=7.8 Hz, 2H), 7.64 (d, J=7.8 Hz, 2H), 7.49 (d, J=7.8 Hz, 2H), 4.96 (s, 2H), 4.49 (t, J=7.6 Hz, 2H), 4.44 (s, 2H), 4.18 (s, 2H), 3.60-3.50 (m, 2H), 3.27-3.19 (m, 2H), 2.22-2.10 (m, 2H), 2.09-1.96 (m, 2H), 1.76 (tt, J=7.6 Hz, 7.6 Hz, 2H), 1.46 (qt, J=7.6 Hz, 7.6 Hz, 2H), 0.95 (t, J=7.6 Hz, 3H). LCMS-ESI⁺: calc'd for C₂₈H₃₅N₆O₂: 487.3 (M+H⁺); Found: 487.1 (M+H⁺) and 244.2 ((M+2H⁺)/2).

Example 101

Prepared by Method LXV

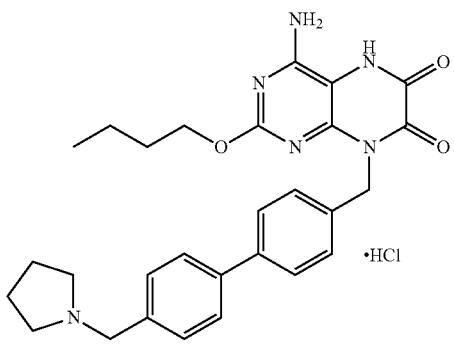

Example 101

Example 101 was obtained in 23% yield as a monohydrochloride salt. ¹H NMR (CD₃OD, 300 MHz): δ (ppm) 7.74 (d, J=7.8 Hz, 2H), 7.62-7.50 (m, 6H), 5.54 (s, 2H), 4.42 (s, 2H), 4.29 (t, J=7.6 Hz, 2H), 3.56-3.41 (m, 2H), 3.38-3.26 (m, 2H), 2.27-2.10 (m, 2H), 2.09-1.96 (m, 2H), 1.69 (tt, J=7.6 Hz, 7.6 Hz, 2H), 1.45 (qt, J=7.6 Hz, 7.6 Hz, 2H), 0.96 (t, J=7.6 Hz, 3H). LCMS-ESI⁺: calc'd for C₂₈H₃₃N₆O₃: 501.3 (M+H⁺); Found 503.1 (M+H⁺).

Compound EA: Prepared by Method I

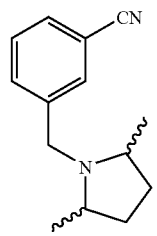

EA

Compound EA was made using THF at 23° C. with a 2 h reaction time. Reaction was quenched with water and chromatoraphed on an ISCO silica column (Eluent: 0→40% B A=DCM B=MeOH/DCM 1:4). Product EA was obtained as a free base. ¹H NMR (DMSO-d⁶, 300 MHz): d (ppm) 7.74-7.73-(d, J=5.1 Hz, 1H), 7.69-7.65 (m, 2H), 7.53-7.48 (m, 1H), 3.81-3.55 (m, 2H), 2.96-2.88 (m, 1H), 2.59-2.56 (m, 1H), 1.99-1.89 (m, 1H), 1.82-1.73 (m, 1H), 1.35-1.26 (m, 2H), 0.92-0.90 (d, J=14.4 Hz, 6H). LCMS-ESI⁺: calc'd for C₁₄H₁₉N₂: 215.3 (M+H⁺); Found: 215.1 (M+H⁺).

Compound EB: Prepared by Method III

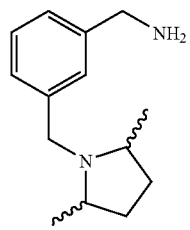

EB

Compound EB was made synthesized in THF over a 100 h reaction timeframe. Crude material was carried forward without further purification, and was obtained as a free base. LCMS-ESI⁺: calc'd for C₁₄H₂₃N₂: 219.3 (M+H⁺); Found: 219.2 (M+H⁺).

Compound EC: Prepared by Method IV

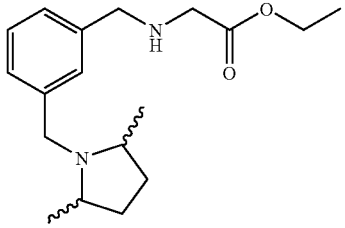

EC

Compound EC was synthesized over a 3 h reaction timeframe and quenched with water. After chromatography on an ISCO silica column (Eluent: 0→40% B over 15 min; A=DCM, B=MeOH/DCM 1:4), EC was obtained as a free base. ¹H NMR (DMSO-d⁶, 300 MHz): d (ppm) 7.26-7.12 (m, 4.12-4.05 (m, 2H), 3.78-3.74 (d, J=20.0 Hz, 1H), 3.68 (s, 2H), 3.62 (s, broad, 1H), 3.47-3.42 (d, J=14.0 Hz, 1H), 3.27-3.26 (d, J=3.6 Hz, 2H), 2.96-2.90 (m, 1H), 1.98-1.89 (m, 2H), 1.79-1.72 (m, 1H), 1.34-1.24 (m, 1.20-1.16 (t, J=7.0 Hz, 3H), 0.94-0.90 (m, 6H). LCMS-ESI⁺: calc'd for C₁₆H₂₉N₂O₂: 305.4 (M+H⁺); Found: 305.2 (M+H⁺).

Compound ED: Prepared by Method LXVI

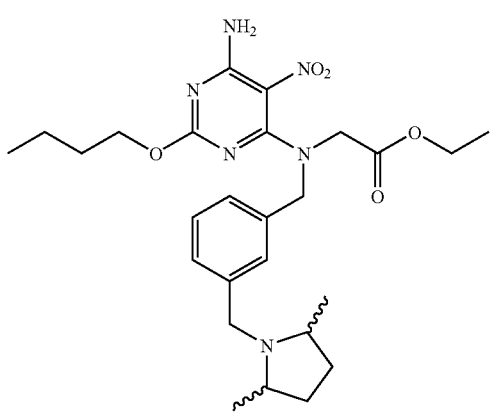

Compound ED was prepared using a 3.5 h reaction timeframe. The product was chromatographed on an 12 gram ISCO silica column (Eluent: 0→30% B ramp over 5 min. A=DCM B=MeOH/DCM 1:4). ED was obtained as a free base. $^1$H NMR (DMSO-d$^6$, 300 MHz): d (ppm) 7.97 (s, broad, 2H), 7.26-7.09 (m, 4H), 4.67 (s, 2H), 4.10-4.06 (m, 6H), 3.76-3.71 (d, J=14.1 Hz, 1H), 3.61 (s, 1H), 3.44-3.39 (d, J=14.1 Hz, 1H), 2.87 (s, broad, 1H), 1.94-1.88 (m, 1H), 1.70 (s, broad, 1H), 1.6-1.51 (m, 2H), 1.37-1.14 (m, 7H), 0.90-0.84 (m, 9H). LCMS-ESI$^+$: calc'd for $C_{26}H_{39}N_6O_5$: 514.6 (M+H$^+$); Found: 515.3 (M+H$^+$).

Example 102

Prepared by Method XIV

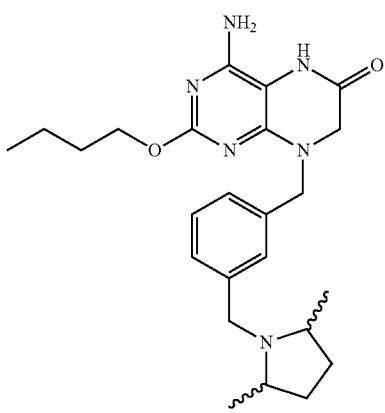

Example 102

Example 102 was synthesized over a 2 h reaction timeframe. Example 102 was obtained as a free base. $^1$H NMR (DMSO d$^6$, 300 MHz): d (ppm) 11.06 (s, broad, 1H), 10.60 (s, broad, 1H), 10.29 (s, broad, 1H), 7.76-7.71 (m, 4H), 4.79 (s, 2H), 4.31-4.17 (m, 4H), 4.07-4.04 (d, J=8.7 Hz, 2H), 3.72 (m, 1H), 3.61-3.50 (m, 1H), 2.28-2.00 (m, broad, 3H), 1.71-1.53 (m, 4H), 1.36-1.16 (m, 7H), 1.13-1.04 (m, 2H), 0.85-0.80 (t, J=7.6 Hz, 3H). LCMS-ESI$^+$: calc'd for $C_{24}H_{35}N_6O_2$: 438.6 (M+H$^+$); Found: 439.3 (M+H$^+$).

Compound EE: Prepared by Method XXXVII

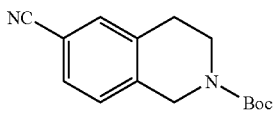

$^1$H NMR (CDCl$_3$, 300MHz) δ (ppm) 7.48-7.45 (m, 2H), 7.21 (d, 1H, J=8.1 Hz), 4.62 (s, 2H), 3.67 (t, J=5.8 Hz, 2H), 2.87 (t, J=5.5 Hz, 2H), 1.50 (s, 9H).

Compound EF: Prepared by Method XXXVIII

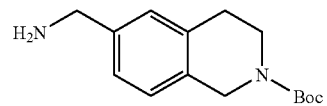

$^1$H NMR (CD$_3$OD, 300 MHz) δ (ppm) 7.14-7.03 (m, 3H), 4.74 (s, 2H), 3.71 (s, 2H), 3.57 (t, J=5.7 Hz, 2H), 2.78 (t, J=5.8 Hz, 2H), 1.48 (s, 9H). LCMS-ESI$^+$: calc'd for $C_{15}H_{23}N_2O_2$: 263.3 (M+H$^4$); Found: 262.9 (M+H$^+$).

Compound EG: Prepared by Method XXXIX

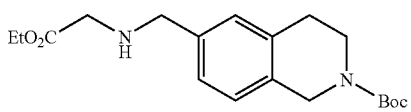

$^1$H NMR (CDCl$_3$, 300 MHz) δ (ppm) 7.18-7.07 (m, 3H), 4.56 (s, 2H), 4.24-4.17 (m, 2H), 3.81 (s, 2H), 3.66-3.64 (m, 2H), 3.43 (s, 2H), 2.83 (t, 2H, J=6.3 Hz), 1.50 (s, 9H), 1.28 (t, J=7.0 Hz, 3H); LCMS-ESI$^+$: calc'd for $C_{19}H_{29}N_2O_4$: 349.4 (M+H$^+$); Found: 349.0 (M+H$^+$).

Compound EH: Prepared by Method LXVI

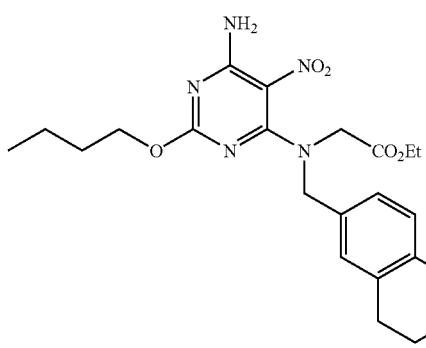

$^1$H NMR (CDCl$_3$, 300 MHz): δ (ppm) 7.30-7.06 (m, 3H), 4.66 (s, 2H), 4.54 (s, 2H), 4.10-4.21 (m, 4H), 4.032 (s, 2H), 3.62-3.34 (m, 2H), 2.79-2.81 (m, 2H), 1.69-1.65 (m, 2H), 1.50 (s, 9H), 1.43-1.48 (m, 2H), 1.22-1.28 (m, 3H), 0.89-0.96

(m, 3H); LCMS-ESI⁺: calc'd for $C_{29}H_{39}N_6O_7$: 559.6 (M+H⁺); Found: 559.0 (M+H⁺).

Example 103

Prepared by Method XL

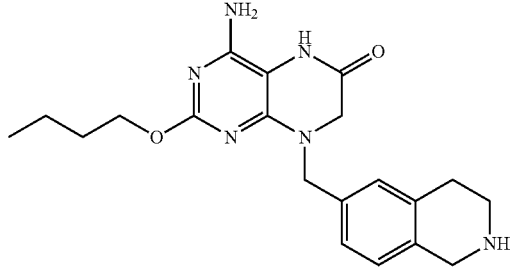

Example 103

Example 103 was made according to Method XL. ¹H NMR (CD₃OD, 300 MHz): d (ppm) 7.26-7.22 (m, 3H), 4.86 (s, 2H), 4.43-4.36 (m, 4H), 4.05 (s, 2H), 3.50 (t, J=6.4 Hz, 2H), 3.12 (t, J=6.1 Hz, 2H), 1.78-1.70 (m, 2H), 1.49-1.42 (m, 2H), 0.95 (t, J=7.5 Hz, 3H). LCMS-ESI⁺: calc'd for $C_{20}H_{27}N_6O_2$: 383.4 (M+H⁺); Found: 383.1 (M+H⁺).

Example 104

Prepared by Method XLI

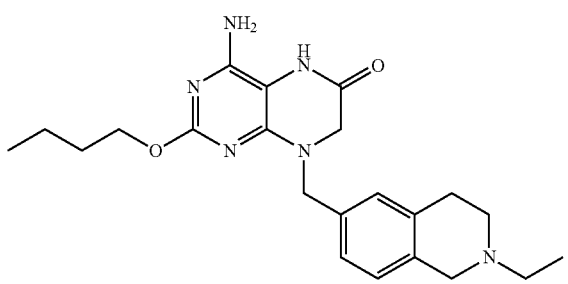

Example 104

Example 104 was made according to Method XLI. ¹H NMR (CD₃OD, 300 MHz): d (ppm) 7.32-7.24 (m, 3H), 4.58-4.56 (m, 2H), 4.38 (t, J=6.5 Hz, 2H), 4.26-4.24 (m, 2H), 4.03 (s, 2H), 3.79-3.71 (m, 2H), 3.21-3.10 (m, 2H), 1.80-1.68 (m, 2H), 1.47-1.39 (m, 2H), 0.96 (t, J=7.4 Hz, 3H). LCMS-ESI⁺: calc'd for $C_{22}H_{31}N_6O_2$: 411.5 (M+H⁺); Found: 411.2 (M+H⁺).

Example 105

Prepared by Method XLVIII

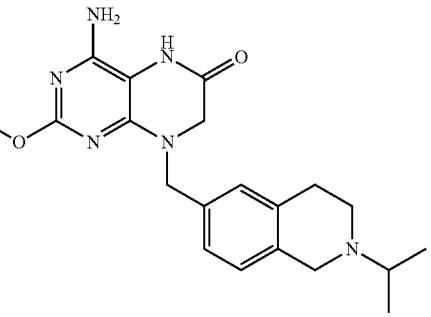

Example 105

Example 105 was made according to Method XLVIII. ¹H NMR (CD₃OD, 300 MHz): d (ppm) 7.29-7.26 (m, 3H), 4.46-4.35 (m, 4H), 4.02 (s, 2H), 3.76-3.72 (m, 2H), 3.23-3.21 (m, 2H), 1.77-1.72 (m, 2H), 1.47-1.44 (m, 8H), 0.96 (t, J=7.0 Hz, 3H); LCMS-ESI⁺: calc'd for $C_{23}H_{33}N_6O_2$: 425.5 (M+H⁺); Found: 425.2 (M+H⁺).

Example 106

Prepared by Method XLVIII

Example 106

Example 106 was made according to Method XLVIII. ¹H NMR (CD₃OD, 300 MHz): d (ppm) 7.30-7.26 (m, 3H), 4.67-4.64 (m, 1H), 4.41-4.37 (m, 3H), 4.04-4.02 (m, 2H), 3.88-3.85 (m, 1H), 3.43-3.41 (m, 1H), 3.34-3.20 (m, 4H), 1.76-1.72 (m, 2H), 1.49-1.44 (m, 2H), 1.24-1.20 (m, 1H), 0.99-0.94 (m, 3H), 0.82 (t, J=6 Hz, 2H), 0.45 (m, 2H). LCMS-ESI⁺: calc'd for $C_{24}H_{33}N_6O_2$: 437.2 (M+H⁺); Found: 437.1 (M+H⁺).

Scheme 90

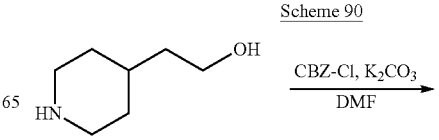

CBZ-Cl, K₂CO₃ / DMF

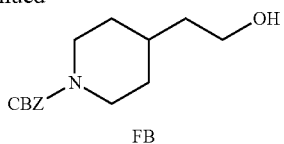
FB

Method XLIX: Compound FB. 2-(Piperidin-4-yl)-ethanol, (520 mg, 4 mmol) was dissolved in anhydrous DMF (8 mL) and to this was added $K_2CO_3$ and the mixture was stirred under $N_2$ in an ice bath. To this was added benzyl chloroformate (623 μL, 4.4 mmol) dropwise. The reaction was allowed to warm to room temperature and then stirred for additional 90 minutes. The reaction was diluted with EtOAc and washed with saturated $NaHCO_3$(aq) (2×) followed with saturated NaCl(aq). The organic extract was dried over anhydrous $Na_2SO_4$ and concentrated under reduced pressure. The residue was purified with silica gel chromatography (20-80% EtOAc in hexanes) to give Compound FB (0.99 g, 3.76 mmol). $^1$H NMR (CDCl$_3$, 300 MHz): d (ppm) 7.36 (m, 5H), 5.13 (s, 2H), 4.18 (bs, 2H), 3.72 (m, 2H), 2.79 (m, 2H), 1.73-1.52 (m, 5H), 1.27-1.18 (m, 3H).

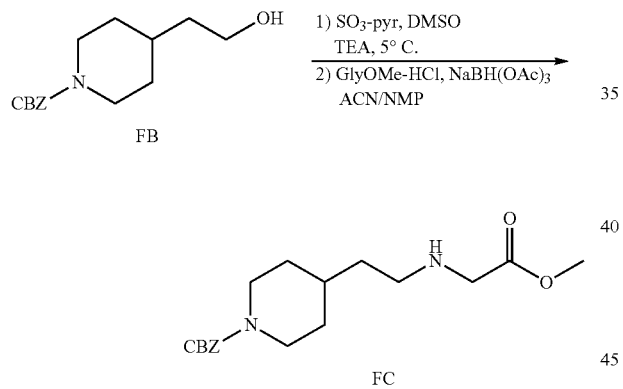

Method XLX: Compound FC. Compound FB (989 mg, 3.76 mmol) was dissolved in anhydrous DMSO (12 mL) and stirred under $N_2$ at 5° C. Triethylamine (1.3 mL, 9.4 mmol) was added followed by sulfur trioxide pyridine complex (1.5 g, 9.4 mmol). The reaction was stirred at 0-5° C. for 90 minutes. Ice and EtOAc were added to the reaction, followed by stirring for several minutes. The organic layer was collected and washed with saturated $NaHCO_3$(aq) (2×) followed with saturated NaCl(aq). The organic extract was dried over anhydrous $Na_2SO_4$ and concentrated under reduced pressure. The resulting oil was dissolved in anhydrous acetonitrile (10 mL) and NMP (3 mL). To this was added glycine methyl ester hydrochloric salt (708 mg, 5.64 mmol) followed by stirring for 15 minutes. NaBH(OAc)$_3$ (1.59 g, 7.52 mmol) was added and the reaction was stirred for 16 hours. Then MeOH was added and the mixture was stirred for 5 minutes. The reaction was diluted with EtOAc and washed with saturated $NaHCO_3$ (aq) (2×) followed with saturated NaCl(aq). The organic extract was dried over anhydrous $Na_2SO_4$, filtered, and concentrated under reduced pressure. The residue was purified with silica gel chromatography (0-10% MeOH in $CH_2Cl_2$) to give Compound FC (142 mg, 0.43 mmol).

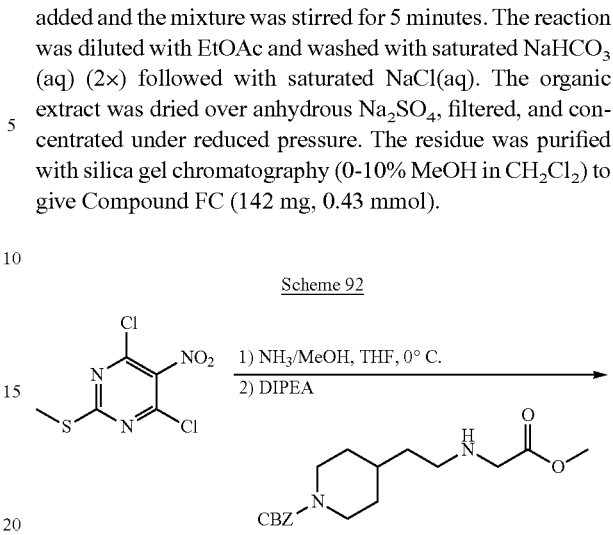

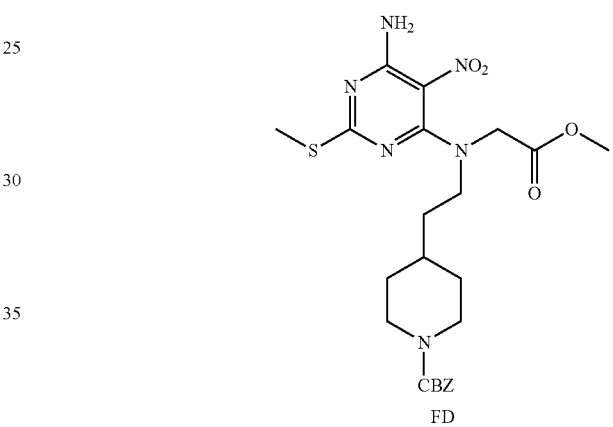

Method XLXI: Compound FD. 4,6-dichloro-5-nitro-2-methylthiopyrimidine (124 mg, 0.468 mmol) was dissolved in anhydrous THF (5 mL) and stirred under $N_2$ (g) in an ice bath. A solution of 7 N $NH_3$ in MeOH (73 μL, 0.51 mmol) in THF (500 μL) was added dropwise over 2-3 minutes. The reaction was stirred for 60 minutes. Additional 7 N $NH_3$ in MeOH solution (73 μL, 0.51 mmol) was added and the mixture was stirred for an additional 60 minutes. A solution of FC (142 mg, 0.42 mmol) in anhydrous THF (0.5 mL) was added to the reaction. The DIPEA (89 μL, 0.51 mmol) was added. The reaction mixture was then stirred for 16 hours at room temperature, diluted with EtOAc, and washed with saturated $NaHCO_3$(aq) solution (2×) followed with saturated NaCl(aq). Ther organic extract was dried over anhydrous $Na_2SO_4$ and concentrated under reduced pressure. The product was purified with silica gel chromatography (20-50% EtOAc in hexanes) to give Compound ED (150 mg, 0.29 mmol). $^1$H NMR: (CDCl$_3$, 300 MHz): d (ppm) 7.36 (m, 5H), 5.13 (s, 2H), 4.12 (m, 4H), 3.76 (s, 3H), 3.41 (m, 2H), 2.76 (m, 2H), 2.42 (s, 3H), 1.67 (m, 4H), 1.45 (m, 1H), 1.20 (m, 2H). LCMS-ESI$^+$: calc'd for $C_{23}H_{31}N_6O_6S$: 519.2 (M+H$^+$); Found: 519.0 (M+H$^+$).

Scheme 93

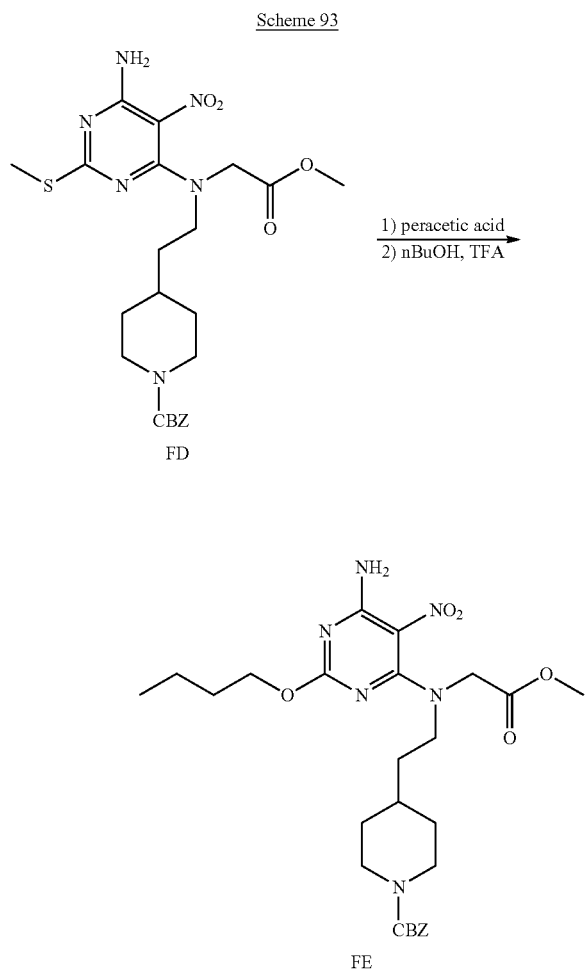

Method XLII: Compound FE. Compound ED (150 mg, 0.29 mmol) was dissolved in anhydrous acetonitrile (10 mL) and stirred under $N_2$ (g) in an ice bath. Aqueous 32% peracetic acid solution (244 µL, 1.16 mmol) was added and the mixture was stirred for 2 hours. Saturated $Na_2S_2O_3$(aq) solution was added and the mixture was stirred for 5 minutes. The mixture was extracted with EtOAc. The organic extract was then washed with $NaHCO_3$(aq) solution followed with saturated NaCl(aq), dried over anhydrous $Na_2SO_4$, filtered, and concentrated under reduced pressure. The residue was added to n-BuOH (5 mL) and TFA (90 µL, 1.16 mmol) and then stirred at 100° C. for 2-3 hours. The mixture was concentrated under reduced pressure, dissolved in EtOAc and washed with saturated $NaHCO_3$(aq) solution (2×) followed with saturated NaCl(aq). The organic extract was dried over anhydrous $Na_2SO_4$ and concentrated under reduced pressure. The product was purified with silica gel chromatography (20-50% EtOAc in hexanes) to give Compound FE (108 mg, 0.20 mmol). $^1$H NMR ($CDCl_3$, 300 MHz): ☐ 7.36 (m, 5H), 5.13 (s, 2H), 4.22-4.10 (m, 6H), 3.76 (s, 3H), 3.40 (m, 2H), 2.76 (m, 2H), 1.71 (m, 6H), 1.45 (m, 3H), 1.20 (m, 2H), 0.95 (t, J=7.2 Hz, 3H). LCMS-ESI$^+$: calc'd for $C_{26}H_{37}N_6O_7$: 545.3 (M+H$^+$): Found: 545.1 (M+H$^+$).

Scheme 94

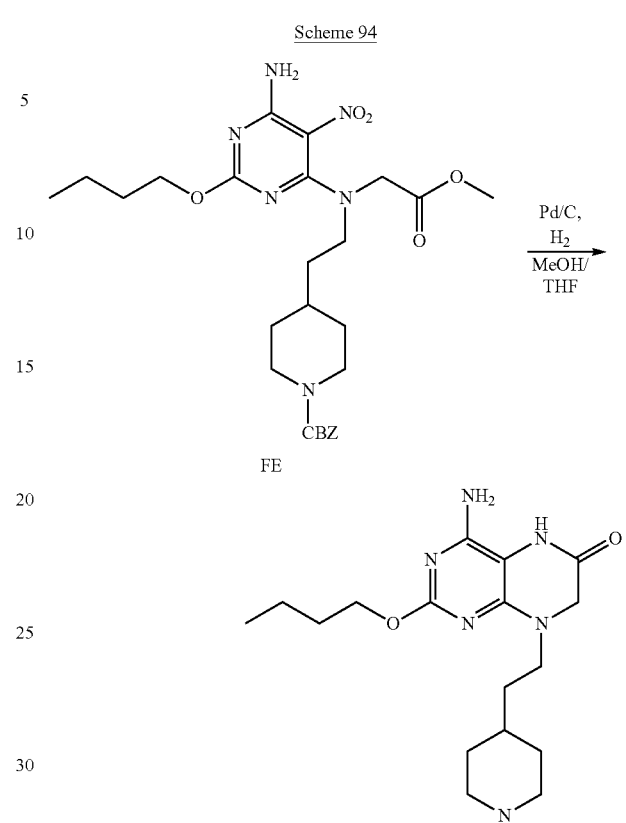

Method XLIII: Example 107. Compound FE (108 mg, 0.20 mmol) was dissolved in THF (4 mL) and MeOH (15 mL). To this was added 10% Pd/C and the reaction was stirred under 1 atmosphere $H_2$ (g) for 16 hours. The reaction was filtered reaction through Celite. Concentration under reduced pressure gave Example 107 (60 mg, 0.17 mmol). $^1$H NMR: ($CDCl_3$, 300 MHz): d (ppm) 5.15 (s, 2H), 3.97 (t, J=6.9 Hz, 2H), 3.75 (s, 2H), 3.35 (m, 2H), 2.76 (m, 2H), 1.65-1.05 (m, 13H), 0.95 (t, J=7.2 Hz, 3H). LCMS-ESI$^+$: calc'd for $C_{17}H_{29}N_6O_2$: 349.2 (M+H$^+$); Found: 349.1 (M+H$^+$).

Scheme 95: Example 108

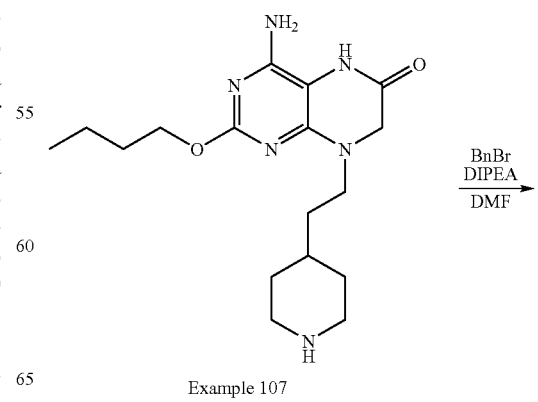

-continued

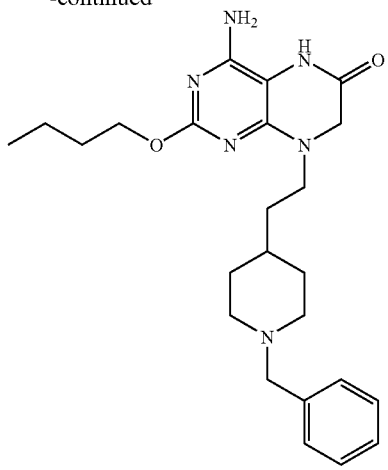

Example 108

Method XLXIV: Example 108: Example 107 (20 mg, 0.057 mmol) was dissolved in anhydrous DMF (0.5 mL). To this was added diisopropylethylamine, DIPEA, (15 μL, 0.086 mmol) and benzyl bromide (8 μL, 0.068 mmol). The reaction was stirred for 16 hours. Reaction was directly purified with Prep HPLC Phenomenex Gemini 5u $C_{18}$ column and eluted with a linear gradient of 5-100% Acetonitrile containing 0.1% TFA to give Example 108 (11.2 mg, 0.025 mmol). $^1$H NMR: (CD$_3$OD, 300 MHz): d (ppm) 7.50 (s, 5H), 4.42 (t, J=6.3 Hz, 2H), 4.30 (s, 2H), 4.20 (s, 2H), 3.69 (m, 2H), 3.51 (m, 2H), 3.00 (m, 2H), 2.03 (m, 2H), 1.80-1.46 (m, 9H), 0.98 (t, J=7.2 Hz, 3H). LCMS-ESI$^+$: calc'd for $C_{24}H_{35}N_6O_2$: 439.3 (M+H$^+$); Found: 439.2 (M+H$^+$).

Scheme 96:

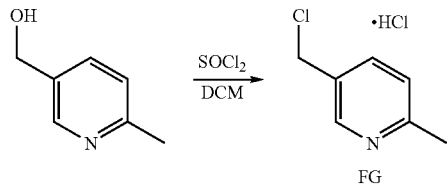

Method XLXV: Compound FG: Starting with (2-methylpyridine-5-yl)-methanol (5.07 g) in CH$_2$Cl$_2$ (50.0 mL), 4 equivs of SOCl$_2$ (12.0 mL) were added at 23° C. The mixture was allowed to stir overnight and was then concentrated in vacuo, giving Compound FG as a monohydrochloride salt, which was used without purification. $^1$H NMR: (DMSO-d$_6$, 300 MHz): δ 8.84 (s, 1H), 8.44 (d, J=6.9 Hz, 1H), 7.86 (d, J=7.8 Hz, 1H), 4.92 (s, 2H), 2.1 (s, 3H).

Scheme 97

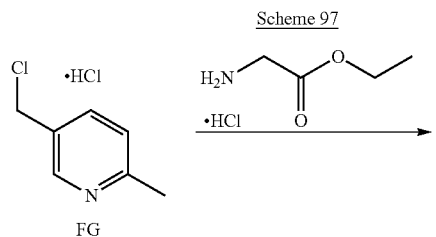

-continued

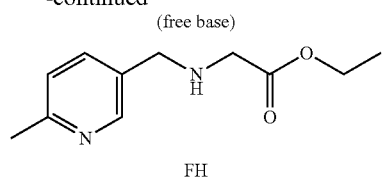

FH

Method XLXVI: Compound FH. Ethyl glycinate hydrochloride (113 mg) was slurried in DMF (3.0 mL) with K$_2$CO$_3$ (270 mg) and the crude pyridinyl chloride (FG)(110 mg). The mixture was heated to 40° C. and allowed to stir overnight. The reaction was quenched by the addition of water and was diluted with EtOAc. The mixture was washed with a 5% solution of LiCl (3×5 ml) to remove DMF, followed by a brine wash, and the organic extracts were dried with sodium sulfate and concentrated in vacua. Chromatography on silica using CH$_2$Cl$_2$ and 20% MeOH/CH$_2$Cl$_2$ as eluent gave rise to the desired pyridyl aminoester product (55 mg). $^1$H NMR: (DMSO-d$_6$, 300 MHz): δ 8.42 (s, 1H), 7.71-7.62 (m, 1H), 7.25 (d, J=7.8 Hz, 1H), 5.03 (s, 2H), 4.12-4.05 (m, 2H), 3.73 (d, J=11.7 Hz, 2H), 2.45 (s, 3H), 1.30 (t, J=7 Hz, 3H). LCMS-ESI$^+$: calc'd for $C_{11}H_{17}N_2O_2$: 208.26 (M+H$^+$); Found: 208.9 (M+H$^+$).

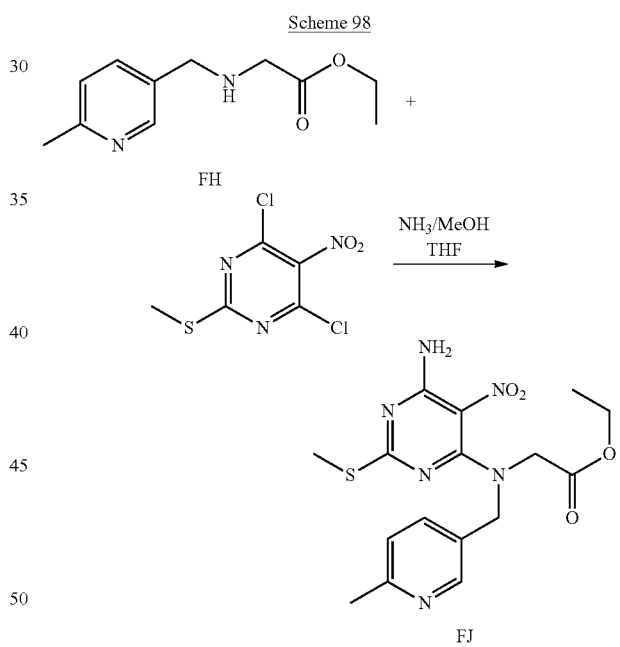

Method XLXVII: Compound FJ. 4,6-dichloro-5-nitro-2-methylmercaptopurine (1.0715 g, 4.502 mmol) was dissolved in 25 mL THF and cooled to 0° C. NH$_3$/MeOH was added (3.5 Equiv) and the mixture was allowed to stir cold for 1 h. Aminoester (1.22 g, 4.37 mmol) was then added dropwise as a solution in 10 mL THF over 10-15 minutes, and the resulting mixture was allowed to warm to room temperature. After 3 h, the reaction was quenched with the addition of water, diluted with EtOAc and the pH was adjusted to =8 using solid K$_2$CO$_3$. The mixture was washed with water, washed with brine then dried with sodium sulfate and concentrated in vacua. The crude product was then chromatographed on silica with a CH$_2$Cl$_2$ and 20% MeOH/CH$_2$Cl$_2$ gradient over 10-15 column volumes. Sometimes mixtures of 6-chloropyrimidine and 6-aminopyrimidine products are obtained (1.02 g) and are sequentially treated with excess NH₃ in MeOH in THF over 45 minutes at room temperature and rechromatographed as above to give pure 6-aminopyrimidine product (716 mg). LCMS-ESI⁺: calc'd for $C_{16}H_{21}N_6O_4S$: 392.43 (M+H⁺); Found: 393.0 (M+H⁺).

Scheme 99:

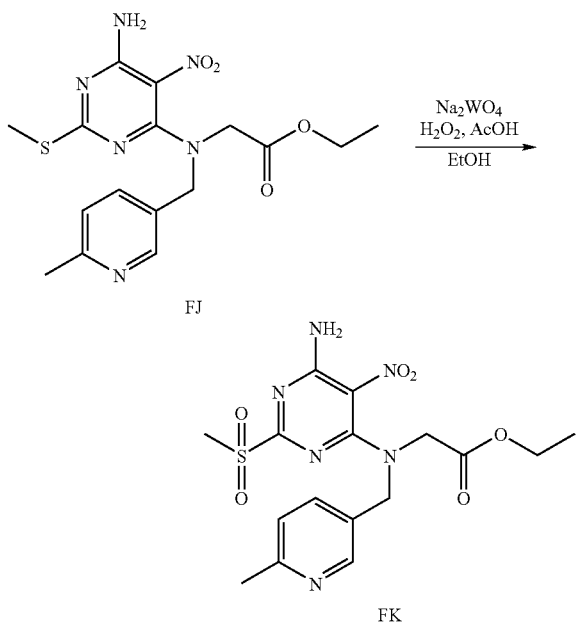

FJ

FK

Method XLXVIII: Compound FK. To a solution a suspension of the sulfide FJ (3.68 g, 8.00 mmol) in EtOH (40 mL) at 0° C. was added sodium tungstate dihydrate (792 mg, 2.40 mmol), acetic acid (4.6 mL, 80 mmol), and hydrogen peroxide (3.4 mL, ~40 mmol, 35% w/w in H₂O) sequentially. After 3 h, additional acetic acid (4.6 mL) and hydrogen peroxide (3.4 mL) were added. The reaction was maintained at 0° C. for 16 h. A saturated solution of Na₂SO₃ (50 mL) was added carefully while at 0° C. followed by CH₂Cl₂ (75 mL). The layers were separated, and the aqueous layer was extracted with CH₂Cl₂ (4×50 mL). The combined organic layers were dried over MgSO₄, filtered, and concentrated under vacuum to give FK which was used without further purification. LCMS-ESI⁺: calc'd for sulfoxide $C_{16}H_{20}N_6O_5S$: 408.43 (M+H⁺); Found: 409.0 (M+H⁺). LCMS-ESI⁺: calc'd for sulfone $C_{16}H_{21}N_6O_6S$: 424.43 (M+H⁺); Found: 425.1 (M+H⁺).

Scheme 100:

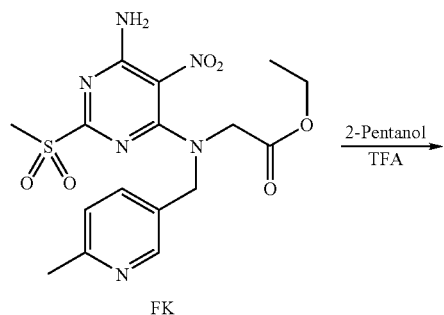

FK

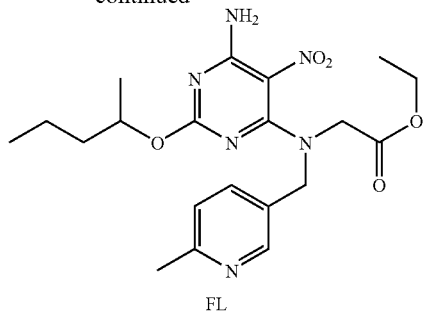

FL

Method XLXIX: Compound FL. To a solution of sulfone FK (1.0 g, 2.0 mmol) in racemic 2-pentanol (10 mL) was added TFA (470 μL, 6.1 mmol). The reaction was stirred at 100° C. for 1 h. The reaction mixture was poured onto a saturated solution of NaHCO₃ (20 mL) and CH₂Cl₂ (30 mL). The layers were separated, and the aqueous layer was extracted with CH₂Cl₂ (30 mL). The combined organic layers were dried over MgSO₄, filtered, and concentrated under vacuum. Purification was conducted by silica gel chromatography (1 g substrate/10 g SiO₂) (2-15% MeOH/CH₂Cl₂). LCMS-ESI⁺: calc'd for $C_{20}H_{29}N_6O_5$: 432.47 (M+H⁺); Found: 433.1 (M+H⁺).

Scheme 101:

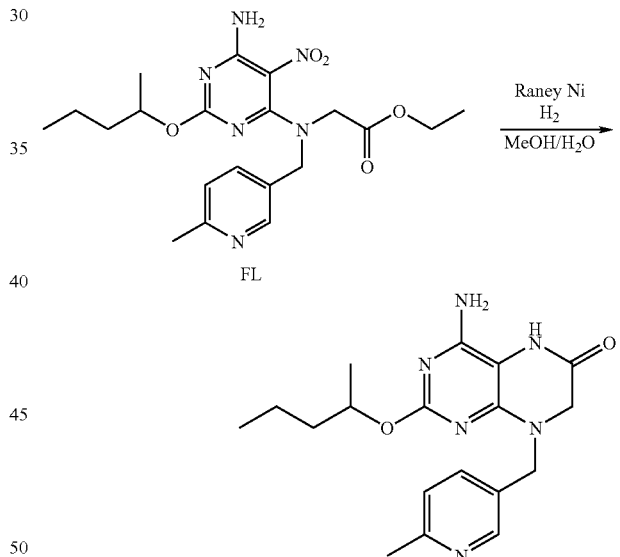

FL

Example 109

Method XLXX: Example 109. To a solution of nitro compound (730 mg, 1.5 mmol) in MeOH (10 mL) was added a Raney Nickel (~200 μL, slurry in H₂O). The reaction vessel was flushed with H₂ and then stirred under an H₂ atmosphere for 1.5 h. The mixture was filtered through celite with CH₂Cl₂ and MeOH (1:1). The filtrate was concentrated under vacuum and left on lyophilizer overnight. The title product was obtained as a free base. ¹H NMR (DMSO-d₆, 300 MHz): δ 9.66 (s, broad, 0.78H), 8.40 (s, 1H), 7.59 (d, J=7.8 Hz, 1H), 7.20 (d, J=7.8 Hz, 1H), 6.18 (s, broad, 1.5H), 5.60-5.56 (m, broad, 0.78H), 4.96-4.85 (m, 1H), 4.61 (s, 2H), 3.82 (s, 2H), 2.42 (s, 3H), 1.53-1.04 (m, 7H), 0.83 (t, J=7 Hz, 3H). LCMS-ESI⁺: calc'd for $C_{18}H_{25}N_6O_2$: 356.42 (M+H⁺); Found: 356.9 (M+H⁺).

Scheme 102: Prepared Via Method XLV:

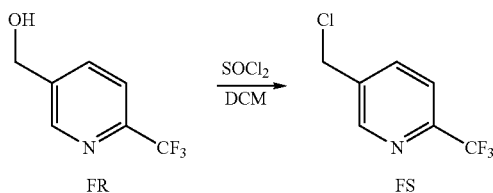

¹H NMR (DMSO-d₆, 300 MHz): δ 8.84 (s, 1H), 8.17 (d, J=8.1 Hz, 1H), 7.94 (d, J=8.4 Hz, 1H), 4.82 (s, 2H). LCMS-ESI⁺: calc'd for $C_7H_6ClF_3N$ 195.57 (M+H⁺): Found: for ³⁵Cl 195.9 (M+H⁺) and ³⁷Cl 197.9 (M+H⁺).

Scheme 103: Prepared Via Method XLVI:

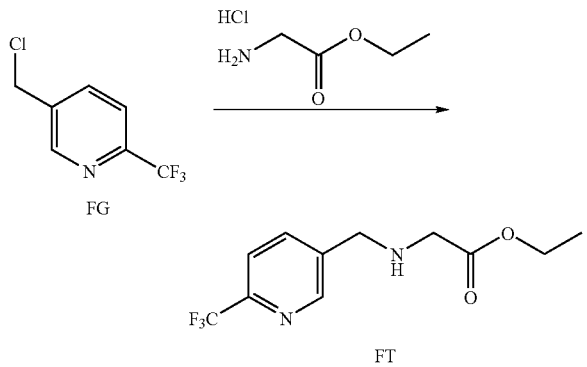

¹⁹F NMR (DMSO-d₆, 282 MHz): δ −66.69. ¹H NMR (DMSO-d₆, 300 MHz): 8.69 (s, 1H), 8.02 (dd, J=7.8 Hz, 1H), 7.85 (d, J=7.8 Hz, 1H), 4.08 (d, 2H), 3.85 (s, 2H), 2.82 (bs, 1H), 1.15-1.19 (t, J=7 Hz, 3H). LCMS-ESI⁺: calc'd for $C_{11}H_{13}F_3N_2O_2$ 262.23 (M+H⁺); found: 262.9 (M+H⁺).

Scheme 104:

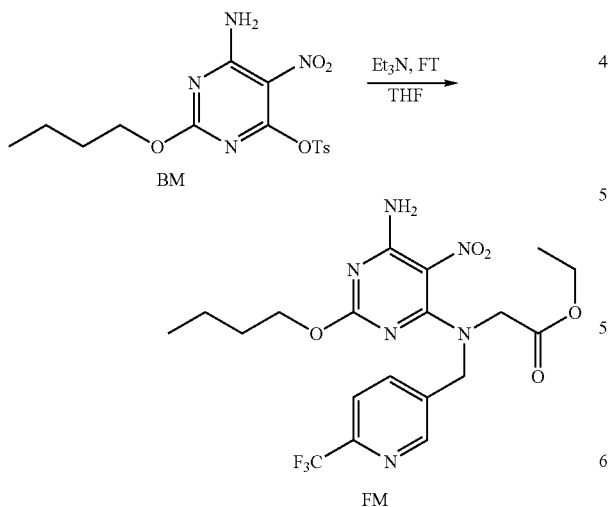

Method XLXXI: Compound FM. Compound FT (6.5 mg, 0.025 mmol) was dissolved in THF (1 mL) and to this was added BM (9.6 mg, 0.025 mmol). Then triethylamine (10 μL, 0.075 mmol) was added and the mixture was stirred for 12 hours. The mixture was added to EtOAc and washed with saturated NaHCO₃(aq) solution followed with saturated NaCl(aq). The organic extract was dried over anhydrous Na₂SO₄, filtered, and concentrated under reduced pressure. The product was then purified with Prep HPLC Phenomenex Gemini 5u C₁₈ column and eluted with a linear gradient of 25-100% Acetonitrile containing 0.1% TFA. LCMS-ESI⁺: calc'd for $C_{19}H_{24}F_3N_6O_5$: 472.42 (M+H⁺); Found: 473.1 (M+H⁺).

Compound FAB: Prepared by Method XLXXI

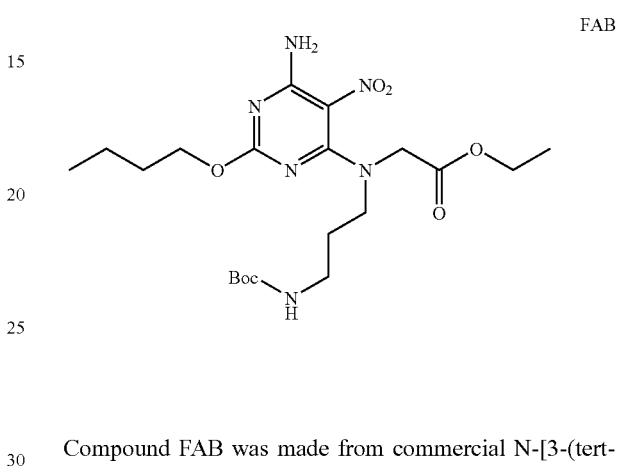

Compound FAB was made from commercial N-[3-(tert-butoxylcarbonylamino)propyl]glycine ethyl ester according to Method XLXXI. To a stirred solution of tosylate (BM) (648.6 mg) in 30 mL of THF was added N-[3-(tert-butoxylcarbonylamino)propyl]glycine ethyl ester (475 mg), and resulting solution became yellow within seconds. Et₃N (500 μL) was added and the mixture was allowed to stir overnight at 23° C. After quenching with water, the mixture was diluted 100% with EtOAc and partitioned with saturated brine solution. The organic layer was collected, dried with sodium sulfate, and concentrated in vacuo. After chromatography on silica gel (Eluent: DCM→MeOH/DCM 1:4) pure FAB was obtained as a free base (852 mg) in 98% yield. ¹H NMR (DMSO d⁶, 300 MHz): d (ppm): 7.98 (s, braod, 2H); 6.79 (m, broad, 1H); 4.18-4.06 (m, 6H); 3.29 (m, 2H); 2.93-2.85 (m, 2H); 1.79-1.70 (m, 2H); 1.66-1.57 (m, 2H); 1.42-1.32 (m, 11H); 1.22 (t, J=7.0 Hz, 3H); 0.90 (t, J=7.6 Hz, 3H). LCMS-ESI⁺: calc'd for $C_{20}H_{35}N_6O_7$: 471.52 (M+H⁺); Found: 471.1 (M+H⁺).

Scheme 105:

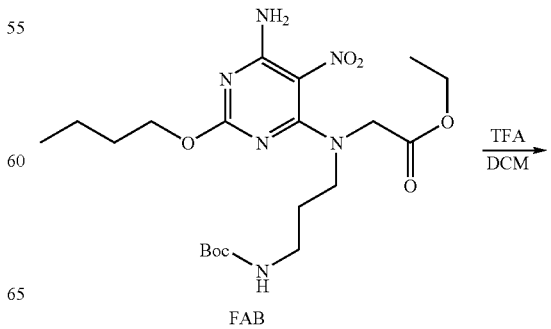

-continued

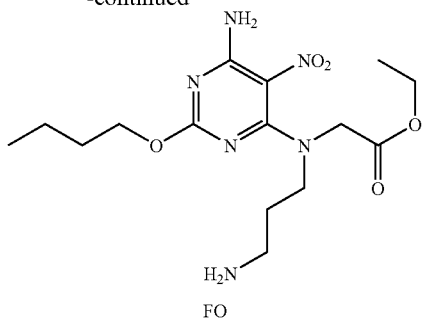

FO

Method XLXXII: Compound FO. Substrate FAB (400 mg) was dissolved in DCM (25 mL) and cooled to 0° C. TFA (2 mL) was added. After an hour at 0° C., the reactions progress was observed to be sluggish; More TFA (1 mL) was added and the mixture continued to stir in the cold bath without any additional ice being added. At 2 h, the temperature was observed to be 6.8° C., and the mixture was observed to be 60:40 (product:starting material). The cold bath was removed and the mixture was allowed to gradually warm to 23° C. After ~7.5 h, reaction had progressed to 95% complete according to HPLC. Water was added and the mixture allowed to stir at 23° C. overnight. Mixture was neutralized to pH=8 with saturated NaHCO$_3$, and extracted with EtOAc. The organic phase was dried with sodium sulfate and concentrated to a syrup. Crude material was not purified. LCMS-ESI$^+$: calc'd for $C_{15}H_{27}N_6O_5$: 371.4 (M+H$^+$); Found: 371.1 (M+H$^+$).

Scheme 106:

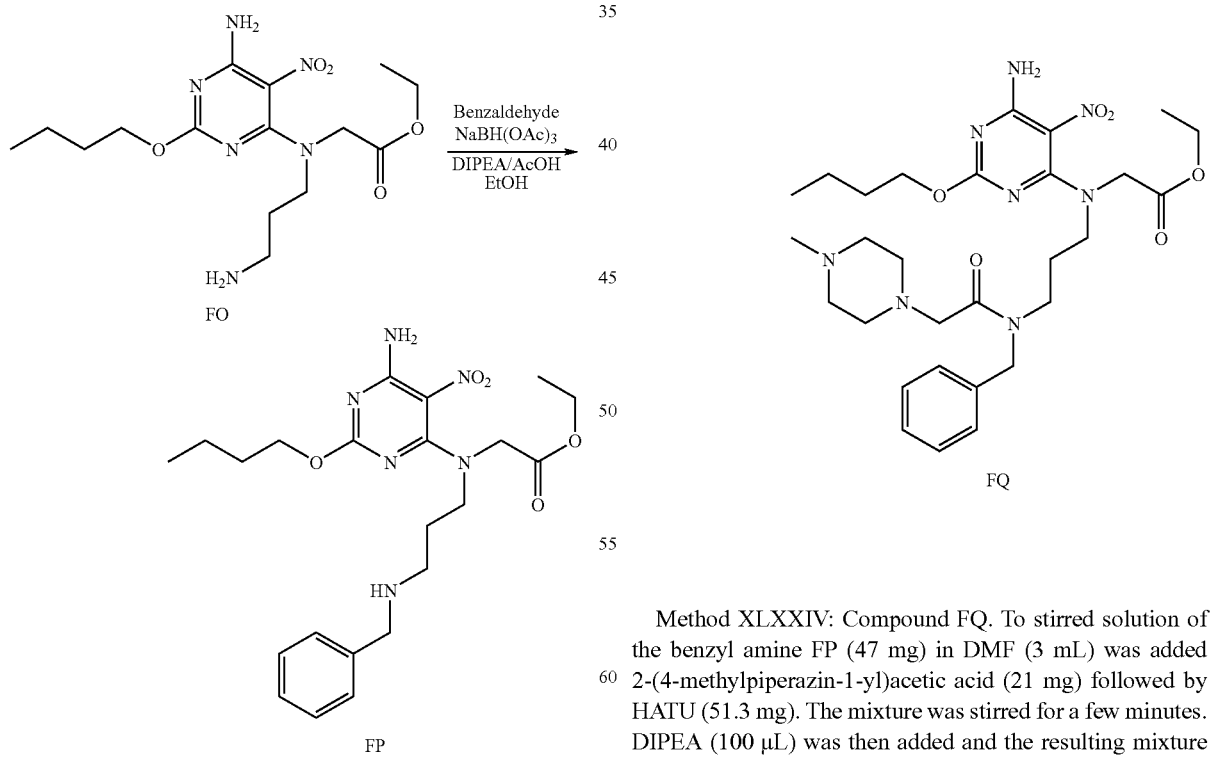

Method XLXXIII: Compound FP. Compound FO (free base form)(200 mg) was dissolved in EtOH and treated with benzaldehyde (65 μL), DIPEA (100 μL), and 1 drop of HOAc so that the mixture was at approximately pH=5.8. After a few minutes of stirring, NaHB(OAc)$_3$ (344 mg, 3 equiv based on pure FO) was added, and the mixture stirred at 23° C. overnight. After dilution with one volume of EtOAc relative to EtOH used previously, the mixture was washed with water, followed by saturated brine. The organic phase was dried with sodium sulfate, filtered, and concentrated in vacuo. Flash chromatography consistently gave rise to mixtures of unreacted starting material, desired product and a double reductive amination product. Thus, multiple runs of gravity column chromatography on silica gel using 5% MeOH in DCM were needed to obtain small amounts of purified desired product FP as a free base (77.1 mg). LCMS-ESI$^+$: calc'd for $C_{22}H_{32}N_6O_5$: 461.53 (M+H$^+$); Found: 461.2 (M+H$^+$).

Scheme 107:

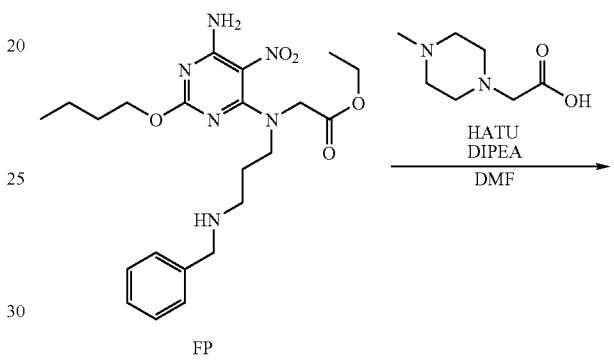

Method XLXXIV: Compound FQ. To stirred solution of the benzyl amine FP (47 mg) in DMF (3 mL) was added 2-(4-methylpiperazin-1-yl)acetic acid (21 mg) followed by HATU (51.3 mg). The mixture was stirred for a few minutes. DIPEA (100 μL) was then added and the resulting mixture was allowed to stir at 23° C. After 45 minutes, the starting material was observed to be consumed according to HPLC analysis, and the reaction was quenched with water and diluted with EtOAc (30 mL). The mixture was washed with 5% w/v aq. LiCl (3×20 mL) then washed with saturated brine. The organic phase was dried with sodium sulfate and filtered. After concentrating in vacua the crude product was chromatographed on an ISCO silica gel column (Eluent: 0→20% B ramp over 20 minutes: A=DCM and solvent B=MeOH/DCM 1:4) to give rise to desired product FQ (60 mg) as a free base. $^1$H NMR (MeOH-d$^4$, 300 MHz): d (ppm) 7.36-7.23 (m, 5H); 4.71-4.36 (m, 2H); 4.28-4.10 (m, 6H); 4.01 (s, 1H); 3.50-3.47 (m, 2H); 3.38-3.17 (m, 4H); 2.59 (app. s, broad, 8H); 2.43-2.36 (m, 3H); 2.10-1.78 (m, 2H); 1.69 (m, broad, 2H); 1.48-1.38 (m, broad, 2H), 1.31-1.22 (t, J=7.0 Hz, 3H), 0.99-0.93 (t, J=7.6 Hz, 3H). LCMS-ESI$^+$: calc'd for $C_{29}H_{45}N_8O_6$: 601.71 (M+H$^+$); Found: 602.3 (M+H$^+$).

Scheme 108: Example 110: Method XLXX:

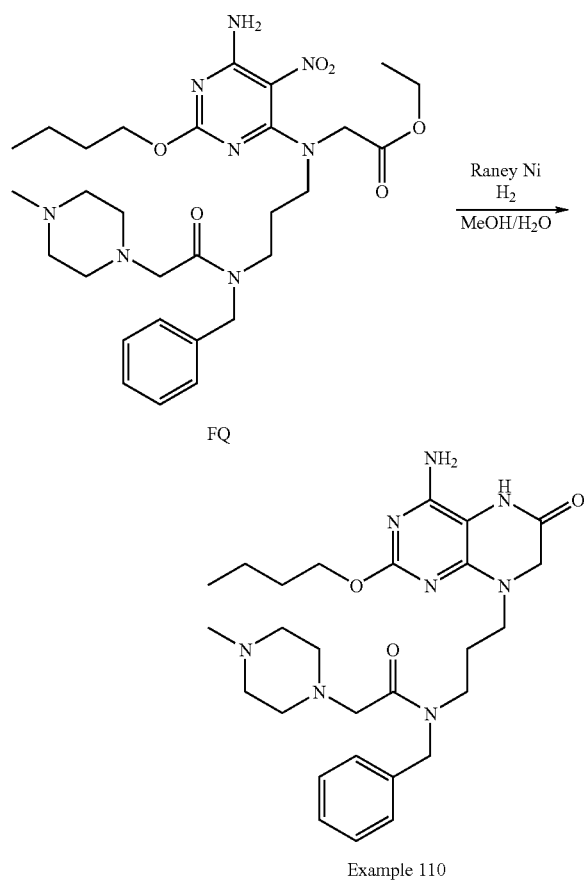

FQ

Example 110

Example 110 was prepared according to Method XLXX. Prep HPLC was utilized to isolate desired Example 110 as a free base (Eluent: CH$_3$CN/H$_2$O gradient). NMR (DMSO-d$^6$, 300 MHz): d (ppm) 9.64-9.62 (d, broad, J=6.9 Hz, 1H), 7.72-7.64 (m, broad, 1H), 7.36-7.15 (m, 5H); 6.12 (s, 2H), 4.67 (s, 1H); 4.51 (d, J=49.8 Hz, 2H), 4.04-3.87 (m, 4H), 3.50-3.23 (m, 2H), 3.12 (s, 2H), 2.37-2.27, (d, broad, J=30.3 Hz, 8H), 2.13 (s, 3H); 1.85 (m, 2H); 1.75-1.50 (m, broad, 4H), 1.36-1.14 (m, 2H), 0.89-0.80 (t, J=7.6 Hz, 3H). LCMS-ESI$^+$: calc'd for $C_{27}H_{41}N_8O_3$: 525.74 (M+H$^+$); Found: 525.3 (M+H$^+$).

Scheme 109: Prepared Via Method XLXIX

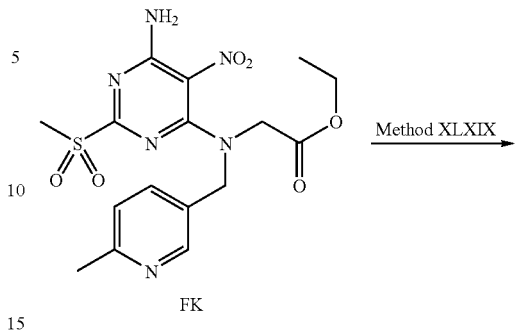

FK

FW

The sulfoxide/sulfone mixture (FK) was advanced with Method XLXIX using to install the (S)-(+)-2-pentanol side chain. LCMS-ESI$^+$: calc'd for $C_{19}H_{27}N_6O_6$: 418.45 (M+H$^+$); Found: 419.1 (M+H$^+$).

Scheme 110: Example 111, Method XLXX

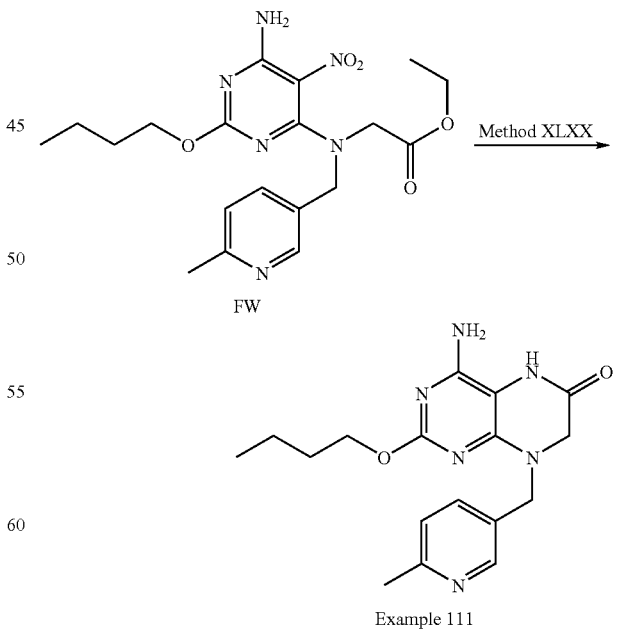

FW

Example 111

Method XLXX was used to produce the final product. $^1$H NMR (DMSO-d$_6$, 300 MHz): δ 9.67 (s, 1H), 8.42 (s, 1H), 7.61 (d, J=7.8 Hz, 1H), 7.20 (d J=7.8 Hz, 1H), 6.22 (s, broad, 2H), 4.62 (s, 2H), 4.10-4.06 (m, 2H), 3.83 (s, 2H), 2.43 (s, 3H), 1.63-1.53 (m, 2H), 1.40-1.30 (m, 2H), 0.88 (t, J=7 Hz, 3H). LCMS-ESI$^+$: calc'd for $C_{17}H_{23}N_6O_2$: 342.4 (M+H$^+$); Found: 343.2 (M+H$^+$).

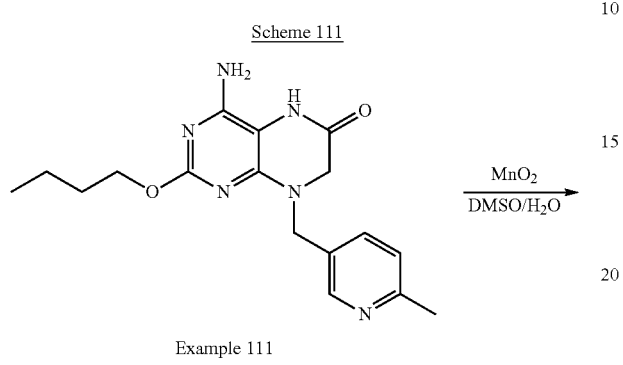

Example 111

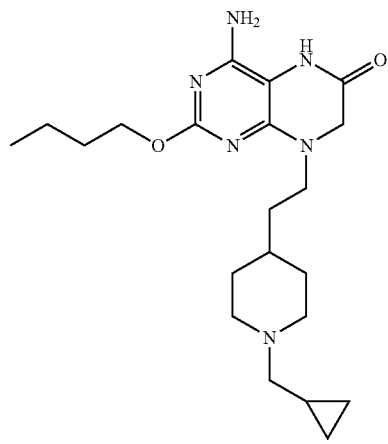

Example 113

Example 113

Prepared by Method XLIV

Example 113 was prepared according to Method XLIV: NMR (CD$_3$OD, 300 MHz): d 4.45 (t, J=6.3 Hz, 2H), 4.24 (s, 2H), 3.69 (m, 4H), 3.02 (m, 4H), 2.07 (m, 2H), 1.82-1.49 (m, 9H), 1.06 (m, 1H), 1.00 (t, J=7.2 Hz, 3H), 0.78 (m, 2H), 0.44 (m, 2H). LCMS-ESI$^+$: calc'd for $C_{21}H_{35}N_6O_2$: 403.3 (M+H$^+$); Found: 403.2 (M+H$^+$).

Scheme 112: Prepared Via Method XLIX

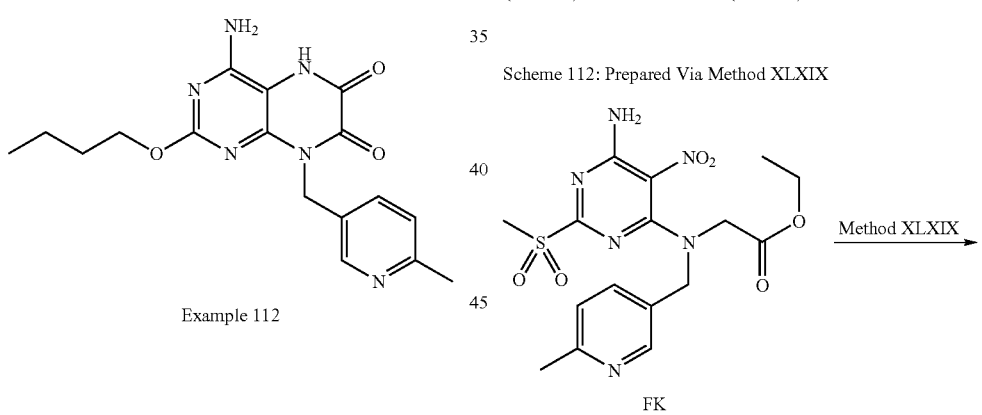

Method LXXV: Example 112. A solution of Example 111 (10.0 mg) in DMSO (2.9 mL) was treated with H$_2$O (750 μL) followed by MnO$_2$ (85%, activated, from Sigma Aldrich) (126 mg) at 23° C. After 5 h, the reaction was filtered through a 0.45 micron Teflon filter cartridge. The filtrate was directly loaded onto a Teledyne Isco 'gold' 5.5 gram column and flashed (Eluent: 0.05% w/v aq. HCl/CH$_3$CN 95:5→0:100), giving Example 112 (4.7 mg, 41% yield) as a white solid in monohydrochloride form. $^1$H NMR (CD$_3$OD, 300 MHz): δ (ppm) 8.80 (s, 1H), 8.57 (d, J=8.2 Hz, 1H), 7.88 (d, J=8.2 Hz, 1H), 5.59 (s, 2H), 4.33 (t, J=7.6 Hz, 2H), 2.76 (s, 3H), 1.73 (tt, J=7.6 Hz, 7.6 Hz, 2H), 1.46 (qt, J=7.6 Hz, 7.6 Hz, 2H), 0.96 (t, J=7.6 Hz, 3H). LCMS-ESI$^+$: calc'd for $C_{17}H_{21}N_6O_3$: 357.2 (M+H$^+$); Found: 357.2 (M+H$^+$).

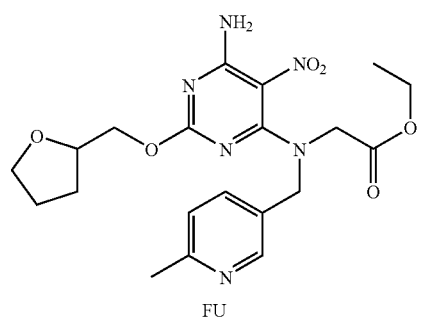

FU

Compound FU. The sulfoxide/sulfone mixture (FK) was advanced with Method XLIX using tetrahydrofurfurol to install the tetrahydrofurfuryl side chain. LCMS-ESI$^+$: calc'd for $C_{20}H_{27}N_6O_6$: 446.46 (M+H$^+$); Found: 447.1 (M+H$^+$).

Scheme 113: Example 114, Method XLXX

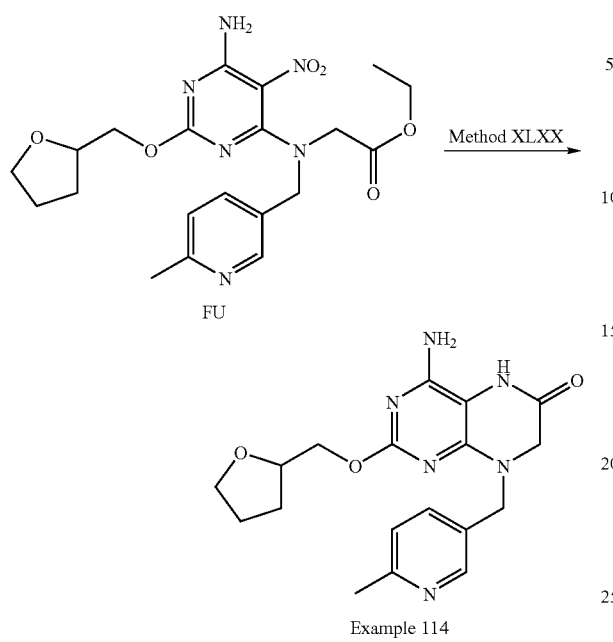

Example 114

Method XLXX was used to produce the final product. $^1$H NMR (DMSO-d$_6$, 300 MHz): δ 9.63 (s, broad, 1H), 8.41 (s, 1H), 7.55-7.62 (m, 1H), 7.19 (d, J=8 Hz, 1H), 6.25 (s, 2H), 4.62 (s, 2H), 4.24-3.96 (m, 3H), 3.83 (s, 2H), 3.77-3.69 (m, 1H), 3.66-3.58 (m, 1H), 2.43 (s, 3H), 1.93-1.72 (m, 3H), 1.62-1.48 (m, 1H). LCMS-ESI$^+$: calc'd for $C_{18}H_{23}N_6O_3$: 370.41 (M+H$^+$); Found: 371.0 (M+H$^+$).

Scheme 114: Prepared Via Method XLXIX

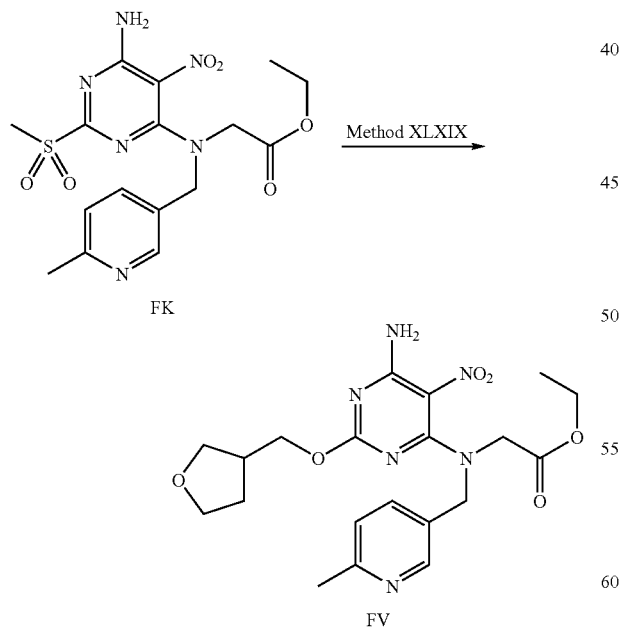

The sulfoxide/sulfone mixture (FK) was advanced with Method XLXIX using tetrahydrofuran-3-methanol to install the alkoxy side chain. LCMS-ESI$^+$: calc'd for $C_{20}H_{27}N_6O_6$: 446.46 (M+H$^+$); Found: 447.1 (M+H$^+$).

Scheme 115: Example 115, Method XLXX

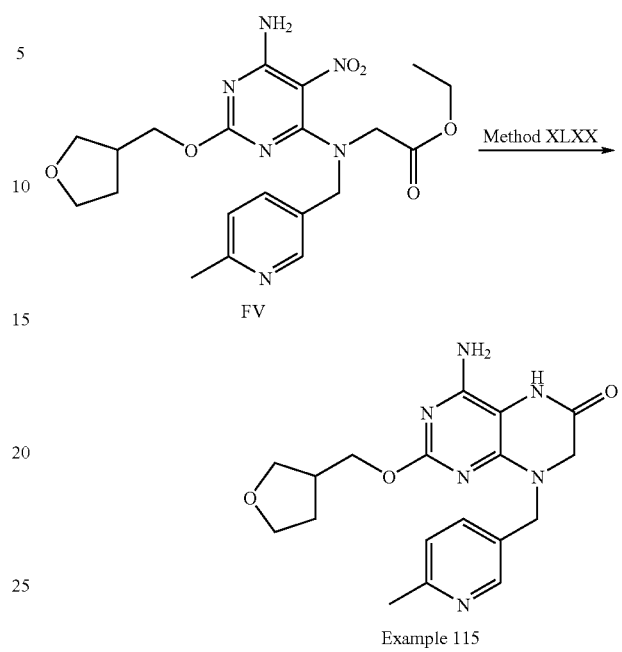

Example 115

Method XLXX was used to produce the final product. $^1$H NMR (DMSO-d$_6$, 300 MHz): δ 9.69 (s, broad, 1H), 8.42 (s, 1H), 7.61 (d, J=7.8 Hz, 1H), 7.19-7.22 (d J=7.5, 1H), 6.25 (s, broad, 2H), 4.62 (s, 2H), 4.1-3.95 (m, 4H), 3.83 (s, 2H), 3.75-3.69 (m, 3H), 3.64-3.57 (m, 2H), 3.46-3.43 (m, 2H), 2.43 (s, 3H), 2.02-1.88 (m, 2H), 1.62-1.50 (m, 2H), 1.22 (s, broad, 1H). LCMS-ESI$^+$: calc'd for $C_{18}H_{23}N_6O_3$: 370.41 (M+H$^+$); Found: 371.1 (M+H$^+$).

Scheme 116: Prepared Via Method XLXIX

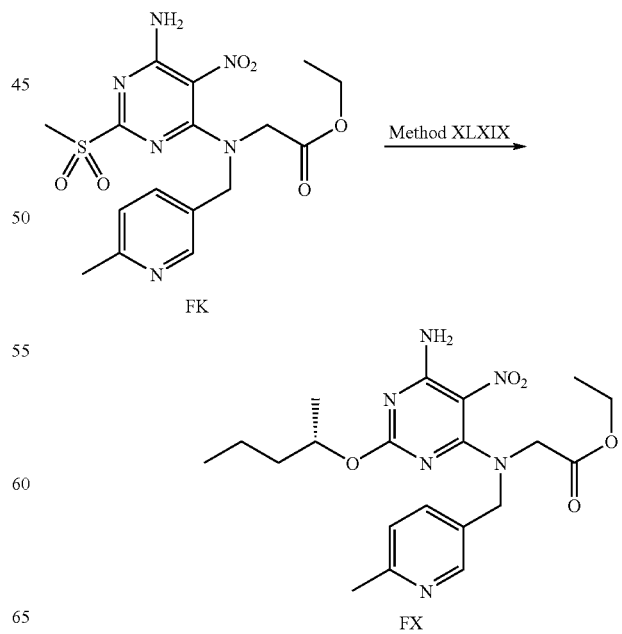

Starting from the sulfone/sulfoxide mixture (FK), Method XLXIX was used to install the chiral 2-pentoxy side chain. LCMS-ESI⁺: calc'd for $C_{20}H_{27}N_6O_5$: 432.47 (M+H⁺); Found: 433.2 (M+H⁺).

Scheme 117: Example 116, Method XLXX

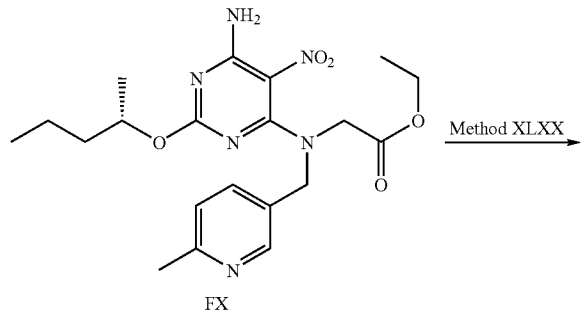

FX

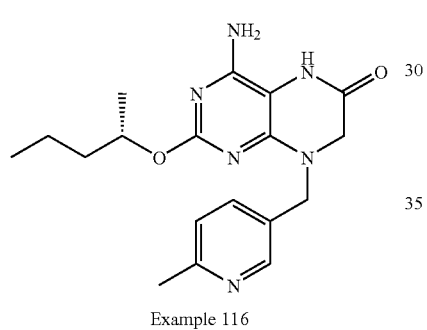

Example 116

Method XLXX was used to produce the final product. ¹H NMR (DMSO-d₆, 300 MHz): δ 9.66 (s, 1H), 8.40 (s, 1H), 7.59 (d, J=8.4 Hz, 1H), 7.20 (d, J=8.1 Hz, 1H), 6.18 (s, broad, 2H), 4.94-4.87 (m, 1H), 4.61 (s, 2H), 3.83 (s, 2H), 2.42 (s, 3H), 1.58-1.07 (m, 7), 0.84 (t, J=7 Hz, 3H). calc'd for $C_{20}H_{27}N_6O_5$: 356.42 (M+H⁺); Found: 357.1 (M+H⁺).

Scheme 118: Example 117, Method XLXX

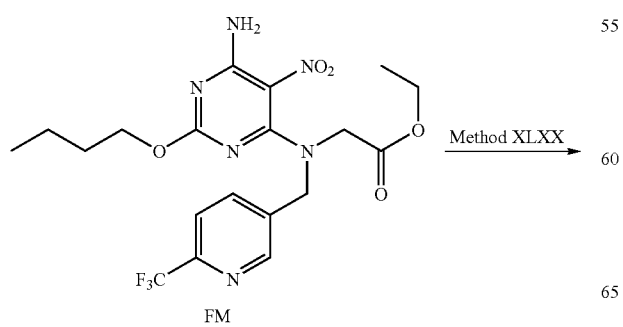

FM

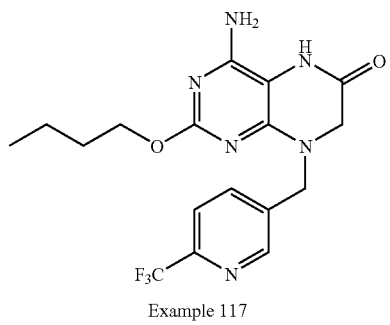

Example 117

The final compound was synthesized using Method XLXX. ¹H NMR (DMSO-d₆, 300 MHz): δ 9.70 (s, 1H), 8.73 (s, 1H), 8.01-7.98 (s, J=7.8 Hz, 1H), 7.86 (d, J=7.8 Hz, 1H), 6.25 (s, broad, 2H), 4.75 (s, 2H), 4.00 (m, 5H), 1.54-1.51 (m, 2H), 1.32-1.22 (m, 4H), 0.84-0.86 (t, J=7 Hz, 3H). LCMS-ESI⁺: calc'd for $C_{17}H_{20}F_3N_6O_2$: 396.37 (M+H⁺); Found: 397.1 (M+H⁺).

Compound FY: Prepared by Method XLXVII

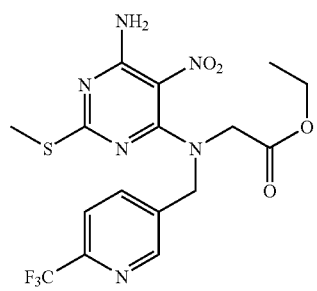

FY

Compound FY was prepared from FT and isolated as a free base. ¹H NMR (DMSO d⁶, 300 MHz): d (ppm) 8.71 (s, 1H), 8.53-8.41 (d, broad, J=38.1 Hz, 1H); 8.22 (s, broad, 2H), 8.04-8.01 (d, J=7.5Hz, 1H), 7.89-7.76 (d, J=7.5 Hz, 1H), 4.81 (s, 2H), 4.19 (s, 2H), 4.15-4.08 (m, 2H); 2.27 (s, 3H), 1.19-1.15 (t, J=7.0 Hz, 3H). LCMS-ESI⁺: calc'd for $C_{16}H_{18}F_3N_6O_4S$: 447.4 (M+H⁺); Found: 446.9 (M+H⁺), Compound FZ: Prepared by Method XLXVIII

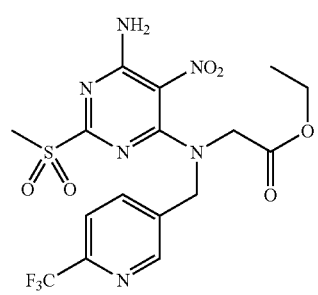

FZ

Compound FZ was prepared from FY according to Method XLXVIII. MS-ESI⁺: calc'd for $C_{16}H_{18}F_3N_6O_6S$: 478.4 (M+H⁺); Found: 478.9 (M+H⁺).

Scheme 119: Compound FAA Prepared Via Method XLXIX

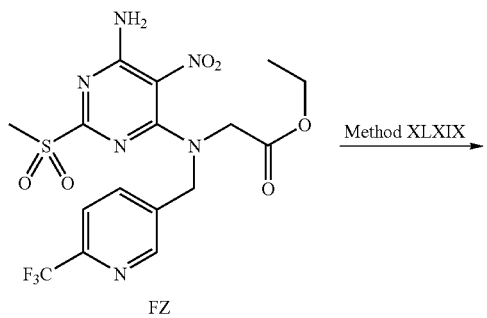

The sulfoxide/sulfone mixture (FZ) was advanced with Method XLXIX using tetrahydropyran-4-methanol to install the alkoxy side chain of Compound FAA. LCMS-ESI+: calc'd for $C_{20}H_{27}N_6O_6$: 446.46 (M+H+); Found: 447.1 (M+H+).

Scheme 120: Example 118, Method XLXX

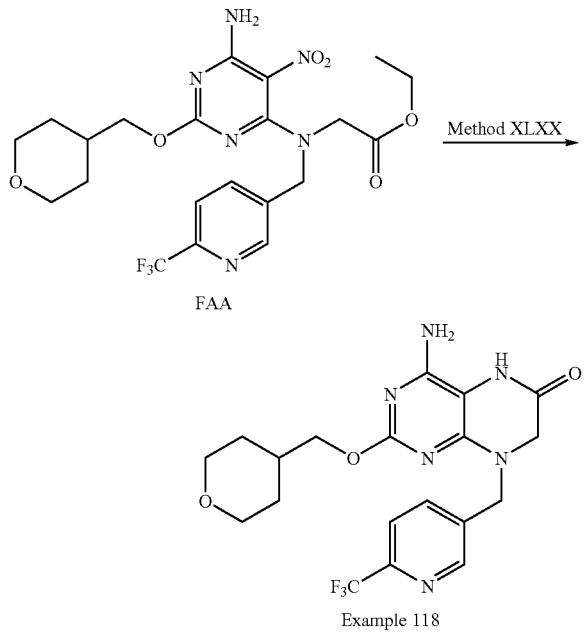

Method XLXX was used to produce the final product. $^1$H NMR (DMSO-$d_6$, 300 MHz): d 9.73 (s, broad, 1H), 8.71 (d, J=13.8 Hz, 1H), 8.00-7.82 (m, 2H), 6.27 (s, 2H), 5.73 (s, broad, 1H), 4.75 (s, 2H), 4.58 (m, 2H), 3.96 (s, 2H), 3.89-3.77 (m, 2H), 3.27-3.16 (m, 2H), 1.56-1.42 (m, 3H), 1.26-1.08 (m, 2H). LCMS-ESI+: calc'd for $C_{19}H_{22}F_3N_6O_3$: 438.4 (M+H+); Found: 439.0 (M+H+).

Prophetic Examples

As with the examples herein described, the following compounds may be prepared using analogous synthetic methods:

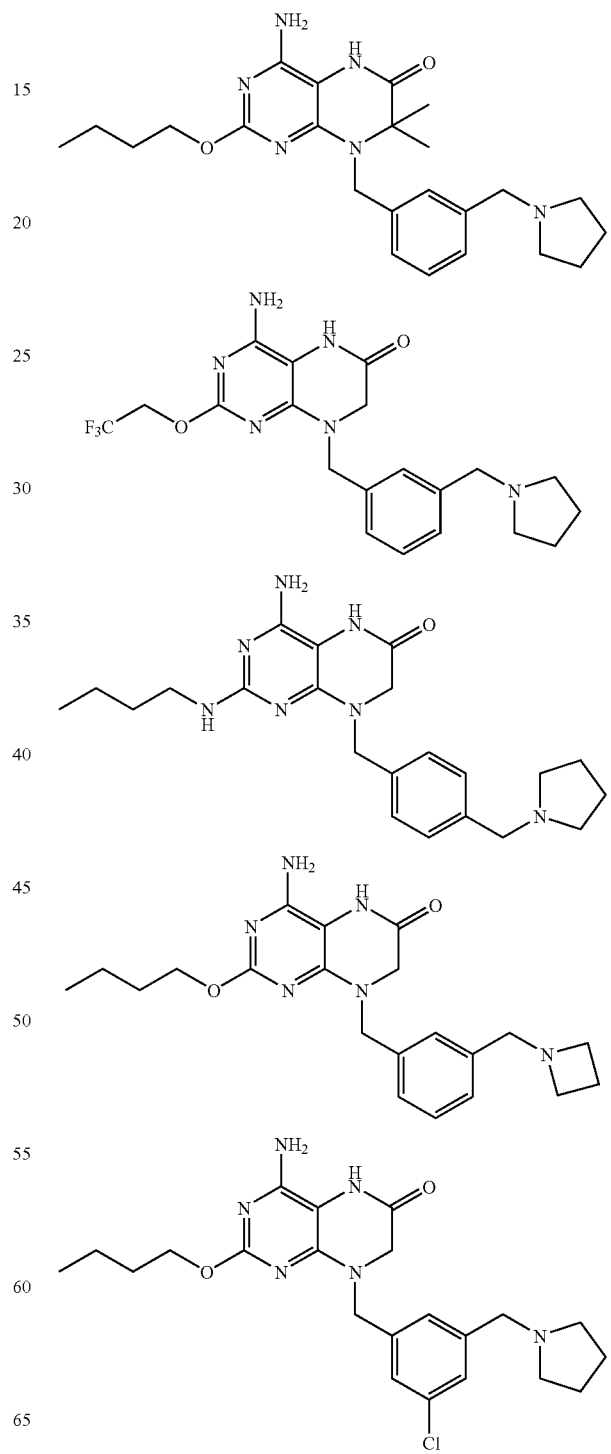

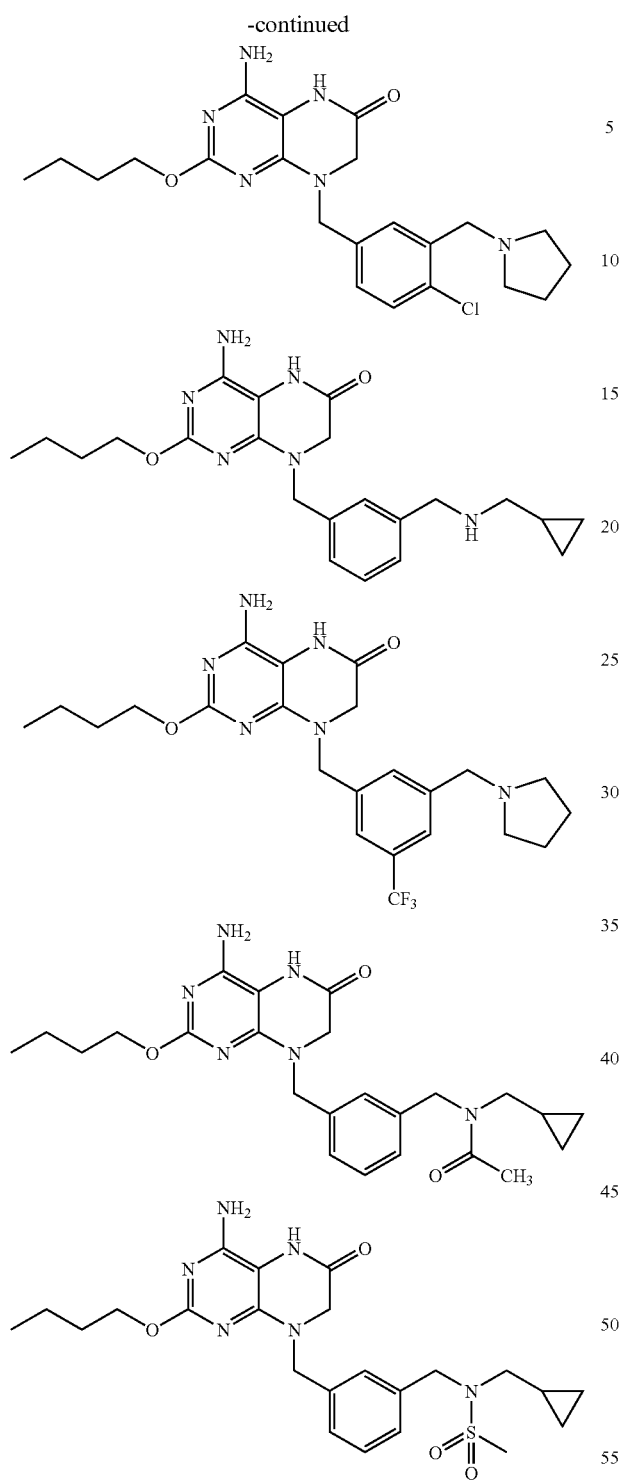
General Scheme Pyrimidinodiazepinone Derivatives
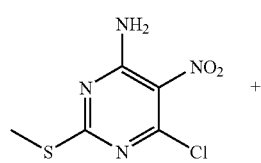
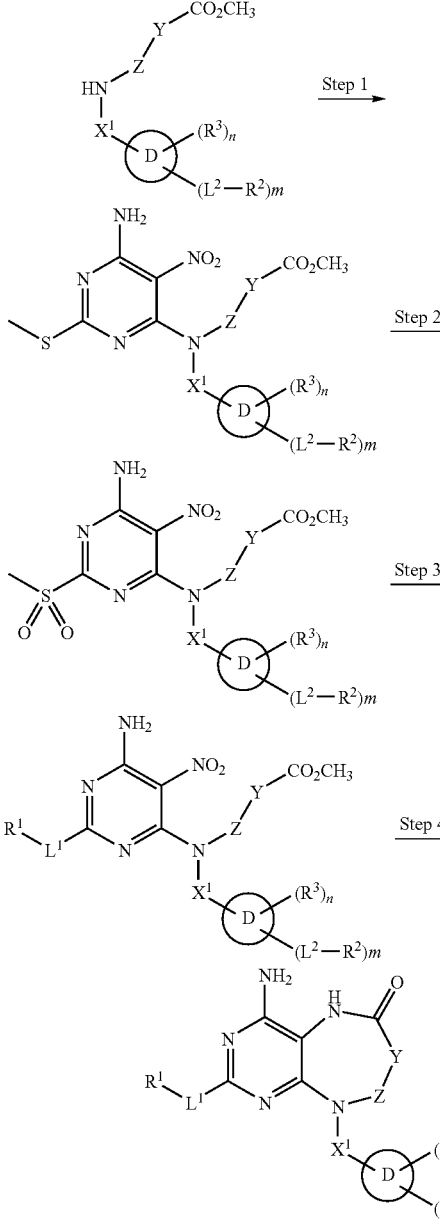
Prophetic Examples
The following compounds may be prepared using analogous synthetic methods:
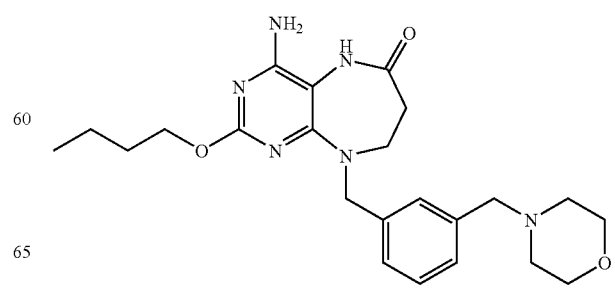

231
-continued
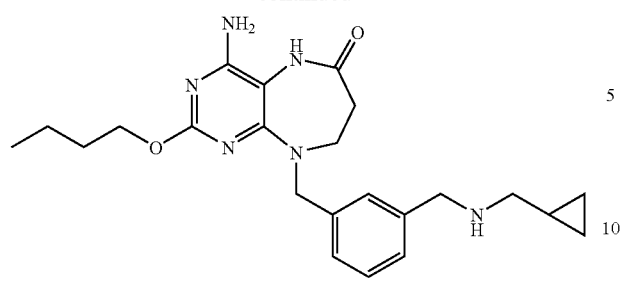
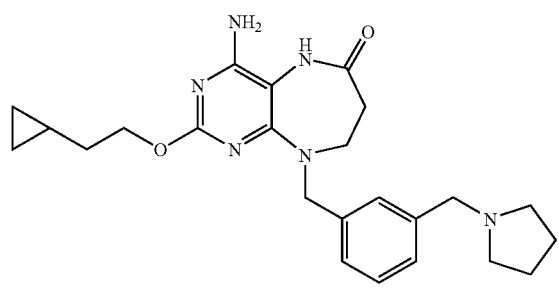
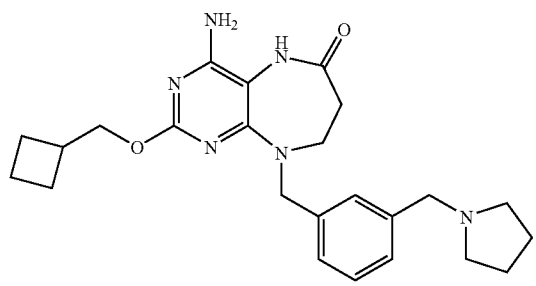
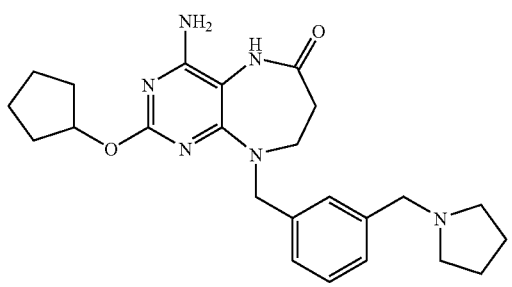
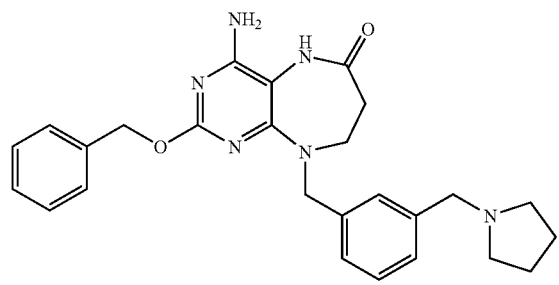
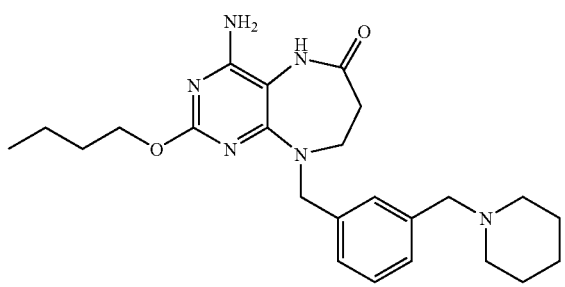
232
-continued
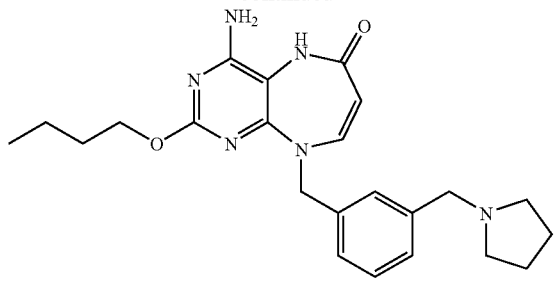
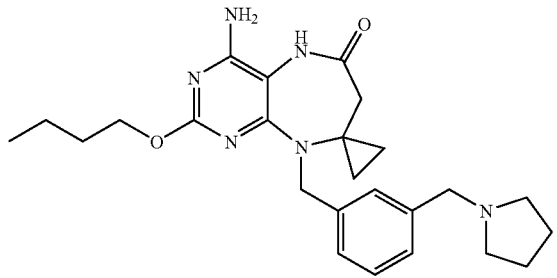
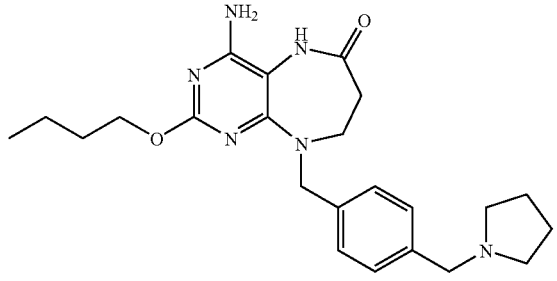
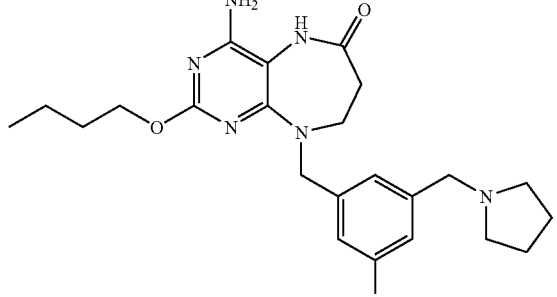
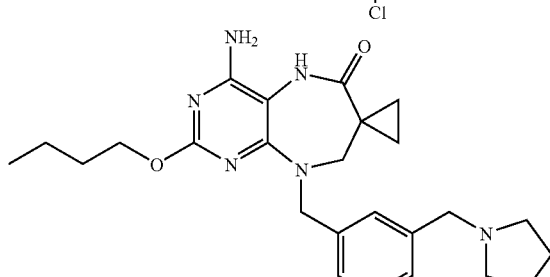
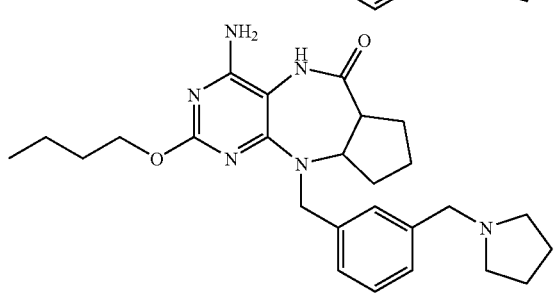

-continued

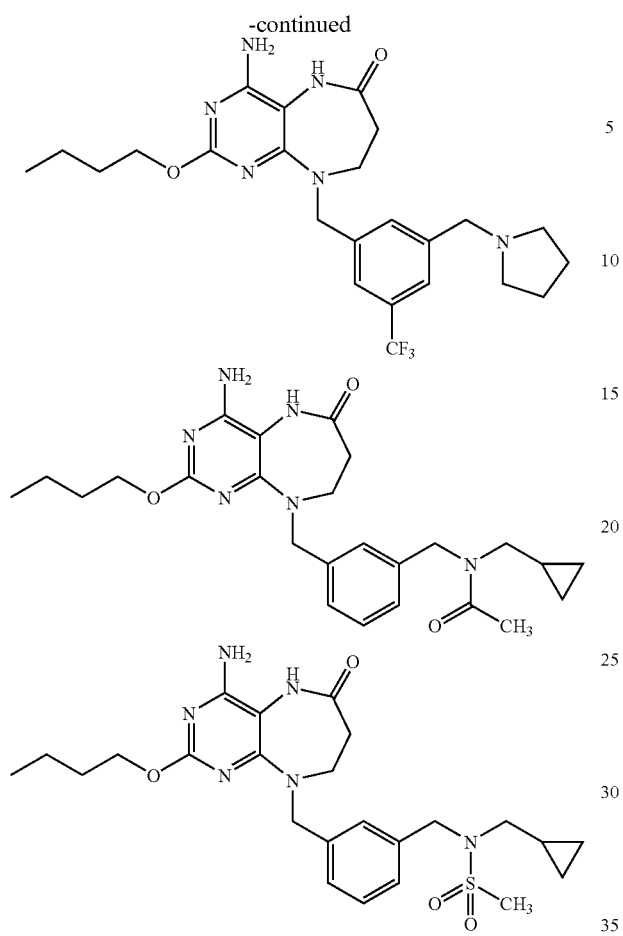

BIOLOGICAL EXAMPLES

PBMC Assay Protocol

Assays were conducted to determine cytokine stimulation at 24 hours from human Peripheral Blood Mononuclear Cell (PMBC) using the compounds of the present invention. The assays were run in duplicate, with 8-point, half-log dilution curves. The compounds of the present invention were diluted from 10 mM DMSO solution. Cell supernatants are assayed directly for IFNa and 1:10 dilution for TNFa. The assays were performed in a similar fashion as described in Bioorg. Med. Chem. Lett. 16, 4559, (2006). Specifically, cryo-preserved PBMCs were thawed and seeded 96 well plates with 750,000 cells/well in 190 μL/well cell media. The PBMCs were then incubated for 1 hour at 37° C. at 5% CO2. Then, the compounds of the present invention were added in 10 μL cell media at 8 point, half-log dilution titration. The plates were incubated at 37° C. and 5% CO2 for 24 hours and then spinned at 1200 rpm for 10 min, which was followed by collecting supernatant and storing the same at −80° C. Cytokine secretion was assayed with Luminex and Upstate multiplex kits, using a Luminex analysis instrument. The IFN-α MEC value for a compound was the lowest concentration at which the compound stimulated IFN-α production at least 3-fold over the background as determined using the assay method above.

The compounds of the present invention have IFN-α MEC values (μM) in the range of >0.03 μM or =0.03 μM. In one embodiment, the compounds of the present invention have IFN MEC values of ≦0.01 μM. Table 1 shows IFN MEC values for the compounds disclosed in Examples 1-118 of the present application.

TABLE 1

| Example | IFN MEC |
|---|---|
| 1 | >0.03 |
| 2 | =0.03 |
| 3 | >0.03 |
| 4 | =0.03 |
| 5 | >0.03 |
| 6 | >0.03 |
| 7 | >0.03 |
| 8 | >0.03 |
| 9 | =0.03 |
| 10 | >0.03 |
| 11 | >0.03 |
| 12 | >0.03 |
| 13 | >0.03 |
| 14 | >0.03 |
| 15 | >0.03 |
| 16 | >0.03 |
| 17 | >0.03 |
| 18 | >0.03 |
| 19 | >0.03 |
| 20 | >0.03 |
| 21 | =0.03 |
| 22 | >0.03 |
| 23 | >0.03 |
| 24 | =0.03 |
| 25 | =0.03 |
| 26 | >0.03 |
| 27 | >0.03 |
| 28 | >0.03 |
| 29 | >0.03 |
| 30 | =0.03 |
| 31 | =0.03 |
| 32 | >0.03 |
| 33 | >0.03 |
| 34 | >0.03 |
| 35 | >0.03 |
| 36 | >0.03 |
| 37 | =0.03 |
| 38 | =0.03 |
| 39 | =0.03 |
| 40 | =0.03 |
| 41 | =0.03 |
| 42 | >0.03 |
| 43 | =0.03 |
| 44 | >0.03 |
| 45 | >0.03 |
| 46 | >0.03 |
| 47 | >0.03 |
| 48 | =0.03 |
| 49 | =0.03 |
| 50 | >0.03 |
| 51 | =0.03 |
| 52 | =0.03 |
| 53 | >0.03 |
| 54 | >0.03 |
| 55 | =0.03 |
| 56 | =0.03 |
| 57 | >0.03 |
| 58 | >0.03 |
| 59 | =0.03 |
| 60 | >0.03 |
| 61 | =0.03 |
| 62 | >0.03 |
| 63 | >0.03 |
| 64 | >0.03 |
| 65 | =0.03 |
| 66 | >0.03 |
| 67 | >0.03 |
| 68 | =0.03 |
| 69 | >0.03 |
| 70 | =0.03 |
| 71 | =0.03 |
| 72 | =0.03 |

TABLE 1-continued

| Example | IFN MEC |
|---|---|
| 73 | >0.03 |
| 74 | >0.03 |
| 75 | >0.03 |
| 76 | >0.03 |
| 77 | >0.03 |
| 78 | >0.03 |
| 79 | =0.03 |
| 80 | >0.03 |
| 81 | >0.03 |
| 82 | =0.03 |
| 83 | =0.03 |
| 84 | =0.03 |
| 85 | >0.03 |
| 86 | =0.03 |
| 87 | =0.03 |
| 88 | =0.03 |
| 89 | =0.03 |
| 90 | >0.03 |
| 91 | >0.03 |
| 92 | >0.03 |
| 93 | =0.03 |
| 94 | =0.03 |
| 95 | =0.03 |
| 96 | =0.03 |
| 97 | =0.03 |
| 98 | =0.03 |
| 99 | =0.03 |
| 100 | =0.03 |
| 101 | >0.03 |
| 102 | =0.03 |
| 103 | =0.03 |
| 104 | =0.03 |
| 105 | =0.03 |
| 106 | >0.03 |
| 108 | >0.03 |
| 109 | >0.03 |
| 110 | =0.03 |
| 111 | >0.03 |
| 112 | >0.03 |
| 113 | =0.03 |
| 114 | >0.03 |
| 115 | >0.03 |
| 116 | >0.03 |
| 117 | >0.03 |
| 118 | >0.03 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Suppression of HCV replicons by exudates of primary leukocytes treated with these compounds can then be measured by the procedure of Thomas, et al. (*Antimicrob. Agents Chemother.* 2007, 51, 2969-2978), which is herein incorporated by reference. Alternatively, the effectiveness of these compounds for suppressing HCV replicons in the presence of PBMCs and pDCs can be determined by the procedure of Goldchild, at al. (*J. Biomol. Screen.* 2009, 14, 723-730), which is herein incorporated by reference.

The compounds of Formula Ia, II, or IIa may also be tested for their ability to induce expression of immunomodulatory cytokines Cynomolgus monkeys (Example B3), mice (Example B4) and healthy woodchucks (Example B5). Moreover, as described in Example B6, the compounds of Formula Ia, II, or IIa may also be tested for their ability to cause seroconversion against Woodchuck Hepatitis Virus (WHV) in chronically infected Eastern Woodchucks (*Marmota monax*) which is an art-recognized model system for HBV infection in human beings (see, e.g., Tennant, B. C., Animal models of hepatitis B virus infection, *Clin. Liver Dis.* 3:241-266 (1999); Menne, S., and P. J. Cote, The woodchuck as an animal model for pathogenesis and therapy of chronic hepatitis B virus infection, *World J. Gastroenterol.* 13:104-124 (2007); and Korba B E, et al., Treatment of chronic WHV infection in the Eastern woodchuck (*M. monax*) with nucleoside analogues is predictive of therapy for chronic hepatitis B virus infection in man, *Hepatology,* 31: 1165-1175 (2000)).

Example B3

Induction of Interferon Alpha by Compounds in Cynomolgus Monkeys

A dose of a compound of Formula II is administered orally or iv to cynomolgus monkeys (3 or more animals per dose group) and serum is collected at 4 hours and 8 hours after dosing. Serum samples are analyzed for levels of interferon-alpha by ELISA. Prior to dosing, serum interferon-alpha levels are usually near or below the level of detection in each animal. The limit of quantitation (LOQ) for IFN-α based on cynomolgus monkey IFN-a standard is about 625 pg/mL.

Additionally, multiple doses of a compound may be administered to Cynomolgus monkeys, and the concentrations of interferon alpha were measured.

Example B4

Induction of Cytokines by Compounds in Mice

A compound of Formula II may be dosed once or more per day for 14 days usually by oral gavage, at 0.5 mg/kg or 2.5 mg/kg, in CD-1 mice. Mouse serum samples are collected at day 1 and day 14, and serum cytokine levels are determined using the following method. Samples are thawed on ice and diluted 2 fold in assay diluent. The assay for interferon-a is done by ELISA (VeriKine™ Mouse Interferon Alpha (Mu-IFN-a) ELISA Kit, Product Number: 42100-1, PBL Biomedical Laboratories, New Brunswick, N.J.) and the other serum cytokines are assayed with Luminex and Milliplex bead kits. Cytokine levels are determined using a nonlinear five point parameter curve for interpolation of data using the fit=(A+((B−A)/(1+(((B−E)/(E−A))*((x/C)^D))))).

Example B5

Induction of Cytokines by Compounds in Healthy Woodchucks

A compound of Formula II may be administered orally to adult, WHV-negative woodchucks at one or more different doses. Three male woodchucks receive a compound of Formula II at about 0.1 to about 0.05 mg/kg and three other male woodchucks at higher doses. Whole blood samples (4 mls) are collected from each woodchuck prior to dosing at T0, and then at 4, 8, 12, and 24 hours post-dose using EDTA-containing collection tubes.

The induction of an immune response in woodchucks following administration of a compound are determined by measuring the mRNA expression of cytokines and interferon-inducible genes in whole blood samples collected at different time points. Total RNA is isolated using the QIAamp RNA Blood Mini Kit (Qiagen) according to the manufacturer's specifications. RNA is eluted into 40 µl nuclease-free water and stored at −70° C. The concentration of RNA is determined spectrophotometrically at OD 260 nm. Two µg of RNA are treated with DNase I (Invitrogen) and reverse transcribed to cDNA with MultiScribe Reverse Transcriptase (Applied Biosystems) using random hexamers. Triplicates of 2 μl cDNA were amplified by real time PCR on an ABI PRISM 7000 Sequence Detection instrument (Applied Biosystems) using SYBR GREEN Master Mix (Applied Biosystems) and woodchuck-specific primers. Amplified target genes include IFN-α, IFN-γ, TNF-α, IL-2, IL-6, IL-10 IL-12, 2'5'-OAS, IDO, and MxA. Woodchuck β-actin mRNA expression is used to normalize target gene expression. Transcription levels of woodchuck cytokines and interferon-inducible genes are represented by the formula 2ΔCt, where ΔCt indicates the difference in the threshold cycle between β-actin and target gene expression. Results may be further represented as a fold-change from the transcription level at T0.

Example B6

Seroconversion in Woodchucks Chronically Infected with Woodchuck Hepatitis Virus (WHV)

A compound of Formula II or placebo is administered orally to five woodchucks per group that are chronic carriers of woodchuck hepatitis virus (WHV). The compound may be administered at a dose of about 1 to about 0.5 mg/kg/day for 28 days. Blood samples are collected prior to dosing and multiple times during and after the 28 day dosing period. Antiviral activity of the compound is assessed by comparing the serum WHV DNA of treated WHV carrier woodchucks with control WHV carrier woodchucks receiving vehicle. The ability of the compound to cause seroconversion in chronically infected animals is assessed by comparing the serum antibody levels against the woodchuck hepatitis virus surface antigen (anti-WHsAg) in infected animals to the anti-WHsAg antibody levels in placebo treated animals.

The woodchucks used in this study are born to WHV-negative females and reared in environmentally controlled laboratory animal facilities. Woodchucks are inoculated at 3 days of age with 5 million woodchuck infectious doses of a standardized WHV inoculum (cWHV7P1 or WHV7P2). Woodchucks selected for use develope WHV surface antigen (WHsAg) serum antigenemia and became chronic WHV carriers. The chronic carrier status of these woodchucks is confirmed prior to initiation of drug treatment.

Serum WHV DNA concentrations are measured before treatment, during treatment, and during the post-treatment follow-up period at frequent intervals. WHV viremia in serum samples is assessed by dot blot hybridization using three replicate volumes (10 μl) of undiluted serum (sensitivity, $1.0 \times 10^7$ WHV genome equivalents per ml [WHVge/ml]) compared with a standard dilution series of WHV recombinant DNA plasmid (pWHV8).

Levels of Woodchuck Hepatitis Virus surface antigen (WHsAg) and antibodies to WHsAg (anti-WHs) are determined before treatment, during treatment, and during the post-treatment follow-up period at frequent intervals, using WHV-specific enzyme immunoassays.

Antiviral activity of a compound of Formula II is assessed by comparing the serum WHV DNA and the hepatic WHV nucleic acids of treated WHV carrier woodchucks with control WHV carrier woodchucks receiving vehicle.

Immune stimulatory activity of a compound required to cause seroconversion is assessed by comparing the serum levels of WHsAg and antibodies to WHsAg (anti-WHsAg).

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

We claim:
1. A compound of Formula II:

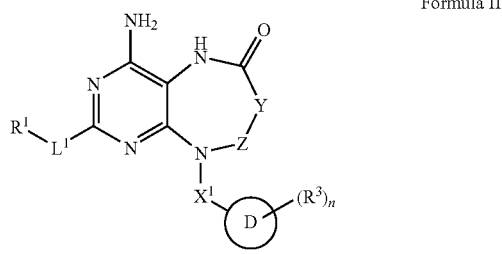

Formula II or a pharmaceutically acceptable salt or tautomeric enol thereof, wherein:

Y—Z is —$CR^4R^5$—;

$L^1$ is —$NR^8$—, —O—, —$N(R^8)C(O)$—, or a covalent bond;

$R^1$ is alkyl, substituted alkyl, haloalkyl, alkenyl, substituted alkenyl, alkynyl, substituted alkynyl, $C_1$-$C_6$ substituted or unsubstituted heteroalkyl containing one or more heteroatoms (selected from N, O, or S), cyclopropyl, substituted cyclopropyl, cyclobutyl, substituted cyclobutyl, cyclopentyl, substituted cyclopentyl, cyclohexyl, substituted cyclohexyl, bicyclo[3.1.0]cyclohexyl, tetrahydropyranyl, substituted tetrahydropyranyl, furanyl, substituted furanyl, pyrrolidinyl, or substituted pyrrolidinyl;

$X^1$ is alkylene, substituted alkylene, heteroalkylene, substituted heteroalkylene, or a bond;

D is phenylene, biphenylene, or pyridinyl, wherein said phenylene, biphenylene, or pyridinyl is substituted with one or two -$L^2$-$NR^6R^7$;

each $L^2$ is independently alkylene, substituted alkylene, heteroalkylene, substituted heteroalkylene, or a covalent bond;

each $R^3$ is independently halogen, cyano, azido, nitro, alkyl, substituted alkyl, hydroxyl, amino, alkoxy, haloalkyl, haloalkoxy, —CHO, —$C(O)OR^8$, —$S(O)R^8$, —$S(O)_2R^8$; —$C(O)NR^9R^{10}$, —$N(R^9)C(O)R^8$, alkenyl, substituted alkenyl, alkynyl, substituted alkynyl, —$S(O)_2NR^9R^{10}$, —$N(R^9)S(O)_2R^8$, —$N(R^9)S(O)_2OR^{10}$, or —$OS(O)_2NR^9R^{10}$;

n is 0, 1, 2, 3, 4 or 5;

$R^4$ and $R^5$ are each independently H, alkyl, substituted alkyl, haloalkyl, $C_1$-$C_6$ substituted or unsubstituted heteroalkyl containing one or more heteroatoms (selected from N, O, or S), cyano, azido, $OR^8$, —$C(O)H$, —$C(O)R^8$, —$S(O)R^8$, —$S(O)_2R^8$, —$C(O)OR^8$, or —$C(O)NR^9R^{10}$;

$R^6$ and $R^7$ are each independently H, alkyl, substituted alkyl, alkenyl, substituted alkenyl, alkynyl, substituted alkynyl, haloalkyl, $C_1$-$C_6$ substituted or unsubstituted heteroalkyl containing one or more heteroatoms (selected from N, O, or S), $C(O)H$, —$C(O)R^8$, —$S(O)R^8$, —$S(O)_2R^8$, —$C(O)OR^8$, or $C(O)NR^9R^{10}$, $S(O)_2NR^9R^{10}$; or $R^6$ and $R^7$, taken together with the nitrogen to which they are both attached, form a substituted or unsubstituted heterocycle, which may contain one or more additional heteroatoms selected from N, O, P, or S; or R$^7$ taken together with L$^2$, and the N to which they are both attached, forms a substituted or unsubstituted 3 to 8 membered heterocycle which may contain one or more additional heteroatoms selected from N, O, S, or P;

R$^8$ is H, alkyl, substituted alkyl, haloalkyl, alkenyl, substituted alkenyl, alkynyl, substituted alkynyl, or C$_1$-C$_6$ substituted or unsubstituted heteroalkyl containing one or more heteroatoms (selected from N, O, or S); and R$^9$ and R$^{10}$ are each independently H, alkyl, substituted alkyl, alkenyl, substituted alkenyl, alkynyl, substituted alkynyl, haloalkyl, C$_1$-C$_6$ substituted or unsubstituted heteroalkyl containing one or more heteroatoms (selected from N, O, or S), wherein each substituted alkyl, substituted alkenyl, substituted alkynyl, substituted cyclopropyl, substituted cyclobutyl, substituted cyclopentyl, substituted cyclohexyl, substituted tetrahydropyranyl, substituted furanyl, or substituted pyrrolidinyl, substituted alkylene, substituted heteroalkylene, substituted alkenylene, substituted alkynylene is independently substituted with one to four substituents selected from the group consisting of -halogen, —R, —O$^-$, =O, —OR, —SR, —S$^-$, —NR$_2$, —N(+)R$_3$, =NR, —C(halogen)$_3$, —CR(halogen)$_2$, —CR$_2$(halogen), —CN, —OCN, —SCN, —N=C=O, —NCS, —NO, —NO$_2$, =N$_2$, —N$_3$, —NRC(=O)R, —NRC(=O)OR, —NRC(=O)NRR, —C(=O)NRR, —O(=O)OR, —OC(=O)NRR, —OC(=O)OR, —C(=O)R, —S(=O)$_2$OR, —S(=O)$_2$R, —OS(=O)$_2$OR, —S(=O)$_2$NR, —S(=O)R, —NRS(=O)$_2$R, —NRS(=O)$_2$NRR, —NRS(=O)$_2$OR, —OP(=O)(OR)$_2$, —P(=O)(OR)$_2$, —P(O)(OR)(O)R, —C(=O)R, —C(=O)OR, —C(=S)OR, —C(=O)SR, —C(=S)SR, —C(=O)NRR, —C(=S)NRR, —C(=NR)NRR, and —NRC(=NR)NRR; wherein each R is independently H or alkyl.

2. The compound of claim 1 wherein L$^1$ is —NH— or —O—.

3. The compound of claim 2 wherein X$^1$ is C$_1$-C$_6$ alkylene, C$_1$-C$_6$ heteroalkylene or C$_1$-C$_6$ substituted heteroalkylene.

4. The compound of claim 3 wherein L$^1$ is —O—.

5. The compound of claim 4 wherein L$^2$ is C$_1$-C$_6$ alkylene or a covalent bond.

6. The compound of claim 5 wherein X$^1$ is —CH$_2$—.

7. The compound of claim 6 wherein R$^6$ and R$^7$ independently are H, alkyl, C$_1$-C$_6$ substituted or unsubstituted heteroalkyl containing one or more heteroatoms (selected from N, O, or S), or, together with the nitrogen atom to which they are attached, form a substituted or unsubstituted pyrrolidine, piperidine or piperazine.

8. The compound of claim 7 wherein R$^6$ and R$^7$ taken together with the nitrogen to which they are attached form a 4- to 10-membered mono- or bicyclic, saturated, partially saturated, or unsaturated ring containing from 0 to 3 additional heteroatoms selected from N, O, or S.

9. The compound of claim 8 wherein L$^2$ is —CH$_2$—.

10. The compound of claim 9 wherein Y—Z is —CH$_2$—.

11. The compound of claim 4 wherein D is pyridinyl.

12. A compound represented by Formula Ia:

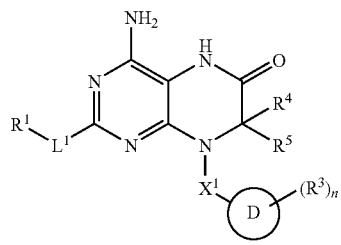

or a pharmaceutically acceptable salt or tautomeric enols thereof, wherein:

L$^1$ is —NH— or —O—;

R$^1$ is alkyl, substituted alkyl, C$_1$-C$_6$ substituted or unsubstituted heteroalkyl containing one or more heteroatoms (selected from N, O or S), cyclopropyl, substituted cyclopropyl, cyclobutyl, substituted cyclobutyl, cyclopentyl, substituted cyclopentyl, cyclohexyl, substituted cyclohexyl, bicyclo[3.1.0]cyclohexyl, tetrahydropyranyl, substituted tetrahydropyranyl, furanyl, substituted furanyl, pyrrolidinyl, or substituted pyrrolidinyl;

each of R$^4$ and R$^5$ independently is H or C$_1$-C$_6$;

X$^1$ is C$_1$-C$_6$ alkylene, C$_1$-C$_6$ heteroalkylene or C$_1$-C$_6$ substituted heteroalkylene;

D is phenyl, biphenyl or pyridinyl, wherein said phenyl, biphenyl or pyridinyl is substituted with -L$^2$-NR$^6$R$^7$; or D is pyridinyl, piperidinyl, piperazinyl or 1,2,3,4-tetrahydroisoquinolinyl, wherein said pyridinyl, piperidinyl, piperazinyl or 1,2,3,4-tetrahydroisoquinolinyl is substituted with one or two -L$^2$-NR$^6$R$^7$; or D is pyridinyl, piperidinyl, piperazinyl or 1,2,3,4-tetrahydroisoquinolinyl;

n is 0 or 1;

R$^3$ is halogen, cyano, alkyl, haloalkyl, —C(O)OR$^8$, —C(O)NR$^9$R$^{10}$ or —CHO;

L$^2$ is C$_1$-C$_6$ alkylene or a covalent bond;

each of R$^6$ and R$^7$ independently is H or alkyl; or

R$^6$ and R$^7$ taken together with the nitrogen to which they are attached form a substituted or unsubstituted 4-6 membered heterocycle comprising 0 to 2 heteroatoms selected from N, O or S.

13. A compound of claim 12 wherein each R$^4$ or R$^5$ is independently H or CH$_3$.

14. A compound of claim 12 wherein L$^1$ is —O—.

15. A compound selected from the group consisting of

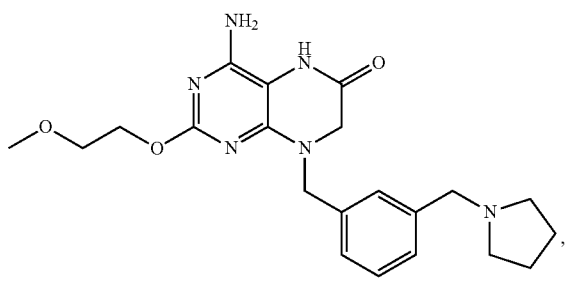

,

241
-continued
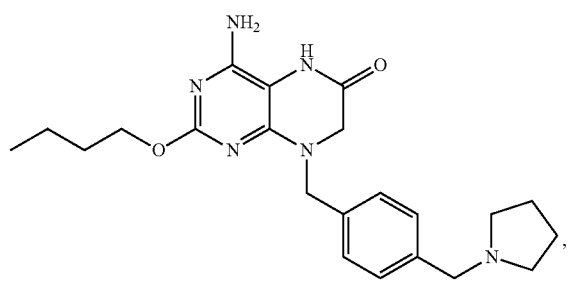
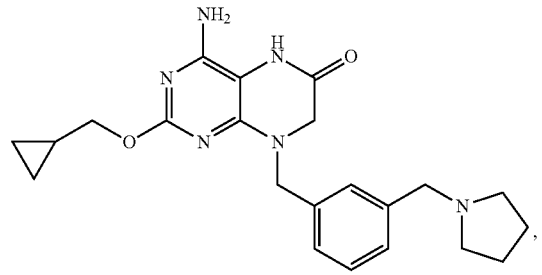
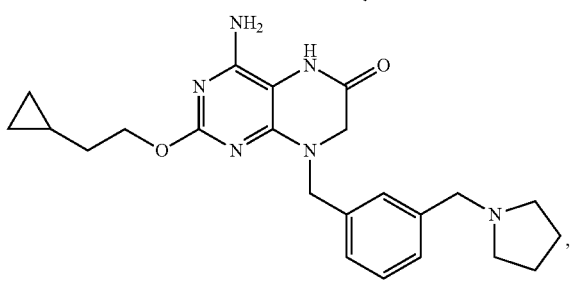
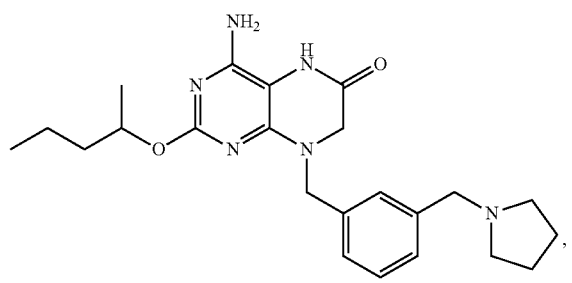
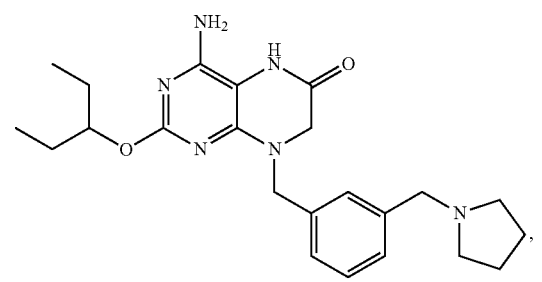
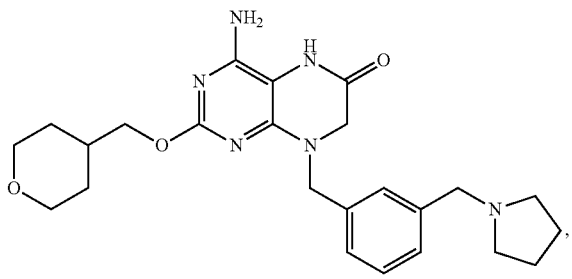
242
-continued
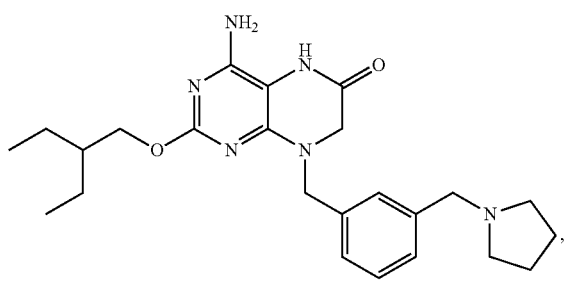
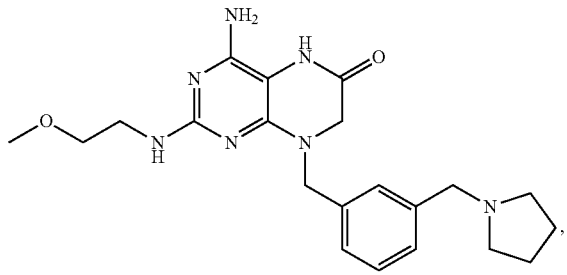
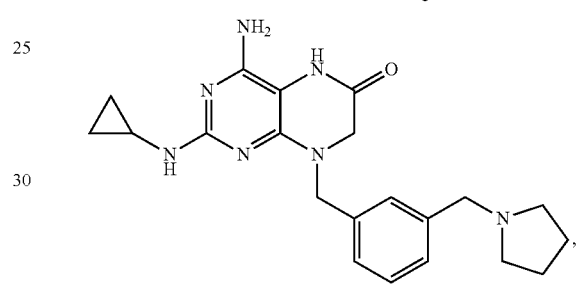
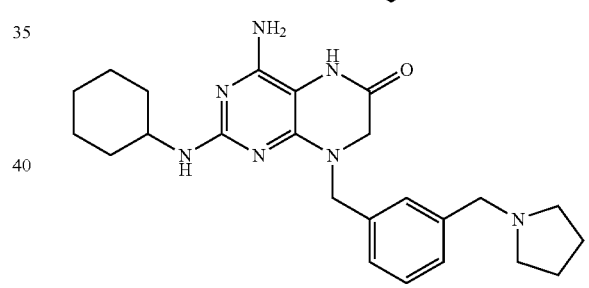
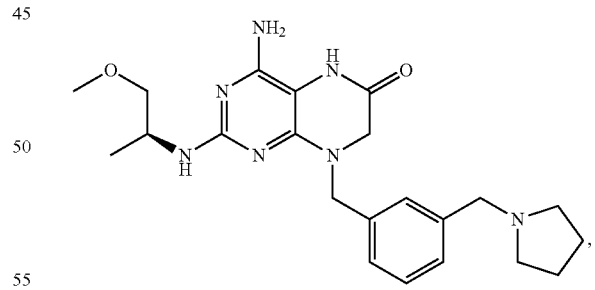
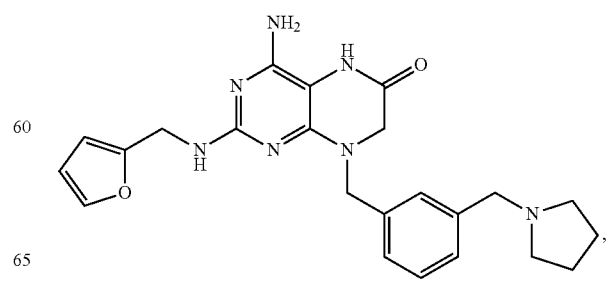

243
-continued
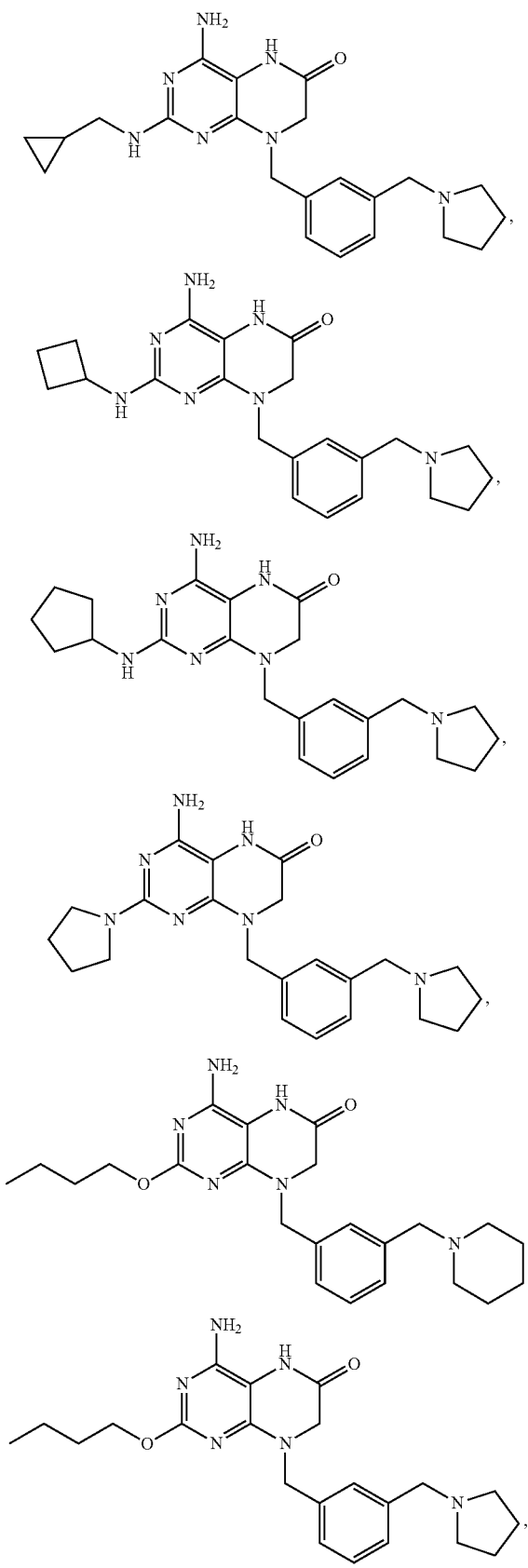
244
-continued
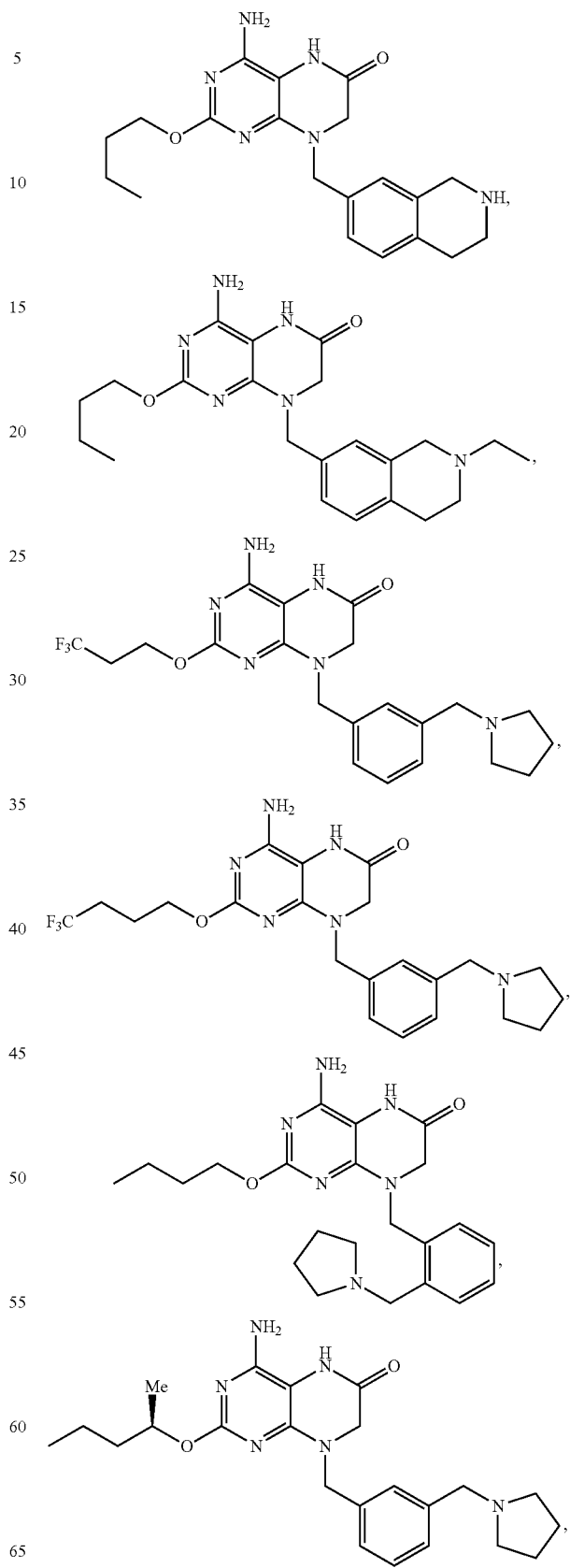

245
-continued
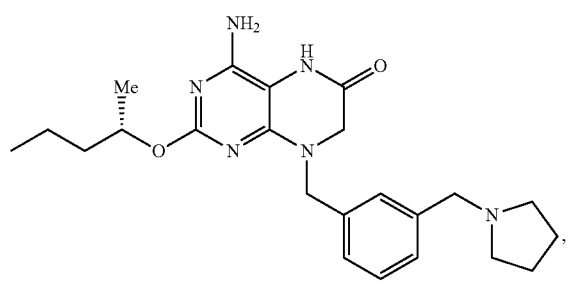
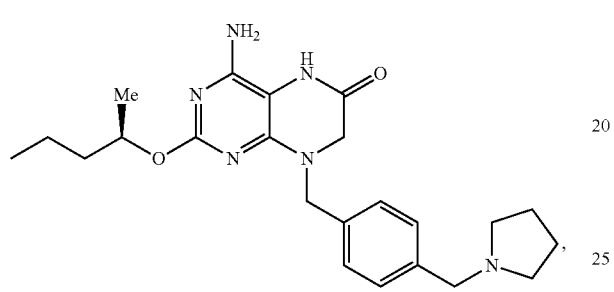
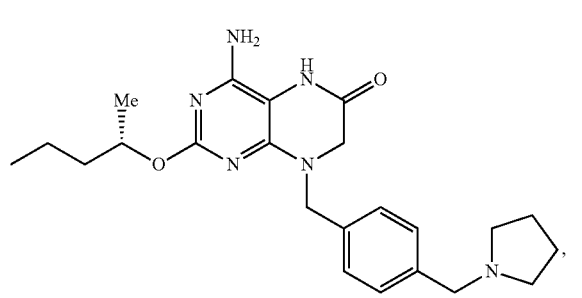
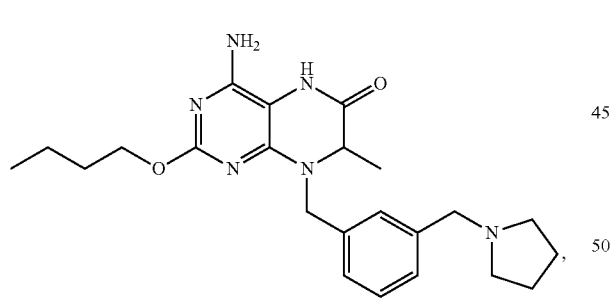
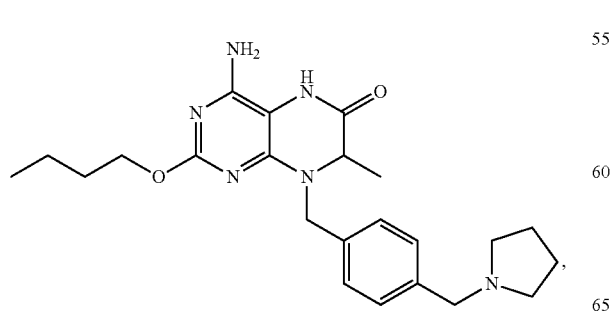
246
-continued
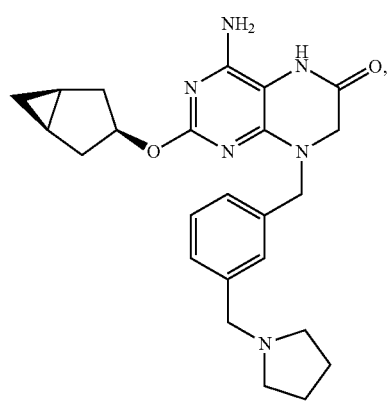
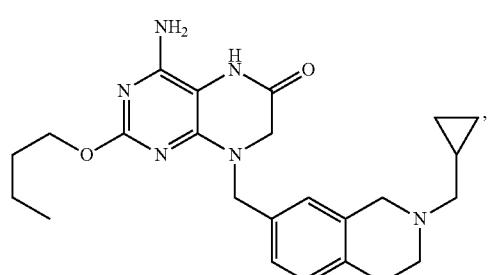
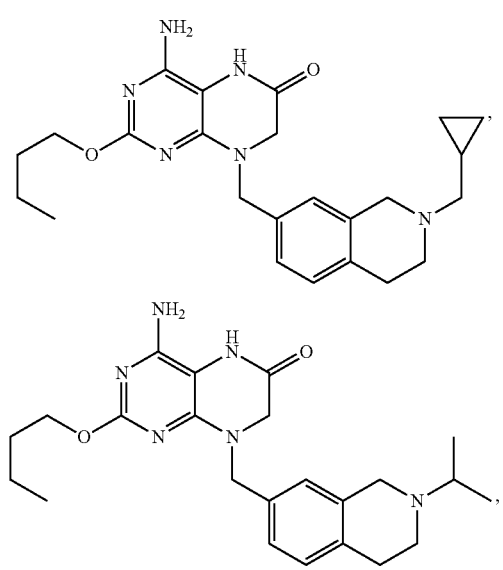
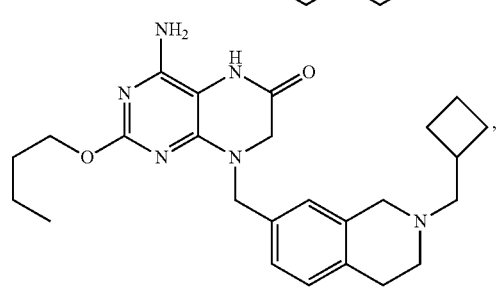
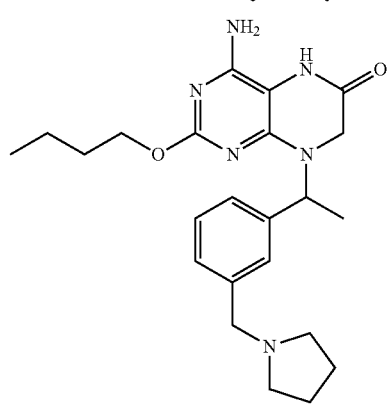

247
-continued
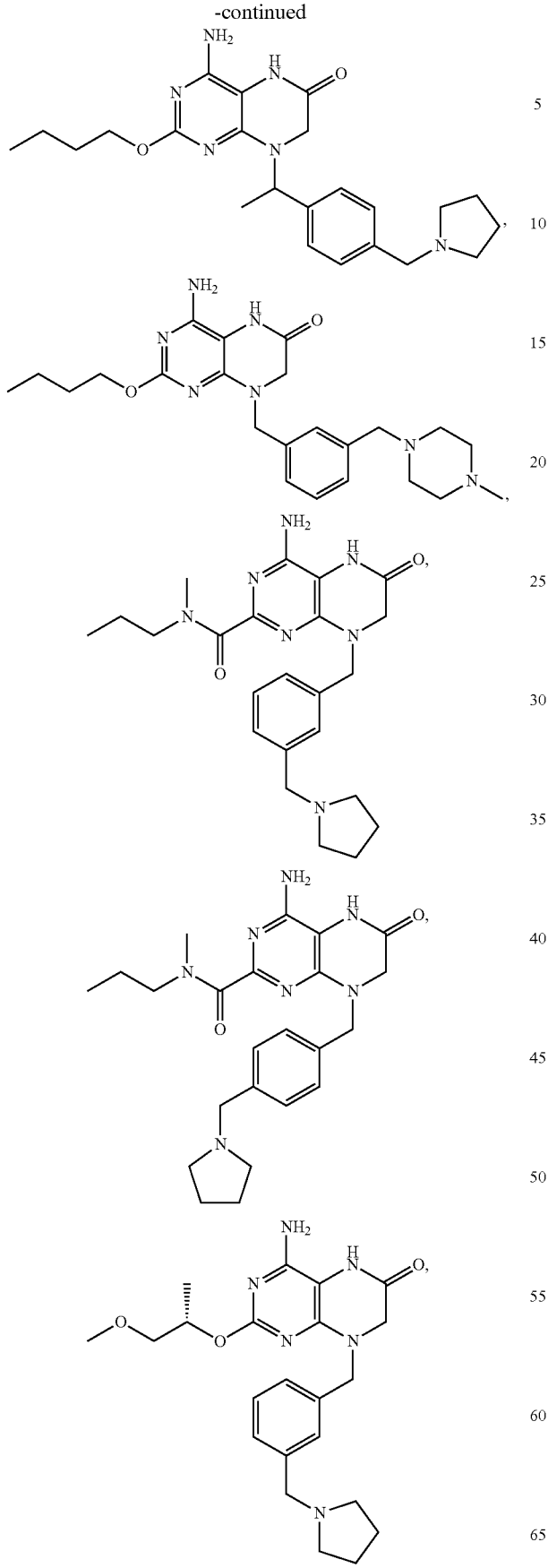
248
-continued
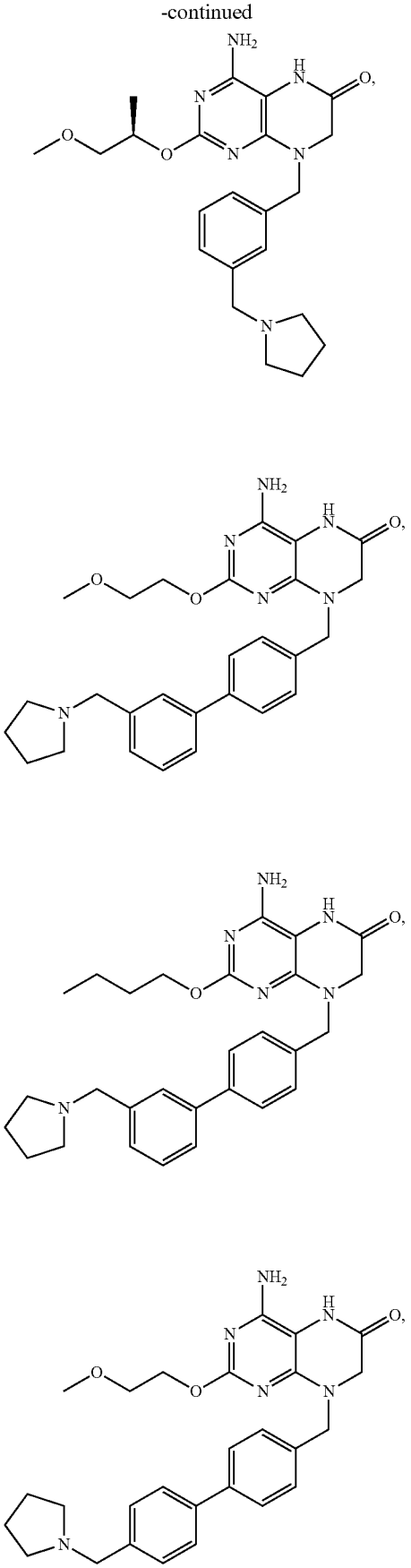

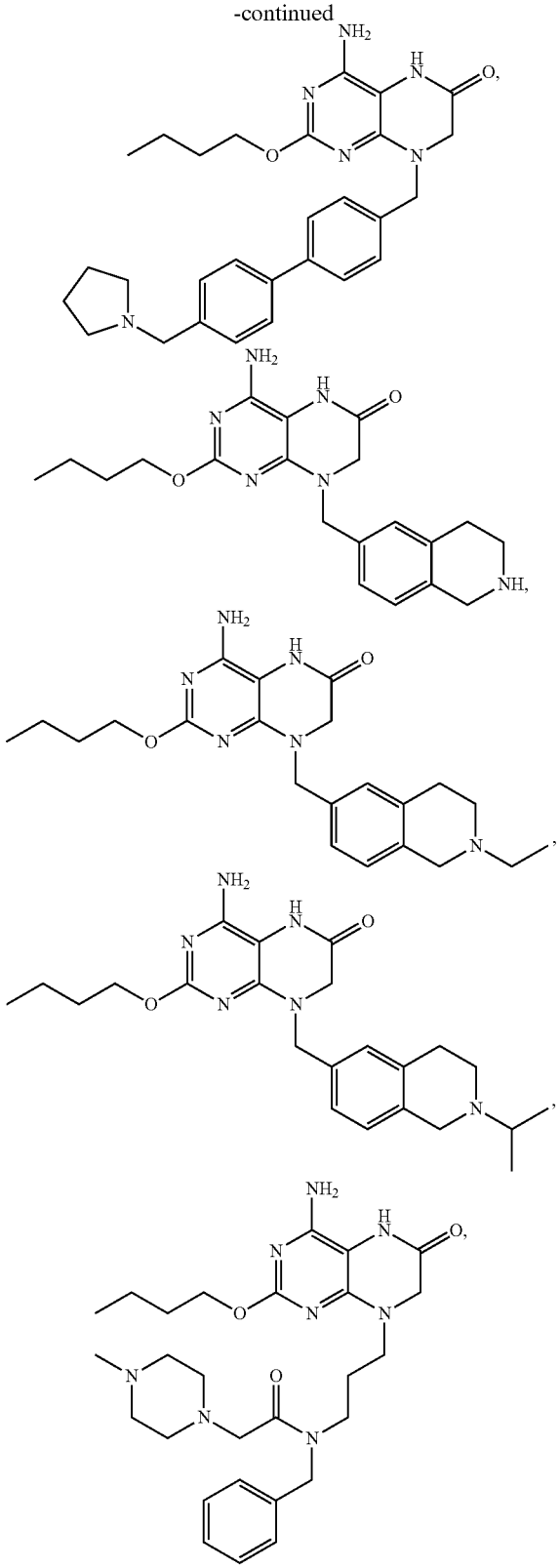

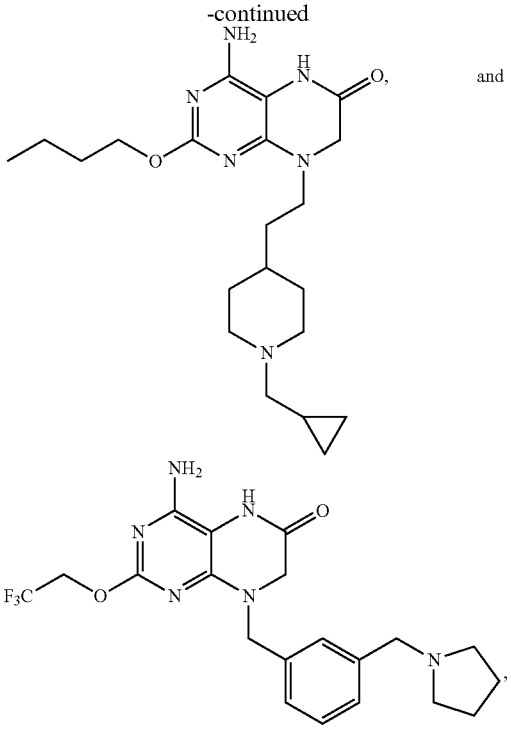

or a pharmaceutically acceptable salt or tautomeric enol thereof.

16. A pharmaceutical composition comprising a therapeutically effective amount of a compound of claim 1 and a pharmaceutically acceptable carrier or excipient.

17. The pharmaceutical composition of claim 16 further comprising at least one additional therapeutic agent selected from the group consisting of interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophilin inhibitors, HCV IRES inhibitors, pharmacokinetic enhancers, and other drugs for treating HCV, or mixtures thereof.

18. The pharmaceutical composition of claim 16 further comprising at least one additional therapeutic agent selected from the group consisting of lamivudine, adefovir, tenofovir, telbivudine, entecavir, interferon alpha-2I), pegylated interferon alpha-2a, interferon alpha 2a, interferon alpha N1, prednisone, predinisolone, Thymalfasin®, retinoic acid receptor agonists, 4-methylumbelliferone, Alamifovir®, Metacavir®, Albuferon®, cytokines and agonists of TLRs.

19. A method of treating a viral infection caused by Hepatitis C virus comprising administering to a mammal in need thereof a therapeutically effective amount of a compound of claim 1.

* * * * *